United States Patent
Yokotani et al.

(10) Patent No.: US 8,327,467 B2
(45) Date of Patent: Dec. 11, 2012

(54) ANTHRANILIC ACID DERIVATIVE OR SALT THEREOF

(75) Inventors: Junichi Yokotani, Toyama (JP); Yoichi Taniguchi, Toyama (JP); Eiji Hara, Toyama (JP); Hitoshi Akitsu, Toyama (JP); Hidehiko Tanaka, Toyama (JP); Shuzo Anzai, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 1067 days.

(21) Appl. No.: 11/908,879

(22) PCT Filed: Mar. 14, 2006

(86) PCT No.: PCT/JP2006/304981
§ 371 (c)(1),
(2), (4) Date: Oct. 23, 2007

(87) PCT Pub. No.: WO2006/098308
PCT Pub. Date: Sep. 21, 2006

(65) Prior Publication Data
US 2009/0105474 A1   Apr. 23, 2009

(30) Foreign Application Priority Data
Mar. 16, 2005 (JP) ................. 2005-074425

(51) Int. Cl.
*C07C 229/00* (2006.01)
(52) U.S. Cl. ............................. 2/433; 562/455; 562/458
(58) Field of Classification Search .................. 562/433, 562/455, 458
See application file for complete search history.

(56) References Cited

U.S. PATENT DOCUMENTS

| 2005/0137236 A1* | 6/2005 | Hattori et al. ................. 514/357 |
| 2005/0197364 A1 | 9/2005 | Kelly et al. |
| 2006/0106048 A1 | 5/2006 | Inoue et al. |

FOREIGN PATENT DOCUMENTS

| GB | 2 406 856 | 4/2005 |
| JP | 49 117442 | 11/1974 |
| JP | 50 34028 | 4/1975 |
| JP | 53 101536 | 9/1978 |
| JP | 54 66645 | 5/1979 |
| JP | 63 216820 | 9/1988 |
| JP | 11171848 | * 6/1990 |
| JP | 11 199565 | 7/1999 |
| JP | 2002-509536 | 3/2002 |
| JP | 2004-67690 | 3/2004 |
| JP | 2004 518726 | 6/2004 |
| JP | 2004 523546 | 8/2004 |
| JP | 2005 502632 | 1/2005 |
| JP | 2007-525482 | 9/2007 |
| WO | WO 99/01421 A1 | 1/1999 |
| WO | WO 2004/050651 A1 | 6/2004 |
| WO | WO 2005032493 | * 10/2004 |
| WO | 2005 019188 | 3/2005 |

OTHER PUBLICATIONS

Igawa et al. STN Document Number: 131:73440 Abstract of JP 11171848.*
Das Gupta et al. Journal of the Indian Chemical Society (1941), 18, 25-8.*
Ramnath, N. et al.,"Matrix Metalloproteinase Inhibitors", Current Oncology Reports, vol. 6, pp. 96-102, 2004.
Close, D. R.,"Matrix Metalloproteinase Inhibitors in Rheumatic Diseases", Annals of the Rheumatic Diseases, vol. 60, pp. iii62-iii67, 2001.
Poole A. R. et al.,"Proteolysis of the Collagen Fibril in Osteoarthritis", Biochem. Soc. Symp., vol. 70, pp. 115-123, 2003.
U.S. Appl. No. 11/721,007, filed Jun. 6, 2007, Yokotani, et al.
Exteded European Search Report issued Sep. 21, 2010, in Application No. 06715640.6-1211 / 1860098 PCT/JP2006304981.
Xuefeng Mei, et al., "Synthesis of a Sterically Crowded Atropisomeric 1,8-Diacridylnaphthalene for Dual-Mode Enantiodelective Fluorosensing", Journal of Organic Chemistry, vol. 71, No. 3, XP-002599058, Mar. 1, 2006, pp. 2854-2861.
Jeremy I. Levin, "The Discovery of Anthranilic Acid-Based MMP Inhibitors., Part1: SAR of the 3-Position", Bioorganic & Medicinal Chemistry Letters, vol. 11, XP-002599059, Jan. 2001, pp. 235-238.
Aventis Res. & Tech, "MMP-13 inhibitors", Expert Opinion on therapeutic Patents, Informa Healthcare, vol. 15, No. 2, XP-002560207, Feb. 1, 2005, pp. 237-241.
U.S. Appl. No. 13/145,813, filed Jul. 22, 2011, Yokotani, et al.
Office Action issued Feb. 1, 2012, in Japanese Patent Application No. 2007-508147.

* cited by examiner

*Primary Examiner* — Nizal Chandrakumar
(74) *Attorney, Agent, or Firm* — Oblon, Spivak, McClelland, Maier & Neustadt, L.L.P.

(57) ABSTRACT

The anthranilic acid derivative or the salt thereof represented by the general formula

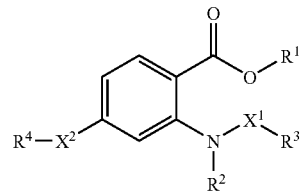

wherein $R^1$ and $R^2$ are hydrogen atom, or the like; $R^3$ is a phenyl, cycloalkyl or bicyclic heterocyclic group which may be substituted, or the like; $R^4$ is a phenyl, cycloalkyl or pyridyl group which may be substituted, or the like; $X^1$ is an alkylene or alkenylene group which may be substituted or a bond; $X^2$ is the general formula $-X^3-X^4-$ or $-X^4-X^3-$, wherein $X^3$ is a sulfur atom, an imino group or a bond, or the like; $X^4$ means an alkylene or alkenylene group which may be substituted or a bond; is useful for a remedy such as rheumatoid arthritis, osteoarthritis and carcinoma, because it shows MMP—13 production inhibitory effect.

17 Claims, No Drawings

ANTHRANILIC ACID DERIVATIVE OR SALT THEREOF

CROSS-REFERENCE TO RELATED APPLICATIONS

The present application is a 35 U.S.C. §371 National Stage patent application of International patent application PCT/JP06/304981, filed on Mar. 14, 2006, which claims priority to Japanese patent application JP 2005-074425, filed on Mar. 16, 2005.

TECHNICAL FIELD

The present invention relates to a novel anthranilic acid derivative or a salt thereof having the inhibitory activity of matrix metalloprotease 13 (MMP-13) production.

BACKGROUND ART

Matrix metalloproteases are a family consisting of zinc-dependent proteases whose substrates are components of extracellular matrix, and they are activated by removal of a propeptide after secretion. More than 20 members of matrix metalloproteases have been identified in human, and they are classified into collagenase (MMP-1, 8, 13), gelatinase (MMP-2, 9), stromelysin (MMP-3, 10), matrilysin (MMP-7, 26), membrane-type MMP (MMP-14, 15, 16, 17, 24, 25) according to the domain structure and substrate specificity. Overexpression of these matrix metalloproteases are observed in various cancer cells, and it is considered to be involved in the proliferation and metastasis thereof. Anticancer agents that inhibit matrix metalloprotease have been developed up to now (Non-Patent Document 1).

Matrix metalloprotease inhibitors have been developed as a therapeutic agent for rheumatoid arthritis and osteoarthritis. The articular cartilage is composed of a cartilage type II collagen network in which cartilage proteoglycans such as aggrecan and hyaluronic acid are retained. Matrix metalloprotease participates in the maintenance of the extracellular matrix. When matrix metalloprotease and TIMP (tissue inhibitor of metalloproteinases), an endogenous inhibitor thereof, are not in balance and matrix metalloprotease becomes excessively present, destruction of the cartilages and bones may progress. Particularly when collagen fibers are damaged, the joints suffer from progressive destruction as observed in rheumatoid arthritis and osteoarthritis. Accordingly, long-term suppression of the progress of joint destruction in rheumatoid arthritis and osteoarthritis can be expected by inhibiting excessive matrix metalloprotease (Non-Patent Document 2).

In osteoarthritis, the production of interleukin-1(IL-1) and tumor necrosis factor (TNF) α also increases and extracellular matrix is degraded. The production of matrix metalloprotease is further increased by degradation products of type II collagen and fibronectin, leading to progress in degradation of matrix in the joints. When this damage of matrix exceeds a certain threshold, character of cartilage cells pathological change, and joint destruction keeps progressing. It is MMP-13 that plays a dominant role in this cleavage of type II collagen (Non-Patent Document 3).

Non-Patent Document 1: Current Oncology Reports, Vol. 6, page 96-102, 2004
Non-Patent Document 2: Annals of the Rheumatic Diseases, Vol. 60, page 62-67, 2001
Non-Patent Document 3: Biochemical Society Symposia, Vol. 70, page 115-123, 2003

DISCLOSURE OF THE INVENTION

Drugs inhibiting the production of matrix metalloproteases, particularly MMP-13, are strongly demanded.

Under the circumstances, the present inventors have conducted extensive studies, and consequently have found that an anthranilic acid derivative represented by general formula [1]

[Formula 1]

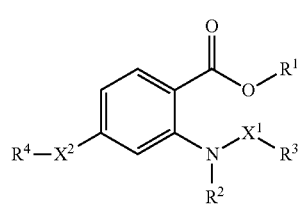

wherein $R^1$ means a hydrogen atom or a carboxyl protecting group; $R^2$ means a hydrogen atom or an imino protecting group; $R^3$ means a monocyclic heterocyclic group which is substituted with a substituted or unsubstituted phenyl group; or a phenyl, cycloalkyl or bicyclic heterocyclic group which may be substituted with one or more group selected from the following group of substituents (1); $R^4$ means a phenyl, thienyl, cycloalkyl, cycloalkenyl or bicyclic heterocyclic group which may be substituted with one or more group selected from the following group of substituents (2) and (3); or a pyridyl group which may be substituted with one or more group selected from the following group of substituents (2) and (4); $X^1$ means a substituted or unsubstituted alkylene or alkenylene group or a bond; $X^2$ means a carbonyl group or the general formula —$X^3$—$X^4$—, —$X^4$—$X^3$—, —O—$X^4$— or —$X^4$—C(O)NH— (provided, however, that the bond on the left side of each general formula should bind to $R^4$.) wherein $X^3$ means a sulfur atom, an imino group which may be protected, a sulfinyl group, a sulfonyl group or a bond; $X^4$ means a substituted or unsubstituted alkylene or alkenylene group or a bond.

[A Group of Substituents (1)]
a halogen atom, a cyano group, a nitro group, an acyl group, an alkanesulfonyl group, an alkanesulfonamide group, an acetamido group, a carbamoyl group, a sulfamoyl group, a lower alkylamino group, an amino group which may be protected, a hydroxyl group which may be protected, an alkyl group which may be substituted, an alkenyl group which may be substituted, an alkynyl group which may be substituted, an alkoxy group which may be substituted, an aryl group which may be substituted, a cyclic amino group which may be substituted, an aralkyl group which may be substituted or a heterocyclic group which may be substituted;

[A Group of Substituents (2)]
an alkyl, alkenyl, alkynyl, alkoxy, aryl, cyclic amino, aralkyl or heterocyclic group which may be substituted with one or more group selected from a halogen atom, a cyano group, a nitro group, an amino group, a cyclic amino group, a lower alkylamino group, a carboxyl group, a hydroxyl group, a lower alkyl group, an alkoxy group and an aryl group

[A Group of Substituents (3)]
a halogen atom, a cyano group, a nitro group, an acyl group, an alkanesulfonyl group, an alkanesulfonamide group, an acetamido group, a carbamoyl group, a sulfamoyl group, a lower alkylamino group, an amino group which may be protected or a hydroxyl group which may be protected

[A Group of Substituents (4)]
a cyano group, a nitro group, an acyl group, an alkanesulfonyl group, an alkanesulfonamide group, an acetamido group, a carbamoyl group, a sulfamoyl group, a lower alkylamino group, an amino group which may be protected or a hydroxyl group which may be protected, or a salt thereof has the inhibitory activity of MMP-13 production and thus completed the present invention.

The novel anthranilic acid derivative or a salt thereof of the present invention has the inhibitory activity of MMP-13 production and is therefore useful as, for example, a therapeutic agent for rheumatoid arthritis, osteoarthritis, cancer and the other diseases in which MMP-13 is involved.

BEST MODE FOR CARRYING OUT THE INVENTION

Hereinbelow, compounds of the present invention are described in detail.

In the present specification, unless otherwise stated in particular, a halogen atom refers to a fluorine atom, a chlorine atom, a bromine atom and an iodine atom; an alkyl group refers to, for example, a linear or branched $C_{1-12}$ alkyl group such as methyl, ethyl, propyl, isopropyl, butyl, sec-butyl, isobutyl, tert-butyl, pentyl, isopentyl, hexyl, heptyl and octyl; a lower alkyl group refers to, for example, a linear or branched $C_{1-6}$ alkyl group such as methyl, ethyl, propyl, isopropyl, butyl, sec-butyl, isobutyl, tert-butyl, pentyl and isopentyl; an alkenyl group refers to, for example, a linear or branched $C_{2-12}$ alkenyl group such as vinyl, allyl, propenyl, isopropenyl, butenyl, isobutenyl, pentenyl, hexenyl, heptenyl and octenyl; an alkynyl group refers to, for example, a linear or branched $C_{2-12}$ alkynyl group such as ethynyl, 2-propynyl and 2-butynyl; a cycloalkyl group refers to, for example, a $C_{3-8}$ cycloalkyl group such as cyclopropyl, cyclobutyl, cyclopentyl and cyclohexyl; a cycloalkenyl group refers to, for example, a $C_{3-8}$ cycloalkenyl group such as cyclopropenyl, cyclobutenyl, cyclopentenyl and cyclohexenyl;

an alkylene group refers to, for example, a linear or branched $C_{1-6}$ alkylene group such as methylene, ethylene, propylene, butylene and hexylene; an alkenylene group refers to, for example, a linear or branched $C_{2-6}$ alkenylene group such as vinylene, propenylene, 1-butenylene and 2-butenylene; an aryl group refers to, for example, a group such as phenyl and naphthyl; an aralkyl group refers to, for example, an ar-$C_{1-6}$ alkyl group such as benzyl, diphenylmethyl, trityl, phenethyl and naphthylmethyl; an alkoxy group refers to, for example, a linear or branched $C_{1-6}$ alkyloxy group such as methoxy, ethoxy, propoxy, isopropoxy, butoxy, isobutoxy, sec-butoxy, tert-butoxy, pentyloxy and isopentyloxy; an alkoxyalkyl group refers to, for example, a $C_{1-6}$ alkyloxy $C_{1-6}$ alkyl group such as methoxymethyl and 1-ethoxyethyl; an aralkyloxyalkyl group refers to, for example, an ar-$C_{1-6}$ alkyloxy $C_{1-6}$ alkyl group such as benzyloxymethyl and phenethyloxymethyl;

an acyl group refers to, for example, a formyl group, a linear or branched $C_{2-12}$ alkanoyl group such as acetyl, propionyl and isovaleryl, an ar-$C_{1-6}$ alkylcarbonyl group such as benzylcarbonyl, a cyclic hydrocarbon carbonyl group such as benzoyl and naphthoyl, a heterocyclic carbonyl group such as nicotinoyl, thenoyl, pyrrolidinocarbonyl and furoyl, a succinyl group, a glutaryl group, a maleoyl group, a phthaloyl group and a linear or branched α-aminoalkanoyl group derived from an amino acid (Examples of the amino acid include glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline and hydroxyproline.) in which the N-terminal may be optionally protected;

an alkyloxycarbonyl group refers to, for example, a linear or branched $C_{1-12}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl and tert-pentyloxycarbonyl; an aralkyloxycarbonyl group refers to, for example, an ar-$C_{1-6}$ alkyloxycarbonyl group such as benzyloxycarbonyl and phenethyloxycarbonyl group; an aryloxycarbonyl group refers to, for example, a group such as phenyloxycarbonyl; an acyloxy group refers to, for example, a linear or branched $C_{2-6}$ alkanoyloxy group such as acetyloxy and propionyloxy and an aroyloxy group such as benzoyloxy; an acylalkyl group refers to, for example, a group such as acetylmethyl, benzoylmethyl, p-nitrobenzoylmethyl, p-bromobenzoylmethyl, p-methoxybenzoylmethyl and 1-benzoylethyl; an acyloxyalkyl group refers to, for example, a group such as acetoxymethyl, propionyloxymethyl and pivaloyloxymethyl;

an arylthio group refers to, for example, a group such as phenylthio; an alkanesulfonyl group refers to, for example, a $C_{1-6}$ alkanesulfonyl group such as methanesulfonyl, ethanesulfonyl and propanesulfonyl; an arylsulfonyl group refers to, for example, a group such as benzenesulfonyl, toluenesulfonyl and naphthalenesulfonyl; an alkylthioalkyl group refers to, for example, a $C_{1-6}$ alkylthio $C_{1-6}$ alkyl group such as methylthiomethyl, ethylthiomethyl and propylthiomethyl; an arylthioalkyl group refers to, for example, a group such as phenylsulfenylmethyl and 2-(p-nitrophenylsulfenyl)ethyl; an alkanesulfonyloxy group refers to, for example, a $C_{1-6}$ alkanesulfonyloxy group such as methanesulfonyloxy and ethanesulfonyloxy; an arylsulfonyloxy group refers to, for example, a group such as benzenesulfonyloxy and toluenesulfonyloxy; an arylsulfonylalkyl group refers to, for example, a group such as p-toluenesulfonylethyl; and an alkanesulfonamide group refers to, for example, a $C_{1-6}$ alkanesulfonamide group such as methanesulfonamide and ethanesulfonamide;

A monocyclic heterocyclic group refers to, for example, a nitrogen-containing monocyclic heterocyclic group containing a nitrogen atom(s) as sole ring-member heteroatom such as pyrrolyl, pyrrolinyl, pyrrolidinyl, piperidyl, piperazinyl, imidazolyl, pyrazolyl, pyridyl, tetrahydropyridyl, pyridazinyl, pyrazinyl, pyrimidinyl, tetrazolyl, imidazolinyl, imidazolidinyl, pyrazolinyl and pyrazolidinyl group; an oxygen-containing monocyclic heterocyclic group containing an oxygen atom(s) as sole ring-member heteroatom such as furyl, pyranyl, tetrahydropyranyl, 1,3-dioxolyl, 1,3-dioxanyl and 1,4-dioxanyl group; a sulfur-containing monocyclic heterocyclic group containing a sulfur atom(s) as sole ring-member heteroatom such as a thienyl group; a nitrogen-and-oxygen-containing monocyclic heterocyclic group containing nitrogen and oxygen atoms as sole ring-member heteroatoms such as oxazolyl, oxadiazolyl, isoxazolyl and morpholinyl group; a nitrogen-and-sulfur-containing monocyclic heterocyclic group containing nitrogen and sulfur atoms as sole ring-member heteroatoms such as thiazolyl, isothiazolyl, thiadiazolyl and thiomorpholinyl group; and an oxygen-and-sulfur-containing monocyclic heterocyclic group containing oxygen and sulfur atoms as sole ring-member heteroatoms such as a thioxanyl group;

A bicyclic heterocyclic group refers to, for example, a nitrogen-containing bicyclic heterocyclic group represented by a condensed or bridged ring containing only nitrogen atom(s) as the heteroatom of the said ring such as indolyl, indolinyl, isoindolyl, indolizinyl, benzimidazolyl, benzotriazolyl, indazolyl, quinolyl, tetrahydroquinolinyl, tetrahydroisoquinolinyl, quinolizinyl, isoquinolyl, phthalazinyl, naphthyridinyl, quinoxalinyl, dihydroquinoxalinyl, quinazolinyl, cinnolinyl, quinuclidinyl and 2,3-dihydrobenzopyrrolyl group; an oxygen-containing bicyclic heterocyclic group represented by a condensed or bridged ring containing only oxygen atom(s) as the heteroatom of the said ring such as benzofuranyl, isobenzofuranyl, chromenyl, isochromanyl, benzo-1,3-dioxolyl, benzo-1,4-dioxanyl and 2,3-dihydrobenzofuranyl group; a sulfur-containing bicyclic heterocyclic group represented by a condensed or bridged ring containing only sulfur atom(s) as the heteroatom of the said ring such as benzothienyl and 2,3-dihydrobenzothienyl group; a nitrogen-and-oxygen-containing bicyclic heterocyclic group represented by a condensed or bridged ring containing only nitrogen and oxygen atom(s) as the heteroatom of the said ring such as benzomorpholinyl and benzomorpholonyl group; and a nitrogen-and-sulfur-containing bicyclic heterocyclic group represented by a condensed or bridged ring containing only nitrogen and sulfur atom(s) as the heteroatom of the said ring such as benzothiazolyl group;

An oxygen-containing heterocyclic group refers to, for example, a group such as 2-tetrahydropyranyl and 2-tetrahydrofuranyl; a sulfur-containing heterocyclic group refers to, for example, a group such as tetrahydrothiopyranyl; a heterocyclic oxycarbonyl group refers to, for example, a group such as 2-furfuryloxycarbonyl and 8-quinolyloxycarbonyl; a nitrogen-containing heterocyclic alkyl group refers to, for example, a group such as phthalimidomethyl and succinimidomethyl;

A heterocyclic group refers to, for example, a nitrogen-containing monocyclic heterocyclic group containing a nitrogen atom(s) as sole ring-member heteroatom such as pyrrolyl, pyrrolinyl, pyrrolidinyl, piperidyl, piperazinyl, imidazolyl, pyrazolyl, pyridyl, tetrahydropyridyl, pyridazinyl, pyrazinyl, pyrimidinyl, tetrazolyl, imidazolinyl, imidazolidinyl, pyrazolinyl and pyrazolidinyl group; an oxygen-containing monocyclic heterocyclic group containing an oxygen atom(s) as sole ring-member heteroatom such as furyl, pyranyl, tetrahydropyranyl, 1,3-dioxolyl, 1,3-dioxanyl and 1,4-dioxanyl group; a sulfur-containing monocyclic heterocyclic group containing a sulfur atom(s) as sole ring-member heteroatom such as a thienyl group; a nitrogen-and-oxygen-containing monocyclic heterocyclic group containing nitrogen and oxygen atoms as sole ring-member heteroatoms such as oxazolyl, oxadiazolyl, isoxazolyl and morpholinyl group; a nitrogen-and-sulfur-containing monocyclic heterocyclic group containing nitrogen and sulfur atoms as sole ring-member heteroatoms such as thiazolyl, isothiazolyl, thiadiazolyl and thiomorpholinyl group; and an oxygen-and-sulfur-containing monocyclic heterocyclic group containing oxygen and sulfur atoms as sole ring-member heteroatoms such as a thioxanyl group; a nitrogen-containing bicyclic heterocyclic group represented by a condensed or bridged ring containing only nitrogen atom(s) as the heteroatom of the said ring such as indolyl, indolinyl, isoindolyl, indolizinyl, benzimidazolyl, benzotriazolyl, indazolyl, quinolyl, tetrahydroquinolinyl, tetrahydroisoquinolinyl, quinolizinyl, isoquinolyl, phthalazinyl, naphthyridinyl, quinoxalinyl, dihydroquinoxalinyl, quinazolinyl, cinnolinyl, purinyl, quinuclidinyl and 2,3-dihydrobenzopyrrolyl group; an oxygen-containing bicyclic heterocyclic group represented by a condensed or bridged ring containing only oxygen atom(s) as the heteroatom of the said ring such as benzofuranyl, isobenzofuranyl, chromenyl, chromanyl, isochromanyl, benzo-1, 3-dioxolyl, benzo-1,4-dioxanyl and 2,3-dihydrobenzofuranyl group; a sulfur-containing bicyclic heterocyclic group represented by a condensed or bridged ring containing only sulfur atom(s) as the heteroatom of the said ring such as benzothienyl and 2,3-dihydrobenzothienyl group; a nitrogen-and-oxygen-containing bicyclic heterocyclic group represented by a condensed or bridged ring containing only nitrogen and oxygen atom(s) as the heteroatom of the said ring such as benzoxazolyl, benzisoxazolyl, benzomorpholinyl and benzomorpholonyl group; and a nitrogen-and-sulfur-containing bicyclic heterocyclic group represented by a condensed or bridged ring containing only nitrogen and sulfur atom(s) as the heteroatom of the said ring such as benzothiazolyl group;

A lower alkylamino group refers to, for example, a mono-$C_{1-6}$ alkylamino group such as methylamino, ethylamino, propylamino, isopropylamino, butylamino, tert-butylamino and pentylamino; a $C_{3-6}$ cycloalkylamino group such as cyclopropylamino, cyclobutylamino and cyclopentylamino; and a di-$C_{1-6}$ alkylamino group such as dimethylamino, diethylamino, dipropylamino and dibutylamino;

A cyclic amino group may be, for example, a saturated cyclic amino group and an unsaturated amino group, may optionally contain one or more heteroatoms such as nitrogen atom, oxygen atom and sulfur atom and carbonyl carbon in the ring, and may be monocyclic, bicyclic or tricyclic; and more specifically refers to a saturated or unsaturated monocyclic 3- to 7-membered cyclic amino group having one nitrogen atom such as aziridin-1-yl, azetidin-1-yl, pyrrolidin-1-yl, pyrrolin-1-yl, pyrrol-1-yl, dihydropyridin-1-yl, piperidin-1-yl, dihydroazepin-1-yl and perhydroazepin-1-yl; a saturated or unsaturated monocyclic 3- to 7-membered cyclic amino group having 2 nitrogen atoms such as imidazol-1-yl, imidazolidin-1-yl, imidazolin-1-yl, pyrazolidin-1-yl, piperazin-1-yl, 1,4-dihydropyrazin-1-yl, 1,2-dihydropyrimidin-1-yl, perhydropyrazin-1-yl and homopiperazin-1-yl; a saturated or unsaturated monocyclic 3- to 7-membered cyclic amino group having 3 or more nitrogen atoms such as 1,2,4-triazol-1-yl, 1,2,3-triazol-1-yl, 1,2-dihydro-1,2,4-triazin-1-yl and perhydro-5-triazin-1-yl; a saturated or unsaturated monocyclic 3- to 7-membered cyclic amino group having 1 to 4 heteroatoms selected from an oxygen atom and a sulfur atom in addition to a nitrogen atom(s) such as oxazolidin-3-yl, isoxazolidin-2-yl, morpholin-4-yl, thiazolidin-3-yl, thiazolidin-2-yl, thiomorpholin-4-yl, homothiomorpholin-4-yl and 1,2,4-thiaziazolin-2-yl; a saturated or unsaturated bicyclic or tricyclic cyclic amino group such as isoindolin-2-yl, indolin-1-yl, 1H-indazol-1-yl, purin-7-yl and tetrahydroquinolin-1-yl; and a saturated or unsaturated 5- to 12-membered spiro or bridged cyclic amino group such as 5-azaspiro[2.4]heptan-5-yl, 2,8-diazabicyclo[4.3.0]nonan-8-yl, 3-azabicyclo[3.1.0]hexan-3-yl, 2-oxa-5,8-diazabicyclo[4.3.0]nonan-8-yl, 2,8-diazaspiro[4.4]nonan-2-yl and 7-azabicyclo[2.2.1]heptan-7-yl; a substituted silyl group refers to, for example, a group such as trimethylsilyl, triethylsilyl and tributylsilyl; and an alkylsilylalkyl group refers to, for example, a group such as 2-(trimethylsilyl)ethyl.

The amino protecting group includes any group which can be normally used as a protecting group of an amino group, and examples thereof include groups described in W. Greene et al., Protective Groups in Organic Synthesis, third edition, pp. 494-615, 1999, John Wiley & Sons, INC. Specific examples thereof include an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkanesulfonyl group, an arylsulfonyl group and a substituted silyl group.

The imino protecting group includes any group which can be normally used as a protecting group of an imino group, and examples thereof include groups described in W. Greene et al., Protective Groups in Organic Synthesis, third edition, pp. 494-615, 1999, John Wiley & Sons, INC. Specific examples thereof include an acyl group, an alkyloxycarbonyl group, an aralkyloxycarbonyl group, an aryloxycarbonyl group, an aralkyl group, an alkoxyalkyl group, an arylthio group, an alkanesulfonyl group, an arylsulfonyl group and a substituted silyl group.

The hydroxyl protecting group includes any group which can be normally used as a protecting group of a hydroxyl group, and examples thereof include groups described in W. Greene et al., Protective Groups in Organic Synthesis, third edition, pp. 17-245, 1999, John Wiley & Sons, INC. Specific examples thereof include an acyl group, an alkyloxycarbonyl group, an aralkyloxycarbonyl group, a heterocyclic oxycarbonyl group, an alkyl group, an alkenyl group, an aralkyl group, an oxygen-containing heterocyclic group, a sulfur-containing heterocyclic group, an alkoxyalkyl group, an aralkyloxyalkyl group, an alkanesulfonyl group, an arylsulfonyl group and a substituted silyl group.

The carboxyl protecting group includes any group which can be normally used as a protecting group of a carboxyl group, and examples thereof include groups described in W. Greene et al., Protective Groups in Organic Synthesis, third edition, pp. 369-453, 1999, John Wiley & Sons, INC. Specific examples thereof include an alkyl group, an alkenyl group, an aryl group, an aralkyl group, an acylalkyl group, an arylthioalkyl group, an arylsulfonylalkyl group, an oxygen-containing heterocyclic group, an alkyl silyl alkyl group, an acyloxyalkyl group, a nitrogen-containing heterocyclic alkyl group, a cycloalkyl group, an alkoxyalkyl group, an aralkyloxyalkyl group, an alkylthioalkyl group and a substituted silyl group.

The phenolic hydroxyl protecting group includes any group which can be normally used as a protecting group of a phenolic hydroxyl group, and examples thereof include groups described in W. Greene et al., Protective Groups in Organic Synthesis, third edition, pp. 246-287, 1999, John Wiley & Sons, INC. Specific examples thereof include an acyl group, an alkyl group, an alkenyl group, an aralkyl group, an oxygen-containing heterocyclic group, a sulfur-containing heterocyclic group, an alkoxyalkyl group, an alkanesulfonyl group, an arylsulfonyl group and a substituted silyl group.

The thiol protecting group includes any group which can be normally used as a protecting group of a thiol group, and examples thereof include groups described in W. Greene et al., Protective Groups in Organic Synthesis, third edition, pp. 454-493, 1999, John Wiley & Sons, INC. Specific examples thereof include an acyl group, an alkyl group, an alkenyl group, an aralkyl group, an alkoxyalkyl group and a substituted silyl group.

Examples of a leaving group include a halogen atom, an alkanesulfonyloxy group, an arylsulfonyloxy group and an acyloxy group.

The salt of a compound of general formula [1] includes commonly known salts formed from a basic group such as an amino group or from an acidic group such as a phenolic hydroxyl group or a carboxyl group.

Examples of salts formed from a basic group include salts with a mineral acid such as hydrochloric acid, hydrogen bromide and sulfuric acid; salts with an organic carboxylic acid such as tartaric acid, formic acid, acetic acid, citric acid, trichloroacetic acid and trifluoroacetic acid; and salts with a sulfonic acid such as methanesulfonic acid, benzenesulfonic acid, p-toluenesulfonic acid, mesitylenesulfonic acid and naphthalenesulfonic acid.

Examples of salts formed from an acidic group include salts with an alkali metal such as sodium and potassium; salts with an alkali earth metal such as calcium and magnesium; ammonium salts; and salts with a nitrogen-containing organic base group such as trimethylamine, triethylamine, tributylamine, pyridine, N,N-dimethylaniline, N-methylpiperidine, N-methylmorpholine, diethylamine,dicyclohexylamine, procaine,dibenzylamine, N-benzyl-β-phenethylamine and N,N'-dibenzylethylenediamine.

Furthermore, as preferable salts of a compound of general formula [1], pharmacologically acceptable salts are included.

An alkyl, alkenyl, alkynyl, alkoxy, aryl, cyclic amino, aralkyl and heterocyclic group, with which a phenyl, cycloalkyl or bicyclic heterocyclic group of $R^3$ in the present invention may be substituted, may be optionally substituted with at least one group selected from a halogen atom, a cyano group, a nitro group, an amino group, a cyclic amino group, a lower alkylamino group, a carboxyl group, a hydroxyl group, a lower alkyl group, an alkoxy group and aryl group.

A phenyl group, with which a monocyclic heterocyclic group of $R^3$ in the present invention is substituted, may be optionally substituted with at least one group selected from a halogen atom, a cyano group, a nitro group, an amino group, a cyclic amino group, a lower alkylamino group, a carboxyl group, a hydroxyl group, a lower alkyl group, an alkoxy group and aryl group.

An alkylene group or an alkenylene group of $X^1$ and $X^4$ in the present invention may be optionally substituted with at least one group selected from a halogen atom, a cyano group, a nitro group, an amino group, a cyclic amino group, a lower alkylamino group, a carboxyl group, a hydroxyl group, a lower alkyl group, an alkoxy group and aryl group.

Among the compounds of the present invention, preferable compounds include the following compounds.

The compounds in which $R^1$ is a hydrogen atom are preferable.

The compounds in which $R^2$ is a hydrogen atom are preferable.

The compounds in which $R^3$ is a monocyclic heterocyclic group which is substituted with a substituted or unsubstituted phenyl group; or a phenyl or bicyclic heterocyclic group which may be optionally substituted with at least one group selected from a halogen atom, a cyano group, a nitro group, an acyl group, an alkanesulfonyl group, an alkanesulfonamide group, an acetamido group, a carbamoyl group, a sulfamoyl group, a lower alkylamino group, an amino group which may be protected, a hydroxyl group which may be protected, an alkyl group which may be substituted, an alkenyl group which may be substituted, an alkynyl group which may be substituted, an alkoxy group which may be substituted, an aryl group which may be substituted, a cyclic amino group which may be substituted, an aralkyl group which may be substituted, and a heterocyclic group which may be substituted are preferable, the compounds in which $R^3$ is a monocyclic heterocyclic group which is substituted with a substituted or unsubstituted phenyl group; or a phenyl or bicyclic heterocyclic group which may be optionally substituted with at least one group selected from a halogen atom, a cyano group, a hydroxyl group, an alkyl group which may be substituted, an alkenyl group which may be substituted, an alkynyl group which may be substituted, an alkoxy group which may be substituted, an aryl group which may be substituted, a cyclic amino group which may be substituted, an aralkyl group which may be substituted, and a heterocyclic group which may be substituted are more preferable, the compounds in which $R^3$ is a monocyclic heterocyclic group which is substituted with a phenyl group; or a phenyl or bicyclic heterocyclic group which may be optionally substituted with at least one group selected from a halogen atom, a hydroxyl group, an alkyl group which may be substituted, an alkoxy group which may be substituted, an aryl group which may be substituted, and a heterocyclic group which may be substituted are still more preferable, and the compounds in which $R^3$ is a pyrazolyl, isoxazolyl, thiazolyl or thiadiazolyl group which is substituted with a phenyl group; or a phenyl group which may be optionally substituted with at least one group selected from a halogen atom, a hydroxyl group, an alkyl group which may be substituted with a halogen atom, and an alkoxy group which may be substituted with a halogen atom are still further more preferable.

The compounds in which $R^4$ is a phenyl or bicyclic heterocyclic group which may be optionally substituted with one or more group selected from the following group of substituents (2a) and (3a) are preferable, the compounds in which $R^4$ is a phenyl or bicyclic heterocyclic group which may be optionally substituted with one or more group selected from the following group of substituents (2b) and (3b) are more preferable, and the compounds in which $R^4$ is a phenyl group which may be optionally substituted with one or more group selected from an alkyl group which may be substituted with a halogen atom, an alkoxy group which may be substituted with a halogen atom, a halogen atom, and a hydroxyl group are still more preferable.

[A Group of Substituents (2a)]
an alkyl, alkenyl, alkynyl, alkoxy, aryl, cyclic amino, aralkyl or heterocyclic group which may be substituted with one or more group selected from a halogen atom, a cyano group, a nitro group, an amino group, a cyclic amino group, a lower alkylamino group, a carboxyl group, a hydroxyl group, a lower alkyl group, an alkoxy group and an aryl group

[A Group of Substituents (2b)]
an alkyl, alkoxy, aryl, cyclic amino or heterocyclic group which may be substituted with one or more group selected from a halogen atom, a cyano group, a nitro group, an amino group, a cyclic amino group, a lower alkylamino group, a carboxyl group, a hydroxyl group, a lower alkyl group, an alkoxy group and an aryl group

[A Group of Substituents (3a)]
a halogen atom, a cyano group, a nitro group, an acyl group, an alkanesulfonyl group, an alkanesulfonamide group, an acetamido group, a carbamoyl group, a sulfamoyl group, a lower alkylamino group, an amino group which may be protected or a hydroxyl group which may be protected

[A Group of Substituents (3b)]
a halogen atom, a cyano group, a lower alkylamino group, an amino group which may be protected or a hydroxyl group which may be protected The compounds in which $X^1$ is an alkylene or alkenylene group which may be substituted with group selected from an alkyl and phenyl group which may be substituted or a bond are preferable, the compounds in which $X^1$ is an alkylene group, an alkenylene group or a bond are more preferable, the compounds in which $X^1$ is an alkenylene group or a bond are still more preferable, and the compounds in which $X^1$ is a bond are still further more preferable.

The compounds in which $X^2$ is a carbonyl group or the general formula —O—$X^{4a}$— or —$X^{4a}$—C(O)NH—; provided, however, that the bond on the left side of the general formula should bind to $R^4$, and $X^{4a}$ represents an alkylene group which may be substituted or a bond, are preferable.

The compounds in which $X^2$ is the general formula —$X^{3a}$—$X^{4b}$— or —$X^{4b}$—$X^{3a}$—; provided, however, that the bond on the left side of the general formula should bind to $R^4$; and $X^{3a}$ represents a sulfur atom, an imino group which may be protected or a bond; and $X^{4b}$ represents an alkylene or alkenylene group which may be optionally substituted with group selected from an alkyl and phenyl group which may be substituted or a bond, are preferable, the compounds in which $X^2$ is an alkylene group, alkenylene group or a bond are more preferable, and the compounds in which $X^2$ is an alkylene group or a bond are still more preferable.

Examples of typical compounds, among the compounds of the present invention, include compounds of the following Tables 1 to 5.

TABLE 1

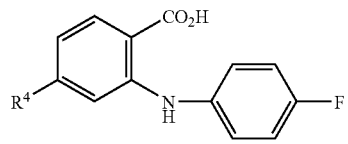

$R^4$

Phenyl
2-Fluorophenyl
3-Fluorophenyl
4-Fluorophenyl
2-Chlorophenyl
3-Chlorophenyl
4-Chlorophenyl
2-Methoxyphenyl
3-Methoxyphenyl
4-Methoxyphenyl
3-Cyanophenyl
4-Cyanophenyl
2-Hydroxyphenyl
3-Hydroxyphenyl
4-Hydroxyphenyl
2-Methylphenyl
3-Methylphenyl
4-Methylphenyl
2,3-Dimethylphenyl
2,6-Dimethylphenyl
3,4-Dimethylphenyl
3-Nitrophenyl
4-Nitrophenyl
4-Acetylphenyl
Thiophen-2-yl
Benzofuran-2-yl
Benzofuran-5-yl
Isoquinolin-4-yl
3-Acetamidephenyl
Indolin-1-yl
Quinoxalin-6-yl
Cyclopentyl
4-tert-Butylphenyl
2,4-Difluorophenyl
3-Fluoro-4-methylphenyl
4-Fluoro-2-methylphenyl
3-Chloro-4-methoxyphenyl
3-Chloro-2-methylphenyl
3-Chloro-4-methylphenyl
3-Chloro-4-hydroxyphenyl
5-Chloro-2-methoxyphenyl
5-Chloro-2-methylphenyl
3,4-Dimethoxyphenyl
2-isopropoxyphenyl TABLE 1-continued

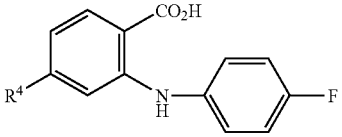

| R⁴ |
|---|
| 4-isopropoxyphenyl |
| 2-(Trifluoromethoxy)phenyl |
| 3-(Trifluoromethoxy)phenyl |
| 4-(Trifluoromethoxy)phenyl |
| 3-(Trifluoromethyl)phenyl |
| 4-(Trifluoromethyl)phenyl |
| 3,5-Dimethyl-4-hydroxyphenyl |
| Benzothiophen-2-yl |
| Benzothiophen-5-yl |
| 2,3-Dihydrobenzo[1,4]dioxin-6-yl |
| Benzo-1,3-dioxol-5-yl |
| 1H-benzimidazol-1-yl |
| 1H-indol-1-yl |
| 1H-indol-4-yl |
| 1H-indol-5-yl |
| 1-Methyl-1H-indol-5-yl |
| 4-Methanesulfonylphenyl |
| 4-Methanesulfonamidephenyl |
| 2-Methoxypyridin-5-yl |
| 1,2,3,4-Tetrahydroisoquinolin-2-yl |

TABLE 2

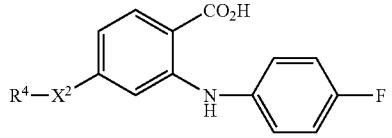

| R⁴ | X² |
|---|---|
| Phenyl | CH₂ |
| Phenyl | CH=CH (E) |
| Phenyl | C=O |
| Phenyl | O |
| Phenyl | S |
| Phenyl | NH |
| Phenyl | (CH₂)₂ |
| Phenyl | (CH₂)₃ |
| Phenyl | (CH₂)₄ |
| Phenyl | CH₂NH |
| Phenyl | (CH₂)₂NH |
| Phenyl | (CH₂)₃NH |
| Phenyl | OCH₂ |
| Phenyl | CH₂S |
| Phenyl | SCH₂ |
| Cyclohexyl | CH=CH (E) |
| Cyclohexyl | CH2CH=CH (E) |
| Cyclohexyl | O |
| Cyclohexyl | (CH₂)₂ |
| Cyclohexyl | (CH₂)₃ |
| 2-Methylphenyl | CH=CH (E) |
| 4-Fluorophenyl | CH=CH (E) |
| 2,4-Difluorophenyl | CH=CH (E) |
| 3-Fluoro-4-methylphenyl | CH=CH (E) |
| 2-Chlorophenyl | CH=CH (E) |
| 3-Chlorophenyl | CH=CH (E) |
| 3-Nitrophenyl | CH=CH (E) |
| 4-Acetylphenyl | CH=CH (E) |
| 3-Methoxyphenyl | CH=CH (E) |
| 4-Methoxyphenyl | CH=CH (E) |
| 2,3-Dihydrobenzo[1,4]dioxin-6-yl | CH=CH (E) |
| Benzo-1,3-dioxol-5-yl | CH=CH (E) |
| 4-Trifluoromethylphenyl | CH=CH (E) |
| Benzofuran-5-yl | CH=CH (E) |

TABLE 2-continued

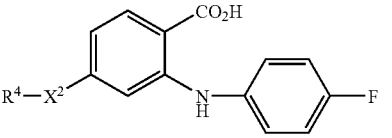

| R⁴ | X² |
|---|---|
| 1H-indol-4-yl | CH=CH (E) |
| 2-Hydroxyphenyl | CH=CH (E) |
| 3-Hydroxyphenyl | CH=CH (E) |
| 4-Hydroxyphenyl | CH=CH (E) |

TABLE 3

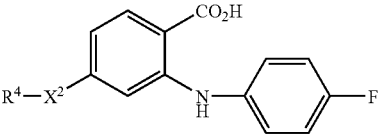

| R⁴ | X² |
|---|---|
| 2-Methylphenyl | (CH₂)₂ |
| 3-Methylphenyl | (CH₂)₂ |
| 4-Methylphenyl | (CH₂)₂ |
| 2,3-Dimethylphenyl | (CH₂)₂ |
| 3,4-Dimethylphenyl | (CH₂)₂ |
| 2-Fluorophenyl | (CH₂)₂ |
| 3-Fluorophenyl | (CH₂)₂ |
| 4-Fluorophenyl | (CH₂)₂ |
| 2,4-Difluorophenyl | (CH₂)₂ |
| 3-Fluoro-4-methylphenyl | (CH₂)₂ |
| 3-Aminophenyl | (CH₂)₂ |
| 4-Ethylphenyl | (CH₂)₂ |
| 2-Methoxyphenyl | (CH₂)₂ |
| 3-Methoxyphenyl | (CH₂)₂ |
| 4-Methoxyphenyl | (CH₂)₂ |
| 3,4-Dimethoxyphenyl | (CH₂)₂ |
| 3-(Trifluoromethoxy)phenyl | (CH₂)₂ |
| 4-(Trifluoromethoxy)phenyl | (CH₂)₂ |
| 3-Acetamidephenyl | (CH₂)₂ |
| 2,3-Dihydrobenzo[1,4]dioxin-6-yl | (CH₂)₂ |
| Benzo-1,3-dioxol-5-yl | (CH₂)₂ |
| 4-Trifluoromethylphenyl | (CH₂)₂ |
| Benzofuran-5-yl | (CH₂)₂ |
| 1H-indol-4-yl | (CH₂)₂ |
| 2-Hydroxyphenyl | (CH₂)₂ |
| 3-Hydroxyphenyl | (CH₂)₂ |
| 4-Hydroxyphenyl | (CH₂)₂ |
| 2,3-Dihydrobenzo[1,4]dioxin-6-yl | CONH |
| Benzothiophen-3-yl | CONH |
| Phenyl | CH=CHCONH (E) |
| Phenyl | SO₂NH |

TABLE 4-1

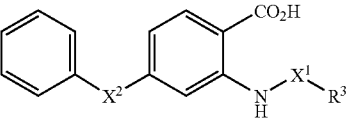

| X² | X¹ | R³ |
|---|---|---|
| Bond | Bond | Phenyl |
| Bond | Bond | 2-Fluorophenyl |
| Bond | Bond | 2,4-Difluorophenyl |

TABLE 4-1-continued

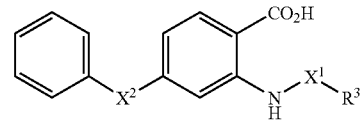

| X² | X¹ | R³ |
|---|---|---|
| Bond | Bond | 2-Chlorophenyl |
| Bond | Bond | 3-Chlorophenyl |
| Bond | Bond | 2-Nitrophenyl |
| Bond | Bond | 3-Nitrophenyl |
| Bond | Bond | 4-Nitrophenyl |
| Bond | Bond | 2-Methylphenyl |
| Bond | Bond | 3-Methylphenyl |
| Bond | Bond | 4-Methylphenyl |
| Bond | Bond | 4-Methoxy-2-methylphenyl |
| Bond | Bond | 2-Methoxyphenyl |
| Bond | Bond | 3-Methoxyphenyl |
| Bond | Bond | 4-Methoxyphenyl |
| Bond | Bond | 2-(Trifluoromethoxy)phenyl |
| Bond | Bond | 3-(Trifluoromethoxy)phenyl |
| Bond | Bond | 4-(Trifluoromethoxy)phenyl |
| Bond | Bond | 3-Fluoro-4-methylphenyl |
| Bond | Bond | 2-Hydroxyphenyl |
| Bond | Bond | 3-Hydroxyphenyl |
| Bond | Bond | 4-Hydroxyphenyl |
| Bond | Bond | 4-Acetylphenyl |
| Bond | Bond | 2-Dimethylaminophenyl |
| Bond | Bond | 4-Dimethylaminophenyl |
| Bond | Bond | Benzo-1,3-dioxol-5-yl |
| Bond | Bond | Benzothiophen-5-yl |
| Bond | Bond | Benzofuran-5-yl |
| Bond | Bond | 2,3-Dihydrobenzo[1,4]dioxin-6-yl |
| Bond | Bond | Quinolin-3-yl |
| Bond | Bond | Quinolin-8-yl |
| Bond | Bond | Isoquinolin-4-yl |
| Bond | Bond | Isoquinolin-5-yl |
| Bond | Bond | 2-Biphenyl |
| Bond | Bond | 3-Biphenyl |
| Bond | Bond | 4-Biphenyl |
| Bond | Bond | 3-(1H-pyrazol-1-yl)phenyl |
| Bond | CH₂CH=CH (E) | Phenyl |

TABLE 4-2

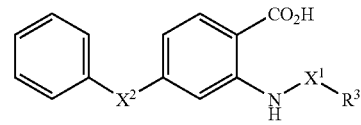

| X² | X¹ | R³ |
|---|---|---|
| (CH₂)₂ | Bond | Phenyl |
| (CH₂)₂ | Bond | Cyclohexyl |
| (CH₂)₂ | Bond | 2-Fluorophenyl |
| (CH₂)₂ | Bond | 3-Fluorophenyl |
| (CH₂)₂ | Bond | 2,5-Difluorophenyl |
| (CH₂)₂ | Bond | 2,4-Difluorophenyl |
| (CH₂)₂ | Bond | 3,4-Difluorophenyl |
| (CH₂)₂ | Bond | 2-Chlorophenyl |
| (CH₂)₂ | Bond | 3-Chlorophenyl |
| (CH₂)₂ | Bond | 4-Chlorophenyl |
| (CH₂)₂ | Bond | 2,6-Dichlorophenyl |
| (CH₂)₂ | Bond | 2-Nitrophenyl |
| (CH₂)₂ | Bond | 3-Nitrophenyl |
| (CH₂)₂ | Bond | 4-Nitrophenyl |
| (CH₂)₂ | Bond | 2-Methylphenyl |
| (CH₂)₂ | Bond | 3-Methylphenyl |
| (CH₂)₂ | Bond | 4-Methylphenyl |
| (CH₂)₂ | Bond | 4-Methoxy-2-methylphenyl |
| (CH₂)₂ | Bond | 2,3-Dimethylphenyl |
| (CH₂)₂ | Bond | 2,4-Dimethylphenyl |

TABLE 4-2-continued

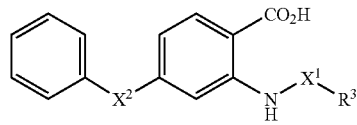

| X² | X¹ | R³ |
|---|---|---|
| (CH₂)₂ | Bond | 3,4-Dimethylphenyl |
| (CH₂)₂ | Bond | 2-Ethylphenyl |
| (CH₂)₂ | Bond | 4-Ethylphenyl |
| (CH₂)₂ | Bond | 2-Methoxyphenyl |
| (CH₂)₂ | Bond | 3-Methoxyphenyl |
| (CH₂)₂ | Bond | 4-Methoxyphenyl |
| (CH₂)₂ | Bond | 2-(Trifluoromethoxy)phenyl |
| (CH₂)₂ | Bond | 3-(Trifluoromethoxy)phenyl |
| (CH₂)₂ | Bond | 4-(Trifluoromethoxy)phenyl |
| (CH₂)₂ | Bond | 2-(Trifluoromethyl)phenyl |
| (CH₂)₂ | Bond | 4-(Trifluoromethyl)phenyl |
| (CH₂)₂ | Bond | 2-Hydroxyphenyl |
| (CH₂)₂ | Bond | 3-Hydroxyphenyl |
| (CH₂)₂ | Bond | 4-Hydroxyphenyl |
| (CH₂)₂ | Bond | 3-Fluoro-4-methylphenyl |
| (CH₂)₂ | Bond | 4-Fluoro-3-methylphenyl |
| (CH₂)₂ | Bond | 4-Acetylphenyl |

TABLE 4-3

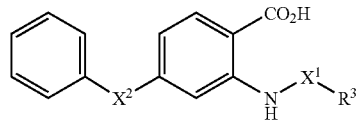

| X² | X¹ | R³ |
|---|---|---|
| (CH₂)₂ | Bond | 2-Dimethylaminophenyl |
| (CH₂)₂ | Bond | 4-Dimethylaminophenyl |
| (CH₂)₂ | Bond | Benzo-1,3-dioxol-5-yl |
| (CH₂)₂ | Bond | Benzothiophen-5-yl |
| (CH₂)₂ | Bond | Benzofuran-5-yl |
| (CH₂)₂ | Bond | 1H-indol-5-yl |
| (CH₂)₂ | Bond | Benzothiazol-6-yl |
| (CH₂)₂ | Bond | 2,3-Dihydrobenzo[1,4]dioxin-6-yl |
| (CH₂)₂ | Bond | Quinolin-3-yl |
| (CH₂)₂ | Bond | Quinolin-8-yl |
| (CH₂)₂ | Bond | Isoquinolin-4-yl |
| (CH₂)₂ | Bond | Isoquinolin-5-yl |
| (CH₂)₂ | Bond | 2-Biphenyl |
| (CH₂)₂ | Bond | 3-Biphenyl |
| (CH₂)₂ | Bond | 4-Biphenyl |
| (CH₂)₂ | Bond | 3-(1H-pyrazol-1-yl)phenyl |
| (CH₂)₂ | Bond | 4-(1H-pyrazol-1-yl)phenyl |
| (CH₂)₂ | Bond | 1-Phenyl-1H-pyrazol-5-yl |
| (CH₂)₂ | Bond | 3-Phenyl-1H-pyrazol-5-yl |
| (CH₂)₂ | Bond | 4-Phenylthiazol-2-yl |
| (CH₂)₂ | Bond | 5-Phenyl-1,3,4-thiadiazol-2-yl |
| (CH₂)₂ | Bond | 3-Phenylisoxazol-5-yl |
| (CH₂)₂ | CH₂ | Phenyl |
| (CH₂)₂ | CH₂ | 4-Fluorophenyl |
| (CH₂)₂ | (CH₂)₂ | Phenyl |
| (CH₂)₂ | CH₂CH=CH (E) | Phenyl |
| O | Bond | Phenyl |
| O | CH₂ | Phenyl |
| O | CH₂ | 4-Fluorophenyl |
| O | CH₂ | 2,4-Difluorophenyl |
| O | Bond | Cyclohexyl |
| O | Bond | 2,4-Dimethoxyphenyl |
| O | Bond | 4-Chlorophenyl |
| O | Bond | 4-Methoxy-2-methylphenyl |
| O | Bond | Quinolin-8-yl |
| O | Bond | Benzo-1,3-dioxol-5-yl |

TABLE 5

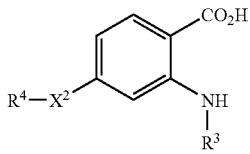

| R⁴—X² | R³ |
|---|---|
| 3-Chlorophenyl | Phenyl |
| 3-Chlorophenyl | 3-Hydroxyphenyl |
| 3-Chlorophenyl | 2-Methylphenyl |
| 3-Chlorophenyl | Benzothiophen-5-yl |
| 3-Chlorophenyl | Benzo-1,3-dioxol-5-yl |
| 4-(Methanesulfonamide)phenyl | Phenyl |
| 4-(Methanesulfonamide)phenyl | 2-Methylphenyl |
| 4-(Methanesulfonamide)phenyl | Benzothiophen-5-yl |
| 4-(Methanesulfonamide)phenyl | Benzo-1,3-dioxol-5-yl |
| 3-Hydroxyphenyl | Phenyl |
| 3-Hydroxyphenyl | 3-Hydroxyphenyl |
| 3-Hydroxyphenyl | 2-Methylphenyl |
| 3-Hydroxyphenyl | Benzothiophen-5-yl |
| 3-Hydroxyphenyl | Benzo-1,3-dioxol-5-yl |
| Indolin-1-yl | Phenyl |
| Indolin-1-yl | 3-Hydroxyphenyl |
| Indolin-1-yl | 2-Methylphenyl |
| Indolin-1-yl | Benzothiophen-5-yl |
| Indolin-1-yl | Benzo-1,3-dioxol-5-yl |
| 2-(3-Methoxyphenyl)ethyl | Phenyl |
| 2-(3-Methoxyphenyl)ethyl | 3-Hydroxyphenyl |
| 2-(3-Methoxyphenyl)ethyl | 2-Methylphenyl |
| 2-(3-Methoxyphenyl)ethyl | Benzothiophen-5-yl |
| 2-(3-Methoxyphenyl)ethyl | Benzo-1,3-dioxol-5-yl |
| 2-(2,3-Dihydrobenzo[1,4]dioxin-6-yl)ethyl | Phenyl |
| 2-(2,3-Dihydrobenzo[1,4]dioxin-6-yl)ethyl | 3-Hydroxyphenyl |
| 2-(2,3-Dihydrobenzo[1,4]dioxin-6-yl)ethyl | 2-Methylphenyl |
| 2-(2,3-Dihydrobenzo[1,4]dioxin-6-yl)ethyl | Benzo-1,3-dioxol-5-yl |

In addition, when any isomer (for example, optical isomer, geometrical isomer, tautomer and the like) is present for the compounds of general formula [1] or a salt thereof, the present invention includes those isomers and, in addition, includes solvates, hydrates and crystals of various kinds.

Next, production processes of the compounds of the present invention are described.

The compound of the present invention can be produced by combining methods well known per se together, but, for example, can be produced following the production processes shown below.

[Manufacturing Process 1]

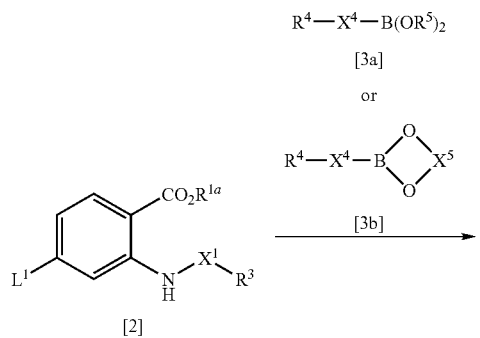

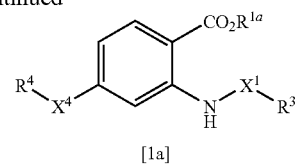

wherein $R^{1a}$ represents a carboxyl protecting group; $R^5$ represents a hydrogen atom or a lower alkyl group; $X^5$ represents an alkylene group which may be substituted; $L^1$ represents a leaving group; $R^3$, $R^4$, $X^1$ and $X^4$ represent the same meanings as described above.

As a compound of general formula [3a], for example, pyridine-3-boronic acid, 4-(methanesulfonamide)phenylboronic acid, thiophene-2-boronic acid, benzofuran-2-boronic acid and 3-methoxyphenylboronic acid are known. As a compound of general formula [3b], for example, 4-(4,4,5,5-tetramethyl-1,3,2-dioxaborolan-2-yl)isoquinoline are known. In addition, the compounds of the general formula [3a] and [3b], for example, can be produced according to the method described in Japanese Patent Laid-Open No. 2003-206290 bulletins or the like method, and can produced from the corresponding halogeno compounds.

The compound of the general formula [1a] can be produced by reacting the compound of the general formula [2] with the compound of the general formula [3a] or [3b] in the presence or absence of base, in the presence of palladium catalyst, in the presence or absence of ligand.

For the solvent used in this reaction, if it does not adversely affect the reaction, it is not limited to particularly, but for example, water; alcohols such as methanol, ethanol, 2-propanol and 2-methyl-2-propanol; aromatic hydrocarbons such as benzene, toluene and xylene; amides such as N,N-dimethylformamide, N,N-dimethylacetamide and 1-methyl-2-pyrrolidone; halogenated hydrocarbons such as dichloromethane, chloroform and dichloroethane; ethers such as dioxane, tetrahydrofuran, anisole, ethylene glycol dimethyl ether,diethylene glycol dimethyl ether and diethylene glycol diethyl ether; ketones such as acetone and 2-butanone; nitrites such as acetonitrile; esters such as ethyl acetate and butyl acetate; and sulfoxides such as dimethyl sulfoxide are given, and these may be mixed and used.

For base used in this reaction if desired, for example, inorganic base such as sodium hydrogen carbonate, sodium carbonate, potassium carbonate and cesium carbonate and organic base such as triethylamine,diisopropylethylamine, tributylamine and N,N-dicyclohexylmethylamine are given. The amount of base used may be 1-50 times mole per the compound of the general formula [2], and may be preferably 2-5 times mole.

For palladium catalyst used in this reaction, for example, metal palladium such as palladium-carbon, palladium black; inorganic palladium salts such as palladium chloride; organic palladium salts such as palladium acetate; organopalladium complex such as tetrakis(triphenylphosphine) palladium(0), bis(triphenylphosphine)palladium (II) chloride, 1,1'-bis(diphenylphosphino)ferrocene palladium (II) dichloride and tris(dibenzylideneacetone)dipalladium (0); and polymer-immobilized organopalladium complex such as polymer supported di(acetato)dicyclohexylphenylphosphine palladium (II) and polymer supported bis(acetato)triphenylphosphine palladium (II) are given, and these may be combined and used. The amount of palladium catalyst used may be 0.00001-1 times mole per the compound of general formula [2], and may be preferably 0.001-0.1 times mole.

For ligand used in this reaction if desired, trialkylphosphine such as trimethylphosphine and tri-tert-butylphosphine; tricycloalkylphosphine such as tricyclohexylphosphine; triarylphosphine such as triphenylphosphine and tritolylphosphine; trialkylphosphite such as trimethylphosphite, triethylphosphite and tributylphosphite; tricycloalkylphosphite such as tricyclohexylphosphite; triarylphosphite such as triphenylphosphite; imidazolium salts such as 1,3-bis(2,4,6-trimethylphenyl) imidazolium chloride; diketones such as acetylacetone and octafluoroacetylacetone; amines such as trimethylamine, triethylamine, tripropylamine and triisopropylamine; and 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-tert-butylphosphino)-2',4',6'-triisopropylbiphenyl and 2-(di-tert-butylphosphino)biphenyl are given, and these may be combined and used. The amount of ligand used may be 0.00001-1 times mole per the compound of general formula [2], and may be preferably 0.001-0.1 times mole.

The amount of the compound of general formula [3a] or [3b] used may be 1-50 times mole per the compound of general formula [2], and may be preferably 1-3 times mole.

This reaction may be carried out preferably under an inert gas (for example, nitrogen, argon) atmosphere at 40 to 220° C. for 1 minute to 96 hours.

[Manufacturing Process 2]

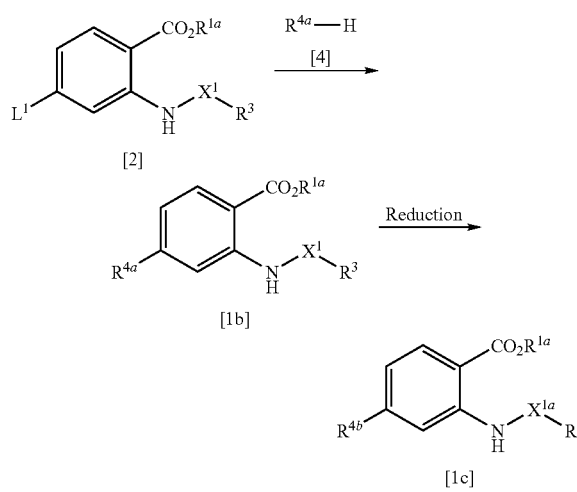

wherein $R^{4a}$ represents a cycloalkenyl group which may be substituted with at least one group selected from a halogen atom, a cyano group, a nitro group, an acyl group, an alkanesulfonyl group, an alkanesulfonamide group, an acetamido group, a carbamoyl group, a sulfamoyl group, a lower alkylamino group, an amino and hydroxy group which may be protected and an alkyl, alkenyl, alkynyl, alkoxy, aryl, cyclic amino, aralkyl and heterocyclic group which may be substituted, $R^{4b}$ represents a cycloalkyl group which may be substituted with at least one group selected from a halogen atom, a cyano group, a nitro group, an acyl group, an alkanesulfonyl group, an alkanesulfonamide group, an acetamido group, a carbamoyl group, a sulfamoyl group, a lower alkylamino group, an amino and hydroxyl group which may be protected and an alkyl, alkenyl, alkynyl, alkoxy, aryl, cyclic amino, aralkyl and heterocyclic group which may be substituted, $X^{1a}$ represents an alkylene group which may be substituted or a bond, $R^{1a}$, $R^3$, $X^1$ and $L^1$ represent the same meanings as described above.

(2-1)

As a compound of general formula [4], for example, cyclopentene and cyclohexene are known. In addition, the compound of general formula [4] can be produced according to the method, for example, described in "Jikken Kagaku Kouza", 4th edition, Vol. 19, Page 53-298, 1992, Maruzen or the like method.

The compound of the general formula [1b] can be produced by reacting the compound of general formula [2] with the compound of general formula [4] in the presence or absence of base, in the presence or absence of phase transfer catalyst, in the presence or absence of ligand, in the presence of palladium catalyst.

For solvent used in this reaction, if it does not adversely affect the reaction, it is not limited to particularly, but for example, water; alcohols such as methanol, ethanol, 2-propanol and 2-methyl-2-propanol; aromatic hydrocarbons such as benzene, toluene and xylene; amides such as N,N-dimethylformamide, N,N-dimethylacetamide and 1-methyl-2-pyrrolidone; halogenated hydrocarbons such as dichloromethane, chloroform and dichloroethane; ethers such as dioxane, tetrahydrofuran, anisole, ethylene glycol dimethyl ether, diethylene glycol dimethyl ether and diethylene glycol diethyl ether; ketones such as acetone and 2-butanone; nitriles such as acetonitrile; esters such as ethyl acetate and butyl acetate; and sulfoxides such as dimethyl sulfoxide are given, and these may be mixed and used.

For base used in this reaction if desired, for example, inorganic base such as sodium hydride, sodium hydrogen carbonate, sodium carbonate, potassium carbonate, cesium carbonate and tripotassium phosphate and organic base such as sodium acetate, potassium acetate, sodium tert-butoxide, triethylamine, diisopropylethylamine, tributylamine and N,N-dicyclohexylmethylamine are given. The amount of base used may be 1-50 times mole per the compound of general formula [2], and may be preferably 2-5 times mole.

For phase transfer catalyst used in this reaction if desired, for example, tetra-ammonium salts such as tetramethylammonium chloride, benzyltrimethylammonium chloride, benzyltriethylammonium chloride, benzyltributylammonium chloride, tetrabutylammonium chloride, tetrabutylammonium bromide, hydrogensulfate tetrabutylammonium and trioctylmethylammonium chloride; N-laurylpyridinium chloride, N-lauryl-4-picolinium chloride, N-laurylpicolinium chloride; and N-benzylpicolinium chloride are given. The amount of phase transfer catalyst used may be 0.01-50 times mole per the compound of general formula [2] or the salt, and may be preferably 0.1-5 times mole.

For ligand used in this reaction if desired, for example, trialkylphosphine such as trimethylphosphine and tri-tert-butylphosphine; tricycloalkylphosphine such as tricyclohexylphosphine; triarylphosphine such as triphenylphosphine and tritolylphosphine; trialkylphosphite such as trimethylphosphite, triethylphosphite and tributylphosphite; tricycloalkylphosphite such as tricyclohexylphosphite; triarylphosphite such as triphenylphosphite; imidazolium salts such as 1,3-bis(2,4,6-trimethylphenyl) imidazolium chloride; diketones such as acetylacetone and octafluoroacetylacetone; amine such as trimethylamine, triethylamine, tripropylamine and triisopropylamine; and 1,1'-bis(diphenylphosphino)ferrocene, 2,2'-bis(diphenylphosphino)-1,1'-binaphthyl, 2-dicyclohexylphosphino-2',4',6'-triisopropylbiphenyl, 2-dicyclohexylphosphino-2',6'-dimethoxybiphenyl, 2-(di-tert-butylphosphino)-2',4',6'-triisopropylbiphenyl and 2-(di-tert-butylphosphino)biphenyl are given, and these may be combined and used. The amount of ligand used may be 0.00001-1 times mole per the compound of general formula [2], and may be preferably 0.001-0.1 times mole.

For palladium catalyst used in this reaction, for example, metal palladium such as palladium-carbon and palladium black; inorganic palladium salts such as palladium chloride; organic palladium salts such as palladium acetate; organopalladium complex such as tetrakis(triphenylphosphine)palladium(0), bis(triphenylphosphine)palladium(II) chloride, 1,1'-bis(diphenylphosphino)ferrocene palladium (II) dichloride, tris(dibenzylideneacetone)dipalladium(0) and (E)-di(μ-acetato)bis(o-(di-o-tolylphosphino)benzyl) dipalladium(II), and polymer immobilization organopalladium complex such as polymer supported bis(acetato)triphenylphosphine palladium(II) and polymer supported di(acetato)dicyclohexylphenylphosphine palladium(II) are given, and these may be combined and used. The amount of palladium catalyst used may be 0.00001-1 times mole per the compound of general formula [2], and may be preferably 0.001-0.5 times mole.

The amount of the compound of general formula [4] used may be 1-50 times mole per the compound of general formula [2], and may be preferably 1-2 times mole.

This reaction may be carried out preferably under an inert gas (for example, nitrogen, argon) atmosphere at 40 to 170° C. for 1 minute to 48 hours.

(2-2)

The compound of the general formula [1c] can be produced by reduction of the compound of the general formula [1b].

For reductive reaction, for example, catalytic hydrogenation reaction using metal catalyst may be given. For solvent used in this reaction, if it does not adversely affect the reaction, it is not limited to particularly, but for example, water; alcohols such as methanol, ethanol, 2-propanol and 2-methyl-2-propanol; amides such as N,N-dimethylformamide, N,N-dimethylacetamide and 1-methyl-2-pyrrolidone; halogenated hydrocarbons such as dichloromethane, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate; carboxylic acid such as acetic acid; and heteroaromatic such as pyridine are given, and these may be mixed and used.

For metal catalyst used in this reaction, for example, metal palladium such as palladium-carbon and palladium black; palladium salts such as palladium oxide and hydroxylated palladium; nickel metals such as Raney nickel; and platinum salts such as platinum oxide are given. The amount of metal catalyst used may be 0.001-1 times quantity(W/W) per the compound of general formula [1b], and may be preferably 0.01-1 times quantity (W/W).

For reducing agent, for example, hydrogen; formic acid; formate such as sodium formate, formic acid ammonium and formic acid triethylammonium; and cyclohexene and cyclohexadiene are given. The amount of reducing agent used may be 2-100 times mole per the compound of the general formula [1b], and may be preferably 2-10 times mole.

This reaction may be carried out at 0 to 200° C., and preferably at 0 to 100° C. for 1 minute to 24 hours.

[Manufacturing Process 3]

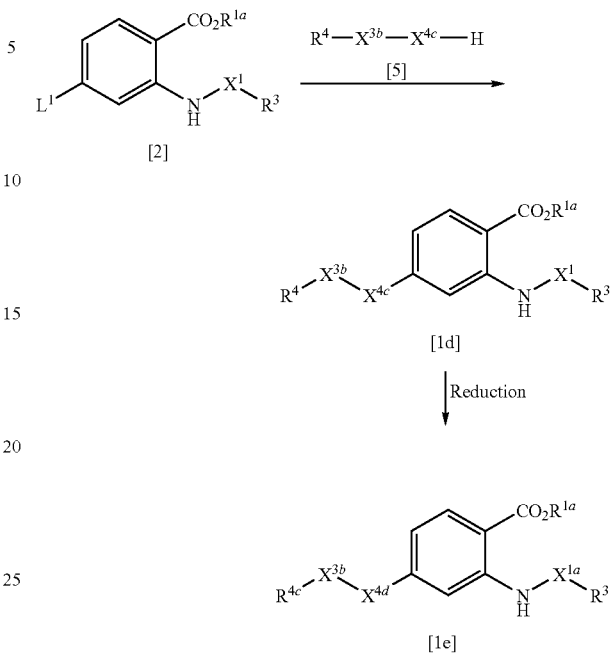

wherein $R^{4c}$ represents a phenyl, thienyl, cycloalkyl or bicyclic heterocyclic group which may be substituted with at least one group selected from a halogen atom, a cyano group, a nitro group, an acyl group, an alkanesulfonyl group, an alkanesulfonamide group, a carbamoyl group, a sulfamoyl group, a lower alkylamino group, an amino and hydroxyl group which may be protected and an alkyl, alkenyl, alkynyl, alkoxy, aryl, cyclic amino, aralkyl and heterocyclic group which may be substituted; or a pyridyl group which may be substituted with at least one group selected from a cyano group, a nitro group, an acyl group, an alkanesulfonyl group, an alkanesulfonamide group, a carbamoyl group, a sulfamoyl group, a lower alkylamino group, an amino and hydroxyl group which may be protected and an alkyl, alkenyl, alkynyl, alkoxy, aryl, cyclic amino, aralkyl and heterocyclic group which may be substituted; $X^{3b}$ represents an oxygen atom, a sulfur atom, an imino group which may be protected, a sulfinyl group, a sulfonyl group or a bond; $X^{4c}$ represents the alkenylene group which may be substituted; $X^{4d}$ represents the alkylene group which may be substituted; $R^{1a}$, $R^3$, $R^4$, $X^1$, $X^{1a}$ and $L^1$ represent the same meanings as described above.

As a compound of general formula [5], styrene, allylbenzene, 4-phenyl-1-butene, vinylcyclohexane and allylcyclohexane are known. In addition, the compound of general formula [5] can be produced according to the method, for example, described in "Jikken Kagaku Kouza", 4th edition, Vol. 19, Page 298-361, 1992, Maruzen or the like method.

(3-1)

The compound of the general formula [1d] can be produced by reacting the compound of general formula [2] with the compound of general formula [5] according to the manufacturing process (2-1).

(3-2)

The compound of the general formula [1e] can be produced by reduction of the compound of the general formula [1d] according to the manufacturing process (2-2).

[Manufacturing Process 4]

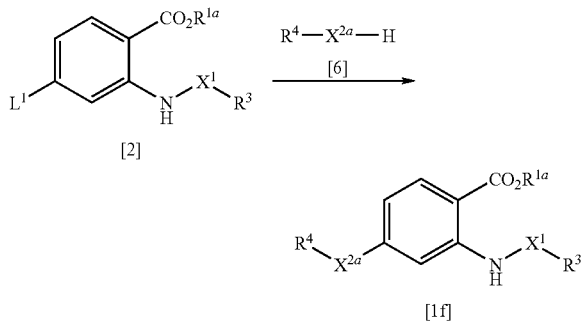

[Manufacturing Process 5]

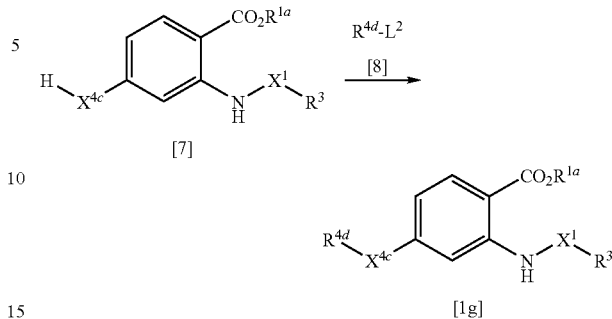

wherein $X^{2a}$ represents an oxygen atom or the general formula $—X^4—X^{3a}—$ (provided, however, that the bond on the left side of each general formula should bind to $R^4$.) wherein $X^{3a}$ and $X^4$ represent the same meanings as described above; $R^{1a}$, $R^3$, $R^4$, $X^1$ and $L^1$ represent the same meanings as described above.

As a compound of general formula [6], for example, aniline, benzylamine, benzenethiol and phenylmethanethiol are known. In addition, for example, the compound of general formula [6] can be produced by conventional methods from the corresponding halogeno compound.

(4-1)

The compound of the general formula [1f] can be produced by reacting the compound of general formula [2] with the compound of general formula [6] according to the manufacturing process (2-1).

(4-2)

In the case that $X^{2a}$ is an oxygen atom, the compound of the general formula [1f] can be produced by reacting the compound of general formula [2] with the compound of general formula [6] in the presence or absence of base, in the presence of copper catalysis.

For solvent used in this reaction, if it does not adversely affect the reaction, it is not limited to particularly, but for example, aromatic hydrocarbons such as benzene, toluene and xylene; amides such as N,N-dimethylformamide, N,N-dimethylacetamide and 1-methyl-2-pyrrolidone; halogenated hydrocarbons such as dichloromethane, chloroform and dichloroethane; ethers such as dioxane, tetrahydrofuran, anisole, ethylene glycol dimethyl ether, diethylene glycol dimethyl ether and diethylene glycol diethyl ether; ketones such as acetone and 2-butanone; nitrites such as acetonitrile; esters such as ethyl acetate and butyl acetate; and sulfoxides such as dimethyl sulfoxide are given, and these may be mixed and used.

For base used in this reaction if desired, for example, sodium hydride and sodium are given. The amount of base used may be 1-50 times mole per the compound of general formula [2], and may be preferably 1-5 times mole.

For copper catalysis used in this reaction, for example, copper powder and copper iodide are given. The amount of copper catalysis used may be 0.00001-1 times mole per the compound of general formula [2], and may be preferably 0.01-1 times mole.

The amount of the compound of general formula [6] used may be 1-50 times mole per the compound of general formula [2], and may be preferably 1-5 times mole.

This reaction may be carried out at 40 to 200° C. for 30 minutes to 72 hours.

wherein $R^{4d}$ represents a phenyl, thienyl and bicyclic heterocyclic group which may be substituted with at least one group selected from a halogen atom, a cyano group, a nitro group, an acyl group, an alkanesulfonyl group, an alkanesulfonamide group, an acetamido group, a carbamoyl group, a sulfamoyl group, a lower alkylamino group, an amino and hydroxyl group which may be protected and an alkyl, alkenyl, alkynyl, alkoxy, aryl, cyclic amino, aralkyl and heterocyclic group which may be substituted; or the pyridyl group which may be substituted with at least one group selected from a cyano group, a nitro group, an acyl group, an alkanesulfonyl group, an alkanesulfonamide group, an acetamido group, a carbamoyl group, a sulfamoyl group, a lower alkylamino group, an amino and hydroxyl group which may be protected and an alkyl, alkenyl, alkynyl, alkoxy, aryl, cyclic amino, aralkyl and heterocyclic group which may be substituted; $L^2$ represents a leaving group; $R^{1a}$, $R^3$, $X^1$ and $X^{4c}$ represent the same meanings as described above.

As a compound of general formula [8], for example, 2-iodotoluene, 3-iodoanisole, 1-iodo-3-nitrobenzene and 6-iodo-2,3-dihydrobenzo[1,4]dioxin are known. In addition, the compound of general formula [8] can be produced according to the method, for example, described in "Jikken Kagaku Kouza", 4th edition, Vol. 19, Page 460-482, 1992, Maruzen or the like method.

The compound of general formula [1g] can be produced by reacting the compound of general formula [7] with the compound of general formula [8] according to the manufacturing process (2-1).

[Manufacturing Process 6]

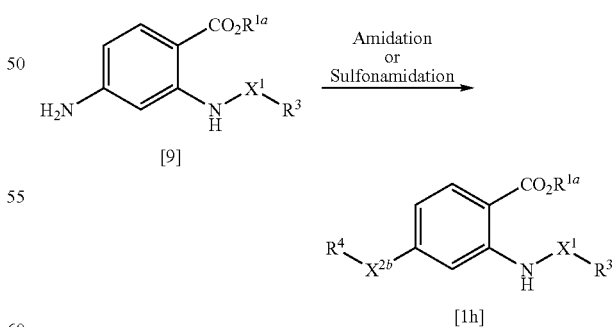

wherein $X^{2b}$ represents the general formula $—X^4—C(O)NH—$ or the general formula $—X^4—SO_2NH—$ (provided, however, that the bond on the left side of each general formula should bind to $R^4$.); wherein $X^4$ represents the same meanings as described above; $R^{1a}$, $R^3$, $R^4$ and $X^1$ represent the same meanings as described above.

(6-1)

In the case that $X^{2b}$ represents the general formula —$X^4$—C(O)NH— (provided, however, that the bond on the left side of each general formula should bind to $R^4$.); $X^4$ represents the same meanings as described above, the compound of the general formula [1 h] can be produced by amidation of the compound of general formula [9]. To be concrete, a method using acid halide in the presence or absence of base and a method using acid anhydride in the presence or absence of base, are given.

For solvent used in this reaction, if it does not adversely affect the reaction, it is not limited to particularly, but for example, amides such as N,N-dimethylformamide, N,N-dimethylacetamide and 1-methyl-2-pyrolidone; halogenated hydrocarbons such as dichloromethane, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate; sulfone such as sulfolane; and sulfoxides such as dimethyl sulfoxide are given, these may be mixed and used.

For acid halide used in this reaction, for example, benzoyl chloride, benzoyl bromide, 2,4-difluorobenzoyl chloride, diphenylacetyl chloride, 2,3-dihydrobenzo[1,4]dioxin-6-carbonyl chloride, cyclohexanecarbonyl chloride, cyclopentanecarbonyl chloride, (trans)-3-phenylacryloyl chloride, phenoxyacetyl chloride, 1-benzofuran-2-carbonyl chloride, 2-thenoyl chloride, nicotinoyl chloride and picolinoyl chloride are given. In addition, acid halide can be produced by reacting the corresponding carboxylic acid with thionyl chloride or oxalyl chloride. The amount of acid halide used may be 1-50 times mole per the compound of general formula [9], and may be preferably 1-5 times mole.

For acid anhydride used in this reaction, for example, benzoic anhydride is given. In addition, acid anhydride can be produced from the corresponding carboxylic acid according to the method, for example, described in "Shin Jikken Kagaku Kouza", Vol. 14, Page 1120-1133, 1977, Maruzen or the like method. The amount of acid anhydride used may be 1-50 times mole per the compound of general formula [9], and may be preferably 1-5 times mole.

For base used in this reaction if desired, for example, inorganic base such as sodium hydrogen carbonate, sodium carbonate, potassium carbonate and cesium carbonate and organic base such as triethylamine and diisopropylethylamine are given. The amount of base used may be 1-50 times mole per the compound of general formula [9], and may be preferably 1-5 times mole.

This reaction may be carried out at −78 to 100° C., and preferably at 0 to 80° C. for 10 minutes to 24 hours.

(6-2)

In the case that $X^{2b}$ represents the general formula —$X^4$—$SO_2NH$— (provided, however, that the bond on the left side of each general formula should bind to $R^4$); $X^4$ represents the same meanings as described above, the general formula [1 h] can be produced by sulfonamidation of the compound of general formula [9]. To be concrete, a method using sulfonyl halide in the presence or absence of base is given.

For solvent used in this reaction, if it does not adversely affect the reaction, it is not limited to particularly, but for example, amides such as N,N-dimethylformamide, N,N-dimethylacetamide and 1-methyl-2-pyrolidone; halogenated hydrocarbons such as dichloromethane, chloroform and dichloroethane; Aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitriles such as acetonitrile; ketones such as acetone and 2-butanone; esters such as ethyl acetate and butyl acetate; sulfone such as sulfolane; and sulfoxides such as dimethyl sulfoxide are given, these may be mixed and used.

For sulfonyl halide used in this reaction, for example, benzenesulfonyl chloride and α-toluenesulfonyl chloride are given. In addition, sulfonyl halide can be produced from the corresponding sulfo acid according to the method, for example, described in "Shin Jikken Kagaku Kouza", Vol. 14, Page 1784-1792, 1978, Maruzen or the like method. The amount of sulfonyl halide used may be 1-50 times mole per the compound of general formula [9], and may be preferably 1-5 times mole.

For base used in this reaction if desired, for example, inorganic base such as sodium hydrogen carbonate, sodium carbonate, potassium carbonate and cesium carbonate and organic base such as triethylamine and diisopropylethylamine are given. The amount of base used may be 1-50 times mole per the compound of general formula [9], and may be preferably 1-5 times mole.

This reaction may be carried out at −78 to 100° C., and preferably at 0 to 80° C. for 10 minutes to 24 hours.

[Manufacturing Process 7]

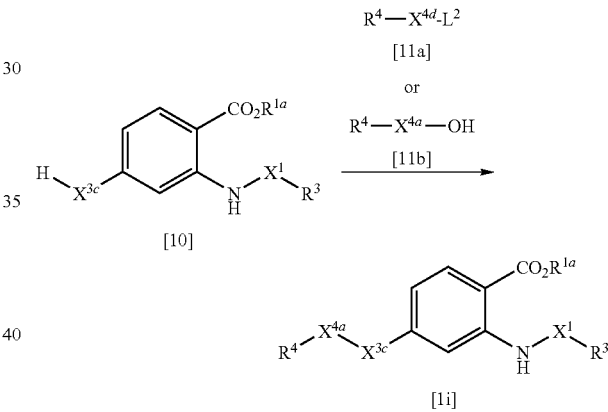

wherein $X^{3c}$ represents an oxygen atom, a sulfur atom or an imino group which may be protected; $R^{1a}$, $R^3$, $R^4$, $X^1$, $X^{4a}$, $X^{4d}$ and $L^2$ represent the same meanings as described above. But in the case that $X^{4a}$ represents a bond, $R^4$ represents the cycloalkyl group may be substituted.

As a compound of the general formula [11a], for example, benzyl bromide and (2-bromoethyl)benzene are known. As a compound of the general formula [11b], for example, 3-phenyl-1-propanol and cyclohexanol are known.

(7-1)

The compound of the general formula [1i] can be produced by reacting in the presence of base, the compound of general formula [10] with the compound of the general formula [11a].

For solvent used in this reaction, if it does not adversely affect the reaction, it is not limited to particularly, but for example, amides such as N,N-dimethylformamide, N,N-dimethylacetamide and 1-methyl-2-pyrolidone; halogenated hydrocarbons such as dichloromethane, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; nitrites such as acetonitrile; ketones such as acetone and 2-butanone;

esters such as ethyl acetate and butyl acetate; sulfone such as sulfolane; and sulfoxides such as dimethyl sulfoxide are given, these may be mixed and used.

The amount of the compound of the general formula [11a] used in this reaction 1-20 times mole per the compound of general formula [10], and may be preferably 1-5 times mole.

For base used in this reaction, for example, organic amine such as dimethylaminopyridine, triethylamine and pyridine; alkali metal hydride such as sodium hydride;
and alkali metal carbonate such as potassium carbonate and sodium carbonate are given. The amount of base used may be 1-20 times mole per the compound of general formula [10], and may be preferably 1-5 times mole.

This reaction may be carried out at 0 to 200° C., and preferably at 25 to 150° C. for 10 minutes to 24 hours.
(7-2)

In the case that $X^{3c}$ is an oxygen atom or a sulfur atom, the compound of the general formula [1i] can be produced by subjecting the compound of general formula [10] and the compound of general formula [11b] to Mitsunobu reaction in the presence of an azodicarbonyl compound and phosphine.

For solvent used in this reaction, if it does not adversely affect the reaction, it is not limited to particularly, but for example, aromatic hydrocarbons such as benzene, toluene, xylene; ethers such as dioxane, tetrahydrofuran, anisole,diethylene glycol dimethyl ether, ethylene glycol monomethyl ether and ethylene glycol dimethyl ether; esters such as methyl acetate, ethyl acetate and butyl acetate; nitrites such as acetonitrile; amides such as N,N-dimethylformamide and N,N-dimethylacetamide; and halogenated hydrocarbon such as chloroform and dichloromethane are given, these may be mixed and used.

For azodicarbonyl compound used in this reaction, for example,diethyl azodicarboxylate, diisopropyl azodicarboxylate and azodicarbonyldipiperidine are given. The amount of azodicarbonyl compound used may be 1-5 times mole per the compound of general formula [10], and may be preferably 1-3 times mole.

For phosphine used in this reaction, for example, triarylphosphine such as triphenylphosphine and trialkylphosphine such as tributylphosphine are given. The amount phosphine used may be 1-5 times mole per the compound of general formula [10], and may be preferably 1-3 times mole.

The amount of compound of the general formula [11b] used may be 1-5 times mole per the compound of general formula [10], and may be preferably 1-3 times mole.

This reaction may be carried out at −20 to 120° C., and preferably at 0 to 50° C. for 30 minutes to 24 hours.
[Manufacturing Process 8]

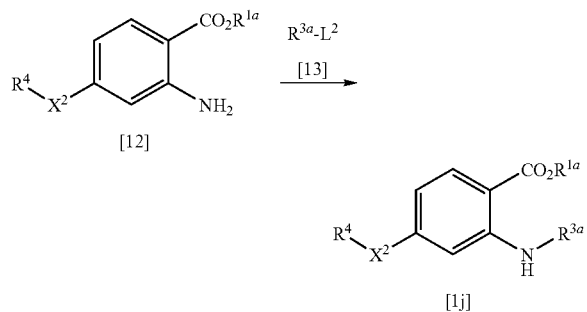

wherein $R^{3a}$ a phenyl or bicyclic heterocyclic group which may be substituted with at least one group selected from a halogen atom, a cyano group, a nitro group, an acyl group, an alkanesulfonyl group, an alkanesulfonamide group, an acetamido group, a carbamoyl group, a sulfamoyl group, a lower alkylamino group, an amino and hydroxyl group which may be protected and an alkyl, alkenyl, alkynyl, alkoxy, aryl, cyclic amino, aralkyl and heterocyclic group which may be substituted; or a monocyclic heterocyclic groups which is substituted with a phenyl group only; $R^{1a}$, $R^4$, $X^2$ and $L^2$ represent the same meanings as described above.

As a compound of general formula [13], for example, iodobenzene, 1-fluoro-4-iodobenzene, 1-iodo-3-nitrobenzene and 6-iodo-2,3-dihydrobenzo[1,4]dioxin are known.
(8-1)

The compound of the general formula [1j] can be produced by the method, for example,described in Journal of American Chemical Society, Vol. 125, Page 6653-6655, 2003 or the like method. To be concrete, it can be produced by reacting the compound of general formula [12] with the compound of general formula [13] in the presence or absence of base, in the presence or absence of phase transfer catalyst, in the presence or absence of ligand, in the presence of palladium catalyst.

For solvent used in this reaction, if it does not adversely affect the reaction, it is not limited to particularly, but for example, water; alcohols such as methanol, ethanol, 2-propanol and 2-methyl-2-propanol; aromatic hydrocarbons such as benzene, toluene and xylene; amides such as N,N-dimethylformamide, N,N-dimethylacetamide and 1-methyl-2-pyrrolidone; halogenated hydrocarbons such as dichloromethane, chloroform and dichloroethane; ethers such as dioxane, tetrahydrofuran, anisole, ethylene glycol dimethyl ether,diethylene glycol dimethyl ether and diethylene glycol diethyl ether; ketones such as acetone and 2-butanone;
nitrites such as acetonitrile; esters such as ethyl acetate and butyl acetate; and sulfoxides such as dimethyl sulfoxide are given, these may be mixed and used.

For base used in this reaction if desired, for example, inorganic base such as sodium hydrogen carbonate, sodium carbonate, potassium carbonate and cesium carbonate and organic base such as sodium acetate, potassium acetate, sodium tert-butoxide, triethylamine,diisopropylethylamine and tributylamine are given. The amount of base used may be 1-50 times mole per the compound of general formula [12], and may be preferably 2-5 times mole.

For phase transfer catalyst used in this reaction if desired, for example, tetra-ammonium salts such as tetramethylammonium chloride, benzyltrimethylammonium chloride, benzyltriethylammonium chloride, benzyltributylammonium chloride, tetrabutylammonium chloride, tetrabutylammonium bromide, tetrabutylammonium hydrogen sulfate and trioctylmethylammonium chloride; N-laurylpyridinium chloride, N-lauryl-4-picolinium chloride, N-laurylpicolinium chloride; and N-benzylpicolinium chloride are given. The amount of phase transfer catalyst used may be 0.01-50 times mole per the compound of general formula [12] or the salt, and may be preferably 0.1-5 times mole.

For ligand used in this reaction if desired, for example, trialkylphosphine such as trimethylphosphine and tri(tert-butyl) phosphine; tricycloalkylphosphine such as tricyclohexylphosphine; triarylphosphine such as triphenylphosphine and tritolylphosphine; trialkylphosphite such as trimethylphosphite, triethylphosphite and tributylphosphite; tricycloalkylphosphite such as tricyclohexylphosphite; triarylphosphite such as triphenylphosphite; imidazolium salts such as 1,3-bis (2,4,6-trimethylphenyl)imidazolium chloride; diketones such as acetylacetone and octafluoroacetylacetone; amine such as trimethylamine, triethylamine, tripropylamine and triisopropylamine; and 1,1'-bis(diphenylphosphino)ferrocene, 2,2'-bis(diphenylphosphino)-1,1'-binaphthyl and 2-dicyclohexylphosphino-2',4',6'-triisopropylbiphenyl are given, and these may be combined and used. The amount of ligand used may be 0.00001-1 times mole per the compound of general formula [12], and may be preferably 0.001-0.2 times mole.

For palladium catalyst used in this reaction, for example, metal palladium such as palladium-carbon and palladium black; inorganic palladium salts such as palladium chloride; organic palladium salts such as palladium acetate; organopalladium complex such as tetrakis(triphenylphosphine)palladium(0), bis(triphenylphosphine)palladium(II) chloride, 1,1'-bis(diphenylphosphino)ferrocene palladium (II) dichloride and tris(dibenzylideneacetone)dipalladium (0); and polymer immobilized organopalladium complex such as polymer supported bis(acetato)triphenylphosphine palladium (II) and polymer supported di(acetato)dicyclohexylphenylphosphine palladium(II) are given, and these may be combined and used. The amount of palladium catalyst used may be 0.00001-1 times mole per the compound of general formula [12], and may be preferably 0.001-0.1 times mole.

The amount of the compound of general formula [13] used may be 1-50 times mole per the compound of general formula [12], and may be preferably 1-3 times mole.

This reaction may be carried out under an inert gas (for example, nitrogen, argon) atmosphere at 40 to 170° C. for 1 minute to 72 hours.

(8-2)

In addition, in the case that $L^2$ is a chlorine atom, a bromine atom or an iodine atom, the compound of the general formula [1j] can be produced by reacting the compound of general formula [12] with the compound of general formula [13] in the presence or absence of base, in the presence or absence of ligand, in the presence of copper catalysis.

For solvent used in this reaction, if it does not adversely affect the reaction, it is not limited to particularly, but for example, water; alcohols such as methanol, ethanol, 2-propanol and 2-methyl-2-propanol; aromatic hydrocarbons such as benzene, toluene and xylene; amides such as N,N-dimethylformamide, N,N-dimethylacetamide and 1-methyl-2-pyrrolidone; halogenated hydrocarbons such as dichloromethane, chloroform and dichloroethane; ethers such as dioxane, tetrahydrofuran, anisole, ethylene glycol dimethyl ether,diethylene glycol dimethyl ether and diethylene glycol diethyl ether; ketones such as acetone and 2-butanone; nitrites such as acetonitrile; esters such as ethyl acetate and butyl acetate; and sulfoxides such as dimethyl sulfoxide are given, and these may be mixed and used.

For base used in this reaction if desired, for example, inorganic base such as sodium hydrogen carbonate, sodium carbonate, potassium carbonate and cesium carbonate and organic base such as triethylamine,diisopropylethylamine and N-methylmorpholine are given. The amount of base used may be 1-50 times mole per the compound of general formula [12], and may be preferably 2-5 times mole. For ligand used in this reaction if desired, for example, amino acid such as proline, N,N-dimethylglycine and alanine are given. The amount of ligand used may be 1-50 times mole per the compound of general formula [12], and may be is preferably 2-5 times mole.

For copper catalysis used in this reaction, for example, copper, copper bromide and copper iodide are given, and these may be combined and used. The amount of copper catalysis used may be 0.01-50 times mole per the compound of general formula [12] or the salt, and may be preferably 0.1-5 times mole.

The amount of compound of general formula [13] used may be 1-50 times mole per the compound of general formula [12], and may be preferably 1-2 times mole.

This reaction may be carried out under an inert gas (for example, nitrogen, argon) atmosphere at 10 to 180° C. for 1 minute to 24 hours.

[Manufacturing Process 9]

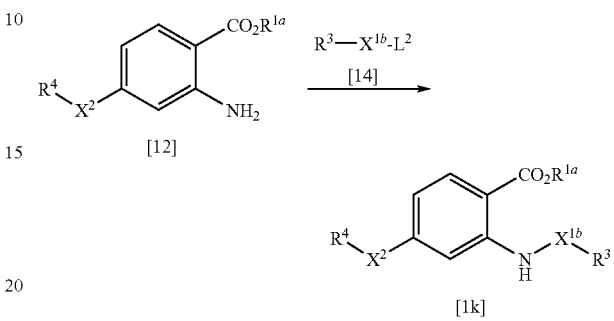

wherein $R^{1a}$, $R^3$, $R^4$, $X^{1b}$, $X^2$ and $L^2$ represent the same meanings as described above.

As a compound of general formula [14], for example, benzyl bromide and (2-bromoethyl)benzene are known.

The compound of the general formula [1k] can be produced by reacting the compound of general formula [12] with compound of general formula [14] in the presence of base.

For solvent used in this reaction, if it does not adversely affect the reaction, it is not limited to particularly, but for example, amides such as N,N-dimethylformamide, N,N-dimethylacetamide and 1-methyl-2-pyrolidone; halogenated hydrocarbons such as dichloromethane, chloroform and dichloroethane; aromatic hydrocarbons such as benzene, toluene and xylene; ethers such as dioxane, tetrahydrofuran, anisole, ethylene glycol dimethyl ether,diethylene glycol dimethyl ether and diethylene glycol diethyl ether; nitrites such as acetonitrile; ketones such as acetone and 2-butanone; esters such as ethyl acetate and butyl acetate; sulfone such as sulfolane; and sulfoxides such as dimethyl sulfoxide are given, and these may be mixed and used.

The amount of the compound of general formula [14] used in this reaction may be 1-5 times mole per the compound of general formula [12], and may be preferably 1-1.5 times mole.

For base used in this reaction, for example, organic amine such as dimethylaminopyridine, triethylamine and pyridine; alkali metal hydride such as sodium hydride and alkali metal carbonate such as potassium carbonate and sodium carbonate are given.

The amount of base used may be 1-20 times mole per the compound of general formula [12], and may be preferably 1-5 times mole.

This reaction usually may be carried out at 0 to 200° C., and preferably at 25 to 150° C. for 10 minutes to 24 hours.

[Manufacturing Process 10]

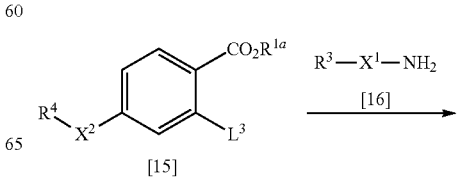

-continued

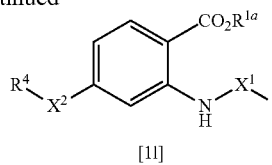

[1l]

wherein $L^3$ represents a leaving group; $R^{1a}$, $R^3$, $R^4$, $X^1$ and $X^2$ represent the same meanings as described above.

As a compound of general formula [16], for example, aniline, cyclohexylamine and benzylamine are known.

The compound of general formula [1l] can be produced by reacting the compound of general formula [15] with the compound of general formula [16] according to the manufacturing process (8-1) or the manufacturing process (8-2).

[Manufacturing Process 11]

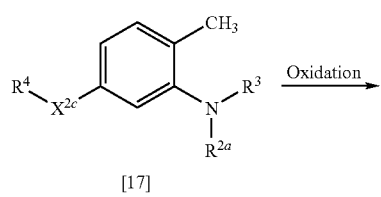

[17]

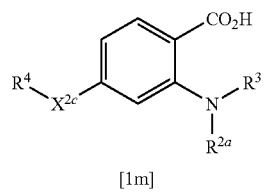

[1m]

wherein $R^{2a}$ represents an imino protecting group; $X^{2c}$ represents an oxygen atom, a carbonyl group or a bond; $R^3$ and $R^4$ represent the same meanings as described above.

The compound of general formula [1m] can be produced by reacting the compound of general formula [17] with oxidizing agent in the presence or absence of acid or base, in the presence or absence of salts.

For solvent used in this reaction, if it does not adversely affect the reaction, it is not limited to particularly, but for example, water; halogenated hydrocarbons such as dichloromethane, chloroform and dichloroethane; aliphatic hydrocarbons such as hexane and cyclohexane; and pyridine are given, and these may be mixed and used.

For acid used in this reaction if desired, for example, mineral acid such as sulfuric acid and nitric acid are given. The amount of acid used may be 1-100 times mole per the compound of general formula [17].

For base used in this reaction if desired, for example, inorganic base such as sodium hydroxide and potassium hydroxide and organic base such as pyridine are given. The amount of base used may be 1-100 times mole per the compound of general formula [17].

For a salt used in this reaction if desired, for example, magnesium sulfate, ammonium sulfate and magnesium chloride are given. The amount of the salt used may be 1-50 times mole per the compound of general formula [17], and may be preferably 1-10 times mole.

For oxidizing agent used in this reaction, for example, chromate such as chromium oxide (VI) and sodium dichromate and permanganate such as potassium permanganate, barium permanganate, calcium permanganate and magnesium permanganate are given. The amount of oxidizing agent used may be 1-50 times mole per the compound of general formula [17], and may be preferably 1-10 times mole.

This reaction usually may be carried out at 0 to 150° C., and may be preferably at 40 to 130° C. for 30 minutes to 48 hours.

[Manufacturing Process 12]

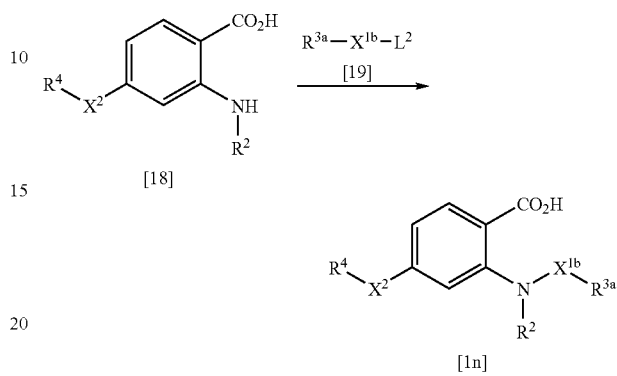

[18]

[1n]

wherein $X^{1b}$ represents an alkylene or alkenylene group which may be substituted; $R^2$, $R^{3a}$, $R^4$, $X^2$ and $L^2$ represent the same meanings as described above.

As a compound of general formula [19], for example, benzyl bromide and (2-bromoethyl)benzene are known.

The compound of the general formula [1n] can be produced by reacting the compound of general formula [18] with the compound of general formula [19] according to the manufacturing process (7-1).

[Manufacturing Process 13]

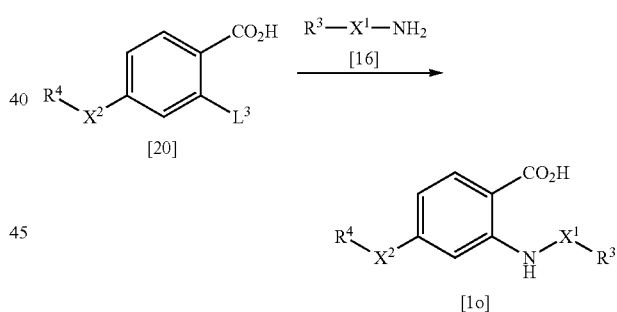

[20]

[1o]

wherein $R^3$, $R^4$, $X^1$, $X^2$ and $L^3$ represent the same meanings as described above.

The compound of the general formula [1o] can be produced by reacting the compound of general formula [20] with the compound of general formula [16] according to the manufacturing process (8-1) or the manufacturing process (8-2).

[Manufacturing Process 14]

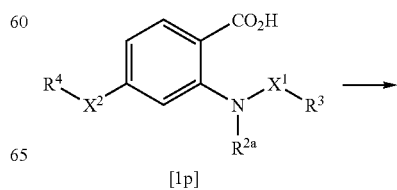

[1p]

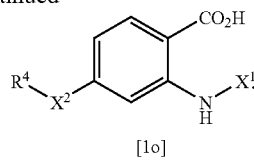

wherein $R^{2a}$, $R^3$, $R^4$, $X^1$ and $X^2$ represent the same meanings as described above.

The compound of the general formula [1o] can be produced by deprotection of the compound of the general formula [1p] according to the method, for example, described in Protective Groups in Organic Synthesis, Page 494-615, 1999, third edition, W. Greene, John Wiley & Sons, INC.

For deprotection reaction, for example, hydrolysis reaction using acid or base, dealkylation reaction with the use of a salt, reductive dealkylation reaction including metal catalyst hydrogenation reaction and hydrazine decomposition reaction are given.

(14-1)

In hydrolysis reaction using acid, for used acid, for example, formic acid, hydrochloric acid, sulfuric acid, hydrogen bromide, trifluoroacetic acid, aluminum chloride and iodination trimethylsilane are given. The amount acid used may be 1-10000 times mole per the compound of the general formula [1p], and may be preferably 1-5000 times mole.

In hydrolysis reaction using base, for base used, for example, inorganic base such as sodium hydroxide, potassium hydroxide, lithium hydroxide, potassium carbonate and sodium carbonate; organic base such as sodium methoxide, sodium ethoxide and potassium tert-butoxide; and tetrabutylammonium fluoride are given. The amount of base used may be 1-1000 times mole per the compound of the general formula [1p], and may be preferably 1-50 times mole.

In dealkylation reaction with the use of a salt, for a salt used, for example, lithium iodide and sodium chloride are given. The amount base used may be 1-100 times mole per the compound of the general formula [1p], and may be preferably 1-10 times mole. A reductive dealkylation reaction including metal catalyst hydrogenation reaction can be carried out according to the manufacturing process (2-2).

For solvent used in these reactions, if it does not adversely affect the reaction, it is not limited to particularly, but for example, water; alcohols such as methanol, ethanol, 2-propanol and 2-methyl-2-propanol; ethers such as dioxane, tetrahydrofuran, anisole, ethylene glycol dimethyl ether, diethylene glycol dimethyl ether and diethylene glycol diethyl ether; halogenated hydrocarbons such as dichloromethane, chloroform and dichloroethane; nitriles such as acetonitrile; aliphatic hydrocarbon such as hexane and cyclohexane; aromatic hydrocarbons such as benzene, toluene and xylene; sulfoxides such as dimethyl sulfoxide; amides such as N,N-dimethylformamide; nitromethane; and pyridine are given, and these may be mixed and used.

This reaction usually may be carried out at −78 to 130° C., and preferably at 0 to 120° C. for 10 minutes to 24 hours.

(14-2)

In hydrazine decomposition reaction, the amount of hydrazine used may be 1-1000 times mole for the compound of the general formula [1p], and may be preferably 1-100 times mole.

For solvent used in this reaction, if it does not adversely affect the reaction, it is not limited to particularly, but for example, water; alcohols such as methanol, ethanol, 2-propanol and 2-methyl-2-propanol; ethers such as dioxane, tetrahydrofuran, anisole, ethylene glycol dimethyl ether, diethylene glycol dimethyl ether and diethylene glycol diethyl ether; halogenated hydrocarbons such as dichloromethane, chloroform and dichloroethane;

nitriles such as acetonitrile; aliphatic hydrocarbons such as hexane and cyclohexane; aromatic hydrocarbons such as benzene, toluene and xylene; sulfoxides such as dimethyl sulfoxide;

amides such as N,N-dimethylformamide; nitromethane; and pyridine are given, and these may be mixed and used. This reaction may usually be carried out at −78 to 170° C., preferably at 0 to 130° C. for 10 minutes to 24 hours.

[Manufacturing Process 15]

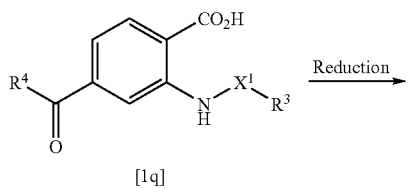

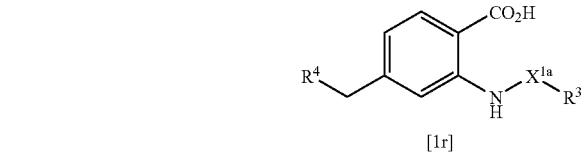

wherein $R^3$, $R^4$, $X^1$ and $X^{1a}$ represent the same meanings as described above.

The compound of the general formula [1r] can be produced by reduction of the compound of the general formula [1q] according to the manufacturing process (2-2).

[Manufacturing Process 16]

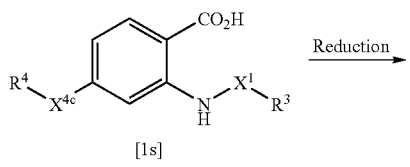

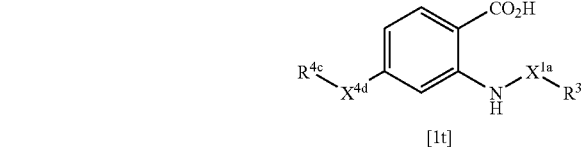

wherein $R^3$, $R^4$, $R^{4c}$, $X^1$, $X^{1a}$, $X^{4c}$ and $X^{4d}$ represent the same meanings as described above.

The compound of general formula [1t] can be produced by reduction of the compound of the general formula [1s] according to the manufacturing process (2-2).

[Manufacturing Process 17]

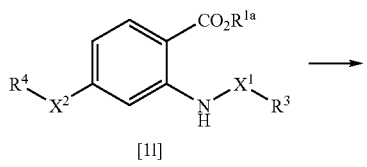

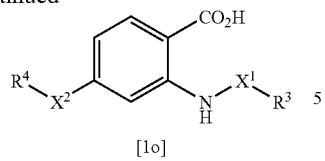

wherein $R^{1a}$, $R^3$, $R^4$, $X^1$ and $X^2$ represent the same meanings as described above.

The compound of the general formula [1o] can be produced by deprotection of the compound of general formula [11] according to the manufacturing process (14-1).

[Manufacturing Process 18]

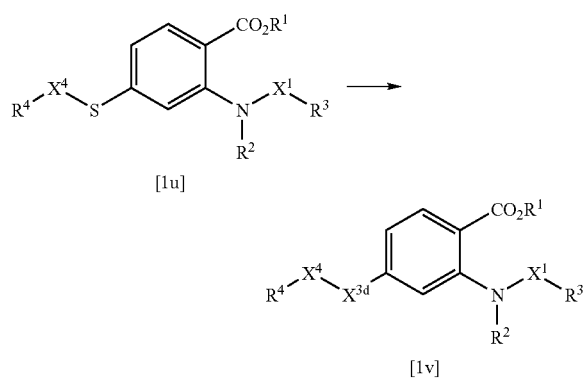

wherein $X^{3d}$ represents a sulfinyl group or a sulfonyl group; $R^1$, $R^2$, $R^3$, $R^4$, $X^1$ and $X^4$ represent the same meanings as described above.

The compound of the general formula [1v] can be produced by oxidation of the compound of the general formula [1u].

For solvent used in this reaction, if it does not adversely affect the reaction, it is not limited to particularly, but for example, water; halogenated hydrocarbons such as dichloromethane, chloroform and dichloroethane; aliphatic hydrocarbons such as hexane, and cyclohexane; and pyridine are given, and these may be mixed and used.

For oxidizing agent used in this reaction, for example, hydrogen peroxide; hyperacids such as peracetic acid, benzoyl hydroperoxide and m-chloroperbenzoic acid; peroxides such as tert-butyl peroxide; and sodium metaperiodate are given. The amount of oxidizing agent used may be 1-50 times mole per the compound of the general formula [1u], and may be preferably 1-10 times mole.

This reaction may usually be carried out at 0 to 150° C., preferably at 10 to 100° C. for 30 minutes to 48 hours.

[Manufacturing Process 19]

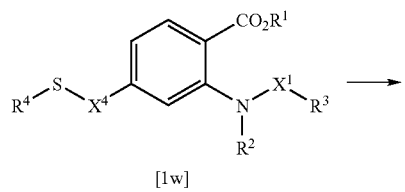

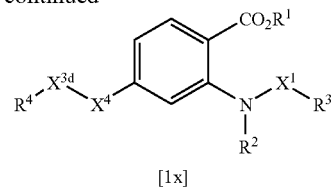

wherein $R^1$, $R^2$, $R^3$, $R^4$, $X^1$, $X^{3d}$ and $X^4$ represent the same meanings as described above.

The compound of the general formula [1x] can be produced by oxidation of the compound of the general formula [1w] according to the manufacturing process 18.

[Manufacturing Process 20]

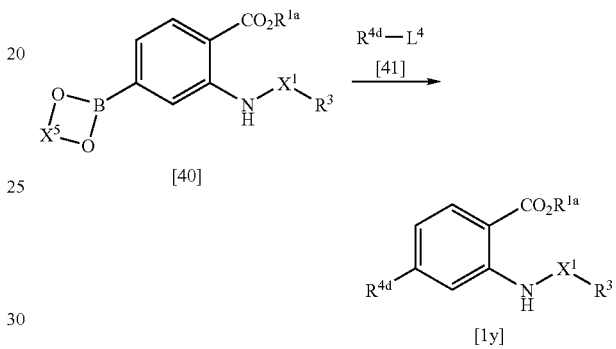

wherein $L^4$ represents a chlorine atom, a bromine atom or an iodine atom. $R^{1a}$, $R^3$, $R^{4d}$, $X^1$ and $X^5$ represent the same meanings as described above.

As a compound of general formula [41], for example, 2-iodotoluene, 3-iodoanisole, 3-iodonitrobenzene and 6-iodo-2,3-dihydrobenzo[1,4]dioxin are known.

The compound of the general formula [1y] can be produced by reacting the compound of general formula [40] with the compound of general formula [41] according to the manufacturing process 1.

[Manufacturing Process 21]

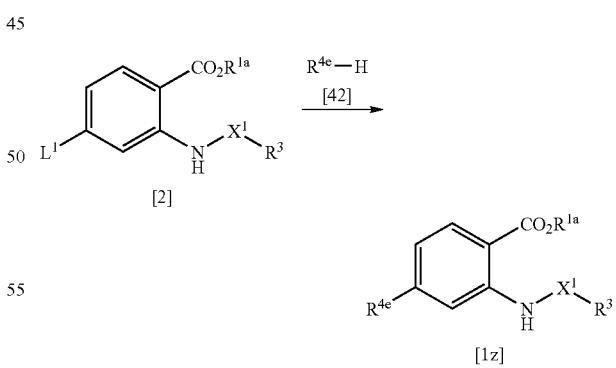

$R^{4e}$ represents a bicyclic heterocyclic group which binds to a nitrogen atom forming the ring, which the bicyclic heterocyclic group may be substituted with at least one group selected from a halogen atom, a cyano group, a nitro group, an acyl group, an alkanesulfonyl group, an alkanesulfonamide group, an acetamido group, a carbamoyl group, a sulfamoyl group, a lower alkylamino group, an amino and hydroxyl group which may be protected and an alkyl, alkenyl, alkynyl, alkoxy, aryl, cyclic amino, aralkyl and heterocyclic group which may be substituted; $R^{1a}$, $R^3$, $X^1$ and $L^1$ represent the same meanings as described above.

As a compound of general formula [42], for example, indoline, benzimidazole and indole are known.

The compound of the general formula [1z] can be produced by reacting the compound of general formula [2] with the compound of general formula [42] according to the manufacturing process (8-1).

The compounds of general formula [1a], [1b], [1c], [1d], [1e], [1f], [1g], [1h], [1i], [1j], [1k], [1l], [1m], [1n], [1o], [1p], [1q], [1r], [1s], [1t], [1u], [1v], [1w], [1x], [1y] and [1z] or those salts obtained in this way can be derived to the compound of other general formula [1] or the salt by a known method per se, for example, such as condensation, addition, oxidation, reduction, rearrangement, substitution, halogenation, dehydration or hydrolysis or by appropriate combination of those reaction.

In addition, in the compound described in above manufacturing process, in the case that isomers (for example, optical isomers, geometrical isomers and tautomers and the like) exist, these isomers can be used, too, and solvates, hydrates and various kinds of crystal forms can be used, too.

Next, manufacturing methods of the compounds of general formula [2], [7], [9], [10], [12], [15], [17], [18], [20] and [40] which are raw materials of production of present invention compounds are explained.

[Manufacturing Process A]

In a method using alkylating agent, for solvent used, if it does not adversely affect the reaction, it is not limited to particularly, but for example, aromatic hydrocarbons such as benzene, toluene and xylene; amides such as N,N-dimethylformamide, N,N-dimethylacetamide and 1-methyl-2-pyrrolidone; halogenated hydrocarbons such as dichloromethane, chloroform and dichloroethane; ethers such as dioxane, tetrahydrofuran, anisole, ethylene glycol dimethyl ether, diethylene glycol dimethyl ether and diethylene glycol diethyl ether; ketones such as acetone and 2-butanone; nitrites such as acetonitrile; esters such as ethyl acetate and butyl acetate; and sulfoxides such as dimethyl sulfoxide are given, and these may be mixed and used.

For phase transfer catalyst used in this reaction if desired, for example, tetra-ammonium salts such as tetramethylammonium chloride, benzyltrimethylammonium chloride, benzyltriethylammonium chloride, benzyltributylammonium chloride and tetrabutylammonium bromide are given. The amount of phase transfer catalyst used may be equal to or more than 0.01 mole per the compound of general formula [21], and may be preferably 0.1-5 times mole.

For base used in this reaction, for example, inorganic base such as sodium carbonate, potassium carbonate and cesium carbonate and organic base such as triethylamine, pyridine, dimethylaminopyridine and N-methylmorpholine are given. The amount of base used may be 1-50 times mole per the compound of general formula [21], and may be preferably 1-5 times mole. For alkylating agent used in this reaction, for

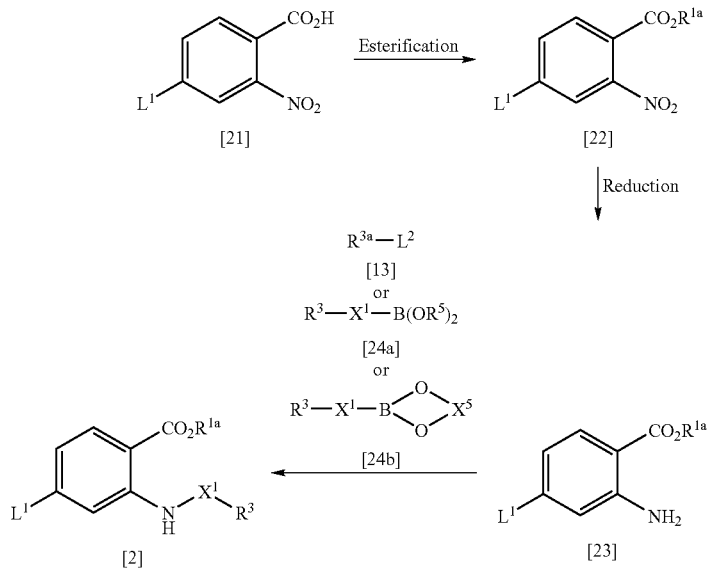

wherein $R^{1a}$, $R^3$, $R^{3a}$, $R^5$, $X^1$, $X^5$, $L^1$ and $L^2$ represent the same meanings as described above.

As a compound of general formula [21], for example, 4-bromo-2-nitrobenzoic acid is known.

(A-1)

The compound of general formula [22] can be produced by esterification of the compound of general formula [21]. This reaction may be carried out by the method described in Protective Groups in Organic Synthesis, third edition, Page 369-453, 1999, W. Greene, John Wiley & Sons, INC. or the like method. To be concrete, a method using alkylating agent in the presence or absence of phase transfer catalyst, in the presence of base, and a method through acid halide of the compound of general formula [21] are given.

example, methyl iodide, ethyl iodide, dimethyl sulfate, 2-bromo-2-methylpropane, benzyl chloride and benzyl bromide are given. The amount of alkylating agent used may be 1-50 times mole per the compound of general formula [21], and may be preferably 1-5 times mole. This reaction may usually be carried out at 0 to 170° C. for 1 minute to 24 hours.

In a method through acid halide, the compound of general formula [21] may be reacted with, for example, thionyl chloride, oxalyl chloride or the like to give acid halide, subsequently it may be reacted with alcohols such as methanol, ethanol, benzyl alcohol and the like in the presence or absence of base.

In this reaction, for solvent used, if it does not adversely affect the reaction, it is not limited to particularly, but for example, aromatic hydrocarbons such as benzene, toluene and xylene; halogenated hydrocarbons such as dichloromethane, chloroform and dichloroethane; ethers such as dioxane, tetrahydrofuran, anisole, ethylene glycol dimethyl ether,diethylene glycol dimethyl ether and diethylene glycol diethyl ether; ketones such as acetone and 2-butanone; nitrites such as acetonitrile; esters such as ethyl acetate and butyl acetate; and sulfoxides such as dimethyl sulfoxide are given, and these may be mixed and used.

For base used in this reaction if desired, for example, inorganic base such as sodium carbonate, potassium carbonate and cesium carbonate and organic base such as triethylamine, pyridine, dimethylaminopyridine and N-methylmorpholine are given. The amount of base used may be 1-50 times mole per the compound of general formula [21], and may be preferably 1-5 times mole.

This reaction may usually be carried out at 0 to 170° C. for 1 minute to 24 hours.

As a compound of general formula [23], for example, methyl 2-amino-4-iodobenzoate is known.

(A-2)

The compound of general formula [23] can be produced by reduction of the compound of general formula [22]. This reaction may be carried out by the method described in Comprehensive Organic Transformations, 2nd Edition, Page 823-827, 1999, Richard C. Larock,John Wiley & Sons, INC. or the like method. To be concrete, reductive reaction using metals such as iron or zinc is given.

In this reaction, for solvent used, if it does not adversely affect the reaction, it is not limited to particularly, but for example, water; alcohols such as methanol, ethanol, 2-propanol and 2-methyl-2-propanol; amides such as N,N-dimethylformamide, N,N-dimethylacetamide and 1-methyl-2-pyrrolidone; halogenated hydrocarbons such as dichloromethane, chloroform and dichloroethane; aromatic hydrocarbons such as benzene, toluene and xylene; ethers such as dioxane, tetrahydrofuran, anisole, ethylene glycol dimethyl ether,diethylene glycol dimethyl ether and diethylene glycol diethyl ether; nitrites such as acetonitrile; ketones such as acetone and 2-butanone; and esters such as ethyl acetate and butyl acetate are given, and these may be mixed and used.

For metal used for this reaction, for example, iron, zinc, stannum and tin (II) chloride are given. The amount of metal used may be 1-50 times mole per the compound of general formula [22], and may be preferably, 1-10 times mole.

For acid used in this reaction if desired, for example, hydrogen chloride, hydrogen bromide and acetic acid are given. The amount of acid used may be 0.001-100 times quantity (W/V) per the compound of general formula [22], and may be preferably 0.01-20 times quantity (W/V).

This reaction may be carried out at 0 to 200° C., and preferably at 0 to 100° C. for 1 minute to 24 hours.

(A-3)

The compound of general formula [23] can be produced by reduction of compound of general formula [22] according to the manufacturing process (2-2)

(A-4)

The compound of general formula [2] can be produced by reacting the compound of general formula [23] with the compound of general formula [13] according to the manufacturing process (8-1) or (8-2).

(A-5)

As a compound of the general formula [24a], for example, 4-(methanesulfonamide)phenylboronic acid, benzofuran-2-boronic acid and 3-methoxyphenylboronic acid are known. As a compound of the general formula [24b], for example, 4-(4,4,5,5-tetramethyl-1,3,2-dioxaborolan-2-yl)isoquinoline is known. In addition, the compound of the general formula [24a] and [24b] can be produced from the corresponding halogeno compound according to the method, for example, described in Japanese Patent Laid-Open No. 2003-206290 bulletins or the like method.

The compound of general formula [2] can be produced according to the method, for example, described in Organic Letters, Vol. 3, Page 2077-2079, 2001 or the like method. To be concrete, it can be produced by reacting the compound of general formula [23] with the compound of general formula [24a] or [24b] in the presence or absence of base, in the presence or absence of myristic acid, in the presence of metal catalyst.

For solvent used in this reaction, if it does not adversely affect the reaction, it is not limited to particularly, but for example, water; alcohols such as methanol, ethanol, 2-propanol and 2-methyl-2-propanol; aromatic hydrocarbons such as benzene, toluene and xylene; amides such as N,N-dimethylformamide, N,N-dimethylacetamide and 1-methyl-2-pyrrolidone; halogenated hydrocarbons such as dichloromethane, chloroform and dichloroethane; ethers such as dioxane, tetrahydrofuran, anisole, ethylene glycol dimethyl ether,diethylene glycol dimethyl ether and diethylene glycol diethyl ether; ketones such as acetone and 2-butanone;

nitrites such as acetonitrile; esters such as ethyl acetate and butyl acetate; and sulfoxides such as dimethyl sulfoxide are given, and these may be mixed and used.

For base used in this reaction if desired, for example, inorganic base such as sodium hydrogen carbonate, sodium carbonate, potassium carbonate and cesium carbonate; and organic base such as triethylamine,diisopropylethylamine, tributyl amine and 2,6-lutidine are given. The amount of base used may be 1-50 times mole per the compound of general formula [23], and may be preferably 1-5 times mole. For metal catalyst used in this reaction, for example, copper (II) acetate or mercury (II) acetate is given. The amount of metal catalyst used may be 0.00001-1 times mole per the compound of general formula [23], and may be preferably 0.001-1 times mole.

The amount of myristic acid used in this reaction if desired may be 0.001-50 times mole per the compound of general formula [23], and may be preferably 0.1-2 times mole.

The amount of the compound of general formula [24a] and [24b] used may be 1-50 times mole per the compound of general formula [23], and may be preferably 1-2 times mole.

This reaction may be preferably carried out under an inert gas (for example, nitrogen, argon) atmosphere at 10 to 170° C. for 1 minute to 96 hours.

[Manufacturing Process B]

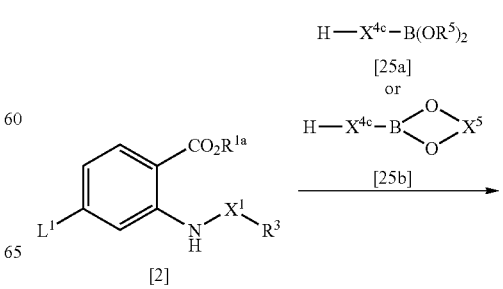

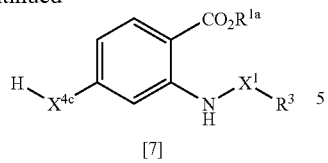

[7]

wherein $R^{1a}$, $R^3$, $R^5$, $X^1$, $X^{4c}$, $X^5$ and $L^1$ represent the same meanings as described above.

The compound of general formula [7] can be produced by reacting the compound of general formula [2] with the compound of the general formula [25a] or [25b] according to the manufacturing process 1.

[Manufacturing Process C]

wherein $R^{1a}$, $R^3$, $X^1$ and $L^3$ represent the same meanings as described above.

As a compound of general formula [26], for example, 2-chloro-4-nitrobenzoic acid is known.

(C-1)

The compound of general formula [27] can be produced by reacting the compound of general formula [26] with the compound of general formula [16] according to the manufacturing process (8-1) or (8-2).

(C-2)

The compound of general formula [28] can be produced by esterification of the compound of general formula [27] according to the manufacturing process (A-1).

(C-3)

The compound of general formula [9] can be produced by reduction of the compound of general formula [28] according to the manufacturing process (2-2) or (A-2).

[Manufacturing Process D]

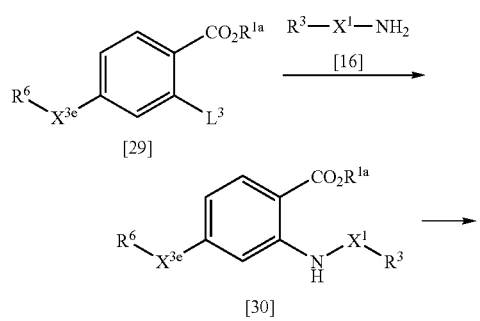

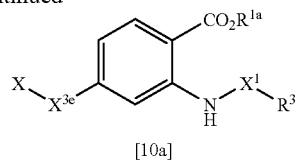

[10a]

wherein $R^6$ represents a phenolic protecting group or a thiol protecting group; $X^{3e}$ represents an oxygen atom or a sulfur atom, $R^{1a}$, $R^3$, $X^1$ and $L^3$ represent the same meanings as described above.

As a compound of general formula [29], for example, methyl 2-iodo-4-methoxybenzoate is known.

(D-1)

The compound of general formula [30] can be produced by reacting the compound of general formula [29] with the compound of general formula [16] according to the manufacturing process (8-1) or (8-2).

(D-2)

The compound of the general formula [10a] can be produced by deprotection of the compound of general formula [30].

In the case that $R^6$ is a phenolic hydroxyl protecting group, the compound of the general formula [10a] can be produced by the method, for example, described in Protective Groups in Organic Synthesis, the third edition, Page 249-287, 1999, W. Greene,John Wiley & Sons, INC or the like method.

In the case that $R^6$ is a thiol protecting group, the compound of the general formula [10a] can be produced by the method, for example,described in Protective Groups in Organic Synthesis the third edition, Page 454-493, 1999, W. Greene,John Wiley & Sons, INC. or the like method.

[Manufacturing Process E]

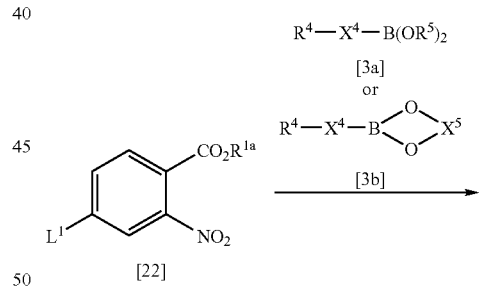

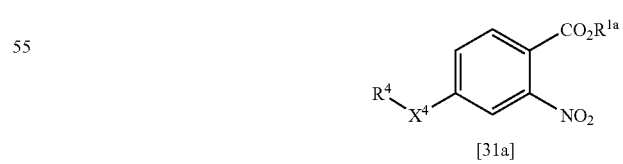

[31a]

wherein $R^{1a}$, $R^4$, $R^5$, $X^4$, $X^5$ and $L^1$ represent the same meanings as described above.

The compound of the general formula [31] can be produced by reacting the compound of general formula [22] with the compound of the general formula [3a] or [3b] according to the manufacturing process 1.

[Manufacturing Process F]

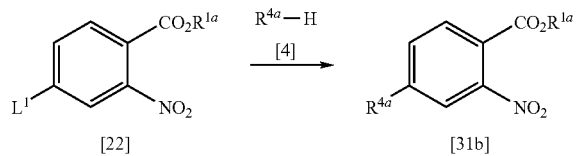

wherein $R^{1a}$, $R^{4a}$ and $L^1$ represent the same meanings as described above.

The compound of the general formula [31b] can be produced by reacting the compound of general formula [22] with the compound of general formula [4] according to the manufacturing process (2-1).

[Manufacturing Process G]

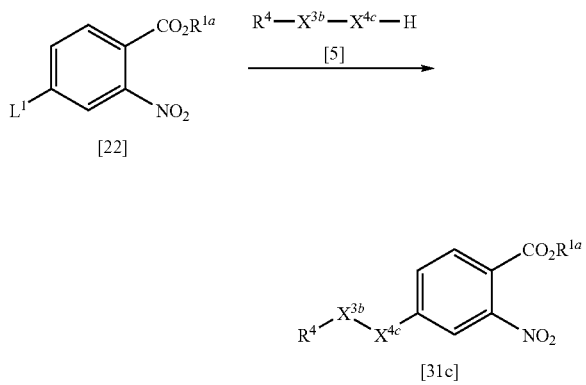

wherein $R^{1a}$, $R^4$, $X^{3b}$, $X^{4c}$ and $L^1$ represent the same meanings as described above.

The compound of the general formula [31c] can be produced by reacting the compound of general formula [22] with the compound of general formula [5] according to the manufacturing process (2-1).

[Manufacturing Process H]

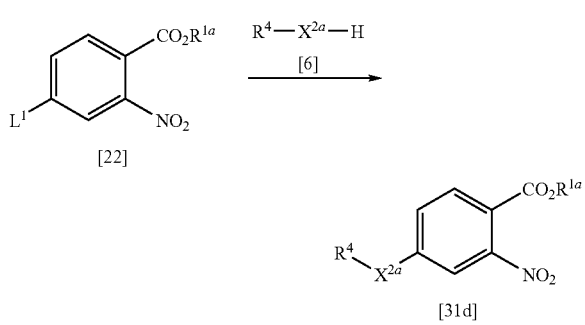

wherein $R^{1a}$, $R^4$, $X^{2a}$ and $L^1$ represent the same meanings as described above.

The compound of the general formula [31d] can be produced by reacting the compound of general formula [22] with the compound of general formula [6] according to the manufacturing process (2-1) or (4-2).

[Manufacturing Process I]

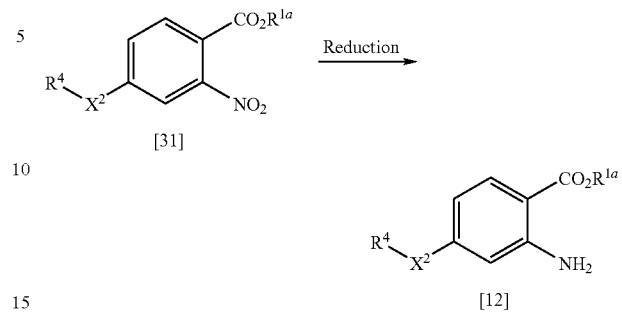

wherein $R^{1a}$, $R^4$ and $X^2$ represent the same meanings as described above.

The compound of general formula [12] can be produced by reduction of the compound of general formula [31] according to the manufacturing process (2-2) or (A-2).

[Manufacturing Process J]

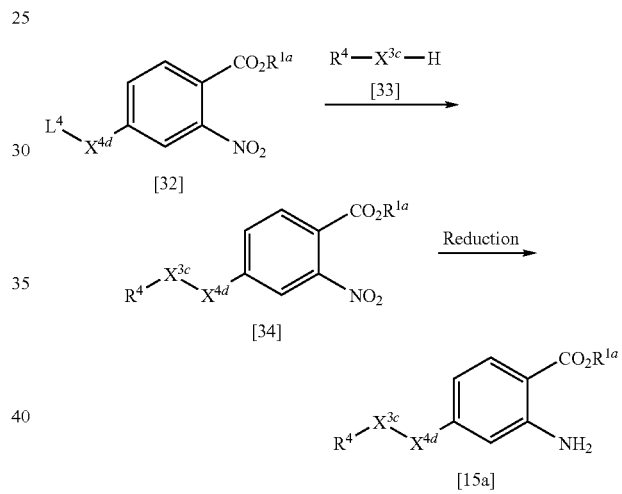

wherein $L^4$ represents a leaving group; $R^{1a}$, $R^4$, $X^{3c}$ and $X^{4d}$ represent the same meanings as described above.

As a compound of general formula [32], for example, methyl 4-(bromomethyl)-2-nitrobenzoate is known. In addition, methyl 4-(bromomethyl)-2-nitrobenzoate can be produced by esterification of 4-(bromomethyl)-2-nitrobenzoic acid which is described in Journal of Medicinal Chemistry, Vol. 29, Page 589-591, 1986 according to conventional methods.

As a compound of general formula [33], for example, aniline, phenol and benzenethiol are known.

(J-1)

The compound of general formula [34] can be produced by reacting the compound of general formula [32] with the compound of general formula [33] according to the manufacturing process (7-1).

(J-2)

The compound of the general formula [15a] can be produced by reduction of compound of general formula [34] according to the manufacturing process (2-2) or (A-2).

[Manufacturing Process K]

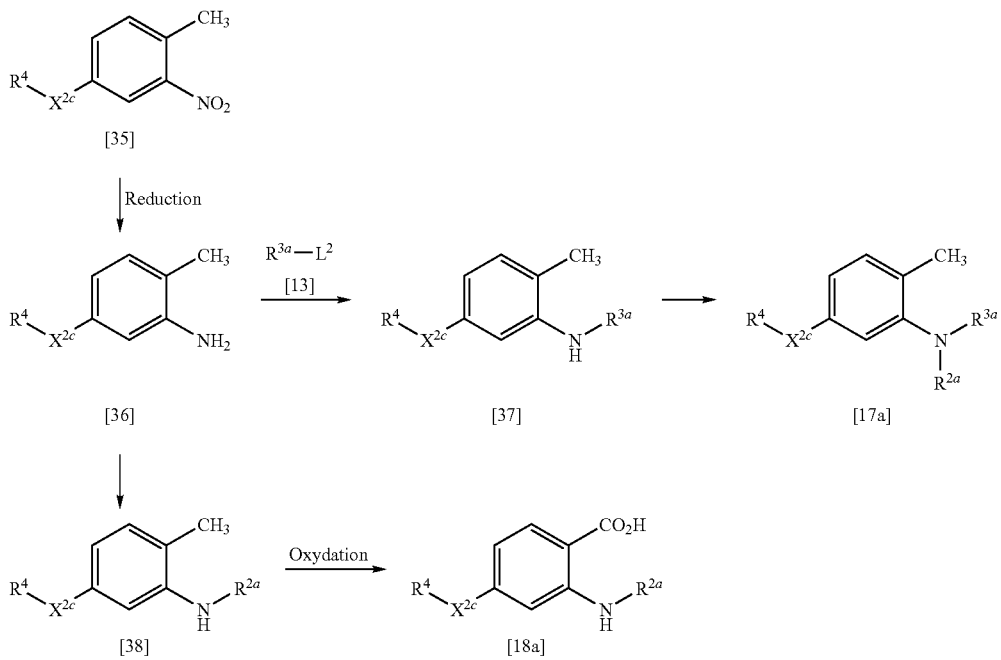

wherein $R^{2a}$, $R^{13a}$, $R^4$, $X^{2c}$ and $L^2$ represent the same meanings as described above.

As a compound of general formula [35], for example, 1-methyl-2-nitro-4-phenoxybenzene is known. As a compound of general formula [36], for example, 3-amino-4-methylbenzophenone is known.

(K-1)

The compound of general formula [36] can be produced by reduction of compound of general formula [35] according to the manufacturing process (A-2).

(K-2)

The compound of general formula [37] can be produced by reacting the compound of general formula [36] with the compound of general formula [13] according to the manufacturing process (8-1) or (8-2).

(K-3)

The compound of the general formula [17a] can be produced by protection of amino group of the compound of general formula [37]. This reaction may be carried out by the method described in Protective Groups in Organic Synthesis, Page 494-615, 1999, W. Greene,John Wiley & Sons, INC. third edition or the like method. For example, in the case of an amide type or a urethane type protecting group, to be concrete, a method using acid anhydride or acid halide is given.

In a method using acid halide, in the presence or absence of base,desirable acid halide and the compound of general formula [37] may be reacted. In this reaction, for solvent used, if it does not adversely affect the reaction, it is not limited to particularly, but for example, aromatic hydrocarbons such as benzene, toluene and xylene; halogenated hydrocarbons such as dichloromethane, chloroform and dichloroethane; amides such as N,N-dimethylformamide, N,N-dimethylacetamide and 1-methyl-2-pyrrolidone; ethers such as dioxane, tetrahydrofuran, anisole, ethylene glycol dimethyl ether,diethylene glycol dimethyl ether and diethylene glycol diethyl ether; ketones such as acetone and 2-butanone; nitrites such as acetonitrile; esters such as ethyl acetate and butyl acetate; and sulfoxides such as dimethyl sulfoxide are given, and these may be mixed and used.

For base used in this reaction if desired, for example, inorganic base such as sodium hydroxide, potassium hydroxide, lithium hydroxide, sodium carbonate, potassium carbonate and cesium carbonate and organic base such as triethylamine, pyridine, dimethylaminopyridine and N-methylmorpholine are given. The amount of base used may be 1-50 times mole per the compound of general formula [37], and may be preferably 1-5 times mole.

For acid halide used in this reaction, for example, acetyl chloride, benzoyl chloride, trimethyl acetyl chloride, methoxy methyl chloride, benzyloxymethyl chloride or benzyloxymethyl carbonyl chloride is given. The amount of acid halide used may be 1-50 times mole per the compound of general formula [37], and may be preferably 1-5 times mole. This reaction may usually be carried out at 0 to 170° C. for 1 minute to 24 hours.

In a method using acid anhydride, in the presence or absence of base,desirable acid anhydride and the compound of general formula [37] may be reacted.

In this reaction, for solvent used, if it does not adversely affect the reaction, it is not limited to particularly, but for example aromatic hydrocarbons such as benzene, toluene and xylene; halogenated hydrocarbons such as dichloromethane, chloroform and dichloroethane; ethers such as dioxane, tetrahydrofuran, anisole, ethylene glycol dimethyl ether,diethylene glycol dimethyl ether and diethylene glycol diethyl ether; ketones such as acetone and 2-butanone; nitriles such as acetonitrile; esters such as ethyl acetate and butyl acetate; and sulfoxides such as dimethyl sulfoxide are given, and these may be mixed and used.

For base used in this reaction if desired, for example, inorganic base such as sodium carbonate, potassium carbonate and cesium carbonate and organic base such as triethylamine, pyridine, dimethylaminopyridine and N-methylmorpholine are given. The amount of base used may be 1-50 times mole per the compound of general formula [37], and may be preferably 1-5 times mole.

For acid anhydride used in this reaction, for example, acetic anhydride, anhydrous trichloroacetic acid or di-tert-butyl dicarbonate is given. The amount of acid anhydride used may be 1-50 times mole per the compound of general formula [37], and may be preferably 1-5 times mole.

This reaction may usually be carried out at 0 to 170° C. for 1 minute to 24 hours.
(K-4)
The compound of general formula [38] can be produced by protection of an amino group of the compound of general formula [36] according to the manufacturing process (K-3).
(K-5)
The compound of the general formula [18a] can be produced by oxidation of the compound of general formula [38] according to the manufacturing process 11.
[Manufacturing Process L]

This reaction may usually carried out at −10 to 15° C. for 1 minute to 24 hours.

The compound of the general formula [20a] can be produced by reacting the diazonium salt of the compound of general formula [39] with metal halide.

In this reaction, for solvent used, if it does not adversely affect the reaction, it is not limited to particularly, but for example, water; ethers such as dioxane and tetrahydrofuran; organic acids such as acetic acid are given, and these may be mixed and used.

For metal halide used in this reaction, for example, copper (I) chloride, copper(I) bromide, copper(I) iodide or potassium iodide is given. The amount of metal halide used may be 1-10 times mole per the compound diazonium salt of general formula [39], and may be preferably 1-3 times mole.

This reaction usually may be carried out at −10 to 80° C. for 1 minute to 24 hours.
[Manufacturing Process M]

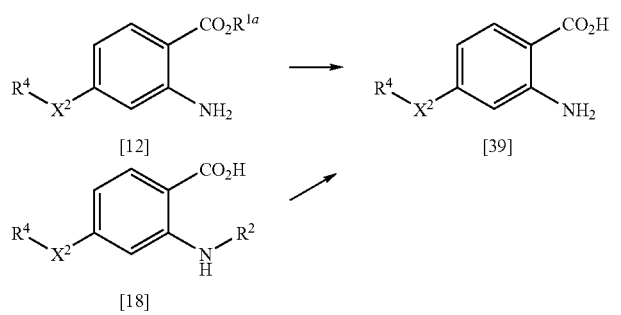

wherein $L^{3a}$ represents a chlorine atom, a bromine atom or an iodine atom; $R^{1a}$, $R^2$, $R^4$ and $X^2$ represent the same meanings as described above.
(L-1)
The compound of general formula [39] can be produced by deprotection of the compound of general formula [12] according to the manufacturing process (14-1).
(L-2)
The compound of general formula [39] can be produced by deprotection of the compound of general formula [18] according to the manufacturing process (14-1) or (14-2).
(L-3)
The Compound of General Formula [20a] can be produced by reacting desirable metal halide after diazotation of the compound of general formula [39] by use of nitrite.

Diazonium salt of compound of general formula [39] can be produced by reacting the compound of general formula [39] with nitrite in the presence of acid.

In this reaction, for solvent used, if it does not adversely affect the reaction, it is not limited to particularly, but for example, water; ethers such as dioxane and tetrahydrofuran; organic acids such as acetic acid are given, and these may be mixed and used.

For acid used in this reaction if desired, for example, hydrochloric acid, sulfuric acid, nitric acid or hydrobromic acid is given. The amount of acid used may be 1-50 times mole per the compound of general formula [39], and may be preferably 1-10 times mole.

For nitrite used in this reaction, for example, sodium nitrite and potassium nitrite are given. The amount of nitrite used may be 1-2 times mole per the compound of general formula [39], and may be preferably 1-1.5 times mole.

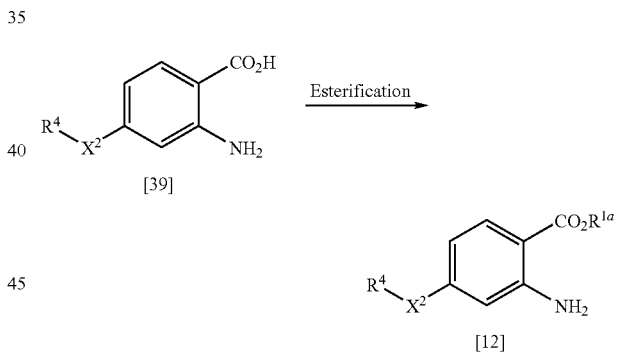

wherein $R^{1a}$, $R^4$ and $X^2$ represent the same meanings as described above.

The compound of general formula [12] can be produced by esterification of the compound of general formula [39] according to the manufacturing process (A-1).
[Manufacturing Process N]

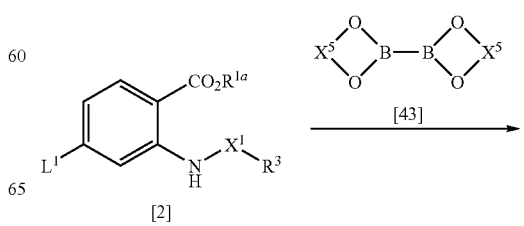

-continued

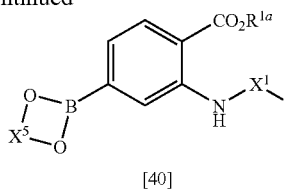

[40]

wherein $R^{1a}$, $R^3$, $X^1$, $X^5$ and $L^1$ represent the same meanings as described above.

As a compound of general formula [43], for example, such as bis(pinacolato)diboron, bis(neopentylglycolato)diboron and bis(hexyleneglycolato)diboron are known.

The compound of general formula [40] can be produced by reacting the compound of general formula [2] with the compound of general formula [43] according to the manufacturing process 1.

[Manufacturing Process O]

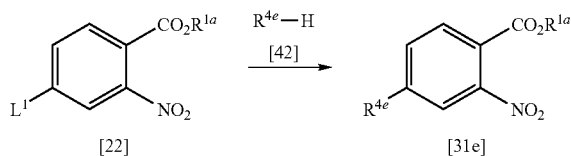

wherein $R^{1a}$, $R^{4e}$ and $L^1$ represent the same meanings as described above.

The compound of the general formula [31e] can be produced by reacting the compound of general formula [22] with the compound of general formula [42] according to the manufacturing process (8-1).

In the compounds used in the production processes mentioned above, compounds which can be in the form of a salt can be used as a salt. Examples of those salts include salts which are similar to the salts of the compound of general formula [1].

When there is any isomer (for example, optical isomer, geometrical isomer, tautomer and the like) for the compounds in the production processes mentioned above, these isomers can be also used. In addition, when there are solvates, hydrates and various kinds of crystals, these solvates, hydrates and various kinds of crystals can be used. Further, when the compounds used in the production process mentioned above have a group which can be protected, for example, an amino group, a hydroxyl group or a carboxyl group, these groups can be protected with ordinary protecting groups beforehand, and these protecting groups can be detached by methods well known per se after the reaction.

When the compounds of the present invention are used as a drug, drug adjuvants usually used for preparation such as excipient, carrier and diluent may be mixed appropriately. They can be administered orally or parenterally in the forms such as tablet, capsule, powder, syrup, granule, pill, suspension, emulsion, solution, powder preparations, suppository, eyedrop, nose drop, eardrop, patch, ointment or injection. The administration method, dosage and times of administration can be selected appropriately according to the age, weight and conditions of the patient. Ordinarily, 0.01 to 1000 mg/kg per day can be administered to an adult orally or parenterally (for example, injection, intravenous feeding and administration to a rectal part) at a time or divided to several times.

Usefulness of some representative compounds of the present invention is described in the following Test Examples.

TEST EXAMPLE 1

MMP-13 Production Inhibition Test $6.8 \times 10^3$ human cartilage derived cell line SW1353 cells were suspended in 100 μL of Dulbecco modified Eagle's medium supplemented with 10% fetal calf serum, plated on 96-well plates and cultured for 3 days. After the culture medium was changed to Dulbecco modified Eagle's medium containing 0.2% lactalbumin hydrolysate and the cells were cultured for 6 hours, test compounds were added and then IL-1β was added to obtain the final concentration of 10 ng/mL 1 hour later. 16 hours after the stimulation, supernatant was collected and the amount of MMP-13 in the culture supernatant was determined with an ELISA kit (Amersham). The inhibition rate was calculated from the amount of MMP-13 in the presence of a test compound assuming that the amount of MMP-13 was 100% in the absence of the test compound.

The results are shown in Table 6.

TABLE 6

| Example No. | Inhibition rate (%) at 30 μmol/L |
|---|---|
| 3 | 53 |
| 7 | 95 |
| 9 | 93 |
| 11 | 62 |
| 12 | 75 |
| 13 | 95 |
| 15 | 91 |
| 37 | 92 |
| 38 | 97 |
| 43 | 93 |
| 45 | 73 |
| 46 | 93 |
| 48 | 85 |
| 49 | 85 |
| 52 | 77 |
| 63 | 67 |
| 67 | 67 |
| 69 | 94 |
| 81 | 97 |
| 87 | 97 |
| 91 | 53 |
| 126 | 94 |
| 132 | 95 |
| 140 | 93 |
| 160 | 93 |
| 166 | 92 |
| 169 | 97 |
| 170 | 97 |
| 172 | 97 |
| 173 | 97 |
| 181 | 97 |
| 185 | 79 |
| 190 | 97 |
| 191 | 97 |
| 199 | 97 |
| 200 | 97 |
| 209 | 82 |
| 214 | 98 |
| 220 | 98 |
| 222 | 98 |
| 225 | 98 |
| 234 | 97 |
| 237 | 97 |
| 243 | 97 |
| 248 | 84 |
| 252 | 96 |
| 259 | 96 |
| 262 | 80 |
| 271 | 97 |
| 273 | 83 |
| 280 | 90 |
| 286 | 96 |
| 290 | 98 |

TABLE 6-continued

| Example No. | Inhibition rate (%) at 30 μmol/L |
|---|---|
| 293 | 87 |
| 329 | 96 |
| 331 | 97 |
| 340 | 97 |
| 343 | 98 |
| 350 | 91 |
| 360 | 97 |
| 362 | 97 |
| 363 | 96 |
| 372 | 97 |

TEST EXAMPLE 2

Type II Collagen-Induced Arthritis in Mice

Eight-week old male DBA/1 J mice were used (Charles River Laboratories Japan Inc.). 4 mg/mL bovine type II collagen (Collagen Gijutsu Kenshukai) dissolved in 0.01 mol/L of acetic acid aqueous solution and an equal amount of Freund's complete adjuvant (Chondorex) containing 1 mg/mL of killed tuberculosis bacillus were added to prepare an emulsion, and 0.1 mL thereof was intradermally injected at the base of tail. Similar treatment was conducted on the 21st day to cause arthritis. The test compound was suspended in 0.5% methylcellulose aqueous solution, and 10 mg/kg was orally administered once a day from the 21st day to the 35th day. In the control group, 0.5% methylcellulose aqueous solution was administered in the same manner. The severity of arthritis was estimated by scoring at zero point for an animal without change; one point for an animal with swelling at the one or two finger joint or light swelling only at the carpal or tarsal joint; two points for an animal with severe swelling at the carpal or tarsal joint or with swelling at three or more finger joints; three points for an animal with severe swelling along the whole foreleg or hindleg and thus counting 12 points at the maximum for the four limbs as arthritis score. Degree of bone destruction was estimated by X-ray photographs of the four limbs on the 36th day observing the interphalangeal joints of the second to fifth fingers, the metacarpophalangeal and metatarsophalangeal joints of the first to fifth fingers, carpal or tarsal parts, calcaneal bone and scoring at 0 or 0.5 point according to the absence or presence of osteoporotic image in the joint and their vicinity, 0 point for the bone image without change, one point for the partially destroyed bone image and, 2 points for the completely destroyed bone image and thus counting 105 points at the maximum for the four limbs as bone destruction score. The inhibitory rate was determined by the following expression.

Inhibitory ratio (%)=100−(score of a test compound treated group/score of the control group)×100

The compound shown in Example 38 exhibited inhibitory action on arthritis and bone destruction.

EXAMPLES

Hereinbelow, the present invention is described by way of Referential Examples and Examples, but the present invention is not limited thereto.

The mixing ratio in the eluent is a volume ratio. Unless indicated otherwise, the carrier in the silica gel column chromatography is B. W. Silica gel, BW-127ZH, manufactured by Fuji Silysia Chemical Ltd., and the carrier in the reversed-phase silica gel column chromatography is ODS-AM12S05-2520WT of YMC Co., Ltd.

Each of the symbols used in each Example has the following meaning.

Ac: acetyl, Boc: tert-butoxycarbonyl, $^t$Bu: tert-butyl, Bz: benzoyl, Et: ethyl, Me: methyl DMSO-$d_6$: deuterated dimethylsulfoxide Referential Example 1

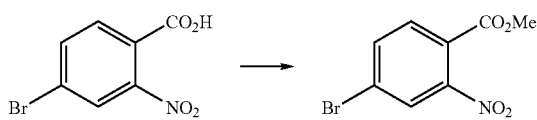

To acetone 40 mL solution of 4-bromo-2-nitrobenzoic acid 4.0 g were added potassium carbonate 3.4 g and dimethylsulfate 2.3 mL at room temperature, and it was stirred at 50° C. for 1 hour. After the reaction mixture was cooled to room temperature, the solvent was removed under reduced pressure. Water and ethyl acetate were added to the obtained residue. The organic layer was separated and collected, dried over anhydrous magnesium sulfate after sequential washing with saturated sodium hydrogen carbonate aqueous solution, 1.0 mol/L hydrochloric acid and saturated sodium chloride aqueous solution, and the solvent was removed under reduced pressure to give methyl 4-bromo-2-nitrobenzoate 4.1 g of white solid.

$^1$H-NMR(CDCl$_3$) δ value:

3.97(3H,s),7.85(1H,d,J=8.3 Hz),8.07(1H,dd,J=8.3,2.0 Hz),8.47 (1H,d,J=2.0 Hz).

Reference Example 2

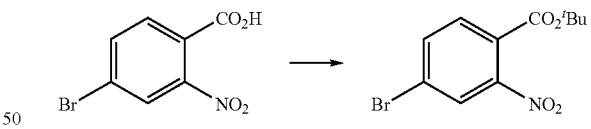

To N,N-dimethylacetamide 50 mL solution of 4-bromo-2-nitrobenzoic acid 5.0 g were added potassium carbonate 41 g, benzyltriethylammonium chloride 4.6 g and 2-bromo-2-methylpropane 69 mL at room temperature and it was stirred at 55° C. for 10 hours. After the reaction mixture was cooled to room temperature, 2-bromo-2-methylpropane 12 mL was added to it, and it was stirred at 55° C. for 4 hours. After the reaction mixture was cooled to room temperature, water and ethyl acetate were added to it. The organic layer was separated and collected, dried over anhydrous magnesium sulfate after sequential washing with 10% citric acid aqueous solution and saturated sodium chloride aqueous solution, and the solvent was removed under reduced pressure. Methanol was added to the obtained residue, solid matter was filtrated to give tert-butyl 4-bromo-2-nitrobenzoate 3.0 g of white solid.

$^1$H-NMR(CDCl$_3$) δ value:
1.55(9H,s),7.63(1H,d,J=8.3 Hz),7.77(1H,dd,J=8.3,1.9 Hz),7.95 (1H,d,J=1.9 Hz).

Reference Example 3

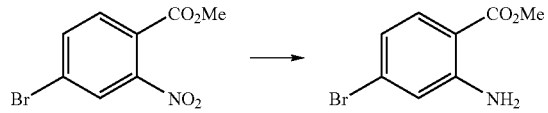

Iron powder 2.6 g was added to a mixed solution of methanol 20 mL and acetic acid 20 mL of methyl 4-bromo-2-nitrobenzoate 4.0 g, it was heated and refluxed for 3 hours. After the reaction mixture was cooled to room temperature, saturated sodium hydrogen carbonate aqueous solution and ethyl acetate were added to it, and insoluble matter was filtrated. The organic layer was separated and collected, dried over anhydrous magnesium sulfate after sequential washing with saturated sodium hydrogen carbonate aqueous solution and saturated sodium chloride aqueous solution, and solvent was removed under reduced pressure. Hexane was added to the obtained residue, solid matter was filtrated to give methyl 2-amino-4-bromobenzoate 2.0 g of white solid.

$^1$H-NMR(CDCl$_3$) δ value:
3.89(3H,s),4.20(2H,s),7.26(1H,dd,J=8.3,2.1 Hz),7.43 (1H,d, J=2.1 Hz),7.47(1H,d,J=8.3 Hz).

Reference Example 4

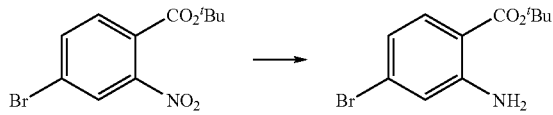

Iron powder 3.0 g were added to a mixed solution methanol 28 mL and acetic acid 28 mL of tert-butyl 4-bromo-2-nitrobenzoate 5.5 g, it was heated and refluxed for 1 hour. After the reaction mixture was cooled to room temperature, saturated sodium hydrogen carbonate aqueous solution and ethyl acetate were added to it, and insoluble matter was filtrated. The organic layer was separated and collected, dried over anhydrous magnesium sulfate after sequential washing with saturated sodium hydrogen carbonate aqueous solution and saturated sodium chloride aqueous solution, the solvent was removed under reduced pressure to give tert-butyl 2-amino-4-bromobenzoate 4.3 g of pale yellow oil.

$^1$H-NMR(DMSO-d$_6$) δ value:
1.52(9H,s),6.65(1H,dd,J=8.5,2.0 Hz),6.78(2H,s),6.98 (1H,d, J=2.0 Hz),7.55(1H,d,J=8.5 Hz).

Reference Example 5

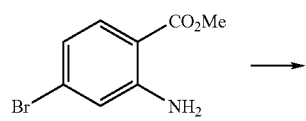

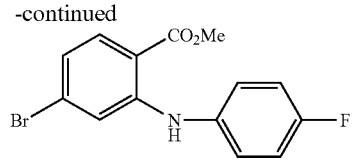

To toluene 12 mL solution of methyl 2-amino-4-bromobenzoate 1.2 g were added 1-fluoro-4-iodobenzene 1.5 mL, cesium carbonate 3.4 g, palladium acetate 12 mg and rac-2,2'-bis(diphenylphosphino)-1,1'-binaphthyl 32 mg at room temperature, and it was heated and refluxed under nitrogen atmosphere for 12 hours. After the reaction mixture was cooled to room temperature, palladium acetate 12 mg and rac-2,2'-bis(diphenylphosphino)-1,1'-binaphthyl 32 mg were added to it, and it was heated and refluxed under nitrogen atmosphere for 12 hours. After the reaction mixture was cooled to room temperature, water was added to it. The organic layer was separated and collected, dried over anhydrous magnesium sulfate after sequential washing with 1.0 mol/L hydrochloric acid and saturated sodium chloride aqueous solution, and the solvent was removed under reduced pressure. The obtained residue was refined by silica gel column chromatography [Fuji SILYSIA Chemical Ltd., PSQ100B (spherical type), eluent; hexane:ethyl acetate=10:1] to give methyl 4-bromo-2-(4-fluoroanilino)benzoate 0.20 g of pale yellow solid.

$^1$H-NMR(DMSO-d$_6$) δ value:
3.86(3H,s),6.94(1H,dd,J=8.6,1.7 Hz),7.04(1H,d,J=1.7 Hz),7.24-7.35(4H,m),7.80(1H,d,J=8.6 Hz),9.27(1H,s).

Reference Example 6

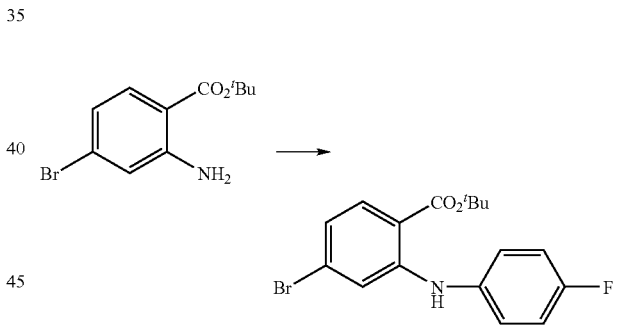

To toluene 15 mL solution of tert-butyl 2-amino-4-bromobenzoate 1.0 g were added 1-fluoro-4-iodobenzene 0.85 mL, cesium carbonate 3.6 g, palladium acetate 8 mg and rac-2,2'-bis(diphenylphosphino)-1,1'-binaphthyl 23 mg at room temperature, and it was heated and refluxed under nitrogen atmosphere for 6 hours. After the reaction mixture was cooled to room temperature, palladium acetate 8 mg and rac-2,2'-bis(diphenylphosphino)-1,1'-binaphthyl 23 mg were added to it, it was heated and refluxed under nitrogen atmosphere for 8 hours. After the reaction mixture was cooled to room temperature, water was added to it, insoluble matter was filtrated. The organic layer was separated and collected, dried over anhydrous magnesium sulfate after sequential washing with 10% citric acid aqueous solution and saturated sodium chloride aqueous solution, the solvent was removed under reduced pressure. The obtained residue was refined by silica gel column chromatography [eluent; hexane:ethyl acetate=20:1] to give tert-butyl 4-bromo-2-(4-fluoroanilino)benzoate 0.55 g of pale yellow oil.

$^1$H-NMR(DMSO-d$_6$) δ value:
 1.56(9H,s),6.93(1H,dd,J=8.6,1.6 Hz),7.04(1H,d,J=1.6 Hz),7.23-7.35(4H,m),7.75(1H,d,J=8.6 Hz),9.34(1H,s).

Reference Example 7

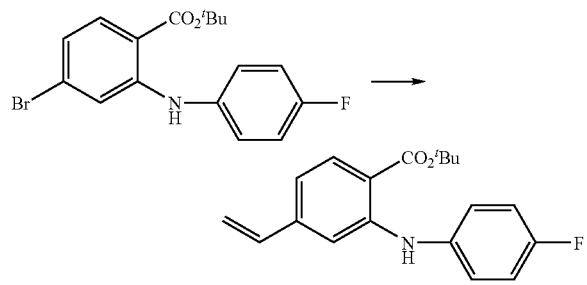

To a mixed solution of ethylene glycol dimethyl ether 50 mL and water 15 mL of tert-butyl 4-bromo-2-(4-fluoroanilino)benzoate 5.0 g were added vinylboronic acid pinacol ester 2.7 mL, potassium carbonate 2.3 g and tetrakis(triphenylphosphine)palladium(0) 0.80 g at room temperature sequentially, and it was heated and refluxed under nitrogen atmosphere for 4 hours. After the reaction mixture was cooled to room temperature, toluene and water were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane: ethyl acetate=20:1] to give tert-butyl 2-(4-fluoroanilino)-4-vinylbenzoate 3.4 g of yellow oil.

$^1$H-NMR(DMSO-d$_6$) δ value:
 1.56(9H,s),5.34(1H,d,J=11.0 Hz),5.81(1H,d,J=17.7 Hz),6.65 (1H,dd,J=17.7,11.0 , Hz),6.94-6.96(1H,m),7.06-7.07(1H,m),7.18-7.23(2H,m),7.27-7.32(2H,m),7.82(1H,d,J=8.3 Hz),9.31(1H,s).

Reference Example 8

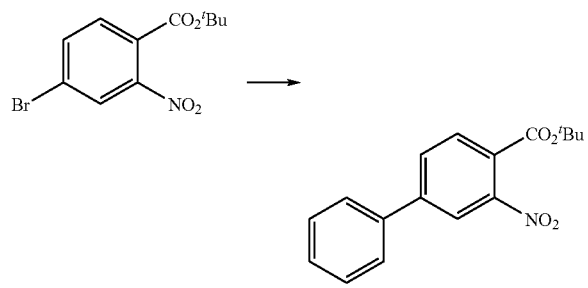

To toluene 70 mL solution of tert-butyl 4-bromo-2-nitrobenzoate 8.8 g were added phenylboronic acid 4.3 g, sodium hydrogen carbonate 6.1 g, ethanol 26 mL, water 13 mL and tetrakis(triphenylphosphine)palladium (0) 1.7 g at room temperature sequentially, and it was heated and refluxed for 3 hours. After the reaction mixture was cooled to room temperature, water was added to it. The organic layer was separated and collected, dried over anhydrous magnesium sulfate after sequential washing with saturated sodium hydrogen carbonate aqueous solution and saturated sodium chloride aqueous solution, and the solvent was removed under reduced pressure. Hexane was added to the obtained residue, solid matter was filtrated to give tert-butyl 2-nitro-4-phenylbenzoate 7.8 g of white solid.

$^1$H-NMR(DMSO-d$_6$) δ value:
 1.52(9H,s),7.47-7.56(3H,m),7.81-7.83(2H,m),7.91(1H,d,J=8.1 Hz),8.11(1H,dd,J=8.1, 2.0 Hz),8.27(1H,d,J=2.0 Hz).

Reference Example 9

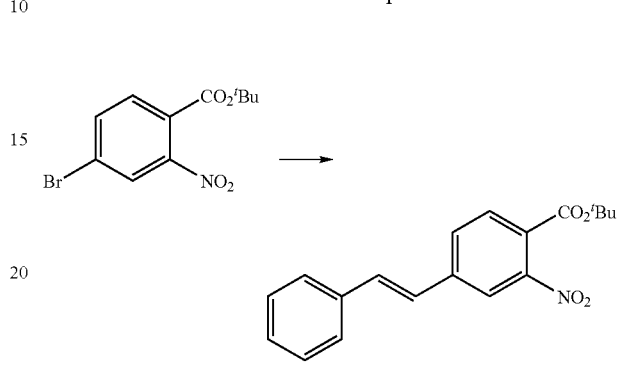

To N,N-dimethylacetamide 48 mL solution of tert-butyl 4-bromo-2-nitrobenzoate 6.0 g were added styrene 2.7 mL, sodium acetate 2.5 g, tetrabutylammonium bromide 3.2 g and palladium acetate 0.22 g sequentially, and it was heated and stirred under nitrogen atmosphere at 90° C. for 3 hours. After the reaction mixture was cooled to room temperature, styrene 0.45 mL and palladium acetate 0.22 g were added to it, and it was stirred at 110° C. for 3 hours. After the reaction mixture was cooled to room temperature, water and ethyl acetate were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [eluent; hexane: ethyl acetate=20:1] to give tert-butyl 2-nitro-4-((E)-2-phenylvinyl)benzoate 3.8 g of white solid.

$^1$H-NMR(DMSO-d$_6$) δ value:
 1.51(9H,s),7.33-7.45(4H,m),7.59(1H,d,J=16.6 Hz),7.66 (2H,d,J=7.4 Hz), 7.84(1H,d,J=8.1 Hz),7.98(1H,dd,J=8.1, 1.5 Hz),8.23(1H,d,J=1.5 Hz).

Reference Example 10

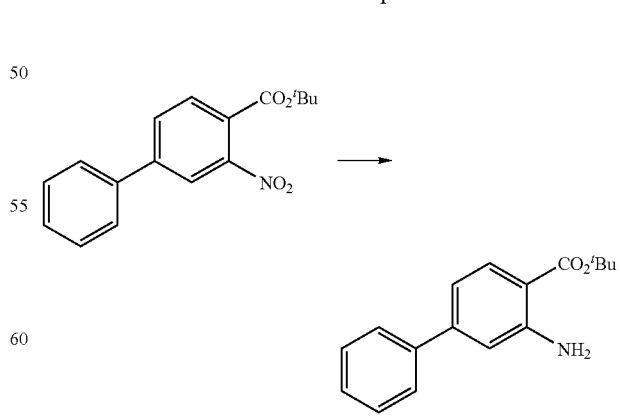

To a suspension of methanol 38 mL and acetic acid 38 mL of tert-butyl 2-nitro-4-phenylbenzoate 7.5 g was added iron powder 4.2 g at room temperature, and it was heated and refluxed for 1 hour. After the reaction mixture was cooled to room temperature, the solvent was removed under reduced pressure. To the obtained residue, saturated sodium hydrogen carbonate aqueous solution and ethyl acetate were added, and insoluble matter was filtrated. The organic layer was separated and collected, dried over anhydrous magnesium sulfate after sequential washing with saturated sodium hydrogen carbonate aqueous solution and saturated sodium chloride aqueous solution, and the solvent was removed under reduced pressure. Hexane was added to the obtained residue, solid matter was filtrated to give tert-butyl 2-amino-4-phenylbenzoate 3.3 g of white solid.

$^1$H-NMR(DMSO-$d_6$) δ value:
1.55(9H,s),6.64-6.68(2H,broad),6.81(1H,dd,J=8.4,1.7 Hz),7.03(1H,d,J=1.7H z),7.39-7.49(3H,m),7.60(2H,d,J=7.6 Hz),7.72(1H,d,J=8.4 Hz).

Reference Example 11

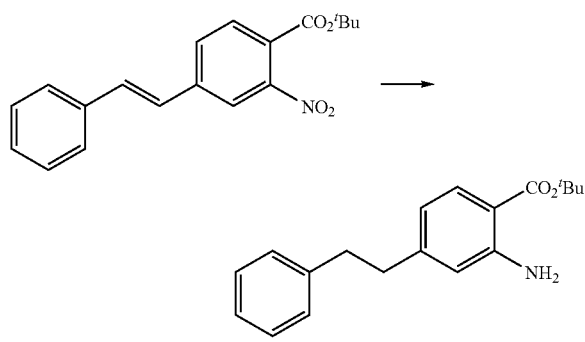

To a mixed solution of methanol 56 mL and ethyl acetate 56 mL of tert-butyl 2-nitro-4-((E)-2-phenylvinyl)benzoate 3.7 g was added 5% palladium-carbon 0.74 g, and it was stirred under hydrogen atmosphere at room temperature for 2 hours. Insoluble matter was filtrated, the solvent was removed under reduced pressure to give tert-butyl 2-amino-4-phenethyl benzoate 3.4 g of white solid.

$^1$H-NMR(CDCl$_3$) δ value:
1.58(9H,s),2.79-2.91(4H,m),5.63(2H,s),6.44(1H,s),6.47 (1H,dd,J=8.3,1.5 Hz), 7.17-7.21(3H,m),7.26-7.30(2H,m), 7.72(1H,d,J=8.3 Hz).

Reference Example 12

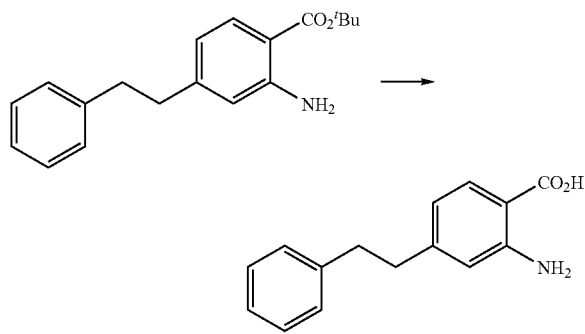

Trifluoroacetic acid 1.0 mL solution of tert-butyl 2-amino-4-phenethyl benzoate 50 mg was stirred at room temperature for 16 hours. The solvent was removed under reduced pressure, ethyl acetate and water were added to the obtained residue, and it was adjusted to pH 6.4 with saturated hydrogen carbonate aqueous solution. The organic layer was separated and collected, dried over anhydrous magnesium sulfate, the solvent was removed under reduced pressure to give 2-amino-4-phenethylbenzoic acid 30 mg of white solid.

$^1$H-NMR(DMSO-$d_6$) δ value:
2.73-2.86(4H,m),6.41(1H,d,J=8.2 Hz),6.58(1H,s),7.15-7.29(5H,m),7.59(1H,d,J=8.2 Hz).

Reference Example 13

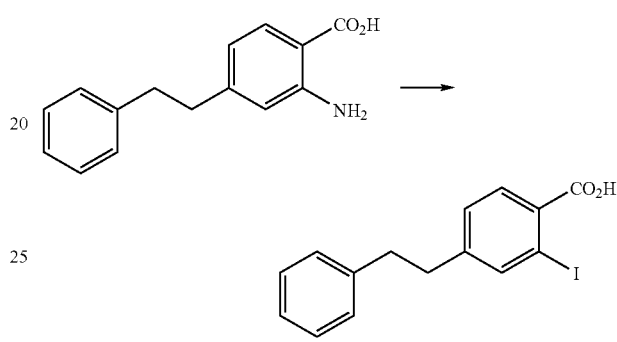

To a suspension of acetic acid 17 mL, water 17 mL and hydrochloric acid 2.1 mL of 2-amino-4-phenethylbenzoic acid 1.7 g, was added water 3.0 mL solution of sodium nitrite 0.58 g at 4° C., and it was stirred at same temperature for 15 minutes. The reaction mixture was added to water 20 mL solution of potassium iodide 2.3 g at 4° C., and it was stirred at room temperature for 30 minutes. The solvent was removed under reduced pressure, and ethyl acetate was added to it. The organic layer was separated and collected, dried over anhydrous magnesium sulfate after sequential washing with 5% sodium thiosulfate aqueous solution and saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate: acetic acid=66:33:1] to give 2-iodo-4-phenethylbenzoic acid 1.5 g of yellow solid.

$^1$H-NMR(DMSO-$d_6$) δ value:
2.88(4H,s),7.16-7.30(5H,s),7.33(1H,dd,J=8.0,1.3 Hz), 7.66(1H,d,J=8.0 Hz),7.86 (1H,d,J=1.3 Hz),13.01-13.29(1H, broad).

Reference Example 14

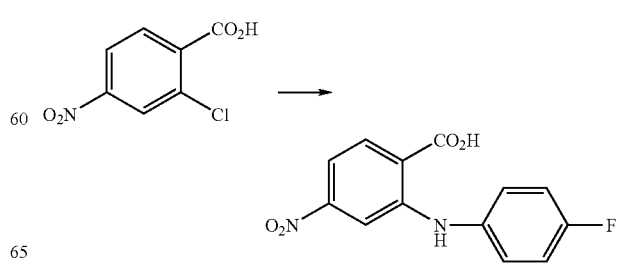

57

To N,N-dimethylacetamide 150 mL solution of 2-chloro-4-nitrobenzoic acid 30 g, were added 4-fluoroaniline 29 mL, copper powder 2.8 g, copper (I) chloride 5.3 g and N-methylmorpholine 33 mL at room temperature, and it was stirred at 110 to 120° C. for 10 hours. After the reaction mixture was cooled to room temperature, insoluble matter was filtrated, and 1.0 mol/L hydrochloric acid 700 mL and ethyl acetate 700 mL were added to it. The organic layer was separated and collected,dried over anhydrous magnesium sulfate after sequential washing with 1.0 mol/L hydrochloric acid and saturated sodium chloride aqueous solution, and the solvent was removed under reduced pressure. Diisopropyl ether was added to the obtained residue, solid matter was filtrated to give 2-(4-fluoroanilino)-4-nitrobenzoic acid 9.7 g of red solid.

$^1$H-NMR(DMSO-$d_6$) δ value:
7.26-7.33(2H,m),7.37-7.42(2H,m),7.50(1H,dd,J=8.6,2.3 Hz),7.66(1H,d,J=2.3 Hz),8.11(1H,d,J=8.6 Hz),9.69(1H,s).

Reference Example 15

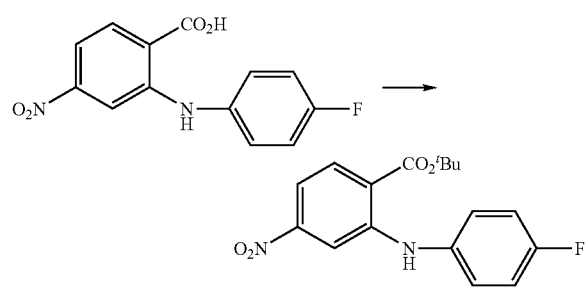

To N,N-dimethylacetamide 15 mL solution of 2-(4-fluoroanilino)-4-nitrobenzoic acid 1.0 g, were added potassium carbonate 9.9 g, benzyltriethylammonium chloride 0.82 g and 2-bromo-2-methylpropane 21 mL at room temperature, and it was stirred at 55° C. for 4 hours. After the reaction mixture was cooled to room temperature,2-bromo-2-methylpropane 21 mL was added to it, and it was stirred at 55° C. for 12 hours. After the reaction mixture was cooled to room temperature, water and ethyl acetate were added to it. The organic layer was separated and collected,dried over anhydrous magnesium sulfate after sequential washing with water and 10% citric acid aqueous solution, and the solvent was removed under reduced pressure. The obtained residue was refined by silica gel column chromatography [eluent; hexane:ethyl acetate=8:1] to give tert-butyl 2-(4-fluoroanilino)-4-nitrobenzoate 1.1 g of red oil.

$^1$H-NMR(DMSO-$d_6$) δ value:
1.59(9H,s),7.26-7.31(2H,m),7.38-7.41(2H,m),7.51(1H, dd,J=8.8,2.3 Hz),7.66(1H,d,J=2.3 Hz), 8.06(1H,d,J=8.8 Hz), 9.44(1H,s).

Reference Example 16

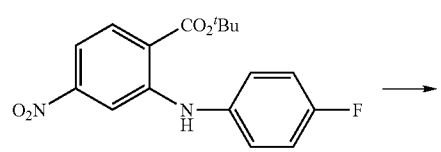

58

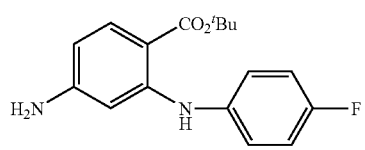

To a mixed solution of methanol 5.0 mL and ethyl acetate 5.0 mL of tert-butyl 2-(4-fluoroanilino)-4-nitrobenzoate 1.0 g, was added 5% palladium-carbon 0.20 g, and it was stirred under hydrogen atmosphere at room temperature for 6 hours. Insoluble matter was filtrated, the solvent was removed under reduced pressure to give tert-butyl 4-amino-2-(4-fluoroanilino)benzoate 0.90 g of white solid.

$^1$H-NMR(DMSO-$d_6$) δ value:
1.51(9H,s),5.78-5.82(2H,broad),5.97(1H,dd,J=8.8,2.1 Hz),6.19(1H,d,J=2.1H z),7.16-7.26(4H,m),7.54(1H,d,J=8.8 Hz),9.43(1H,s).

Reference Example 17

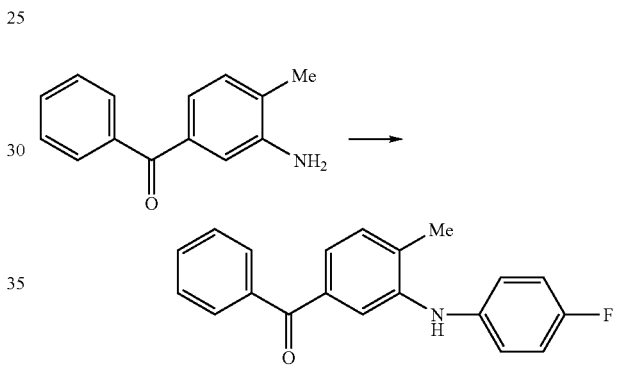

To toluene 5 mL solution of 3-amino-4-methylbenzophenone 0.50 g,1-fluoro-4-iodobenzene 0.30 mL and 1,1'-bis(diphenylphosphino)ferrocene 0.16 g were added sodium tert-butoxide 0.25 g and (1,1'-bis(diphenylphosphino)ferrocene)palladium(II) dichloride dichloromethane complex 0.077 g at room temperature, it was stirred at 100° C. under nitrogen atmosphere for 1 hour. After the reaction mixture was cooled to room temperature, it was refined by silica gel column chromatography [eluent; hexane:ethyl acetate=5:1] to give 3-(4-fluoroanilino)-4-methylbenzophenone 0.59 g of brownish-red oil.

$^1$H-NMR(CDCl$_3$) δ value:
2.33(3H,s),6.98-7.00(4H,m),7.25-7.30(2H,m),7.43-7.47 (2H,m),7.53-7.56(2H,m),7.76-7.78(2H,m).

Reference Example 18

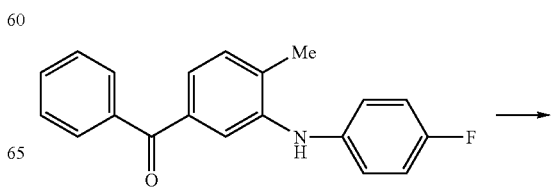

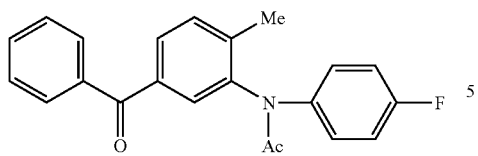

60% sodium hydride 79 mg and acetyl chloride 0.14 mL were added to N,N-dimethylformamide 5.0 mL solution of 3-(4-fluoroanilino)-4-methylbenzophenone 0.50 g under ice cooling sequentially, and it was stirred at room temperature for 4 hours. After the reaction mixture was cooled to ice temperature, 60% sodium hydride 79 mg and acetyl chloride 0.14 mL were added sequentially, and it was stirred at room temperature for 5 hours and 30 minutes. Ethyl acetate and 1.0 mol/L hydrochloric acid were added to the reaction mixture. The organic layer was separated and collected, dried over anhydrous magnesium sulfate after sequential washing with 1.0 mol/L hydrochloric acid and saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=2:1] to give N-(5-benzoyl-2-methylphenyl)-N-(4-fluorophenyl)acetamide 82 mg of orange oil.

$^1$H-NMR(CDCl$_3$) δ value:
2.01-2.14(3H,m),2.31-2.42(3H,m),7.00-7.10(2H,m),7.24-7.28(2H,m),7.44-7.80(8H,m).

Reference Example 19

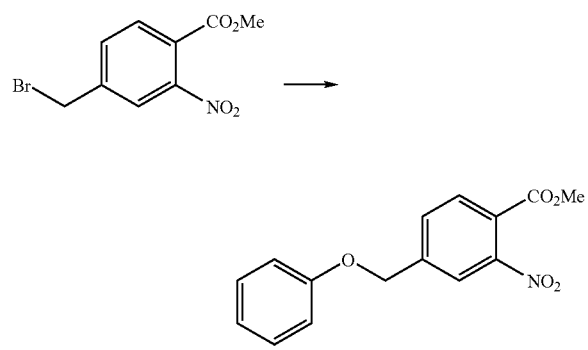

To N,N-dimethylformamide 5.0 mL solution of phenol 0.18 g were added potassium carbonate 0.50 g and methyl 4-(bromomethyl)-2-nitrobenzoate 0.50 g at room temperature, and it was stirred at same temperature for 10 hours. Ethyl acetate and 1.0 mol/L hydrochloric acid were added to the reaction mixture. The organic layer was separated and collected, dried over anhydrous magnesium sulfate after washing with saturated sodium chloride aqueous solution, and the solvent was removed under reduced pressure. The obtained residue was refined by silica gel column chromatography [eluent; hexane:ethyl acetate=6:1] to give methyl 2-nitro-4-(phenoxymethyl)benzoate 0.53 g of colorless oil.

$^1$H-NMR(CDCl$_3$) δ value:
3.93(3H,s),5.17(2H,s),6.95-7.03(3H,m),7.30-7.34(2H,m),7.72-7.79(2H,m),7.99(1H,s).

Reference Example 20

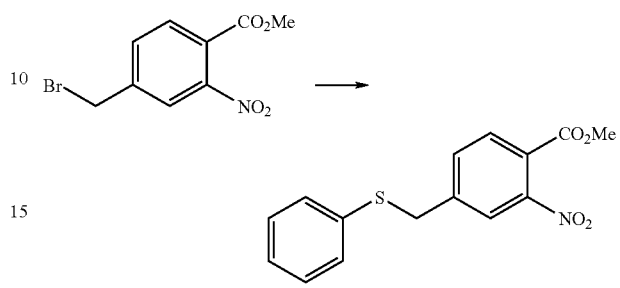

To N,N-dimethylformamide 10 mL solution of methyl 4-(bromomethyl)-2-nitrobenzoate 1.0 g, were added potassium carbonate 1.0 g and benzenethiol 0.39 mL at room temperature, and it was stirred at same temperature for 7 hours. Ethyl acetate was added to the reaction mixture, insoluble matter was filtrated, and water was added to it. The organic layer was separated and collected, dried over anhydrous magnesium sulfate after sequential washing with saturated sodium hydrogen carbonate aqueous solution and saturated sodium chloride aqueous solution, the solvent was removed under reduced pressure. The obtained residue was refined by silica gel column chromatography [eluent; hexane:ethyl acetate=4:1] to give methyl 2-nitro-4-((phenylthio)methyl)benzoate 0.70 g of pale yellow oil.

$^1$H-NMR(CDCl$_3$) δ value:
3.86(3H,s),4.27(2H,s),6.60-6.74(5H,m),7.15-7.19(2H,m),7.82(1H,d,J=8.3 Hz).

Reference Example 21

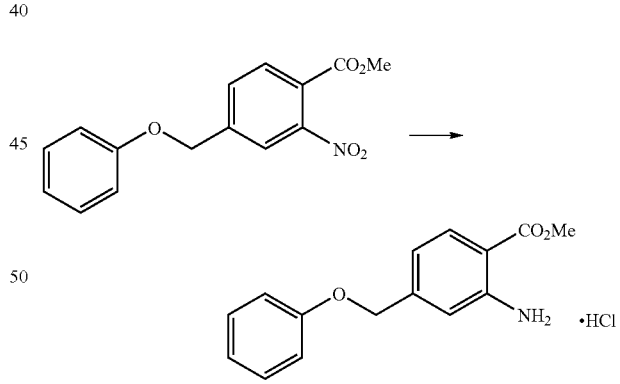

To a mixed solution of methanol 6.6 mL and acetic acid 2.0 mL of methyl 2-nitro-4-(phenoxymethyl)benzoate 0.66 g was added iron powder 0.38 g, and it was heated and refluxed for 3 hours. After the reaction mixture was cooled to room temperature, ethyl acetate and saturated sodium hydrogen carbonate aqueous solution were added to it, and insoluble matter was filtrated. The organic layer was separated and collected, dried over anhydrous magnesium sulfate after washing with saturated sodium chloride aqueous solution, and the solvent was removed under reduced pressure. The obtained residue was dissolved in diethyl ether 6.6 mL, hydrochloric acid 0.2 mL was added to it under ice cooling, and solid matter was filtrated to give methyl 2-amino-4-(phenoxymethyl)benzoate hydrochloride 0.58 g of white solid.

¹H-NMR(DMSO-d₆) δ value:
3.78(3H,s),4.40-4.80(2H,broad),5.03(2H,s),6.61(1H,dd, J=8.3,1.7 Hz),6.86(1H,s),6.92-7.00(3H,m),7.27-7.32(2H, m),7.71(1H,d,J=8.3 Hz).

Reference Example 22

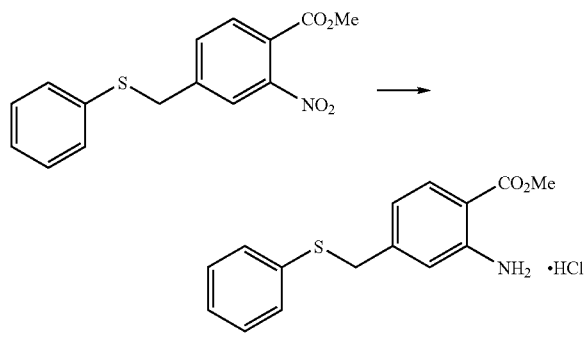

To a mixed solution of methanol 7.0 mL and acetic acid 2.1 mL of methyl 2-nitro-4-((phenylthio)methyl)benzoate 0.70 g was added iron powder 0.39 g, and it was heated and refluxed for 3 hours. After the reaction mixture was cooled to room temperature, ethyl acetate and saturated sodium hydrogen carbonate aqueous solution were added to it, and insoluble matter was filtrated. The organic layer was separated and collected,dried over anhydrous magnesium sulfate after sequential washing with saturated sodium hydrogen carbonate aqueous solution and saturated sodium chloride aqueous solution, and the solvent was removed under reduced pressure. The obtained residue was dissolved in diethyl ether 10 mL, 1.9 mol/L hydrogen chloride/ethyl acetate 1.2 mL was added under ice cooling, solid matter was filtrated to give methyl 2-amino-4-((phenylthio) methyl)benzoate hydrochloride 0.39 g of white solid.

¹H-NMR(DMSO-d₆) δ value:
3.76(3H,s),4.13(2H,s),4.30-4.70(2H,broad),6.55(1H,dd, J=8.2,1.7 Hz),6.79(1H,d,1.7 Hz), 7.15-7.19(1H,m),7.26-7.33(4H,m),7.62(1H,d,J=8.2 Hz).

Reference Example 23

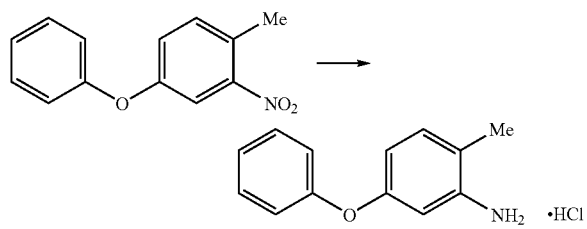

To a mixed solution of methanol 57 mL and acetic acid 17 mL of 1-methyl-2-nitro-4-phenoxy benzene 5.7 g was added iron powder 4.2 g, and it was heated and refluxed for 5 hours. After the reaction mixture was cooled to room temperature, ethyl acetate and saturated sodium hydrogen carbonate aqueous solution were added to it, and insoluble matter was filtrated. The organic layer was separated and collected,dried over anhydrous magnesium sulfate after sequential washing with saturated sodium hydrogen carbonate aqueous solution and saturated sodium chloride aqueous solution, and the solvent was removed under reduced pressure. The obtained residue was dissolved in diethyl ether 60 mL, hydrochloric acid 2.1 mL was added to it under ice cooling. Solid matter was filtrated to give 2-methyl-5-phenoxyaniline hydrochloride 4.7 g of white solid.

¹H-NMR(DMSO-d₆) δ value:
2.27(3H,s),6.82(1H,dd,J=8.3,2.4 Hz),6.96(1H,d,J=2.4 Hz),7.03 (2H,d,J=7.5 Hz),7.17(1H,t,J=7.5 Hz),7.26(1H,d, J=8.3 Hz), 7.39-7.43(2H,m).

Reference Example 24

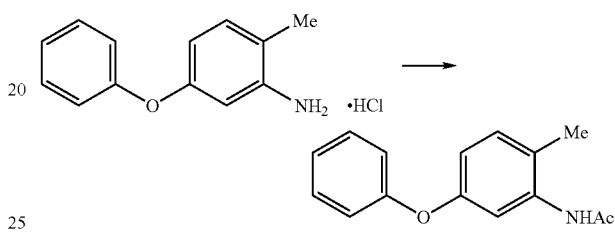

To dichloromethane 5.0 mL solution of 2-methyl-5-phenoxyaniline hydrochloride 0.50 g were added pyridine 0.34 mL and acetic anhydride 0.24 mL under ice cooling, and it was stirred at room temperature for 6 hours and 30 minutes. The solvent was removed under reduced pressure,1.0 mol/L hydrochloric acid and ethyl acetate were added to the obtained residue. The organic layer was separated and collected,dried over anhydrous magnesium sulfate after sequential washing with saturated sodium hydrogen carbonate aqueous solution and saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=2:1] to give N-(2-methyl-5-phenoxyphenyl)acetamide 0.44 g of white solid.

¹H-NMR(DMSO-d₆) δ value:
2.18(3H,s),2.23(3H,s),6.74(1H,d,J=7.6 Hz),6.92-6.98 (1H,broad),7.00(2H,d,J=7.8 Hz),7.06-7.13(2H,m),7.32(2H, t,J=7.8 Hz),7.60(1H,s).

Reference Example 25

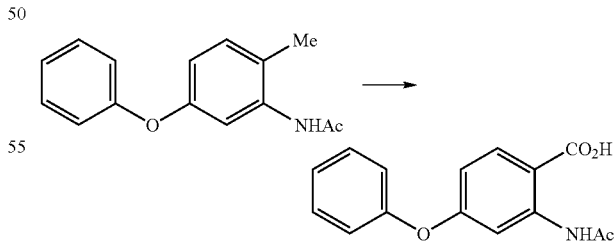

To a suspension of 2-methyl-2-propanol 10 mL and water 20 mL of N-(2-methyl-5-phenoxyphenyl)acetamide 1.1 g were added potassium permanganate 1.4 g and anhydrous magnesium sulfate 2.7 g at room temperature, and it was heated and refluxed for 1 hour. After the reaction mixture was cooled to room temperature, potassium permanganate 0.72 g was added to it, and it was heated and refluxed for 1 hour.

After the reaction mixture was cooled to room temperature, potassium permanganate 0.72 g was added to it, and it was heated and refluxed for 1 hour. After the reaction mixture was cooled to room temperature, potassium permanganate 0.36 g were added to it, and it was heated and refluxed for 1 hour. After the reaction mixture was cooled to room temperature, ethanol 5 mL was added to it, insoluble matter was filtrated, and 1.0 mol/L hydrochloric acid and ethyl acetate were added to it. The organic layer was separated and collected, dried over anhydrous magnesium sulfate, the solvent was removed under reduced pressure. Diisopropyl ether and hexane were added to the obtained residue, solid matter was filtrated to give 2-(acetamido)-4-phenoxybenzoic acid 0.88 g of white solid.

$^1$H-NMR(DMSO-$d_6$) δ value:
2.11(3H,s),6.68(1H,dd,J=8.9,2.4 Hz),7.11-7.14(2H,m), 7.23-7.27(1H,m),7.43-7.49(2H,m),7.99(1H,d,J=8.9 Hz), 8.20(1H,d,J=2.4Hz),11.29(1H,s),13.40-13.58(1H,broad).

Reference Example 26

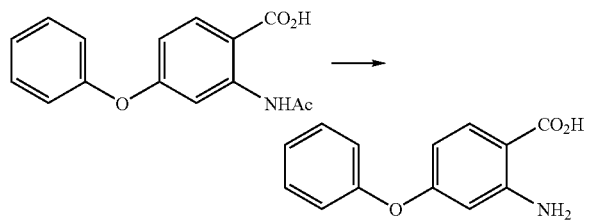

A suspension of hydrazine monohydrate 5.0 mL of 2-(acetamido)-4-phenoxybenzoic acid 1.5 g was heated and refluxed for 4 hours. After the reaction mixture was cooled to room temperature, acetic acid 10 mL, ethyl acetate and saturated sodium chloride aqueous solution were added to it. The organic layer was separated and collected, dried over anhydrous magnesium sulfate, the solvent was removed under reduced pressure. Diisopropyl ether and hexane were added to the obtained residue, solid matter was filtrated to give 2-amino-4-phenoxybenzoic acid 1.2 g of white solid.

$^1$H-NMR(DMSO-$d_6$) δ value:
6.11(1H,dd,J=8.8, 2.5 Hz),6.20(1H,d,J=2.5 Hz),7.06-7.09 (2H,m),7.17-7.22(1H,m),7.40-7.45(2H,m),7.70(1H,d,J=8.8 Hz).

Reference Example 27

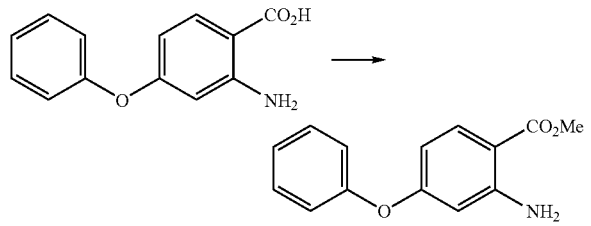

To N,N-dimethylformamide 5.0 mL solution of 2-amino-4-phenoxybenzoic acid 0.40 g were added potassium carbonate 0.29 g and dimethyl sulfate 0.20 mL, and it was stirred at room temperature for 2 hours. Ethyl acetate was added to the reaction mixture, it was dried over anhydrous magnesium sulfate after sequential washing with saturated sodium hydrogen carbonate aqueous solution and saturated sodium chloride aqueous solution, and the solvent was removed under reduced pressure. The obtained residue was refined by silica gel column chromatography [eluent; hexane:ethyl acetate=10:1] to give methyl 2-amino-4-phenoxybenzoate 0.33 g of colorless oil.

$^1$H-NMR(DMSO-$d_6$) δ value:
3.76(3H,s),6.16(1H,dd,J=8.9,2.4 Hz),6.23(1H,d,J=2.4 Hz),6.76(2H,s),7.08-7.12(2H,m),7.20-7.24(1H,m),7.42-7.47(2H,m),7.70(1H,d,J=8.9 Hz).

Reference Example 28

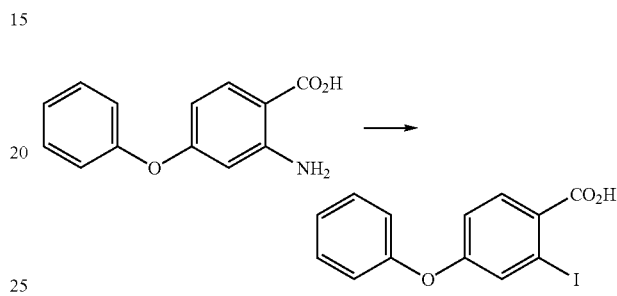

To a suspension of water 6.0 mL, acetic acid 10 mL and concentrated sulfuric acid 0.95 mL of 2-amino-4-phenoxybenzoic acid 2.0 g was added water 2.0 mL solution of sodium nitrite 0.66 g at 4° C., and it was stirred at same temperature for 30 minutes. The reaction mixture was added dropwise to water 30 mL solution of potassium iodide 3.2 g at same temperature, and it was stirred at room temperature for 3 hours. Ethyl acetate was added to the reaction mixture. The organic layer was separated and collected, dried over anhydrous magnesium sulfate, and the solvent was removed under reduced pressure. The obtained residue was refined by silica gel column chromatography [eluent; hexane:ethyl acetate: acetic acid=80:20:1] to give 2-iodo-4-phenoxybenzoic acid 1.6 g of red solid.

$^1$H-NMR(CDCl$_3$) δ value:
6.98(1H,dd,J=8.7,2.4 Hz),7.07-7.09(2H,m),7.22-7.26 (1H,m),7.40-7.45(2H,m),7.64(1H,d,J=2.4 Hz),8.04(1H,d, J=8.7Hz).

Reference Example 29

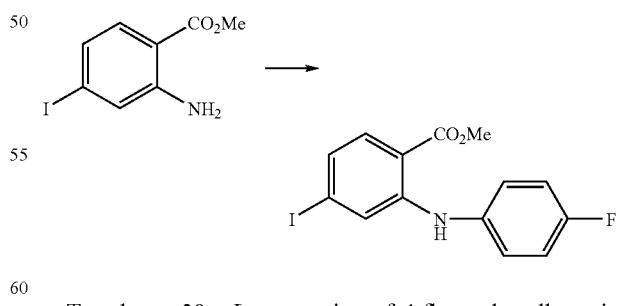

To toluene 20 mL suspension of 4-fluorophenylboronic acid 1.4 g, anhydrous copper(II) acetate 0.35 g and myristic acid 0.89 g was added 2,6-lutidine 0.76 mL, and it was stirred at room temperature for 5 minutes. Methyl 2-amino-4-iodobenzoate 1.8 g was added to the reaction mixture, and it was stirred at room temperature for 3 hours. 4-fluorophenylboronic acid 0.45 g and anhydrous copper(II) acetate 0.35 g were added to the reaction mixture, and it was stirred at room temperature for 8 hours. Ethyl acetate and 1.0 mol/L hydrochloric acid were added to the reaction mixture. The organic layer was separated and collected,dried over anhydrous magnesium sulfate after washing with saturated sodium chloride aqueous solution, and the solvent was removed under reduced pressure. The obtained residue was refined by silica gel column chromatography [eluent; hexane:ethyl acetate=10:1] to give methyl 2-(4-fluoroanilino)-4-iodobenzoate 0.63 g of pale yellow solid.

$^1$H-NMR(CDCl$_3$) δ value:
3.89(3H,s),7.03-7.11(3H,m),7.17-7.20(2H,m),7.34(1H,d, J=1.7 Hz),7.61(1H,d,J=8.5Hz) 9.32(1H,s).

Reference Example 30

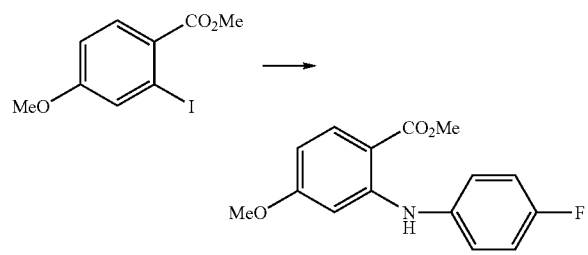

To toluene 30 mL suspension of methyl 2-iodo-4-methoxybenzoate 2.7 g, rac-2,2'-bis(diphenylphosphino)-1,1'-binaphthyl 58 mg, palladium acetate 20 mg and cesium carbonate 6.0 g was added 4-fluoroaniline 1.3 mL, and it was heated and refluxed under nitrogen atmosphere for 5 hours. After the reaction mixture was cooled to room temperature, insoluble matter was filtrated, and ethyl acetate and 1.0 mol/L hydrochloric acid were added to it. The organic layer was separated and collected,dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=10:1] to give methyl 2-(4-fluoroanilino)-4-methoxybenzoate 2.2 g of white solid.

$^1$H-NMR(CDCl$_3$) δ value:
3.73(3H,s),3.87(3H,s),6.29(1H,dd,J=8.9,2.4 Hz),6.48 (1H,d, J=2.4 Hz),7.02-7.08(2H,m),7.19-7.23(2H,m),7.90 (1H,d,J=8.9 Hz),9.47(1H,s).

Reference Example 31

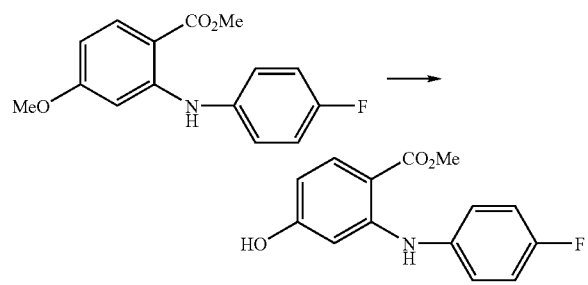

Methyl 2-(4-fluoroanilino)-4-methoxybenzoate 2.2 g was added to 1.0 mol/L boron tribromide/dichloromethane 24 mL, and it was stirred at room temperature for 5 hours. Saturated sodium chloride aqueous solution and ethyl acetate were added to the reaction mixture. The organic layer was separated and collected,dried over anhydrous magnesium sulfate, and the solvent was removed under reduced pressure. The obtained residue was refined by silica gel column chromatography [Fuji SILYSIA Chemical Ltd., PSQ100B (spherical type), eluent; hexane:ethyl acetate=5:1] to give methyl 2-(4-fluoroanilino)-4-hydroxybenzoate 0.60 g of purple solid.

$^1$H-NMR(CDCl$_3$) δ value:
3.87(3H,s),5.04-5.18(1H,broad),6.19(1H,dd,J=8.8,2.3 Hz),6.40(1H,d,J=2.3H z),7.02-7.08(2H,m),7.18-7.23(2H, m),7.87(1H,d,J=8.8 Hz),9.46(1H,s).

Reference Example 32

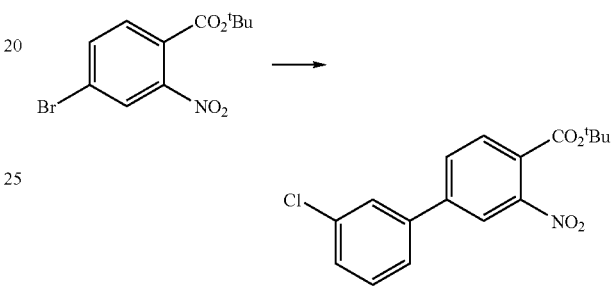

To toluene 20 mL solution of tert-butyl 4-bromo-2-nitrobenzoate 2.0 g were added ethanol 6.0 mL, water 3.0 mL,3-chlorophenylboronic acid 1.2 g, sodium carbonate 1.7 g and tetrakis(triphenylphosphine)palladium(0) 0.23 g sequentially, and it was heated and refluxed under nitrogen atmosphere for 3 hours. After the reaction mixture was cooled to room temperature, water was added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=10: 1] to give tert-butyl 4-(3-chlorophenyl)-2-nitrobenzoate 0.70 g of white solid.

$^1$H-NMR(DMSO-d$_6$) δ value:
1.52(9H,s),7.53-7.59(2H,m),7.77-7.82(1H,m),7.89-7.95 (2H,m),8.15(1H,dd,J=8.1,1.6 Hz),8.34(1H,d,J=1.6 Hz).

Reference Example 33

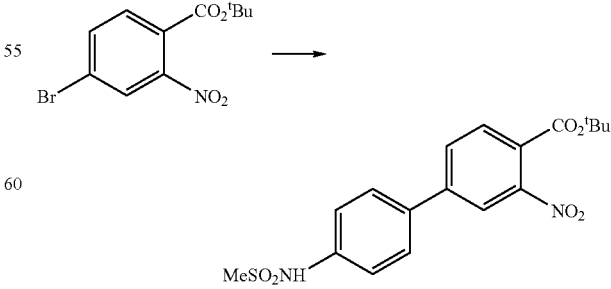

To toluene 24 mL solution of tert-butyl 4-bromo-2-nitrobenzoate 3.0 g were added ethanol 9.0 mL, water 4.5 mL,4-N-(methanesulfonamide)phenylboronic acid 2.6 g, sodium hydrogen carbonate 2.1 g and tetrakis(triphenylphosphine)palladium(0) 0.57 g, and it was heated and refluxed under nitrogen atmosphere for 4 hours and 30 minutes. After the reaction mixture was cooled to room temperature, ethyl acetate and water were added to it. After insoluble matter was filtrated, the organic layer was separated and collected,dried over anhydrous magnesium sulfate after washing with saturated sodium chloride aqueous solution, and the solvent was removed under reduced pressure. Hexane and diisopropyl ether were added to the obtained residue, solid matter was filtrated to give tert-butyl 4-(4-N-(methanesulfonamido)phenyl)-2-nitrobenzoate 3.9 g of white solid.

$^1$H-NMR(DMSO-$d_6$) δ value:
1.51(9H,s),3.06(3H,s),7.32-7.37(2H,m),7.79-7.84(2H,m),7.89(1H,d,J=8.2 Hz),8.07(1H,dd,J=8.2, 1.8 Hz),8.23(1H,d,J=1.8 Hz),10.02-10.08(1H,broad).

Reference Example 34

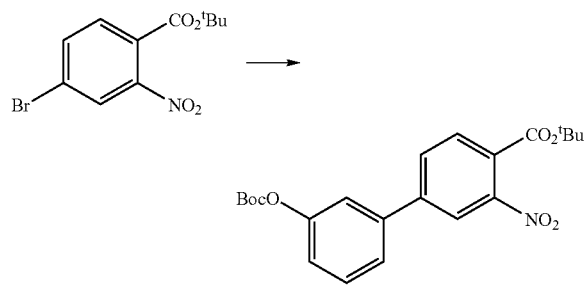

To toluene 24 mL solution of tert-butyl 4-bromo-2-nitrobenzoate 3.0 g were added ethanol 9.0 mL, water 4.5 mL, tert-butyl 3-(4,4,5,5-tetramethyl-1,3,2-dioxaborolan-2-yl)phenyl carbonate 3.8 g, sodium hydrogen carbonate 2.1 g and tetrakis (triphenylphosphine)palladium(0) 0.57 g sequentially, and it was heated and refluxed under nitrogen atmosphere for 6 hours. After the reaction mixture was cooled to room temperature, ethyl acetate and water were added to it. After insoluble matter was filtrated, the organic layer was separated and collected,dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B (spherical type), eluent; hexane:ethyl acetate=3:1] to give tert-butyl 4-(3-(tert-butoxycarbonyl)oxyphenyl)-2-nitrobenzoate 3.6 g of yellow oil.

$^1$H-NMR(DMSO-$d_6$) δ value:
1.51(9H,s),1.52(9H,s),7.29-7.34(1H,m),7.55-7.60(1H,m),7.70-7.76(2H,m),7.91(1H,d,J=8.0 Hz),8.14(1H,dd,J=8.0, 1.7 Hz),8.32 (1H,d,J=1.7 Hz).

Reference Example 35

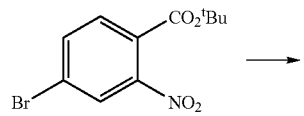

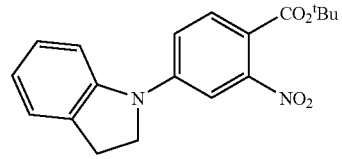

To toluene 30 mL solution of tert-butyl 4-bromo-2-nitrobenzoate 3.0 g were added indoline 2.1 mL, cesium carbonate 8.0 g,2-dicyclohexylphosphino-2',4',6'-triisopropylbiphenyl 0.29 g, tris(dibenzylideneacetone)dipalladium(0) 0.11 g and palladium acetate 55 mg at room temperature, and it was heated and refluxed under nitrogen atmosphere for 3 hours and 30 minutes. After the reaction mixture was cooled to room temperature,2-dicyclohexylphosphino-2',4',6'-triisopropylbiphenyl 0.29 g, tris(dibenzylideneacetone)dipalladium(0) 0.11 g and palladium acetate 55 mg were added to it, and it was heated and refluxed under nitrogen atmosphere for 3 hours. After the reaction mixture was cooled to room temperature, ethyl acetate and 10% citric acid aqueous solution were added to it. The organic layer was separated and collected,dried over anhydrous magnesium sulfate after washing with saturated sodium chloride aqueous solution, and the solvent was removed under reduced pressure. Toluene was added to the obtained residue,dried over anhydrous magnesium sulfate after sequential washing with 1.0 mol/L hydrochloric acid and saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=10:1] to give tert-butyl 4-(indolin-1-yl)-2-nitrobenzoate 2.0 g of yellow solid.

$^1$H-NMR(DMSO-$d_6$) δ value:
1.48(9H,s),3.15(2H,t,J=8.4 Hz),4.04(2H,t,J=8.4 Hz),6.91 (1H,t,J=7.4 Hz),7.17(1H,t,J=7.4 Hz),7.25-7.30(1H,m),7.35 (1H,d,J=8.0 Hz),7.50-7.55(2H,m),7.81(1H,d,J=8.6 Hz).

Reference Example 36

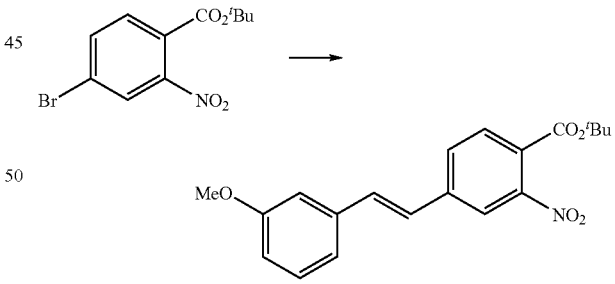

To N,N-dimethylacetamide 5 mL solution of tert-butyl 4-bromo-2-nitrobenzoate 0.50 g were added 3-vinylanisole 0.37 mL, triethylamine 0.47 mL and palladium acetate 0.11 g at room temperature, and it was stirred under nitrogen atmosphere at 110° C. for 4 hours. After the reaction mixture was cooled to room temperature, ethyl acetate and water were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane: ethyl acetate=10:1] to give tert-butyl 4-((E)-2-(3-methoxyphenyl)vinyl)-2-nitrobenzoate 0.20 g of pale yellow solid.

$^1$H-NMR(DMSO-$d_6$) δ value:
1.51(9H,s),3.81(3H,s),6.90-6.94(1H,m),7.20-7.27(2H, m),7.34(1H,t,J=7.9 Hz),7.43(1H,d,J=16.6 Hz),7.55(1H,d, J=16.6 Hz),7.84(1H,d,J=8.0 Hz),7.97(1H,d,J=7.8 Hz),8.21 (1H,s).

Reference Example 37

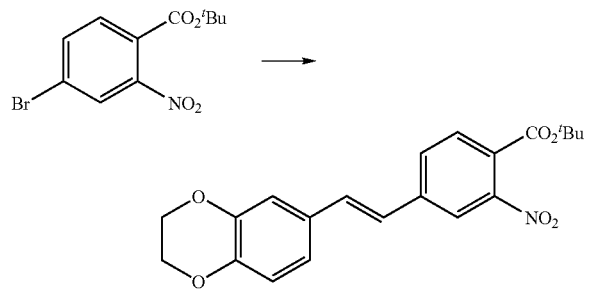

To N,N-dimethylacetamide 24 mL solution of tert-butyl 4-bromo-2-nitrobenzoate 3.0 g were added 2,3-dihydro-6-vinylbenzo[1,4]dioxin 2.4 g, N,N-dicyclohexylmethylamine 4.0 mL and palladium acetate 0.11 g at room temperature, and it was stirred under nitrogen atmosphere at 120° C. for 3 hours. After the reaction mixture was cooled to room temperature, ethyl acetate and water were added to it, and insoluble matter was filtrated. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=10:1] to give tert-butyl 4-((E)-2-(2,3-dihydrobenzo[1,4]dioxin-6-yl)vinyl)-2-nitrobenzoate 1.5 g of yellow solid.

$^1$H-NMR(DMSO-$d_6$) δ value:
1.50(9H,s),4.27(4H,s),6.90(1H,d,J=8.3 Hz),7.11-7.16 (1H,m),7.17-7.20(1H,m),7.23(1H,d,J=16.5 Hz),7.45(1H,d, J=16.5 Hz),7.81 (1H,d,J=8.0 Hz),7.89-7.93(1H,m),8.14(1H, s).

Reference Example 38

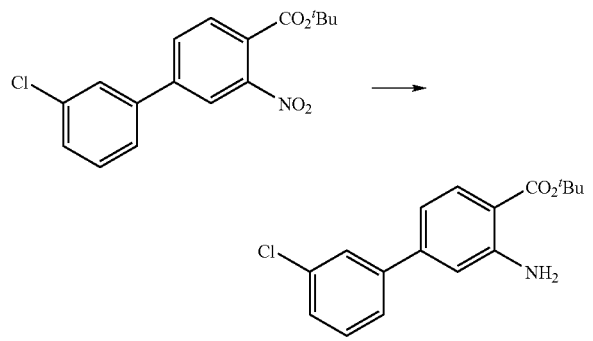

To a mixed solution of methanol 11 mL and ethyl acetate 11 mL of tert-butyl 4-(3-chlorophenyl)-2-nitrobenzoate 1.1 g was added 10% palladium-carbon 0.33 g, and it was stirred under hydrogen atmosphere at room temperature for 3 hours. The solvent was removed under reduced pressure after insoluble matter was filtrated. To the obtained residue, were added acetic acid 11 mL, methanol 11 mL and 10% palladium-carbon 0.33 g sequentially, and it was stirred under hydrogen atmosphere at room temperature for 2 hours. The solvent was removed under reduced pressure after insoluble matter was filtrated to give tert-butyl 2-amino-4-(3-chlorophenyl)benzoate 0.70 g of white solid.

$^1$H-NMR(DMSO-$d_6$) δ value:
1.55(9H,s),6.63-6.69(2H,broad),6.83(1H,dd,J=8.5,1.9 Hz),7.06(1H,d,J=1.9H z),7.46(1H,dt,J=7.8,1.6 Hz),7.50(1H, t,J=7.8 Hz),7.57(1H,d t,J=7.8,1.6 Hz),7.63(1H,t,J=1.6 Hz), 7.73(1H,d,J=8.5 Hz).

Reference Example 39

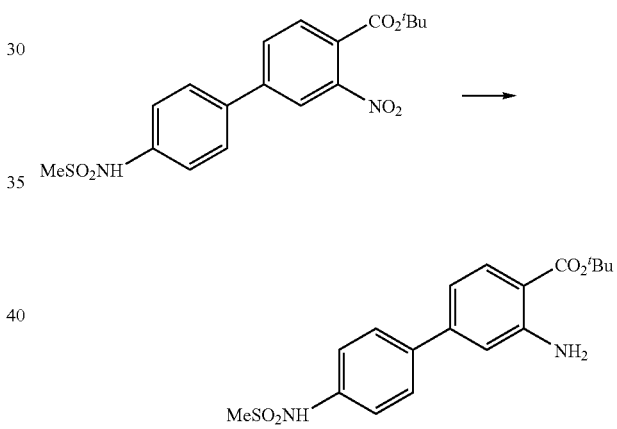

To a suspension of methanol 19 mL of tert-butyl 4-(4-N-(methanesulfonamido)phenyl)-2-nitrobenzoate 3.8 g were added acetic acid 19 mL and iron powder 1.6 g sequentially, and it was heated and refluxed for 1 hour. After the reaction mixture was cooled to room temperature, the solvent was removed under reduced pressure, saturated sodium hydrogen carbonate aqueous solution and ethyl acetate were added to it, and insoluble matter was filtrated. The organic layer was separated and collected, dried over anhydrous magnesium sulfate after sequential washing with saturated sodium hydrogen carbonate aqueous solution and saturated sodium chloride aqueous solution, and the solvent was removed under reduced pressure. Diisopropyl ether was added to the obtained residue, and solid matter was filtrated to give tert-butyl 2-amino-4-(4-N-(methanesulfonamido)phenyl)benzoate 2.8 g of yellow solid.

$^1$H-NMR(DMSO-$d_6$) δ value:

1.54(9H,s),3.03(3H,s),6.61-6.68(2H,broad),6.79(1H,dd,
J=8.5,1.9 Hz),6.99(1H,d,J=1.9H z),7.27-7.32(2H,m),7.56-
7.61(2H,m),7.70(1H,d,J=8.5 Hz),9.86-9.94(1H,broad).

Reference Example 40

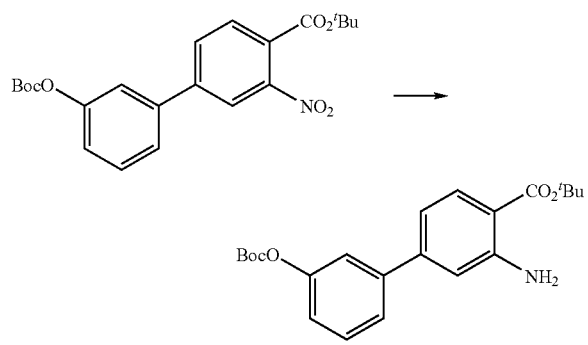

To a mixed solution of methanol 18 mL and ethyl acetate 18 mL of tert-butyl 4-(3-(tert-butoxycarbonyl)oxyphenyl)-2-nitrobenzoate 3.5 g was added 5% palladium-carbon 0.70 g, and it was stirred under hydrogen atmosphere at room temperature for 3 hours and 30 minutes. The solvent was removed under reduced pressure after insoluble matter was filtrated to give tert-butyl 2-amino-4-(3-(tert-butoxycarbonyl)oxyphenyl)benzoate 3.2 g of yellow oil.

$^1$H-NMR(DMSO-$d_6$) δ value:

1.51(9H,s),1.55(9H,s),6.64-6.69(2H,broad),6.82(1H,dd,
J=8.4,1.8 Hz),7.05(1H,d,J=1.8H z),7.20-7.24(1H,m),7.38-
7.42(1H,m),7.49-7.53(2H,m),7.73(1H,d,J=8.4 Hz).

Reference Example 41

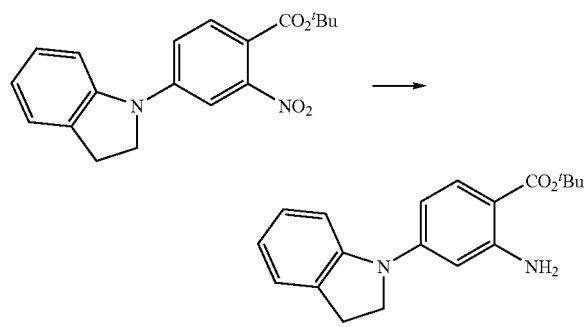

To a mixed solution of methanol 29 mL and ethyl acetate 29 mL of tert-butyl 4-(indolin-1-yl)-2-nitrobenzoate 1.9 g was added 5% palladium-carbon 0.58 g, and it was stirred under hydrogen atmosphere at room temperature for 3 hours. The solvent was removed under reduced pressure after insoluble matter was filtrated.

The obtained residue was refined by silica gel column chromatography [Fuji SILYSIA Chemical Ltd., PSQ100B (spherical type), eluent; hexane:ethyl acetate=8:1] to give tert-butyl 2-amino-4-(indolin-1-yl)benzoate 1.20 g of pale yellow solid.

$^1$H-NMR(DMSO-$d_6$) δ value:

1.52(9H,s),3.08(2H,t,J=8.3 Hz),3.91(2H,t,J=8.3 Hz),6.45
(1H,dd,J=8.9, 2.3 Hz),6.52(1H,d,J=2.3 Hz),6.56-6.63(2H,
broad),6.78(1H,t,J=7.6 Hz),7.08(1H,t,J=7.6 Hz),7.18-7.26
(2H,m),7.61(1H,d,J=8.9 Hz).

Reference Example 42

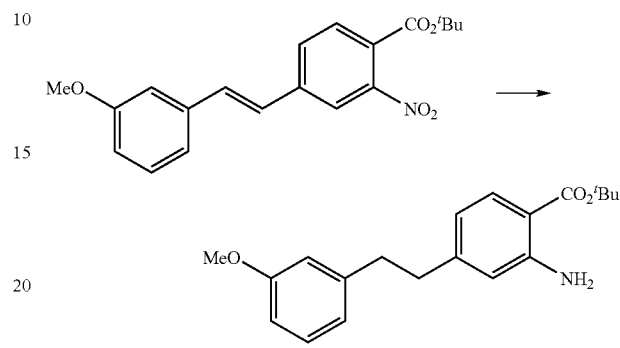

To a mixed solution of methanol 22 mL and ethyl acetate 22 mL of tert-butyl 4-((E)-2-(3-methoxyphenyl)vinyl)-2-nitrobenzoate 2.2 g was added 10% palladium-carbon 0.66 g, and it was stirred under hydrogen atmosphere at room temperature for 2 hours. The solvent was removed under reduced pressure after insoluble matter was filtrated. The obtained residue was refined by silica gel column chromatography [Fuji SILYSIA Chemical Ltd., PSQ100B(spherical type), eluent; hexane:ethyl acetate=8:1] to give tert-butyl 2-amino-4-(2-(3-methoxyphenyl)ethyl)benzoate 1.6 g of colorless oil.

$^1$H-NMR(DMSO-$d_6$) δ value:

1.52(9H,s),2.72-2.84(4H,m),3.72(3H,s),6.41(1H,dd,
J=8.2,1.5 Hz),6.46-6.54(2H,broad),6.56-6.59(1H,m),6.72-
6.80(3H,m),7.15-7.20(1H,m),7.55(1H,d,J=8.2 Hz).

Reference Example 43

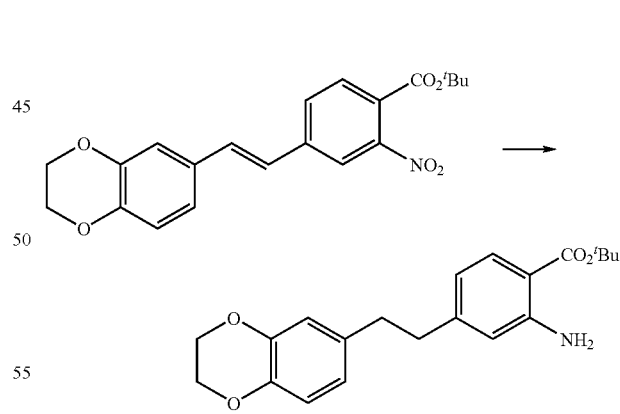

To a mixed solution of methanol 15 mL and ethyl acetate 15 mL of tert-butyl 4-((E)-2-(2,3-dihydrobenzo[1,4]dioxin-6-yl)vinyl)-2-nitrobenzoate 1.5 g was added 10% palladium-carbon 0.44 g, and it was stirred under hydrogen atmosphere at room temperature for 2 hours and 30 minutes. The solvent was removed under reduced pressure after insoluble matter was filtrated. The obtained residue was refined by silica gel column chromatography [Fuji SILYSIA Chemical Ltd., PSQ100B(spherical type), eluent; hexane:ethyl acetate=4:1]

to give tert-butyl 2-amino-4-((E)-2-(2,3-dihydrobenzo[1,4]dioxin-6-yl)ethyl)benzoate 1.3 g of colorless oil.

$^1$H-NMR(DMSO-d$_6$) δ value:

1.52(9H,s),2.68-2.72(4H,m),4.17-4.21(4H,m),6.39(1H,dd,J=8.2,1.6 Hz),6.47-6.53(2H,broad),6.56(1H,d,J=1.2 Hz),6.63-6.66(1H,m),6.69-6.74(2H,m),7.54(1H,d,J=8.3 Hz).

Reference Example 44

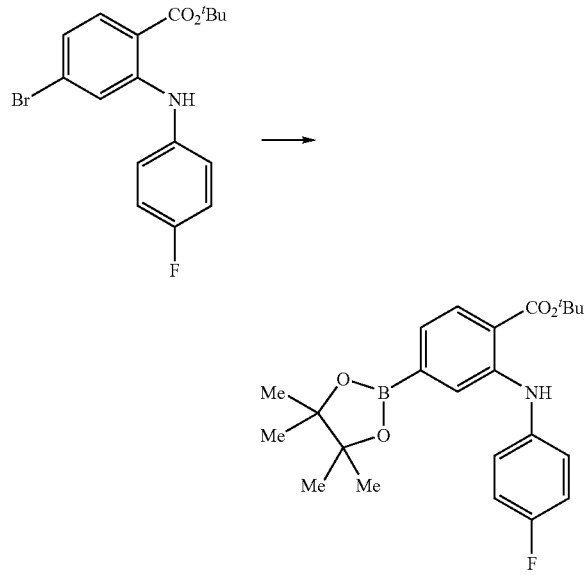

To dioxane 12 mL solution of tert-butyl 4-bromo-2-(4-fluoroanilino)benzoate 1.2 g were added sequentially potassium acetate 0.97 g, bis (pinacolate)diboron 1.8 g and (1,1-bis(diphenylphosphino)palladium (II) dichloride dichloromethane complex 0.14 g at room temperature, and it was heated and refluxed for 2 hours. After the reaction mixture was cooled to room temperature, ethyl acetate was added to it, insoluble matter was filtrated, and the solvent was removed under reduced pressure. The obtained residue was refined by silica gel column chromatography [Fuji SILYSIA Chemical Ltd., PSQ100B(spherical type), eluent; hexane:ethyl acetate=20:1] to give tert-butyl 2-(4-fluoroanilino)-4-(4,4,5,5-tetramethyl-1,3,2-dioxaborolan-2-yl)benzoate 0.86 g of white solid.

$^1$H-NMR(DMSO-d$_6$) δ value:

1.25(12H,s),1.56(9H,s),7.04(1H,d,J=7.9 Hz),7.19-7.30 (4H,m),7.34(1H,s),7.82(1H,d,J=7.9 Hz),9.18(1H,s).

Example 1

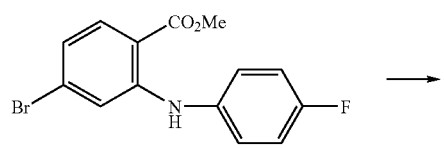

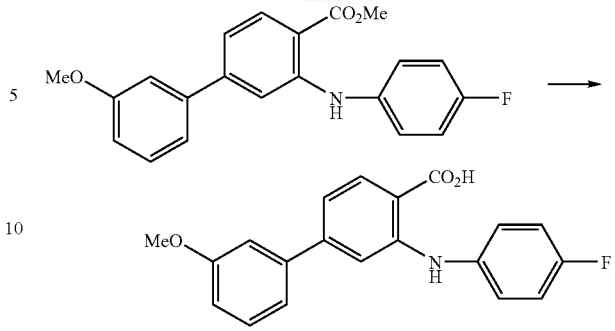

To N,N-dimethylacetamide 2.5 mL solution of methyl 4-bromo-2-(4-fluoroanilino)benzoate 70 mg were added 3-methoxyphenylboronic acid 49 mg, sodium carbonate 57 mg and polymer-carried bis(acetato)triphenylphosphine palladium (II) 31 mg at room temperature, and it was stirred at 90° C. for 12 hours. After the reaction mixture was cooled to room temperature, insoluble matter was filtrated, ethyl acetate and 1.0 mol/L hydrochloric acid were added to it. The organic layer was separated and collected, dried over anhydrous magnesium sulfate after sequential washing with 1.0 mol/L hydrochloric acid and saturated sodium chloride aqueous solution, and the solvent was removed under reduced pressure. To the obtained residue were added 2.0 mol/L sodium hydroxide aqueous solution 1.0 mL and ethanol 6.0 mL, and it was stirred at room temperature for 1 hour. 0.5 mol/L Hydrochloric acid was added to the reaction mixture, solid matter was filtrated to give 2-(4-fluoroanilino)-4-(3-methoxyphenyl)benzoic acid 10 mg of pale yellow solid.

$^1$H-NMR(DMSO-d$_6$) δ value:

3.79(3H,s),6.96(1H,dd,J=8.1, 2.4 Hz),7.05(1H,dd,J=8.4, 1.6 Hz),7.08(1H,t,J=1.9 Hz),7.12(1H,d,J=7.8 Hz),7.20-7.25 (3H,m),7.34-7.39(3H,m),7.97(1H,d,J=8.3 Hz).

Example 2

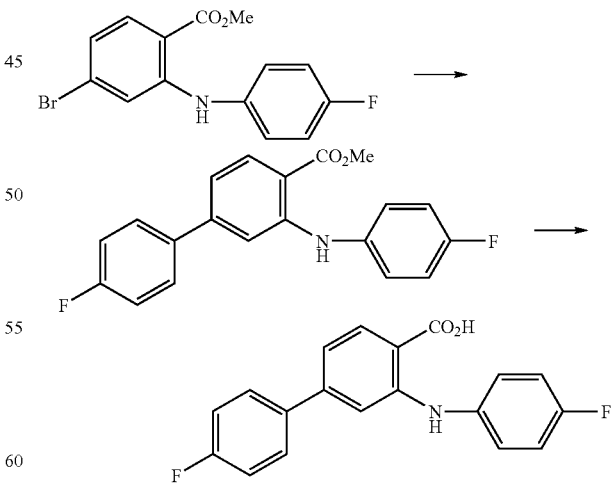

To N,N-dimethylacetamide 2.5 mL solution of methyl 4-bromo-2-(4-fluoroanilino)benzoate 70 mg were added 4-fluorophenylboronic acid 45 mg, sodium carbonate 57 mg and polymer-carried bis(acetato)triphenylphosphine palladium (II) 31 mg at room temperature, and it was stirred at 90°

C. for 12 hours. After the reaction mixture was cooled to room temperature, insoluble matter was filtrated, and ethyl acetate and 1.0 mol/L hydrochloric acid were added to it. The organic layer was separated and collected, dried over anhydrous magnesium sulfate after sequential washing with 1.0 mol/L hydrochloric acid and saturated sodium chloride aqueous solution, and the solvent was removed under reduced pressure. 1.0 mol/L Sodium hydroxide aqueous solution 1.0 mL and ethanol 3.0 mL were added to the obtained residue, and it was stirred at room temperature for 1 hour. 6.0 mol/L Hydrochloric acid was added to the reaction mixture, solid matter was filtrated, and it was refined by silica gel column chromatography [Trikonex company, Flash Tube,2008, eluent; hexane:ethyl acetate:acetic acid=20:10:1] to give 2-(4-fluoroanilino)-4-(4-fluorophenyl)benzoic acid 7.8 mg of pale yellow solid.

$^1$H-NMR(DMSO-$d_6$) δ value:
7.03(1H,d,J=8.5 Hz),7.20-7.32(5H,m),7.36-7.39(2H,m), 7.60-7.64(2H,m),7.97(1H,d,J=8.5 Hz),9.60-9.75(1H,broad), 13.00-13.30(1H,broad).

Example 3

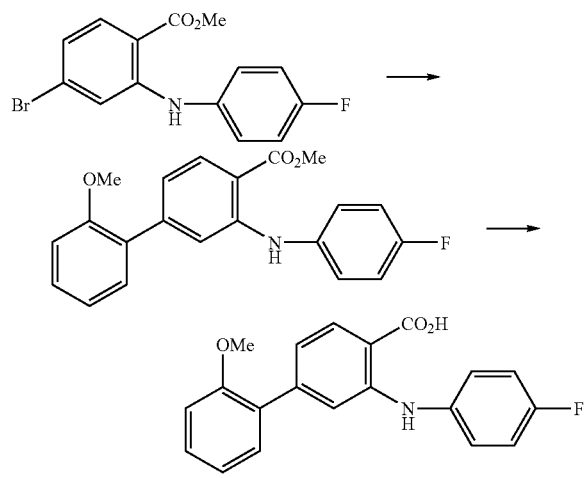

The following compound was obtained in the same manner as in Example 2.

2-(4-fluoroanilino)-4-(2-methoxyphenyl)benzoic acid $^1$H-NMR(DMSO-$d_6$) δ value:
3.78(3H,s),6.85-6.90(1H,m),7.01(1H,t,J=7.6 Hz),7.10 (1H,d,J=8.3 Hz),7.19-7.37(7H,m),7.91(1H,d,J=8.3 Hz), 9.52-9.63(1H,broad),12.98-13.10(1H,broad).

Example 4

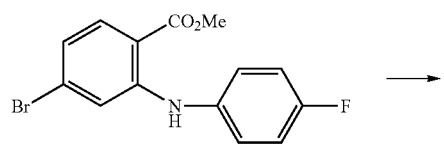

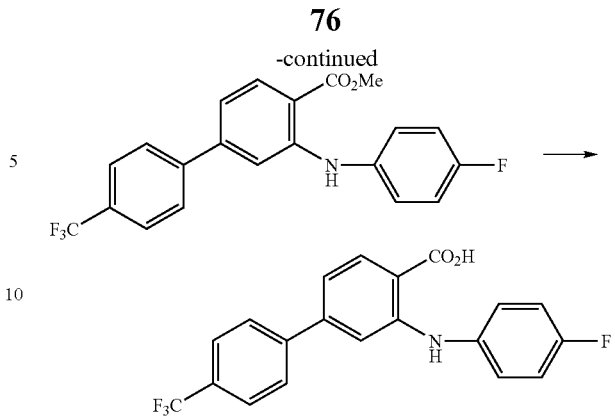

To N,N-dimethylacetamide 2.5 mL solution of methyl 4-bromo-2-(4-fluoroanilino)benzoate 70 mg were added 4-(trifluoromethyl)phenylboronic acid 62 mg, sodium carbonate 57 mg and polymer-carried bis(acetato) triphenylphosphine palladium (II) 31 mg at room temperature, and it was stirred at 90° C. for 12 hours. After the reaction mixture was cooled to room temperature, insoluble matter was filtrated, and ethyl acetate and 1.0 mol/L hydrochloric acid were added to it. The organic layer was separated and collected, dried over anhydrous magnesium sulfate after sequential washing with 1.0 mol/L hydrochloric acid and saturated sodium chloride aqueous solution, and the solvent was removed under reduced pressure. 2.0 mol/L Sodium hydroxide aqueous solution 1.0 mL and ethanol 6.0 mL were added to the obtained residue, and it was stirred at room temperature for 1 hour. 0.5 mol/L Hydrochloric acid was added to the reaction mixture. Solid matter was filtrated, it was refined by reversed-phase silica gel column chromatography [eluent; 50-100% acetonitrile/0.1% trifluoroacetic acid aqueous solution] to give 2-(4-fluoroanilino)-4-(4-(trifluoromethyl)phenyl)benzoic acid 18 mg of pale yellow solid.

$^1$H-NMR(DMSO-$d_6$) δ value:
7.10(1H,dd,J=8.3,1.8 Hz),7.20-7.24(2H,m),7.29(1H,d, J=1.8 Hz),7.37-7.40(2H,m),7.80(4H,s),8.02(1H,d,J=8.3 Hz),9.64(1H,s).

Example 5-8

The compounds shown in Table 7 were obtained in the same manner as in Example 4.

TABLE 7

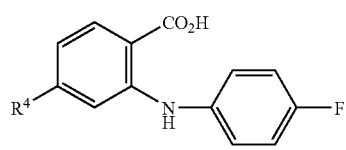

| Example No. | R$^4$ |
|---|---|
| 5 | ![2,4-difluorophenyl] |
| 6 | ![3-trifluoromethylphenyl] |

TABLE 7-continued

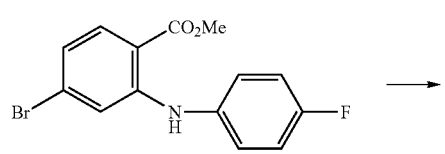

| Example No. | R⁴ |
|---|---|
| 7 | (7-methylbenzo[1,3]dioxol-5-yl) |
| 8 | (2-methylbenzofuran-2-yl) |

4-(2,4-Difluorophenyl)-2-(4-fluoroanilino)benzoic acid $^1$H-NMR(DMSO-$d_6$) δ value:
6.92(1H,dt,J=8.6,1.6 Hz),7.16-7.23(4H,m),7.32-7.36(3H,m),7.56(1H,td,J=8.6,6.7 Hz),7.98(1H,d,J=8.2 Hz),9.60(1H,s),13.06-13.29(1H,broad).

2-(4-Fluoroanilino)-4-(3-(trifluoromethyl)phenyl)benzoic acid $^1$H-NMR(DMSO-$d_6$) δ value:
7.12(1H,dd,J=8.2,1.8 Hz),7.20-7.24(2H,m),7.30(1H,d,J=1.8 Hz),7.37-7.41(2H,m),7.69(1H,t,J=7.6 Hz),7.76(1H,d,J=7.7 Hz),7.87-7.88(2H,m),8.01(1H,d,J=8.2 Hz),9.64(1H,s).

4-(Benzo-1,3-dioxol-5-yl)-2-(4-fluoroanilino)benzoic acid $^1$H-NMR(DMSO-$d_6$) δ value:
6.05(2H,s),6.97-7.00(2H,m),7.06(1H,dd,J=8.2,1.9 Hz),7.15(1H,d,J=1.8 Hz),7.19(1H,d,J=1.7 Hz),7.20-7.24(2H,m),7.34-7.38(2H,m),7.93(1H,d,J=8.2 Hz),9.60(1H,s).

4-(Benzofuran-2-yl)-2-(4-fluoroanilino)benzoic acid $^1$H-NMR(DMSO-$d_6$) δ value:
7.25-7.30(3H,m),7.32-7.35(2H,m),7.37-7.40(2H,m),7.48(1H,d,J=0.9 Hz),7.53(1H,d,J=1.7 Hz),7.61(1H,dd,J=8.2, 0.7 Hz),7.66-7.67(1H,m),8.00(1H,d,J=8.2 Hz),9.67(1H,s).

Example 9

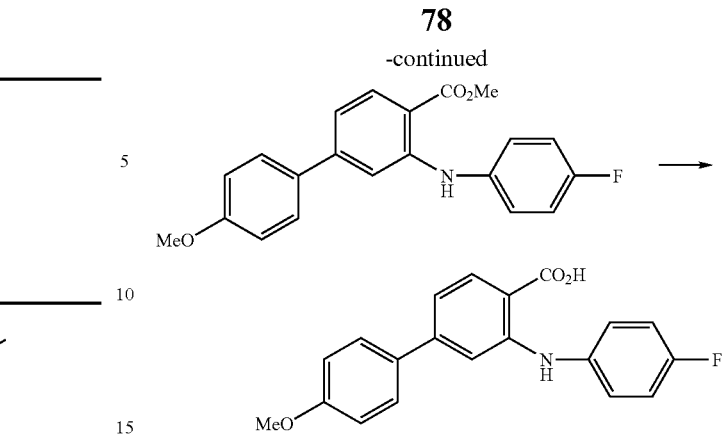

To N,N-dimethylacetamide 3.0 mL solution of methyl 4-bromo-2-(4-fluoroanilino)benzoate 70 mg were added 4-methoxyphenylboronic acid 66 mg, sodium carbonate 69 mg and polymer-carried bis(acetato)triphenylphosphine palladium(II) 31 mg at room temperature, and it was stirred under application of pressure at 160° C. for 5 minutes. After the reaction mixture was cooled to room temperature, it was stirred under application of pressure at 180° C. for 5 minutes. After the reaction mixture was cooled to room temperature, it was stirred under application of pressure at 200° C. for 5 minutes. After the reaction mixture was cooled to room temperature, it was stirred under application of pressure at 220° C. for 5 minutes. After the reaction mixture was cooled to room temperature, insoluble matter was filtrated, and ethyl acetate and 0.5 mol/L hydrochloric acid were added to it. The organic layer was separated and collected, dried over anhydrous magnesium sulfate after sequential washing with 1.0 mol/L hydrochloric acid and saturated sodium chloride aqueous solution, and the solvent was removed under reduced pressure. 2.0 mol/L sodium hydroxide aqueous solution 1.0 mL and ethanol 4.0 mL were added to the obtained residue, and it was stirred at room temperature for 1 hour and 30 minutes. 0.7 mol/L hydrochloric acid and ethyl acetate were added to the reaction mixture, the organic layer was separated and collected, and the solvent was removed under reduced pressure. The obtained residue was refined by reversed-phase silica gel column chromatography [eluent; 50-100% acetonitrile/0.1% trifluoroacetic acid aqueous solution] to give 2-(4-fluoroanilino)-4-(4-methoxyphenyl)benzoic acid 19 mg of pale yellow solid.

$^1$H-NMR(DMSO-$d_6$) δ value:
3.78(3H,s),6.98-7.03(3H,m),7.19-7.25(3H,m),7.34-7.38(2H,m),7.50-7.55(2H,m),7.94(1H,d,J=8.3 Hz),9.62(1H,s),12.86-13.25(1H,broad).

Example 10

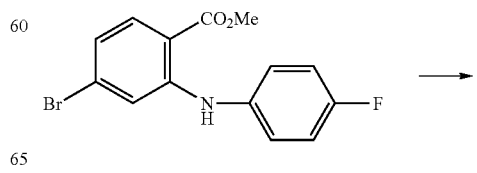

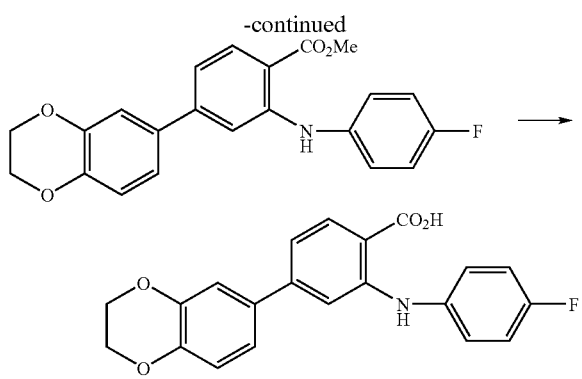

The following compound was obtained in the same manner as in Example 9.

4-(2,3-Dihydrobenzo[1,4]dioxin-6-yl)-2-(4-fluoroanilino)benzoic acid $^1$H-NMR(DMSO-$d_6$) δ value:
4.26(4H,s),6.92(1H,dd,J=7.3,1.5 Hz),6.98(1H,dd,J=8.4, 1.8 Hz),7.03-7.05(2H,m),7.17(1H,d,J=1.8 Hz),7.21-7.26 (2H,m),7.33-7.38(2H,m),7.92(1H,d,J=8.4 Hz),9.60(1H,s), 12.93-13.18(1H,broad).

Example 11

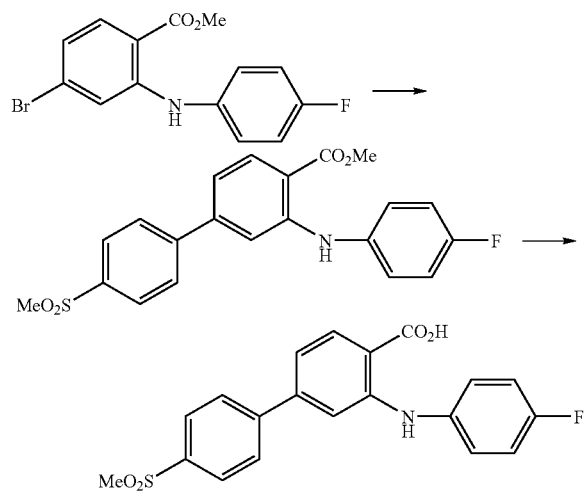

To N,N-dimethylacetamide 2.5 mL solution of methyl 4-bromo-2-(4-fluoroanilino)benzoate 70 mg were added 4-(methanesulfonyl)phenylboronic acid 86 mg, sodium carbonate 69 mg and polymer-carried bis(acetato)triphenylphosphine palladium(II) 31 mg at room temperature, and it was stirred at 90° C. for 12 hours. After the reaction mixture was cooled to room temperature, insoluble matter was filtrated, and ethyl acetate and 1.0 mol/L hydrochloric acid were added to it. The organic layer was separated and collected, dried over anhydrous magnesium sulfate after sequential washing with 1.0 mol/L hydrochloric acid and saturated sodium chloride aqueous solution, and the solvent was removed under reduced pressure. 2.0 mol/L Sodium hydroxide aqueous solution 1.0 mL and ethanol 6.0 mL were added to the obtained residue, and it was stirred at room temperature for 1 hour. 0.5 mol/L Hydrochloric acid and ethyl acetate were added to the reaction mixture. The organic layer was separated and collected, and the solvent was removed under reduced pressure. The obtained residue was refined by reversed-phase silica gel column chromatography [eluent; 40-100% acetonitrile/0.1% trifluoroacetic acid aqueous solution] to give 2-(4-fluoroanilino)-4-(4-(methanesulfonyl)phenyl)benzoic acid 28 mg of pale yellow solid.

$^1$H-NMR(DMSO-$d_6$) δ value:
3.24(3H,s),7.11(1H,d,J=8.1 Hz),7.22(2H,t,J=8.8 Hz),7.31 (1H,s),7.37-7.40(2H,m),7.84(2H,d,J=8.3 Hz),7.97-8.03(3H, m),9.66(1H,s),13.11-13.38(1H,broad).

Example 12, 13

The compounds shown in Table 8 were obtained in the same manner as in Example 11.

TABLE 8

| Example No. | R$^4$ |
|---|---|
| 12 | MeSO$_2$NH—⟨phenyl⟩— |
| 13 | 5-methylindol-yl |

2-(4-Fluoroanilino)-4-(4-(methanesulfonamido)phenyl)benzoic acid $^1$H-NMR(DMSO-$d_6$) δ value:
3.02(3H,s),7.02(1H,dd,J=8.3,1.6 Hz),7.16-7.28(5H,m), 7.34-7.38(2H,m),7.56(2H,d,J=8.8 Hz),7.95(1H,d,J=8.3 Hz), 9.91(1H,s).

2-(4-Fluoroanilino)-4-(1H-indol-5-yl)benzoic acid $^1$H-NMR(DMSO-$d_6$) δ value:
6.48(1H,s),7.09(1H,dd,J=8.3,1.7 Hz),7.20-7.26(2H,m), 7.29-7.31(2H,m),7.36-7.40(3H,m),7.45(1H,d,J=8.5 Hz), 7.76(1H,s),7.96(1H,d,J=8.3 Hz),9.62(1H,s),11.20(1H,s), 12.87-13.10(1H,broad).

Example 14

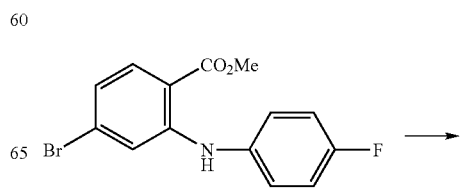

-continued

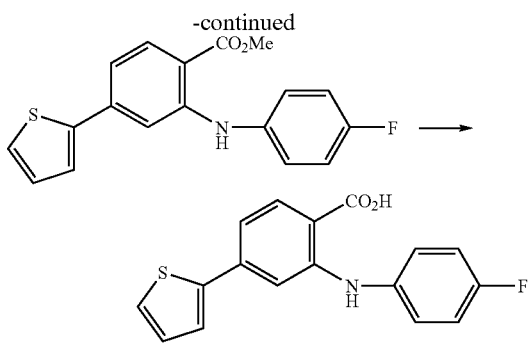

To a mixed solution of toluene 2.0 mL, ethanol 0.6 mL and water 0.4 mL of methyl 4-bromo-2-(4-fluoroanilino)benzoate 70 mg were added thiophene-2-boronic acid 42 mg, sodium carbonate 64 mg and tetrakis(triphenylphosphine) palladium(0) 13 mg at room temperature, and it was stirred under application of pressure at 160° C. for 5 minutes. After the reaction mixture was cooled to room temperature, insoluble matter was filtrated, and ethyl acetate and 0.5 mol/L hydrochloric acid were added to it. The organic layer was separated and collected, dried over anhydrous magnesium sulfate after sequential washing with 1.0 mol/L hydrochloric acid and saturated sodium chloride aqueous solution, and the solvent was removed under reduced pressure. The obtained residue was refined by silica gel column chromatography [Trikonex company, Flash Tube 2008, eluent; hexane] to give methyl 2-(4-fluoroanilino)-4-(thiophen-2-yl)benzoate. 2.0 mol/L Sodium hydroxide aqueous solution 1.0 mL was added to ethanol 7.0 mL solution of the obtained methyl 2-(4-fluoroanilino)-4-(thiophen-2-yl)benzoate, and it was stirred at room temperature for 1 hour and 30 minutes. 0.5 mol/L Hydrochloric acid and ethyl acetate were added to the reaction mixture, the organic layer was separated and collected, and the solvent was removed under reduced pressure. The obtained residue was refined by reversed-phase silica gel column chromatography [eluent; 50-100% acetonitrile/0.1% trifluoroacetic acid aqueous solution] to give 2-(4-fluoroanilino)-4-(thiophen-2-yl)benzoic acid 3.5 mg of pale yellow solid.

$^1$H-NMR(DMSO-$d_6$) δ value:
7.08(1H,dd,J=8.3,1.4 Hz),7.13(1H,dd,J=5.0, 3.6 Hz),7.22-7.27(3H,m),7.34-7.37(2H,m),7.49(1H,d,J=3.6 Hz),7.60(1H,d,J=5.0 Hz),7.92(1H,d,J=8.3 Hz),9.57-9.69(1H,broad).

Example 15

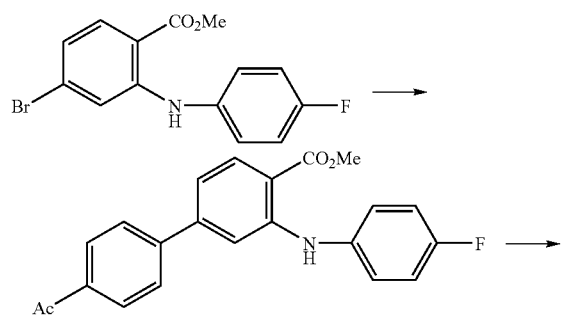

-continued

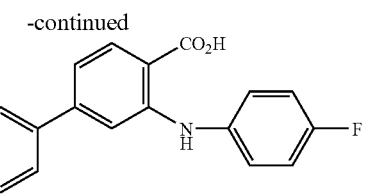

The following compound was obtained in the same manner as in Example 14.

4-(4-Acetylphenyl)-2-(4-fluoroanilino)benzoic acid $^1$H-NMR(DMSO-$d_6$) δ value:
2.60(3H,s),7.11(1H,dd,J=8.3,1.5 Hz),7.21-7.25(2H,m),7.31(1H,d,J=1.5 Hz),7.37-7.40(2H,m),7.72(2H,d,J=8.3 Hz),8.00-8.03(3H,m),9.59-9.74(1H,broad).

Example 16

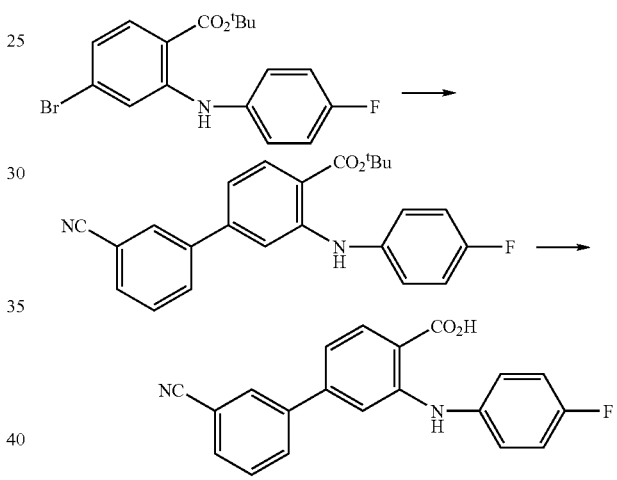

To N,N-dimethylacetamide 2.5 mL solution of tert-butyl 4-bromo-2-(4-fluoroanilino)benzoate 80 mg were added 3-cyanophenyl boronic acid 48 mg, sodium carbonate 58 mg and polymer-carried di(acetato)dicyclohexylphenylphosphine palladium(II) 7 mg, and it was stirred at 110° C. for 19 hours. After the reaction mixture was cooled to room temperature, polymer-carried di(acetato)dicyclohexylphenylphosphine palladium(II) 7 mg was added to it, and it was stirred at 110° C. for 30 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after sequential washing with 10% citric acid aqueous solution and saturated sodium chloride aqueous solution, and the solvent was removed under reduced pressure.

The obtained residue was refined by silica gel column chromatography [Trikonex company, Flash Tube 2008, eluent; hexane:ethyl acetate=4:1] to give tert-butyl 4-(3-cyanophenyl)-2-(4-fluoroanilino)benzoate.

Trifluoroacetic acid 10 mL was added to the obtained tert-butyl 4-(3-cyanophenyl)-2-(4-fluoroanilino)benzoate, and it was stirred at room temperature for 1 hour. The solvent was removed under reduced pressure, methanol was added to the obtained residue, and solid matter was filtrated to give 4-(3-cyanophenyl)-2-(4-fluoroanilino)benzoic acid 13 mg of pale yellow solid.

¹H-NMR(DMSO-d₆) δ value:
7.11(1H,dd,J=8.3,1.7 Hz),7.18-7.26(2H,m),7.31(1H,d,J=1.7 Hz),7.36-7.42(2H,m),7.66(1H,dd,J=7.8,7.7 Hz),7.86(1H,d,J=7.7 Hz),7.91(1H,d,J=7.8 Hz),8.00(1H,d,J=8.3 Hz),8.09(1H,s),9.66(1H, s),13.10-13.35(1H,broad).

Example 17

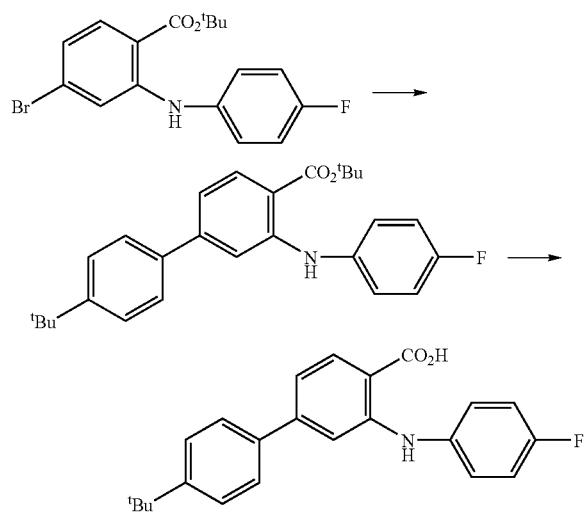

The following compound was obtained in the same manner as in Example 16.

4-(4-(tert-Butyl)phenyl)-2-(4-fluoroanilino)benzoic acid

¹H-NMR(DMSO-d₆) δ value:
1.29(9H,s),7.03(1H,dd,J=8.3,1.2 Hz),7.19-7.26(3H,m),7.34-7.40(2H,m),7.44-7.52(4H,m),7.96(1H,d,J=8.3 Hz),9.61(1H,s),13.07(1H,s).

Example 18

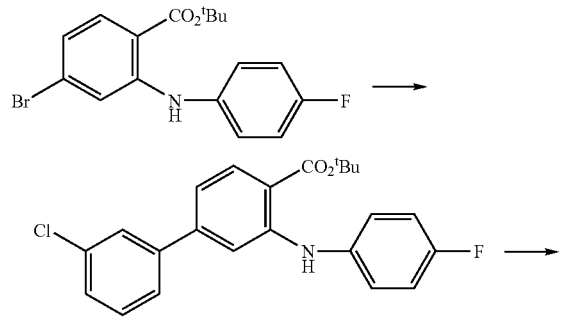

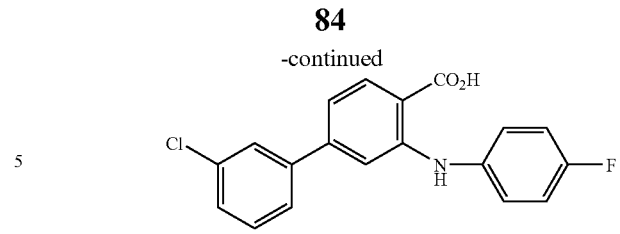

To N,N-dimethylacetamide 2.5 mL solution of tert-butyl 4-bromo-2-(4-fluoroanilino)benzoate 80 mg were added 3-chlorophenylboronic acid 51 mg, sodium carbonate 58 mg and polymer-carried di(acetato)dicyclohexylphenylphosphine palladium(II) 7 mg, and it was stirred at 110° C. for 19 hours. After the reaction mixture was cooled to room temperature, polymer-carried di(acetato)dicyclohexylphenylphosphine palladium(II) 7 mg was added to it, and it was stirred at 110° C. for 30 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after sequential washing with 10% citric acid aqueous solution and saturated sodium chloride aqueous solution, the solvent was removed under reduced pressure. The obtained residue was refined by silica gel column chromatography [Trikonex company, Flash Tube 2008, eluent; hexane:ethyl acetate=4:1] to give tert-butyl 4-(3-chlorophenyl)-2-(4-fluoroanilino)benzoate.

Trifluoroacetic acid 10 mL was added to the obtained tert-butyl 4-(3-chlorophenyl)-2-(4-fluoroanilino)benzoate, and it was stirred at room temperature for 1 hour. The solvent was removed under reduced pressure, the obtained residue was refined by reversed-phase silica gel column chromatography [eluent; 70-100% acetonitrile/0.1% trifluoroacetic acid aqueous solution] to give 4-(3-chlorophenyl)-2-(4-fluoroanilino)benzoic acid 19 mg of pale yellow solid.

¹H-NMR(DMSO-d₆) δ value:
7.07(1H,dd,J=8.3,1.7 Hz),7.19-7.28(2H,m),7.25(1H,d,J=1.7 Hz),7.34-7.42(2H,m),7.43-7.51(2H,m),7.53(1H,dt,J=6.7,1.9 Hz),7.63(1H,s),7.98(1H,d, J=8.3 Hz),9.64(1H,s),13.05-13.30(1H,broad).

Example 19-22

The compounds shown in Table 9 were obtained in the same manner as in Example 18.

TABLE 9

| Example No. | R⁴ |
|---|---|
| 19 | 2-methylphenyl |
| 20 | 4-methylphenyl |

TABLE 9-continued

[Structure: benzoic acid with R⁴ substituent and 4-fluoroanilino group]

| Example No. | R⁴ |
|---|---|
| 21 | [4-cyanophenyl group] |
| 22 | [3-hydroxyphenyl group] |

2-(4-Fluoroanilino)-4-(2-methylphenyl)benzoic acid $^1$H-NMR(DMSO-$d_6$) δ value:

δ 2.21(3H,s),6.73(1H,dd,J=8.1,1.6 Hz),6.88(1H,d,J=1.6 Hz),7.14-7.35(8H,m),7.94(1H,d,J=8.1 Hz),9.59(1H,s),13.00-13.15(1H,broad).

2-(4-Fluoroanilino)-4-(4-methylphenyl)benzoic acid $^1$H-NMR(DMSO-$d_6$) δ value:

2.33(3H,s),7.03(1H,dd,J=8.3,1.7 Hz),7.19-7.29(5H,m),7.33-7.40(2H,m),7.46(2H,d,J=8.3 Hz),7.96(1H,d,J=8.3 Hz),9.61(1H,s),12.90-13.25(1H,broad).

4-(4-Cyanophenyl)-2-(4-fluoroanilino)benzoic acid $^1$H-NMR(DMSO-$d_6$) δ value:

7.11(1H,dd,J=8.3, 1.6 Hz),7.18-7.27(2H,m),7.29(1H,d,J=1.6 Hz),7.34-7.42(2H,m),7.78(2H,d,J=8.3 Hz),7.91(2H,d,J=8.3 Hz),8.01(1H,d,J=8.3 Hz),9.65(1H,s),13.00-13.50(1H,broad).

2-(4-Fluoroanilino)-4-(3-hydroxyphenyl)benzoic acid $^1$H-NMR(DMSO-$d_6$) δ value:

6.78(1H,dd,J=8.3,2.3 Hz),6.91(1H,t,J=1.9 Hz),6.95-7.02(2H,m),7.18-7.28(4H,m),7.32-7.40(2H,m),7.95(1H,d,J=8.3 Hz),9.56(1H,s),9.59(1H,s),12.95-13.20(1H,broad).

Example 23

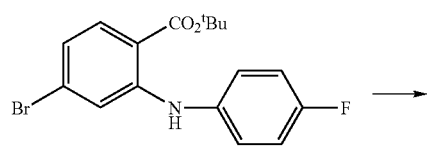

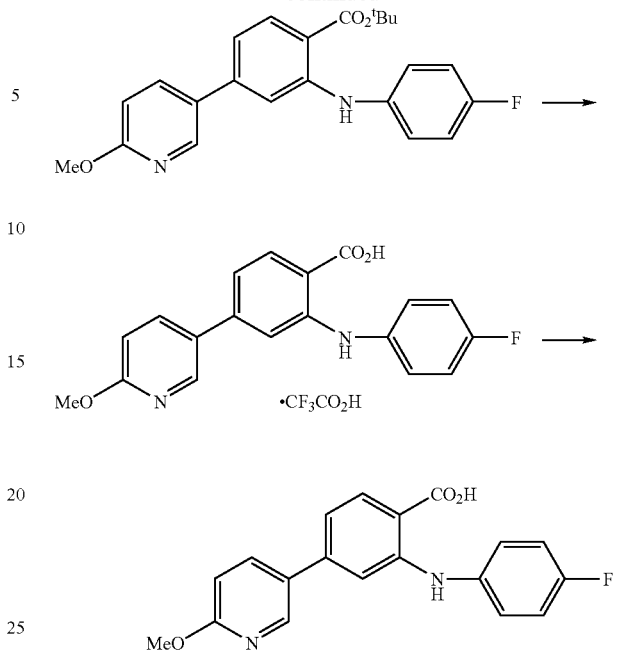

To N,N-dimethylacetamide 2.5 mL solution of tert-butyl 4-bromo-2-(4-fluoroanilino)benzoate 0.10 g were added 2-methoxy-5-pyridinboronic acid 63 mg, sodium carbonate 72 mg and polymer-carried di(acetato)dicyclohexylphenylphosphine palladium(II) 8 mg, and it was stirred at 110° C. for 15 hours. After the reaction mixture was cooled to room temperature, 2-methoxy-5-pyridinboronic acid 21 mg and polymer-carried di(acetato)dicyclohexylphenylphosphine palladium(II) 8 mg were added to it, and it was stirred at 110° C. for 36 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-(4-fluoroanilino)-4-(2-methoxypyridin-5-yl)benzoate.

Trifluoroacetic acid 10 mL was added to the obtained tert-butyl 2-(4-fluoroanilino)-4-(2-methoxypyridin-5-yl)benzoate, and it was stirred at room temperature for 1 hour. The solvent was removed under reduced pressure, the obtained residue was refined by reversed-phase silica gel column chromatography [eluent; 55-90% acetonitrile/0.1% trifluoroacetic acid aqueous solution] to give 2-(4-fluoroanilino)-4-(2-methoxypyridin-5-yl)benzoic acid trifluoroacetate.

Ethyl acetate and water were added to 2-(4-fluoroanilino)-4-(2-methoxypyridin-5-yl)benzoic acid trifluoroacetate, and it was adjusted to pH6.0 with saturated sodium hydrogen carbonate aqueous solution. The organic layer was separated and collected, dried over anhydrous magnesium sulfate after sequential washing with water and saturated sodium chloride aqueous solution, and the solvent was removed under reduced pressure. Hexane was added to the obtained residue, and solid matter was filtrated to give 2-(4-fluoroanilino)-4-(2-methoxypyridin-5-yl)benzoic acid 15 mg of pale yellow solid.

¹H-NMR(DMSO-d₆) δ value:
3.88(3H,s),6.89(1H,d,J=8.7 Hz),7.05(1H,dd,J=8.3,1.0 Hz),7.18-7.26(3H,m),7.34-7.41(2H,m),7.92(1H,dd,J=8.7, 2.5 Hz),7.97(1H,d,J=8.3 Hz),8.41 (1H,d,J=2.5 Hz),9.66(1H, s),12.90-13.30(1H,broad).

Example 24

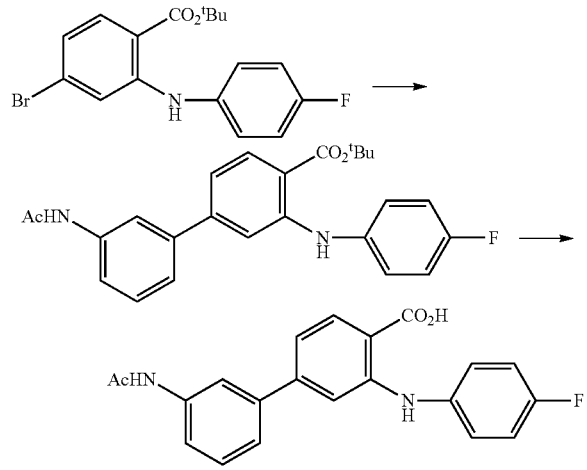

To N,N-dimethylacetamide 2.5 mL solution of tert-butyl 4-bromo-2-(4-fluoroanilino)benzoate 0.10 g were added 3-(acetamido)phenylboronic acid 98 mg, sodium carbonate 72 mg and tetrakis(triphenylphosphine)palladium(0) 3.2 mg, and it was stirred at 110° C. for 4 hours. After the reaction mixture was cooled to room temperature, insoluble matter was filtrated, and ethyl acetate and 10% citric acid aqueous solution were added to it. The organic layer was separated and collected,dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=2:1] to give tert-butyl 4-(3-(acetamido)phenyl)-2-(4-fluoroanilino)benzoate.

Trifluoroacetic acid 10 mL was added to the obtained tert-butyl 4-(3-(acetamido)phenyl)-2-(4-fluoroanilino)benzoate, and it was stirred at room temperature for 1 hour. The solvent was removed under reduced pressure, methanol was added to the obtained residue, and solid matter was filtrated to give 4-(3-(acetamido)phenyl)-2-(4-fluoroanilino)benzoic acid 32 mg of pale yellow solid.

¹H-NMR(DMSO-d₆) δ value:
2.05(3H,s),6.99(1H,dd,J=8.3,1.7 Hz),7.19-7.28(4H,m), 7.32-7.41(3H,m),7.61(1H,d,J=8.0 Hz),7.77(1H,s),7.98(1H, d,J=8.3 Hz),9.62(1H,s),10.02(1H,s),12.95-13.30(1H,broad).

Example 25

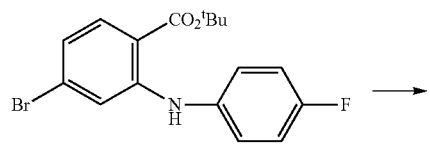

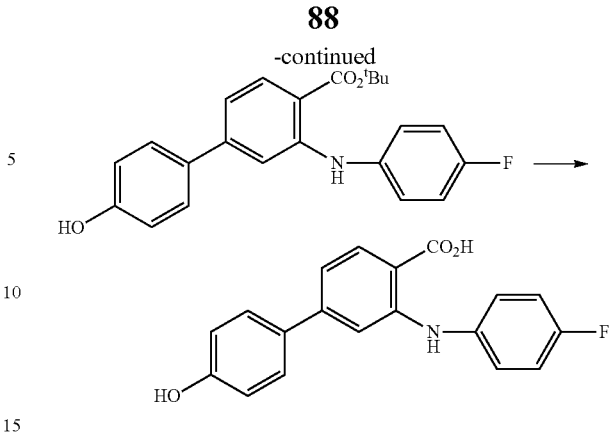

To N,N-dimethylacetamide 2.5 mL solution of tert-butyl 4-bromo-2-(4-fluoroanilino)benzoate 0.10 g were added 4-hydroxyphenylboronic acid 75 mg, sodium carbonate 72 mg and tetrakis(triphenylphosphine)palladium(0) 3.2 mg, and it was stirred at 110° C. for 4 hours. After the reaction mixture was cooled to room temperature, insoluble matter was filtrated, and ethyl acetate and 10% citric acid aqueous solution were added to it. The organic layer was separated and collected,dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-(4-fluoroanilino)-4-(4-hydroxyphenyl) benzoate.

Trifluoroacetic acid 10 mL was added to the obtained tert-butyl 2-(4-fluoroanilino)-4-(4-hydroxyphenyl)benzoate, and it was stirred at room temperature for 1 hour. The solvent was removed under reduced pressure, the obtained residue was refined by reversed-phase silica gel column chromatography [eluent; 55-90% acetonitrile/0.1% trifluoroacetic acid aqueous solution] to give 2-(4-fluoroanilino)-4-(4-hydroxyphenyl)benzoic acid 14 mg of pale yellow solid.

¹H-NMR(DMSO-d₆) δ value:
6.82(2H,d,J=8.3 Hz),6.98(1H,dd,J=8.3,1.2 Hz),7.18-7.27 (3H,m),7.32-7.38(2H,m),7.41(2H,d,J=8.3 Hz),7.92(1H,d, J=8.3 Hz),9.60(1H,s),9.68(1H,s),12.85-13.10(1H,broad).

Example 26

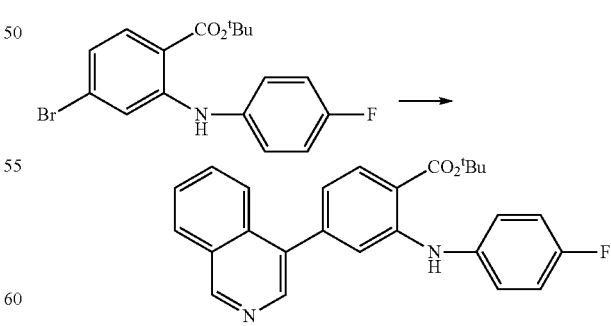

To a mixed solution of toluene 4.0 mL, ethanol 1.2 mL and water 0.6 mL of tert-butyl 4-bromo-2-(4-fluoroanilino)benzoate 0.20 g were added 4-(4,4,5,5-tetramethyl-1,3,2-dioxaborolan-2-yl)isoquinoline 0.17 g, sodium hydrogen carbonate 0.12 g and tetrakis(triphenylphosphine)palladium(0) 35 mg, and it was heated and refluxed under nitrogen atmosphere for 4 hours. After the reaction mixture was cooled to room temperature, tetrakis(triphenylphosphine)palladium(0) 35 mg was added to it, and it was heated and refluxed under nitrogen atmosphere for 4 hours. After the reaction mixture was cooled to room temperature, and water was added to it. The organic layer was separated and collected,dried over anhydrous magnesium sulfate after sequential washing with saturated sodium hydrogen carbonate aqueous solution and saturated sodium chloride aqueous solution, and the solvent was removed under reduced pressure. The obtained residue was refined by silica gel column chromatography [eluent; hexane:ethyl acetate=2:1] to give tert-butyl 2-(4-fluoroanilino)-4-(isoquinolin-4-yl)benzoate 0.11 g of pale red solid.

$^1$H-NMR(DMSO-d$_6$) δ value:

1.61(9H,s),6.96(1H,dd,J=8.1,1.2 Hz),7.11(1H,d,J=1.2 Hz),7.17 (2H,t,J=8.8 Hz),7.36-7.40(2H,m),7.74(1H,t,J=7.5 Hz),7.82(1H,t,J=7.5 Hz),7.88(1H,d,J=8.0 Hz),8.02(1H,d,J=8.0 Hz),8.21(1H,d,J=8.3 Hz),8.43 (1H,s),9.34(1H,s),9.42 (1H,s).

Example 27

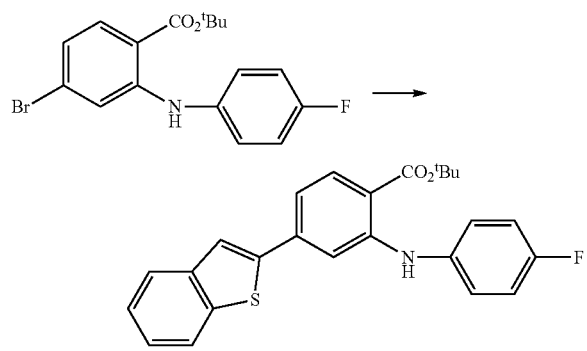

The following compound was obtained in the same manner as in Example 26.

tert-butyl 4-(Benzothiophen-2-yl)-2-(4-fluoroanilino) benzoate $^1$H-NMR(CDCl$_3$) δ value:

1.63(9H,s),7.05(1H,dd,J=8.4,1.8 Hz),7.07-7.13(2H,m),7.24-7.37(4H,m),7.40(1H,d,J=1.8 Hz),7.50(1H,s),7.73-7.81 (2H,m),7.95(1H,d,J=8.4 Hz),9.54(1H,s).

Example 28

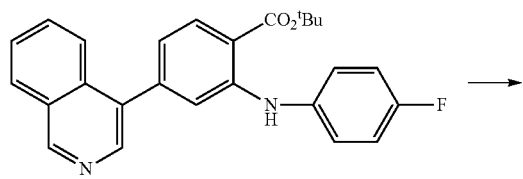

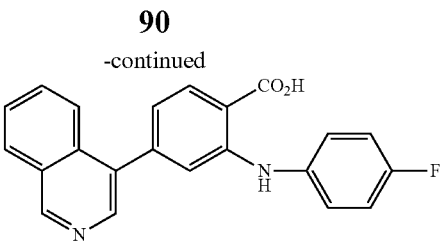

Trifluoroacetic acid 3.0 mL solution of tert-butyl 2-(4-fluoroanilino)-4-(isoquinolin-4-yl)benzoate 110 mg was stirred at room temperature for 1 hour. Water and ethyl acetate were added to the reaction mixture, and it was adjusted to pH6.0 with 1.0 mol/L sodium hydroxide aqueous solution. The organic layer was separated and collected,dried over anhydrous magnesium sulfate after washing with saturated sodium chloride aqueous solution, and the solvent was removed under reduced pressure. Hexane and diisopropyl ether were added to the obtained residue, and solid matter was filtrated to give 2-(4-fluoroanilino)-4-(isoquinolin-4-yl)benzoic acid 50 mg of pale green solid.

$^1$H-NMR(DMSO-d$_6$) δ value:

6.95(1H,dd,J=8.0,1.5 Hz),7.11(1H,d,J=1.5 Hz),7.17(2H,t,J=8.7 Hz),7.37-7.40(2H,m),7.74(1H,t,J=7.4 Hz),7.83(1H,t,J=7.4 Hz),7.90(1H,d,J=8.6 Hz),8.07(1H,d,J=8.3 Hz),8.22 (1H,d,J=7.6 Hz),8.44 (1H,s),9.35(1H,s),9.67(1H,s),13.20-13.26(1H,broad).

Example 29

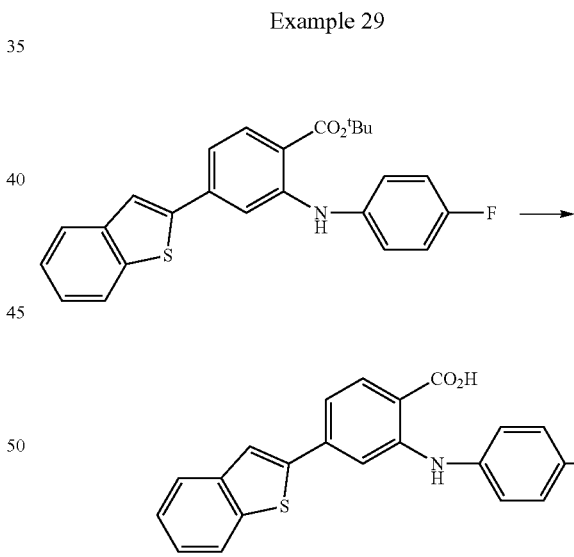

The following compound was obtained in the same manner as in Example 28.

4-(Benzothiophen-2-yl)-2-(4-fluoroanilino)benzoic acid $^1$H-NMR(DMSO-d$_6$) δ value:

7.22(1H,d,J=8.3 Hz),7.24-7.32(2H,m),7.33-7.44(5H,m),7.84-7.90(2H,m),7.95-8.02(2H,m),9.64(1H,s),13.05-13.35 (1H,broad).

Example 30

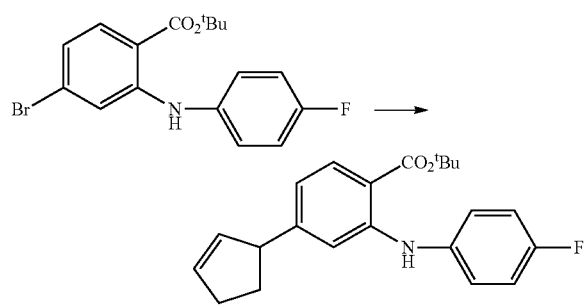

To N,N-dimethylformamide 1 mL solution of tert-butyl 4-bromo-2-(4-fluoroanilino)benzoate 0.20 g were added potassium acetate 0.16 g, tetrabutylammonium chloride 0.15 g, cyclopentene 0.24 mL, palladium acetate 3.1 mg and triphenylphosphine 3.6 mg, and it was stirred under nitrogen atmosphere at room temperature for 17 hours. Ethyl acetate and 10% citric acid aqueous solution were added to the reaction mixture. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [eluent; hexane:toluene=5:1] to give tert-butyl 4-(2-cyclopenten-1-yl)-2-(4-fluoroanilino)benzoate 73 mg of yellow oil.

$^1$H-NMR(CDCl$_3$) δ value:
1.59(9H,s),1.61-1.72(1H,m),2.28-2.48(3H,m),3.70-3.80(1H,m),5.66-5.70(1H,m),5.88-5.92(1H,m),6.54(1H,dd,J=8.3,1.6 Hz),6.92(1H,d,J=1.6 Hz),6.99-7.06(2H,m),7.16-7.22(2H,m),7.83(1H,d,J=8.3 Hz),9.44(1H,s).

Example 31

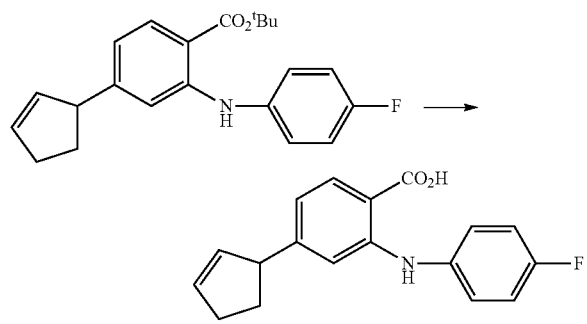

Trifluoroacetic acid 10 mL was added to tert-butyl 4-(2-cyclopenten-1-yl)-2-(4-fluoroanilino)benzoate 27 mg, and it was stirred at room temperature for 1 hour. The solvent was removed under reduced pressure, methanol was added to the obtained residue, and solid matter was filtrated to give 4-(2-cyclopenten-1-yl)-2-(4-fluoroanilino)benzoic acid 22 mg of white solid.

$^1$H-NMR(DMSO-d$_6$) δ value:
1.52-1.65(1H,m),2.24-2.44(3H,m),3.73-3.83(1H,m),5.66-5.76(1H,m),5.88-5.96(1H,m),6.58(1H,dd,J=8.3,1.5 Hz),6.90(1H,d,J=1.5 Hz),7.16-7.31(4H,m),7.82(1H,d,J=8.3 Hz),9.55(1H,s),12.75-13.05(1H,broad).

Example 32

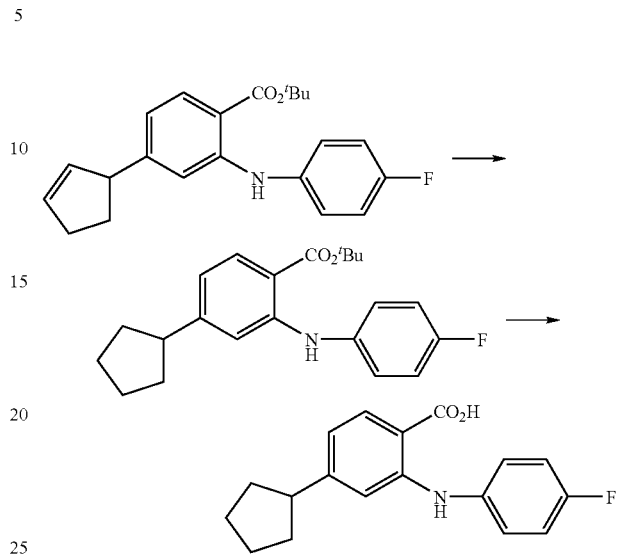

To methanol 2.0 mL solution of tert-butyl 4-(2-cyclopenten-1-yl)-2-(4-fluoroanilino)benzoate 45 mg was added 5% palladium-carbon 9 mg, and it was stirred under hydrogen atmosphere at room temperature for 6 hours. Insoluble matter was filtrated, and the solvent was removed under reduced pressure. Trifluoroacetic acid 10 mL was added to the obtained residue, and it was stirred at room temperature for 1 hour. The solvent was removed under reduced pressure, methanol was added to the obtained residue, and solid matter was filtrated to give 4-cyclopentyl-2-(4-fluoroanilino)benzoic acid 24 mg of white solid.

$^1$H-NMR(DMSO-d$_6$) δ value:
1.38-1.52(2H,m),1.54-1.76(4H,m),1.89-2.00(2H,m),2.82-2.93(1H,m),6.67(1H,dd,J=8.3,1.5 Hz),6.94(1H,d,J=1.5 Hz),7.16-7.32(4H,m),7.81(1H,d,J=8.3 Hz),9.53(1H,s),12.87(1H,s).

Example 33

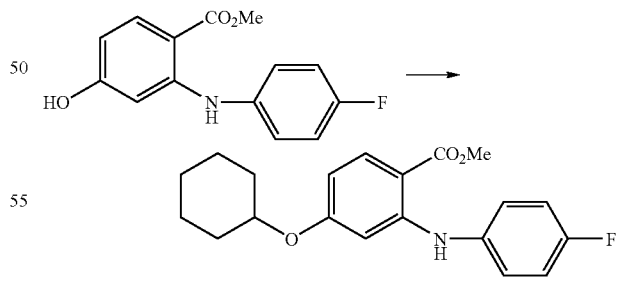

To N,N-dimethylformamide 3.0 mL solution of methyl 2-(4-fluoroanilino)-4-hydroxybenzoate 0.30 g were added potassium carbonate 0.16 g and cyclohexyl bromide 0.42 mL at room temperature, and it was stirred at 80° C. for 8 hours. After the reaction mixture was cooled to room temperature, 11.0 mol/L hydrochloric acid and ethyl acetate were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=8:1] to give methyl 4-(cyclohexyloxy)-2-(4-fluoroanilino)benzoate 40 mg of colorless oil.

$^1$H-NMR(CDCl$_3$) δ value:
1.22-1.38(3H,m),1.41-1.64(3H,m),1.70-1.82(2H,m), 1.86-1.99(2H,m),3.86(3H,s),4.15-4.20(1H,m),6.27(1H,dd, J=8.9,2.4 Hz),6.48(1H,d,J=2.4 Hz),7.02-7.07(2H,m),7.18-7.22(2H,m),7.88(1H,d,J=8.9 Hz),9.44(1H,s).

Example 34

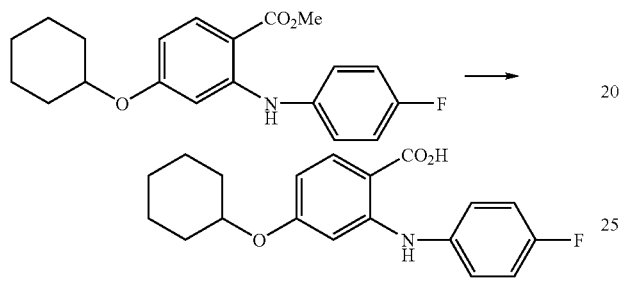

10% Sodium hydroxide aqueous solution 0.25 mL was added to a suspension of 2-propanol 2.0 mL of methyl 4-(cyclohexyloxy)-2-(4-fluoroanilino)benzoate 40 mg at room temperature, and it was heated and refluxed for 5 hours. After the reaction mixture was cooled to room temperature,1.0 mol/L hydrochloric acid and ethyl acetate were added to it. The organic layer was separated and collected,dried over anhydrous magnesium sulfate, and the solvent was removed under reduced pressure. Diisopropyl ether and hexane were added to the obtained residue, and solid matter was filtrated to give 4-(cyclohexyloxy)-2-(4-fluoroanilino)benzoic acid 8 mg of white solid.

$^1$H-NMR(DMSO-d$_6$) δ value:
1.17-1.54(6H,m),1.62-1.71(2H,m),1.83-1.91(2H,m), 4.25-4.29(1H,m),6.37(1H,dd,J=8.9,2.3 Hz),6.40(1H,d,J=2.3 Hz),7.18-7.25(2H,m),7.26-7.30(2H,m),7.81(1H,d,J=8.9 Hz),9.57-9.66(1H,broad).

Example 35

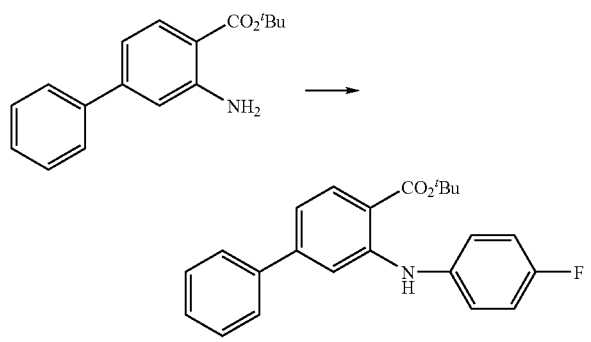

To toluene 7.5 mL solution of tert-butyl 2-amino-4-phenylbenzoate 0.50 g were added 1-fluoro-4-iodobenzene 0.22 mL, cesium carbonate 1.3 g, palladium acetate 4.3 mg and rac-2,2'-bis(diphenylphosphino)-1,1'-binaphthyl 12 mg at room temperature, and it was heated and refluxed for 4 hours. After the reaction mixture was cooled to room temperature, palladium acetate 4.3 mg and rac-2,2'-bis(diphenylphosphino)-1,1'-binaphthyl 12 mg were added to it, and it was heated and refluxed for 13 hours. After the reaction mixture was cooled to room temperature, water and ethyl acetate were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-(4-fluoroanilino)-4-phenylbenzoate 0.44 g of brown oil.

$^1$H-NMR(CDCl$_3$) δ value:
1.63(9H,s),6.93(1H,dd,J=8.3,1.9 Hz),7.03-7.07(2H,m), 7.24-7.28(3H,m),7.32-7.43(3H,m),7.48-7.52(2H,m),7.97 (1H,d,J=8.3 Hz),9.52(1H,s).

Example 36

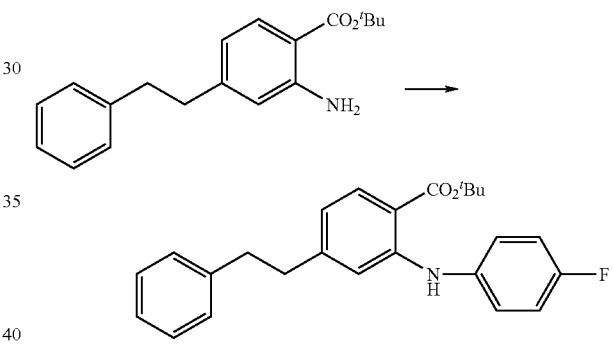

To toluene 10 mL solution of tert-butyl 2-amino-4-phenethylbenzoate 1.0 g were added 1-fluoro-4-iodobenzene 0.98 mL, cesium carbonate 2.2 g, palladium acetate 8 mg and rac-2,2'-bis(diphenylphosphino)-1,1'-binaphthyl 21 mg at room temperature, and it was heated and refluxed under nitrogen atmosphere for 6 hours. After the reaction mixture was cooled to room temperature, palladium acetate 8 mg and rac-2,2'-bis(diphenylphosphino)-1,1'-binaphthyl 21 mg were added, and it was heated and refluxed under nitrogen atmosphere for 10 hours. After the reaction mixture was cooled to room temperature, water was added to it, and insoluble matter was filtrated. The organic layer was separated and collected, dried over anhydrous magnesium sulfate after sequential washing with saturated sodium hydrogen carbonate aqueous solution and saturated sodium chloride aqueous solution, and the solvent was removed under reduced pressure. The obtained residue was refined by silica gel column chromatography [eluent; hexane:ethyl acetate=5:1] to give tert-butyl 2-(4-fluoroanilino)-4-phenethylbenzoate 0.80 g of pale yellow oil.

$^1$H-NMR(DMSO-d$_6$) δ value:
1.55(9H,s),2.78-2.84(4H,m),6.67(1H,dd,J=8.3,1.5 Hz), 6.77(1H,d,J=1.5 Hz),7.04-7.22(7H,m),7.25-7.29(2H,m), 7.75(1H,d,J=8.3 Hz),9.25(1H,s).

Example 37

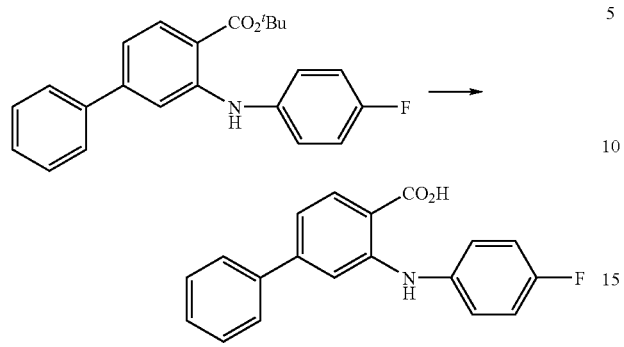

Trifluoroacetic acid 9.0 mL solution of tert-butyl 2-(4-fluoroanilino)-4-phenylbenzoate 0.44 g was stirred at room temperature for 1 hour. The solvent of reaction mixture was removed under reduced pressure, ethyl acetate and water were added to it, and it was adjusted to pH5.0 with saturated sodium hydrogen carbonate aqueous solution. The organic layer was separated and collected, and the solvent was removed under reduced pressure. Diisopropyl ether was added to the obtained residue, and solid matter was filtrated to give 2-(4-fluoroanilino)-4-phenylbenzoic acid 0.11 g of pale yellow solid.

$^1$H-NMR(DMSO-$d_6$) δ value:

7.05(1H,dd,J=8.1,1.8 Hz),7.20-7.25(2H,m),7.26(1H,d,J=1.8 Hz),7.36-7.47(5H,m),7.56-7.58(2H,m),7.98(1H,d,J=8.1 Hz),9.63(1H,s),13.08-13.14(1H,broad).

Example 38

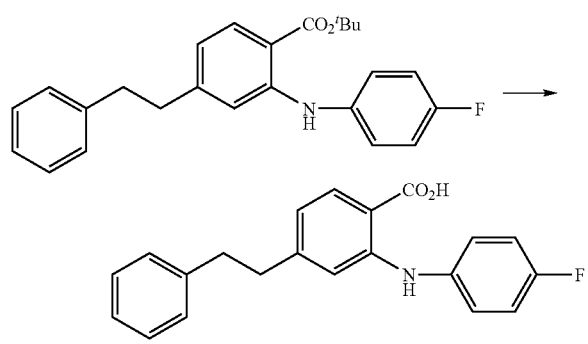

The following compound was obtained in the same manner as in Example 37.

2-(4-Fluoroanilino)-4-phenethylbenzoic acid $^1$H-NMR(DMSO-$d_6$) δ value:

2.77-2.86(4H,m),6.67(1H,dd,J=8.3,1.3 Hz),6.79(1H,d,J=1.3 Hz),7.06-7.22(7H,m),7.25-7.29(2H,m),7.80(1H,d,J=8.3 Hz),9.51(1H,s),12.88-12.93(1H,broad).

Example 39

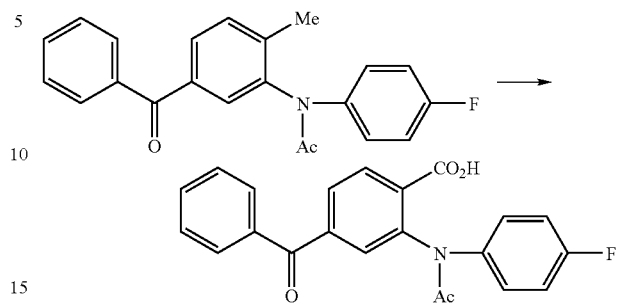

Potassium permanganate 0.24 g was added to a mixed solution of pyridine 5.0 mL and water 5.0 mL of N-(5-benzoyl-2-methylphenyl)-N-(4-fluorophenyl)acetamide 0.52 g at room temperature, and it was heated and refluxed for 30 minutes. After the reaction mixture was cooled to room temperature, potassium permanganate 0.24 g was added to it, it was heated and refluxed for 30 minutes. After the reaction mixture was cooled to room temperature, potassium permanganate 0.24 g was added to it, it was heated and refluxed for 30 minutes. After the reaction mixture was cooled to room temperature, furthermore, potassium permanganate 0.24 g was added to it, and it was heated and refluxed for 30 minutes. After the reaction mixture was cooled, ethyl acetate was added to it, it was adjusted to pH2.3 with 6.0 mol/L hydrochloric acid, and insoluble matter was filtrated. The organic layer was separated and collected, dried over anhydrous magnesium sulfate after sequential washing with 1.0 mol/L hydrochloric acid and saturated sodium chloride aqueous solution, the solvent was removed under reduced pressure. The obtained residue was refined by silica gel column chromatography [eluent; hexane:ethyl acetate=1:2] to give 4-benzoyl-2-(N-(4-fluorophenyl)acetamido)benzoic acid 0.39 g of white solid.

$^1$H-NMR(DMSO-$d_6$) δ value:

1.92(3H,s),7.15-7.19(1H,m),7.31(2H,t,J=8.4 Hz),7.47-7.82(8H,m),7.93(1H,t,J=8.8 Hz),13.33-13.39(1H,broad).

Example 40

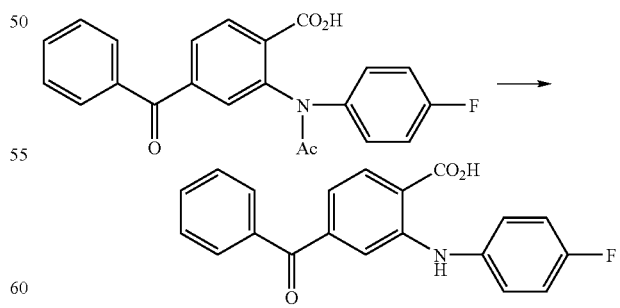

6.0 mol/L Hydrochloric acid 2.0 mL was added to dioxane 2.0 mL solution of 4-benzoyl-2-(N-(4-fluorophenyl)acetamido)benzoic acid 0.39 g, and it was heated and refluxed for 2 hours and 30 minutes. After the reaction mixture was cooled to room temperature, 6.0 mol/L hydrochloric acid 1.0 mL was added to it, and it was heated and refluxed for 4 hours. After the reaction mixture was cooled to room temperature, the solvent was removed under reduced pressure, and ethyl acetate and 1.0 mol/L hydrochloric acid were added to it. The organic layer was separated and collected, dried over anhydrous magnesium sulfate after washing with saturated sodium chloride aqueous solution, the solvent was removed under reduced pressure. The obtained residue was refined by silica gel column chromatography [eluent; chloroform:methanol:acetic acid=20:1:1] to give 4-benzoyl-2-(4-fluoroanilino)benzoic acid 0.27 g of yellow solid.

$^1$H-NMR(DMSO-$d_6$) δ value:
7.06(1H,d,J=8.1 Hz),7.18-7.22(2H,m),7.30(1H,s),7.34-7.37(2H,m),7.56(2H,t,J=7.6 Hz),7.67(1H,t,J=7.6 Hz),7.75 (2H,d,J=7.6 Hz),8.04(1H,d,J=8.1 Hz),9.56(1H,s),13.42-13.52(1H,broad).

Example 41

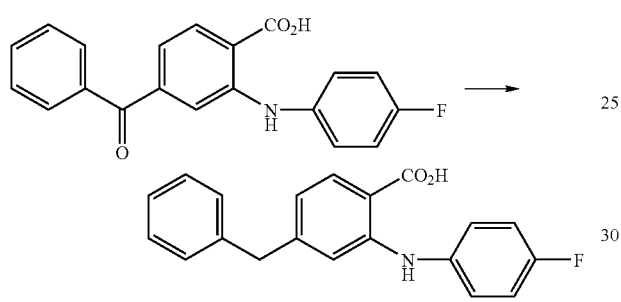

To a mixed solution of methanol 1.3 mL and ethyl acetate 1.3 mL of 4-benzoyl-2-(4-fluoroanilino)benzoic acid 0.13 g was added 5% palladium-carbon 26 mg, and it was stirred under hydrogen atmosphere at room temperature for 6 hours. Insoluble matter was filtrated, and the solvent was removed under reduced pressure. Hexane and diisopropyl ether were added to the obtained residue, and solid matter was filtrated to give 4-benzyl-2-(4-fluoroanilino)benzoic acid 85 mg of white solid.

$^1$H-NMR(DMSO-$d_6$) δ value:
3.86(2H,s),6.60(1H,d,J=8.1 Hz),6.95(1H,s),7.14-7.24 (7H,m),7.28(2H,t,J=7.5 Hz),7.80(1H,d,J=8.1 Hz).

Example 42

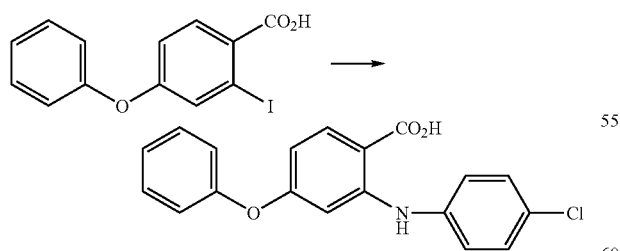

To N,N-dimethylformamide 0.9 mL solution of 2-iodo-4-phenoxybenzoic acid 45 mg were added 4-chloroaniline 27 mg, copper powder 5 mg and N-methylmorpholine 0.036 mL, and it was stirred under application of pressure at 180° C. for 15 minutes. After the reaction mixture was cooled to room temperature, 1.0 mol/L hydrochloric acid and ethyl acetate were added to it. The organic layer was separated and collected, dried over anhydrous magnesium sulfate, the solvent was removed under reduced pressure. The obtained residue was refined by reversed-phase silica gel column chromatography [eluent; 65-100% acetonitrile/0.1% trifluoroacetic acid aqueous solution] to give 2-(4-chloroanilino)-4-phenoxybenzoic acid 9 mg of white solid.

$^1$H-NMR(DMSO-$d_6$) δ value:
6.37(1H,dd,J=8.9,2.4 Hz),6.64(1H,d,J=2.4 Hz),7.12-7.14 (2H,m),7.20-7.25(3H,m),7.32-7.36(2H,m),7.41-7.46(2H, m),7.91(1H,d,J=8.9 Hz),9.77(1H,s),12.84-13.18(1H,broad).

Example 43-47

The compounds shown in Table 10 were obtained in the same manner as in Example 42.

TABLE 10

| Example No. | R$^3$ |
|---|---|
| 43 | ![benzodioxole-methyl] |
| 44 | ![4-isopropylphenyl] |
| 45 | ![2,4-dimethoxy-methylphenyl] |
| 46 | ![phenyl] |
| 47 | ![methoxy-methylphenyl] |

2-((Benzo-1,3-dioxol-5-yl)amino)-4-phenoxybenzoic acid $^1$H-NMR(DMSO-$d_6$) δ value:
6.00(2H,s),6.25(1H,dd,J=8.8,2.4 Hz),6.45(1H,d,J=2.4 Hz),6.67 (1H,dd,J=8.3,2.2 Hz),6.84(1H,d,J=2.2 Hz),6.86 (1H,d,J=8.3 Hz),7.08-7.10(2H,m),7.19(1H,t,J=7.4 Hz),7.38-7.43(2H,m),7.86(1H,d,J=8.8 Hz),9.49-9.67(1H,broad).

2-(4-Isopropylanilino)-4-phenoxybenzoic acid $^1$H-NMR(DMSO-$d_6$) δ value:
1.18(6H,d,J=6.8 Hz),2.79-2.90(1H,m),6.29(1H,dd,J=8.8, 2.3 Hz),6.58(1H,d,J=2.3 Hz),7.09-7.13(4H,m),7.17-7.21 (3H,m),7.39-7.44(2H,m),7.89(1H,d,J=8.8 Hz),9.71(1H,s), 12.75-13.03(1H,broad).

2-(2,4-Dimethoxyanilino)-4-phenoxybenzoic acid $^1$H-NMR(DMSO-$d_6$) δ value:
3.74(3H,s),3.75(3H,s),6.23(1H,dd,J=8.8,2.3 Hz),6.26(1H,d, J=2.3 Hz),6.47(1H,dd,J=8.7,2.7 Hz),6.63(1H,d,J=2.7 Hz),7.06 (2H,d,J=7.8 Hz),7.14(1H,d,J=8.8 Hz),7.18(1H,t, J=7.4 Hz), 7.38-7.42(2H,m),7.85(1H,d,J=8.7 Hz),9.37(1H, s).

2-Anilino-4-phenoxybenzoic acid $^1$H-NMR(DMSO-$d_6$) δ value:
6.34(1H,dd,J=8.9,2.3 Hz),6.64(1H,d,J=2.3 Hz),7.05(1H,t, J=7.5 Hz),7.11-7.13(2H,m),7.18-7.22(3H,m),7.31(2H,t, J=7.7 Hz),7.42(2H,t,J=7.8 Hz),7.91(1H,d,J=8.9 Hz),9.78 (1H,s),12.82-13.07(1H,broad).

2-(4-Methoxy-2-methylanilino)-4-phenoxybenzoic acid $^1$H-NMR(DMSO-$d_6$) δ value:
2.13(3H,s),3.73(3H,s),6.03(1H,d,J=2.3 Hz),6.19(1H,dd, J=8.8, 2.3 Hz),6.75(1H,dd,J=8.6,2.8 Hz),6.87(1H,d,J=2.8 Hz),7.04 (2H,d,J=7.7 Hz),7.12(1H,d,J=8.6 Hz),7.17(1H,t, J=7.7 Hz), 7.38(2H,t,J=7.7 Hz),7.86(1H,d,J=8.8 Hz),9.39 (1H,s),12.63-12.95(1H,broad).

Example 48

To N,N-dimethylformamide 1.0 mL solution of 2-iodo-4-phenoxybenzoic acid 40 mg, were added cyclohexylamine 0.027 mL, copper(I) iodide 3 mg, copper powder 3 mg and N-methylmorpholine 0.040 mL, and it was stirred under application of pressure at 180° C. for 15 minutes. After the reaction mixture was cooled to room temperature,10% citric acid aqueous solution and ethyl acetate were added to it. The organic layer was separated and collected,dried over anhydrous magnesium sulfate, the solvent was removed under reduced pressure. The obtained residue was refined by silica gel column chromatography [Trikonex company, Flash Tube 2008, eluent; hexane:ethyl acetate:acetic acid=20:10:1] to give 2-(cyclohexylamino)-4-phenoxybenzoic acid 5 mg of white solid.

$^1$H-NMR(DMSO-$d_6$) δ value:
1.14-1.38(5H,m),1.48-1.57(1H,m),1.59-1.67(2H,m), 1.81-1.91(2H,m),3.20-3.40(1H,broad),6.04(1H,dd,J=9.0, 2.0 Hz),6.25(1H,d,J=2.0H z),7.09(2H,d,J=7.7 Hz),7.21(1H, t,J=7.7 Hz),7.43(2H,t,J=7.7 Hz),7.76(1H,d,J=9.0 Hz),7.95-8.06(1H,broad),12.35-12.49(1H,broad).

Example 49

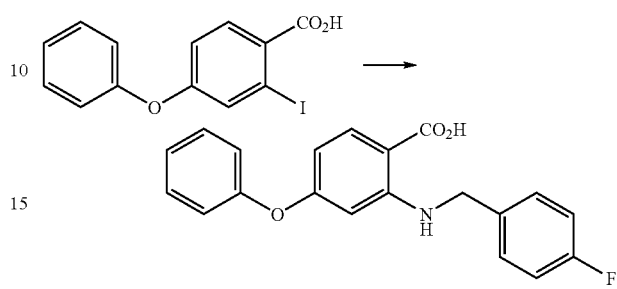

The following compound was obtained in the same manner as in Example 48.

2-(4-Fluorobenzylamino)-4-phenoxybenzoic acid $^1$H-NMR(DMSO-$d_6$) δ value:
4.34(2H,s),6.09-6.12(2H,m),6.98(2H,d,J=8.0 Hz),7.11-7.28(5H,m),7.38(2H,t,J=7.7 Hz),7.79(1H,d,J=8.6 Hz),8.38-8.48(1H,broad),12.48-12.60(1H,broad).

Example 50

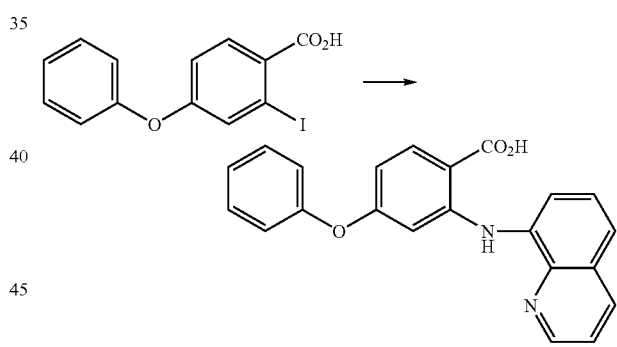

To N,N-dimethylformamide 8.8 mL solution of 2-iodo-4-phenoxybenzoic acid 0.88 g were added quinolin-8-amine 0.75 g, N-methylmorpholine 0.85 mL, copper(I) iodide 0.15 g and copper powder 49 mg, and it was stirred at 90° C. for 6 hours and 30 minutes. After the reaction mixture was cooled to room temperature, ethyl acetate and water were added to it, it was adjusted to pH6.5 with 10% citric acid aqueous solution, and insoluble matter was filtrated. The organic layer was separated and collected,dried over anhydrous magnesium sulfate after washing with saturated sodium chloride aqueous solution, and the solvent was removed under reduced pressure. The obtained residue was refined by silica gel column chromatography [eluent; hexane:ethyl acetate=2:1] to give 4-phenoxy-2-(quinolin-8-ylamino)benzoic acid 0.15 g of pale yellow solid.

$^1$H-NMR(DMSO-$d_6$) δ value:
6.49(1H,dd,J=8.8, 2.2 Hz),7.16-7.20(3H,m),7.23(1H,t, J=7.3 Hz),7.42-7.51(4H,m),7.59-7.63(2H,m),8.00(1H,d, J=8.8 Hz),8.35(1H,dd,J=8.3, 1.5 Hz),8.89 (1H,dd,J=4.2,1.7 Hz),11.07(1H,s),12.89-12.96(1H,broad).

Example 51

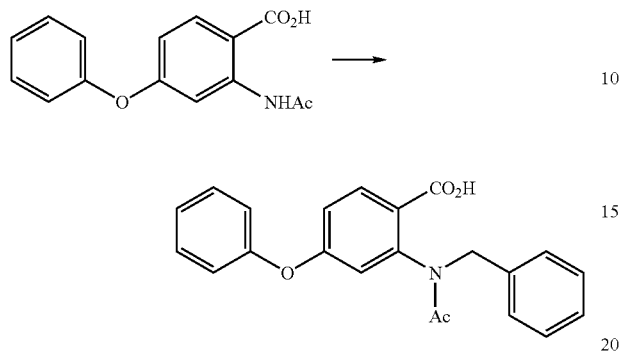

60% Sodium hydride 30 mg was added to N,N-dimethylformamide 2.0 mL solution of 2-(acetamido)-4-phenoxybenzoic acid 0.10 g at room temperature, and it was stirred at same temperature for 30 minutes. Benzyl bromide 0.092 mL was added to the reaction mixture at room temperature, and it was stirred at same temperature for 2 hours and 30 minutes. 60% Sodium hydride 15 mg was added to the reaction mixture at room temperature, and it was stirred at same temperature for 30 minutes. Benzyl bromide 0.022 mL was added to the reaction mixture at room temperature, and it was stirred at same temperature for 1 hour and 30 minutes. 1.0 mol/L Hydrochloric acid and ethyl acetate were added to the reaction mixture. The organic layer was separated and collected, dried over anhydrous magnesium sulfate, and the solvent was removed under reduced pressure. The obtained residue was refined by silica gel column chromatography [eluent; hexane:ethyl acetate:acetic acid=40:10:1] to give 2-(N-benzylacetamido)-4-phenoxybenzoic acid 0.10 g of colorless oil.

$^1$H-NMR(DMSO-$d_6$) δ value:
1.72(3H,s),3.93(1H,d,J=14.8 Hz),5.42(1H,d,J=14.8 Hz),6.42 (1H,d,J=2.5 Hz),6.90(2H,d,J=8.6 Hz),7.03(1H,dd, J=8.6, 2.5H z),7.11-7.14(2H,m),7.18-7.25(4H,m),7.38(2H,t, J=7.7 Hz),7.98(1H,d,J=8.6 Hz).

Example 52

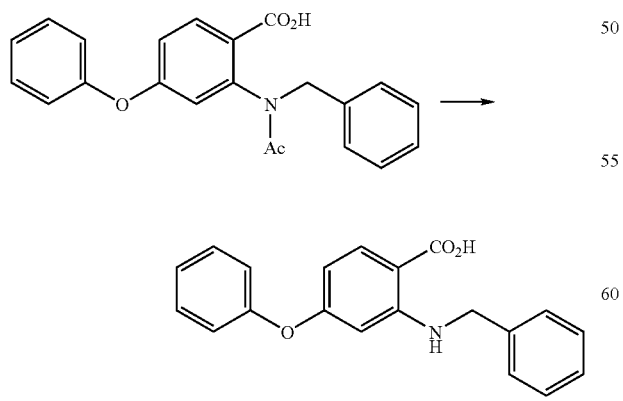

A suspension of hydrazine monohydrate 2.0 mL of 2-(N-benzylacetamido)-4-phenoxybenzoic acid 0.10 g was heated and refluxed for 3 hours. After the reaction mixture was cooled to room temperature, acetic acid 5.0 mL was added to it, and ethyl acetate and saturated sodium chloride aqueous solution were added to it. The organic layer was separated and collected, dried over anhydrous magnesium sulfate, and the solvent was removed under reduced pressure. The obtained residue was refined by silica gel column chromatography [eluent; hexane:ethyl acetate:acetic acid=80:20:1] to give 2-(benzylamino)-4-phenoxybenzoic acid 20 mg of white solid.

$^1$H-NMR(DMSO-$d_6$) δ value:
4.35(2H,s),6.09(1H,dd,J=8.8,2.4 Hz),6.16(1H,d,J=2.4 Hz),6.98-7.00(2H,m),7.17-7.27(4H,m),7.30-7.40(4H,m), 7.79(1H,d,J=8.8 Hz),8.36-8.49(1H,broad),12.32-12.70(1H, broad).

Example 53

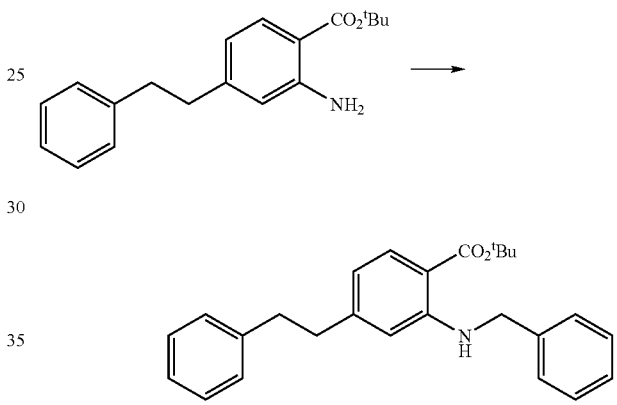

To N,N-dimethylformamide 2.0 mL solution of tert-butyl 2-amino-4-phenethylbenzoate 0.20 g were added potassium carbonate 0.093 g and benzyl bromide 0.080 mL at room temperature, and it was stirred at same temperature for 24 hours. 1.0 mol/L Hydrochloric acid and ethyl acetate were added to the reaction mixture.

The organic layer was separated and collected,dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane: ethyl acetate=5:1] to give tert-butyl 2-(benzylamino)-4-phenethylbenzoate 0.16 g of colorless oil.

$^1$H-NMR(CDCl$_3$) δ value:
1.56(9H,s),2.76-2.85(4H,m),4.38(2H,d,J=5.4 Hz),6.39-6.42(2H,m),7.11-7.34(10H,m),7.78(1H,d,J=8.0 Hz),8.10-8.17(1H,broad).

Example 54, 55

The compounds shown in Table 11 were obtained in the same manner as in Example 53.

TABLE 11

![Structure with CO2tBu, phenethyl, NH-X1-R3]

| Example No. | X1—R3 |
|---|---|
| 54 | [4-fluorobenzyl group: CH2-C6H4-F] |
| 55 | [cinnamyl group: CH2-CH=CH-C6H5] | tert-Butyl 2-(4-fluorobenzylamino)-4-phenethylbenzoate $^1$H-NMR(CDCl$_3$) δ value:
1.56(9H,s),2.78-2.85(4H,m),4.34(2H,s),6.34(1H,d,J=1.4 Hz),6.43(1H,dd,J=8.1, 1.4 Hz),6.98-7.05(2H,m),7.11-7.13(2H,m),7.16-7.20(2H,m),7.24-7.31(3H,m),7.79(1H,d,J=8.1 Hz),7.98-8.26(1H,broad).

tert-Butyl 2-(cinnamylamino)-4-phenethylbenzoate $^1$H-NMR(CDCl$_3$) δ value:
1.57(9H,s),2.83-2.92(4H,m),3.97(2H,s),6.29(1H,dt, J=16.0,5.7 Hz),6.44(1H, d,J=8.2 Hz),6.47(1H,s),6.60(1H,d, J=16.0 Hz),7.15-7.38(10H,m),7.79(1H,d,J=8.2 Hz),7.93 (1H,s).

Example 56

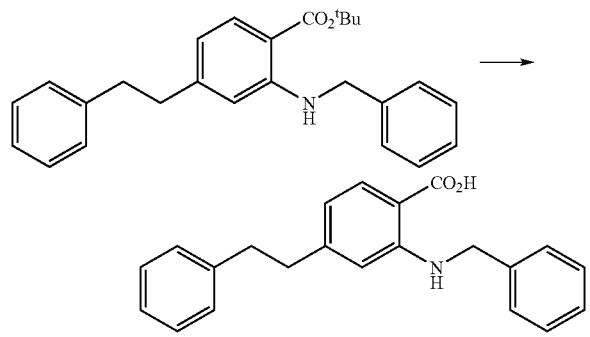

Trifluoroacetic acid 2.0 mL was added to tert-butyl 2-(benzylamino)-4-phenethylbenzoate 0.16 g, it was stirred at room temperature 4 hours, and the solvent was removed under reduced pressure. Toluene was added to it, and the solvent was removed under reduced pressure. Diisopropyl ether and hexane were added to the obtained residue, solid matter was filtrated to give 2-(benzylamino)-4-phenethylbenzoic acid 0.11 g of white solid.

$^1$H-NMR(DMSO-d$_6$) δ value:
2.74-2.81(4H,m),4.41(2H,s),6.44(1H,d,J=8.1 Hz),6.57 (1H,s),7.14-7.18(3H,m),7.23-7.28(3H,m),7.34-7.36(4H,m), 7.69(1H,d,J=8.1 Hz).

Example 57, 58

The compounds shown in Table 12 were obtained in the same manner as in Example 56.

TABLE 12

![Structure with CO2H, phenethyl, NH-X1-R3]

| Example No. | X1—R3 |
|---|---|
| 57 | [4-fluorobenzyl group] |
| 58 | [cinnamyl group] |

2-(4-Fluorobenzylamino)-4-phenethylbenzoic acid $^1$H-NMR(DMSO-d$_6$) δ value: δ 2.73-2.82(4H,m),4.40 (2H,s),6.44(1H,dd,J=8.2,1.2 Hz),6.54(1H,s), 7.13-7.19(5H, m),7.22-7.26(2H,m),7.36-7.39(2H,m),7.68(1H,d,J=8.2 Hz).

2-(Cinnamylamino)-4-phenethylbenzoic acid $^1$H-NMR(DMSO-d$_6$) δ value:
2.80-2.87(4H,m),4.00(2H,d,J=5.5 Hz),6.38(1H,dt,J=15.9, 5.5 Hz), 6.46(1H,d,J=8.0 Hz),6.59-6.63(2H,m),7.13-7.27 (6H,m),7.33(2H,t,J=7.6 Hz),7.43(2H,d,J=7.6 Hz),7.69(1H, d,J=8.0 Hz).

Example 59

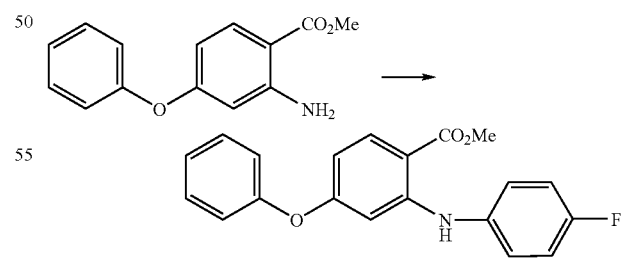

To dioxane 5.0 mL solution of methyl 2-amino-4-phenoxybenzoate 0.34 g were added 1-fluoro-4-iodobenzene 0.18 mL,1,1'-bis(diphenylphosphino)ferrocene 93 mg,1,1'-bis (diphenylphosphino)ferrocene palladium(II) dichloride dichloromethane complex 46 mg and sodium tert-butoxide 0.15 g at room temperature, and it was heated and refluxed under nitrogen atmosphere for 3 hours. After the reaction mixture was cooled to room temperature,10% citric acid aqueous solution and ethyl acetate were added to it. The organic layer was separated and collected,dried over anhydrous magnesium sulfate after washing with saturated sodium chloride aqueous solution, and the solvent was removed under reduced pressure. The obtained residue was refined by silica gel column chromatography [eluent; hexane:ethyl acetate=20:1] to give methyl 2-(4-fluoroanilino)-4-phenoxybenzoate 0.036 g of colorless oil.

$^1$H-NMR(CDCl$_3$) δ value:

3.88(3H,s),6.26(1H,dd,J=8.9,2.3 Hz),6.62(1H,d,J=2.3 Hz),6.97-7.04(4H,m),7.12-7.17(3H,m),7.31-7.38(2H,m), 7.90(1H,d,J=8.9 Hz),9.49(1H,s).

Example 60

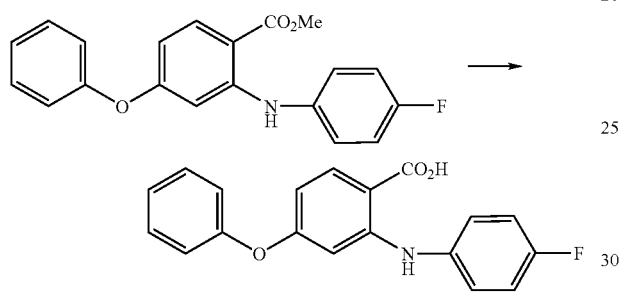

To a suspension of ethanol 3.0 mL of methyl 2-(4-fluoroanilino)-4-phenoxybenzoate 36 mg was added 10% sodium hydroxide aqueous solution 1.0 mL at room temperature, and it was stirred at 60° C. for 1 hour and 30 minutes. After the reaction mixture was cooled to room temperature,10% sodium hydroxide aqueous solution 1.0 mL was added, and it was heated and refluxed for 30 minutes. After the reaction mixture was cooled to room temperature,10% citric acid aqueous solution and ethyl acetate were added to it. The organic layer was separated and collected,dried over anhydrous magnesium sulfate, and the solvent was removed under reduced pressure. Diisopropyl ether and hexane were added to the obtained residue, and insoluble matter was filtrated. The solvent of filtrate was removed under reduced pressure, hexane was added to the residue, and solid matter was filtrated to give 2-(4-fluoroanilino)-4-phenoxybenzoic acid 10 mg of white solid.

$^1$H-NMR(DMSO-d$_6$) δ value:

6.31(1H,dd,J=8.9,2.3 Hz),6.49(1H,d,J=2.3 Hz),7.09-7.27 (7H,m),7.39-7.44(2H,m),7.89(1H,d,J=8.9 Hz),9.66(1H,s), 12.79-13.03(1H,broad).

Example 61

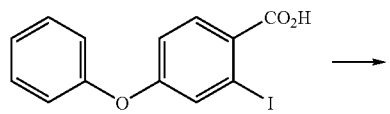

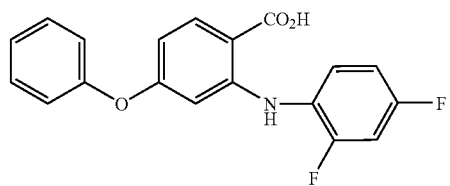

To N,N-dimethylformamide 15 mL solution of 2-iodo-4-phenoxybenzoic acid 1.5 g, were added 2,4-difluoroaniline 0.67 mL, copper powder 0.084 g and N-methylmorpholine 1.2 mL, and it was stirred at 100° C. for 5 hours. After the reaction mixture was cooled to room temperature,1.0 mol/L hydrochloric acid and ethyl acetate were added to it. The organic layer was separated and collected,dried over anhydrous magnesium sulfate, and the solvent was removed under reduced pressure. The obtained residue was refined by silica gel column chromatography [eluent; hexane:ethyl acetate=2:1] to give 2-(2,4-difluoroanilino)-4-phenoxybenzoic acid 0.60 g of white solid.

$^1$H-NMR(DMSO-d$_6$) δ value:

6.29-6.30(1H,m),6.33(1H,dd,J=8.7,2.2 Hz),7.04-7.10 (3H,m),7.20(1H,t,J=7.4 Hz),7.33-7.50(4H,m),7.90(1H,d, J=8.7 Hz),9.59(1H,s),12.85-13.19(1H,broad).

Example 62

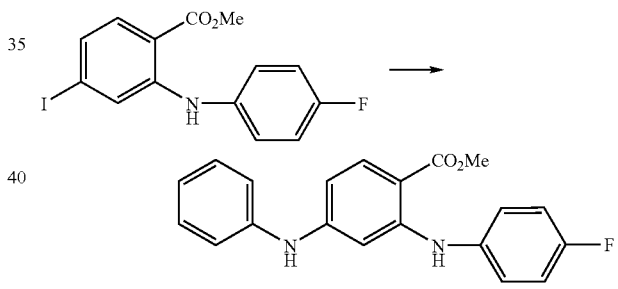

To toluene 2.0 mL suspension of methyl 2-(4-fluoroanilino)-4-iodobenzoate 0.20 g, rac-2,2'-bis(diphenylphosphino)-1,1'-binaphthyl 10 mg, palladium acetate 4 mg and cesium carbonate 0.35 g was added aniline 0.074 mL, and it was heated and refluxed under nitrogen atmosphere for 3 hours. The reaction mixture was cooled to room temperature, rac-2,2'-bis(diphenylphosphino)-1,1'-binaphthyl 10 mg and palladium acetate 4 mg were added to it, and it was heated and refluxed under nitrogen atmosphere for 3 hours. The reaction mixture was cooled to room temperature, insoluble matter was filtrated, and the solvent was removed under reduced pressure. The obtained residue was refined by silica gel column chromatography [Fuji SILYSIA Chemical Ltd., PSQ100B(spherical type), eluent; hexane:ethyl acetate=10:1] to give methyl 4-anilino-2-(4-fluoroanilino)benzoate 0.13 g of pale yellow solid.

$^1$H-NMR(DMSO-d$_6$) δ value:

3.78(3H,s),6.42(1H,dd,J=8.9,2.2 Hz),6.63(1H,d,J=2.2 Hz),6.95 (1H,t,J=7.4 Hz),7.10(2H,d,J=7.6 Hz),7.19-7.32 (6H,m),7.74(1H,d,J=8.9 Hz),8.65(1H,s),9.36(1H,s).

Example 63

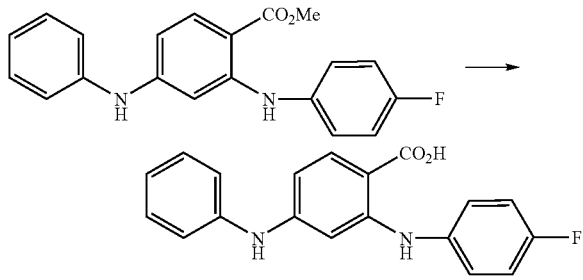

To a suspension of ethanol 2.0 mL of methyl 4-anilino-2-(4-fluoroanilino)benzoate 0.25 g was added water 1.0 mL solution of sodium hydroxide 0.060 g at room temperature, and it was heated and refluxed for 2 hours. After the reaction mixture was cooled to room temperature,1.0 mol/L hydrochloric acid and ethyl acetate were added to it. The organic layer was separated and collected,dried over anhydrous magnesium sulfate, and the solvent was removed under reduced pressure. Diisopropyl ether and hexane were added to the obtained residue, and solid matter was filtrated to give 4-anilino-2-(4-fluoroanilino)benzoic acid 0.24 g of white solid.

$^1$H-NMR(DMSO-$d_6$) δ value:
6.40(1H,dd,J=8.9,2.2 Hz),6.64(1H,d,J=2.2 Hz),6.91-6.95(1H,m),7.09-7.12(2H,m),7.17-7.23(2H,m),7.26-7.32(4H,m),7.73(1H,d,J=8.9 Hz),8.60(1H,s),9.64(1H,s).

Example 64

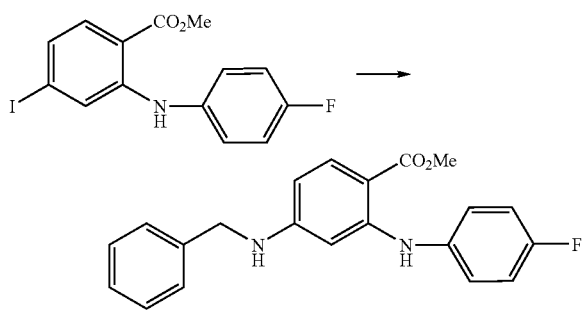

To toluene 3.0 mL solution of methyl 2-(4-fluoroanilino)-4-iodobenzoate 0.30 g were added benzylamine 0.13 mL, rac-2,2'-bis(diphenylphosphino)-1,1'-binaphthyl 0.050 g, tris(dibenzylideneacetone)dipalladium(0) 0.022 g and sodium tert-butoxide 0.093 g at room temperature, and it was stirred under nitrogen atmosphere at 80° C. for 1 hour. After the reaction mixture was cooled to room temperature, acetic acid 1.0 mL was added to it, and the solvent was removed under reduced pressure. The obtained residue was refined by silica gel column chromatography [eluent; hexane:ethyl acetate=5:1] to give methyl 4-(benzylamino)-2-(4-fluoroanilino)benzoate 0.24 g of brown oil.

$^1$H-NMR(CDCl$_3$) δ value:
3.82(3H,s),4.27(2H,s),6.03(1H,dd,J=8.9,2.1 Hz),6.09(1H,d, J=2.1 Hz),6.90-6.95(2H,m),7.01-7.04(2H,m),7.25-7.35(5H,m),7.77(1H,d,J=8.9 Hz),9.47(1H,s).

Example 65, 66

The compounds shown in Table 13 were obtained in the same manner as in Example 64.

TABLE 13

| Example No. | R$^4$—X$^2$ |
|---|---|
| 65 | phenethyl-NH-methyl |
| 66 | 3-phenylpropyl-NH-methyl |

Methyl 2-(4-fluoroanilino)-4-(phenethylamino)benzoate $^1$H-NMR(CDCl$_3$) δ value:
2.84(2H,t,7.1 Hz),3.32(2H,t,7.1 Hz),3.83(3H,s),3.98-4.08(1H,broad),5.97(1H,dd,J=8.8,2.2 Hz),6.13(1H,d,J=2.2Hz),7.02-7.07(2H,m),7.13-7.31(7H,m),7.77(1H,d,J=8.8 Hz),9.48(1H,s).

Methyl 2-(4-fluoroanilino)-4-((3-phenylpropyl)amino)benzoate $^1$H-NMR (CDCl$_3$) δ value:
1.85-1.93(2H,m),2.67(2H,t,7.6 Hz),3.07(2H,t,6.9 Hz),3.83(3H,s), 3.91-3.98(1H,broad),5.93(1H,dd,J=8.8,2.2 Hz),6.07(1H,d,J=2.2H z),7.00-7.05(2H,m),7.14-7.30(7H,m),7.76(1H,d,J=8.8 Hz),9.47(1H,s).

Example 67

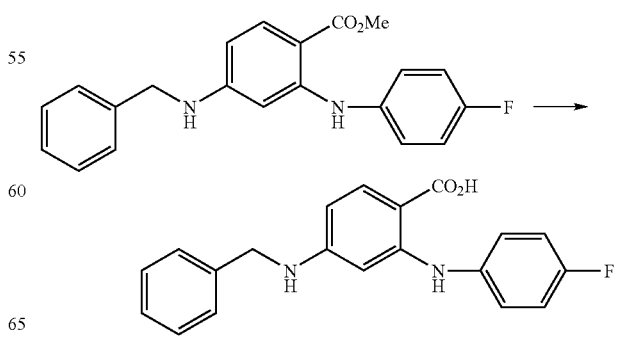

10% Sodium hydroxide aqueous solution 0.82 mL was added to a suspension of ethanol 3.0 mL of methyl 4-(benzylamino)-2-(4-fluoroanilino)benzoate 0.24 g at room temperature, and it was heated and refluxed for 2 hours. After the reaction mixture was cooled to room temperature, 10% sodium hydroxide aqueous solution 0.82 mL was added, and it was heated and refluxed for 3 hours. After the reaction mixture was cooled to room temperature, acetic acid 2.0 mL, saturated sodium chloride aqueous solution and ethyl acetate were added to it. The organic layer was separated and collected, dried over anhydrous magnesium sulfate, and the solvent was removed under reduced pressure. Diisopropyl ether and hexane were added to the obtained residue, and solid matter was filtrated to give 4-(benzylamino)-2-(4-fluoroanilino)benzoic acid 0.17 g of white solid.

$^1$H-NMR (DMSO-$d_6$) δ value:
4.22(2H,d,J=5.6 Hz),6.07-6.09(2H,m),6.99-7.08(5H,m),7.24-7.27(3H,m),7.32-7.35(2H,m),7.60(1H,d,J=8.8 Hz),9.55-9.90(1H,broad).

Example 68, 69

The compounds shown in Table 14 were obtained in the same manner as in Example 67.

TABLE 14

| Example No. | R$^4$—X$^2$ |
|---|---|
| 68 | ![phenethylamino group] |
| 69 | ![3-phenylpropylamino group] |

2-(4-Fluoroanilino)-4-(phenethylamino)benzoic acid $^1$H-NMR (DMSO-$d_6$) δ value:
2.75(2H,t,7.6 Hz),3.15-3.20(2H,m),6.04(1H,dd,J=8.9,2.1 Hz),6.16(1H,d,J=2.1 Hz),6.50 (1H,t,5.5 Hz),7.16-7.29(9H,m),7.62(1H,d,J=8.9 Hz),9.68(1H,s),12.02(1H,s).

2-(4-Fluoroanilino)-4-((3-phenylpropyl)amino)benzoic acid $^1$H-NMR (DMSO-$d_6$) δ value:
1.74-1.81(2H,m),2.62(2H,t,7.7 Hz),2.93-2.98(2H,m),6.00 (1H,dd,J=9.0,2.1 Hz),6.14(1H,d,J=2.1 Hz),6.41 (1H,t,5.3 Hz),7.15-7.28(9H,m),7.61(1H,d,J=9.0 Hz),9.67(1H,s),12.00 (1H,s).

Example 70

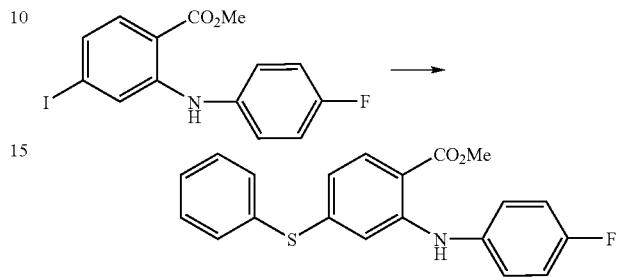

To 2-methyl-2-propanol 4.0 mL solution of methyl 2-(4-fluoroanilino)-4-iodobenzoate 0.20 g were added benzenethiol 0.067 mL, tetrakis(triphenylphosphine) palladium (0) 0.03 g and sodium tert-butoxide 0.10 g, and it was heated and refluxed under nitrogen atmosphere for 30 minutes.

After the reaction mixture was cooled to room temperature, 1.0 mol/L hydrochloric acid and ethyl acetate were added to it. The organic layer was separated and collected, dried over anhydrous magnesium sulfate after washing with saturated sodium hydrogen carbonate aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=20:1] to give methyl 2-(4-fluoroanilino)-4-(phenylthio)benzoate 30 mg of colorless oil.

$^1$H-NMR (CDCl$_3$) δ value:
3.87(3H,s),6.49(1H,dd,J=8.5,1.8 Hz),6.71(1H,d,J=1.8 Hz),6.91-6.96(2H,m),7.00-7.04(2H,m),7.34-7.37(3H,m),7.44-7.47(2H,m),7.80(1H,d,J=8.5 Hz),9.37(1H,s).

Example 71

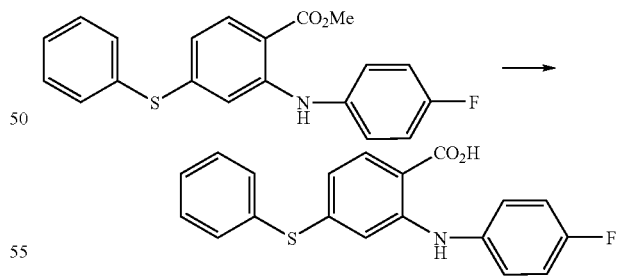

10% Sodium hydroxide aqueous solution 1.0 mL was added to a suspension of 2-propanol 2.0 mL of methyl 2-(4-fluoroanilino)-4-(phenylthio)benzoate 0.21 g at room temperature, and it was heated and refluxed for 2 hours. After the reaction mixture was cooled to room temperature, 1.0 mol/L hydrochloric acid and ethyl acetate were added to it. The organic layer was separated and collected, dried over anhydrous magnesium sulfate, the solvent was removed under reduced pressure to give 2-(4-fluoroanilino)-4-(phenylthio)benzoic acid 0.16 g of pale yellow solid.

¹H-NMR (DMSO-d₆) δ value:
6.54-6.59(2H,m),7.06-7.13(4H,m),7.42-7.51(5H,m),7.80 (1H,d,J=8.3 Hz),9.55(1H,s).

Example 72

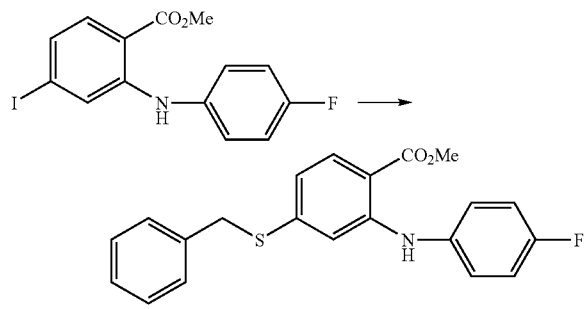

To toluene 4.0 mL suspension of methyl 2-(4-fluoroanilino)-4-iodobenzoate 0.40 g, 1,1'-bis(diphenylphosphino)ferrocene 0.072 g and tris(dibenzylideneacetone)dipalladium (0) 0.050 g were added triethylamine 0.30 mL and phenylmethanethiol 0.15 mL, and it was stirred under argon atmosphere at 80° C. for 2 hours. After the reaction mixture was cooled to room temperature, 1.0 mol/L hydrochloric acid and ethyl acetate were added to it. The organic layer was separated and collected,dried over anhydrous magnesium sulfate, and the solvent was removed under reduced pressure. The obtained residue was refined by silica gel column chromatography [Fuji SILYSIA Chemical Ltd., PSQ100B (spherical type), eluent, hexane:ethyl acetate=10:1] to give methyl 4-(benzylthio)-2-(4-fluoroanilino)benzoate 0.36 g of white solid.
¹H-NMR (CDCl₃) δ value:
3.87(3H,s),4.06(2H,s),6.61(1H,dd,J=8.5,1.5 Hz),6.79 (1H,d, J=1.5 Hz),6.98-7.08(4H,m),7.23-7.28(5H,m),7.81 (1H,d,J=8.5 Hz),9.36(1H,s).

Example 73

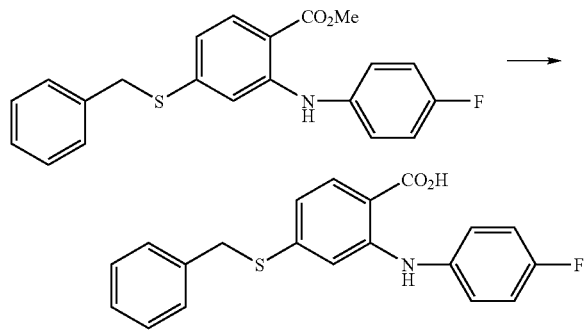

10% Sodium hydroxide aqueous solution 1.0 mL was added to a suspension of 2-propanol 4.0 mL of methyl 4-(benzylthio)-2-(4-fluoroanilino)benzoate 0.36 g at room temperature, and it was heated and refluxed for 2 hours. After the reaction mixture was cooled to room temperature, 1.0 mol/L hydrochloric acid and ethyl acetate were added to it. The organic layer was separated and collected,dried over anhydrous magnesium sulfate, and the solvent was removed under reduced pressure. Diisopropyl ether and hexane were added to the obtained residue, solid matter was filtrated to give 4-(benzylthio)-2-(4-fluoroanilino)benzoic acid 0.30 g of white solid.
¹H-NMR (DMSO-d₆) δ value:
4.20(2H,s),6.69(1H,dd,J=8.5,1.7 Hz),6.78(1H,dd,J=3.9, 1.7 Hz),7.18-7.29(9H,m),7.76(1H,d,J=8.5 Hz),9.56(1H,s).

Example 74

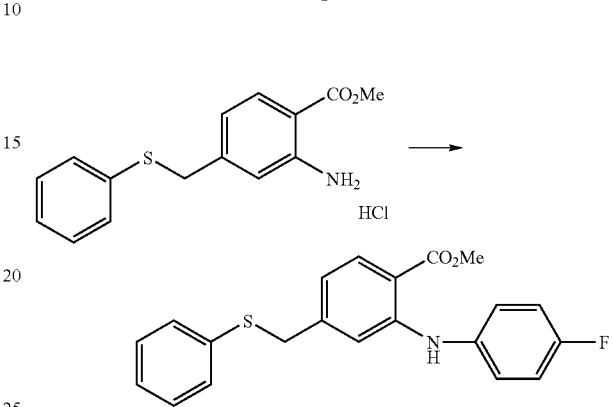

To toluene 9.5 mL suspension of methyl 2-amino-4-((phenylthio)methyl)benzoate hydrochloride 0.96 g, rac-2,2'-bis (diphenylphosphino)-1,1'-binaphthyl 19 mg, palladium acetate 7 mg and cesium carbonate 3.0 g was added 1-fluoro-4-iodobenzene 1.1 mL, and it was heated and refluxed under nitrogen atmosphere for 3 hours. After the reaction mixture was cooled to room temperature, palladium acetate 7.0 mg was added to it, and it was heated and refluxed for 14 hours. After the reaction mixture was cooled to room temperature, insoluble matter was filtrated, and the solvent was removed under reduced pressure. The obtained residue was refined by silica gel column chromatography [Fuji SILYSIA Chemical Ltd., PSQ100B(spherical type), eluent; hexane:ethyl acetate=20:1] to give methyl 2-(4-fluoroanilino)-4-((phenylthio)methyl)benzoate 0.48 g of pale yellow oil.
¹H-NMR (CDCl₃) δ value:
3.88(3H,s),3.94(2H,s),6.67(1H,dd,J=8.3,1.5 Hz),6.84 (1H,d, J=1.5 Hz),6.95-7.02(4H,m),7.20-7.28(5H,m),7.88 (1H,d,J=8.3 Hz),9.33(1H,s).

Example 75

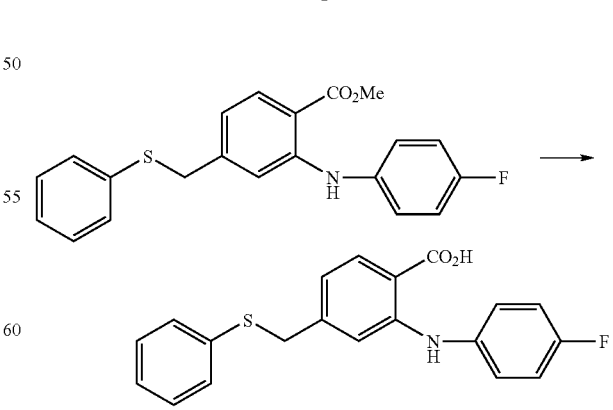

2.0 mol/L Sodium hydroxide aqueous solution 2.0 mL was added to a mixed solution of methanol 2.4 mL and tetrahydrofuran 2.4 mL of methyl 2-(4-fluoroanilino)-4-((phenylthio)methyl)benzoate 0.48 g, and it was stirred at room temperature for 17 hours. The solvent was removed under reduced pressure, ethyl acetate and water were added to it, and it was adjusted to pH4.0 with 1.0 mol/L hydrochloric acid. The organic layer was separated and collected, dried over anhydrous magnesium sulfate after washing with saturated sodium chloride aqueous solution, and the solvent was removed under reduced pressure. Hexane and diisopropyl ether were added to the obtained residue, and solid matter was filtrated to give 2-(4-fluoroanilino)-4-((phenylthio)methyl)benzoic acid 0.40 g of pale yellow solid.

$^1$H-NMR (DMSO-$d_6$) δ value:
4.14(2H,s),6.76(1H,d,J=8.2 Hz),6.97-6.98(1H,m),7.06-7.10(2H,m),7.12-7.18(2H,m),7.20-7.25(1H,m),7.30-7.31(4H,m),7.81(1H,d,J=8.2 Hz),9.51(1H,s),12.94-13.03(1H, broad).

Example 76

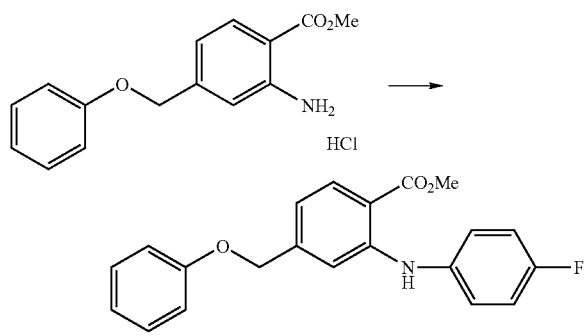

To toluene 4.0 mL suspension of methyl 2-amino-4-(phenoxymethyl)benzoate hydrochloride 0.40 g, rac-2,2'-bis(diphenylphosphino)-1,1'-binaphthyl 8 mg, palladium acetate 3 mg and cesium carbonate 0.89 g was added 1-fluoro-4-iodobenzene 0.47 mL, and it was heated and refluxed under nitrogen atmosphere for 16 hours. After the reaction mixture was cooled to room temperature, insoluble matter was filtrated, and the solvent was removed under reduced pressure. The obtained residue was refined by silica gel column chromatography [eluent; hexane:ethyl acetate=20:1] to give methyl 2-(4-fluoroanilino)-4-(phenoxymethyl)benzoate 0.22 g of pale yellow oil.

$^1$H-NMR (CDCl$_3$) δ value:
3.90(3H,s),4.98(2H,s),6.76(1H,dd,J=8.3,1.7 Hz),6.88-7.03(5H,m),7.09-7.14(3H,m),7.25-7.30(6H,m),7.96(1H,d,J=8.3 Hz),9.40(1H,s).

Example 77

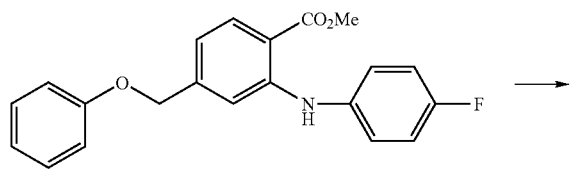

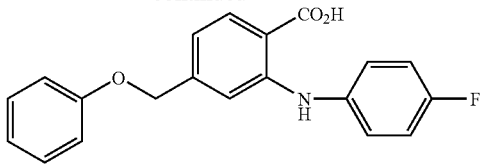

2.0 mol/L Sodium hydroxide aqueous solution 0.92 mL was added to a mixed solution of methanol 2.0 mL and tetrahydrofuran 2.0 mL of methyl 2-(4-fluoroanilino)-4-(phenoxymethyl)benzoate 0.22 g, and it was stirred at room temperature for 24 hours. The solvent was removed under reduced pressure, water was added to it, and it was adjusted to pH4.0 with 1.0 mol/L hydrochloric acid. Solid matter was filtrated to give 2-(4-fluoroanilino)-4-(phenoxymethyl)benzoic acid 0.14 g of white solid.

$^1$H-NMR (DMSO-$d_6$) δ value:
5.07(2H,s),6.81(1H,dd,J=8.2,1.3 Hz),6.92-6.96(3H,m),7.12-7.22(5H,m),7.26-7.31(2H,m),7.90(1H,d,J=8.2 Hz).

Example 78

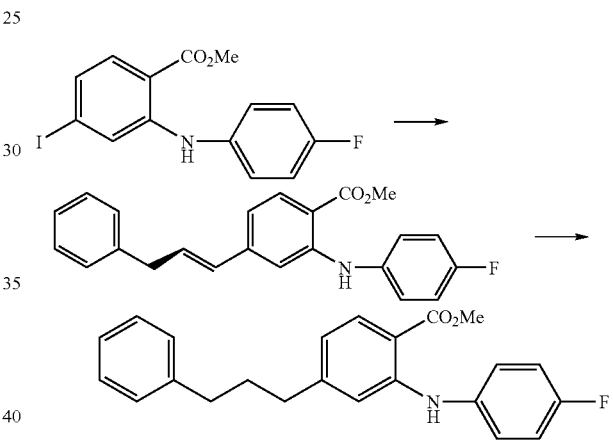

To toluene 3.0 mL solution of methyl 2-(4-fluoroanilino)-4-iodobenzoate 0.30 g, allylbenzene 0.16 mL and triethylamine 0.11 mL was added palladium acetate 9 mg, and it was heated and refluxed under nitrogen atmosphere for 2 hours. After the reaction mixture was cooled to room temperature, palladium acetate 18 mg was added to it, and it was heated and refluxed under nitrogen atmosphere for 2 hours. After the reaction mixture was cooled to room temperature, palladium acetate 18 mg was added, and it was heated and refluxed under nitrogen atmosphere for 1 hour. After the reaction mixture was cooled to room temperature, palladium acetate 18 mg was added, and it was heated and refluxed for 2 hours. After the reaction mixture was cooled to room temperature, insoluble matter was filtrated, and the solvent was removed under reduced pressure. The obtained residue was refined by silica gel column chromatography [eluent; hexane:ethyl acetate=20:1] to give methyl 2-(4-fluoroanilino)-4-(3-phenyl-1-propenyl)benzoate.

To a mixed solution of methanol 8 mL and ethyl acetate 2 mL of the obtained methyl 2-(4-fluoroanilino)-4-(3-phenyl-1-propenyl)benzoate, 5% palladium-carbon 0.060 g was added, and it was stirred under hydrogen atmosphere at room temperature for 1 hour. Insoluble matter of the reaction mixture was filtrated, and the solvent was removed under reduced pressure. The obtained residue was refined by silica gel column chromatography [Trikonex company, Flash Tube 2008, eluent; hexane:ethyl acetate=10:1] to give methyl 2-(4-fluoroanilino)-4-(3-phenylpropyl)benzoate 0.10 g of colorless oil.

$^1$H-NMR (CDCl$_3$) δ value:

1.85-1.93(2H,m),2.53(2H,t,J=7.6 Hz),2.61(2H,t,J=7.6 Hz),3.88(3H,s),6.56(1H,d,J=8.3 Hz),6.86(1H,s),7.03-7.07 (2H,m),7.13-7.28(7H,m),7.87(1H,d,J=8.3 Hz),9.34(1H,s).

Example 79, 80

The compounds shown in Table 15 were obtained in the same manner as in Example 78.

TABLE 15

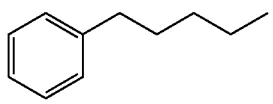

| Example No. | R$^4$—X$^2$ |
|---|---|
| 79 | 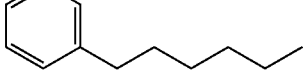 |
| 80 | 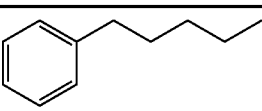 |

Methyl 2-(4-fluoroanilino)-4-(4-phenylbutyl)benzoate $^1$H-NMR (CDCl$_3$) δ value:

1.58-1.64(4H,m),2.51(2H,t,J=6.9 Hz),2.60(2H,t,J=7.2 Hz),3.88(3H,s),6.54(1H,dd,J=8.2,1.5 Hz),6.84(1H,d,1.5 Hz),7.00-7.05(2H,m),7.12-7.28(7H,m),7.85(1H,d,J=8.2 Hz),9.33(1H,s).

Methyl 2-(4-fluoroanilino)-4-(5-phenylpentyl)benzoate $^1$H-NMR (CDCl$_3$) δ value:

1.30-1.38(2H,m),1.51-1.65(4H,m),2.48(2H,t,J=7.8 Hz), 2.58(2H,t,J=7.7 Hz),3.88(3H,s),6.54(1H,dd,J=8.3,1.6 Hz), 6.85(1H,d,J=1.6 Hz),7.01-7.07(2H,m),7.13-7.28(7H,m), 7.86(1H,d,J=8.3 Hz),9.34(1H,s).

Example 81

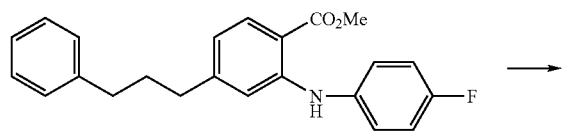 → 

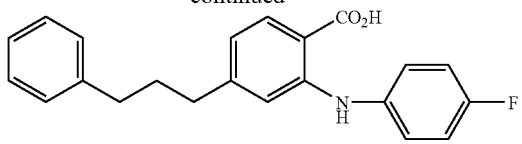

10% Sodium hydroxide aqueous solution 0.2 mL was added to a suspension of ethanol 2.0 mL of methyl 2-(4-fluoroanilino)-4-(3-phenylpropyl)benzoate 0.10 g at room temperature, and it was heated and refluxed for 2 hours. After the reaction mixture was cooled to room temperature, 1.0 mol/L hydrochloric acid and ethyl acetate were added to it. The organic layer was separated and collected, dried over anhydrous magnesium sulfate, and the solvent was removed under reduced pressure. Hexane was added to the obtained residue, and solid matter was filtrated to give 2-(4-fluoroanilino)-4-(3-phenylpropyl)benzoic acid 70 mg of white solid.

$^1$H-NMR (DMSO-d$_6$) δ value:

1.78-1.86(2H,m),2.48-2.58(4H,m),6.62(1H,d,J=8.1 Hz), 6.87(1H,s),7.15-7.30(9H,m),7.81(1H,d,J=8.1 Hz),9.53(1H, s),12.74-13.01(1H,broad).

Example 82, 83

The compounds shown in Table 16 were obtained in the same manner as in Example 81.

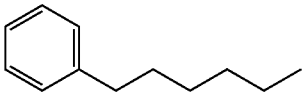

| Example No. | R$^4$—X$^2$ |
|---|---|
| 82 | |
| 83 | |

2-(4-Fluoroanilino)-4-(4-phenylbutyl)benzoic acid $^1$H-NMR (DMSO-d$_6$) δ value: δ 1.52-1.56(4H,m),2.49-2.56(4H,m),6.60(1H,d,J=8.3 Hz),6.87(1H,s),7.13-7.20(5H, m),7.23-7.28(4H,m),7.79(1H,d,J=8.3 Hz),9.51(1H,s),12.75-13.02(1H,broad).

2-(4-Fluoroanilino)-4-(5-phenylpentyl)benzoic acid $^1$H-NMR (DMSO-d$_6$) δ value:

1.23-1.31(2H,m),1.49-1.59(4H,m),2.45-2.55(4H,m),6.60 (1H,d,J=8.3 Hz),6.88(1H,d,J=2.7 Hz),7.10-7.28(9H,m),7.79 (1H,d,J=8.3 Hz),9.52(1H,s),12.77-12.98(1H,broad).

Example 84

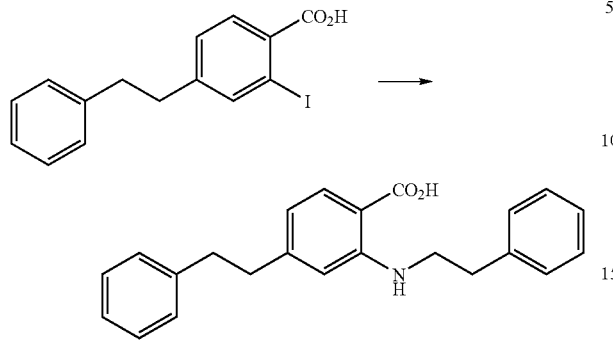

To dimethylsulfoxide 2.0 mL solution of 2-iodo-4-phenethylbenzoic acid 0.20 g were added phenethylamine 0.11 mL, copper (I) iodide 0.010 g, proline 0.013 g and potassium carbonate 0.16 g, and it was stirred at 60° C. for 4 hours. After the reaction mixture was cooled to room temperature, 1.0 mol/L hydrochloric acid and ethyl acetate were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate:acetic acid=90:10:1] to give 4-phenethyl-2-(phenethylamino)benzoic acid 0.12 g of white solid.

$^1$H-NMR (DMSO-$d_6$) δ value:
2.80-2.90(6H,m),3.37(2H,t,J=7.1 Hz),6.45(1H,dd,J=8.1, 1.3 Hz),6.57 (1H,s),7.14-7.33(10H,m),7.67(1H,d,J=8.1 Hz).

Example 85

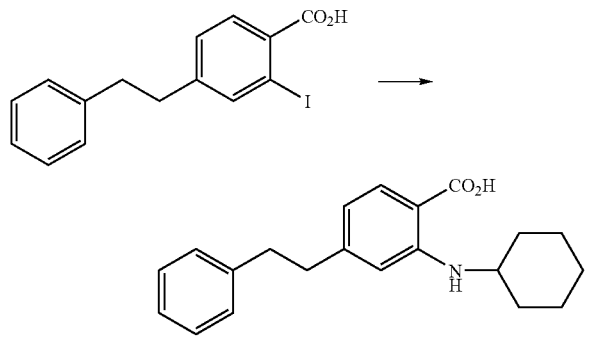

The following compound was obtained in the same manner as in Example 84.

2-(Cyclohexylamino)-4-phenethylbenzoic acid $^1$H-NMR (DMSO-$d_6$) δ value:
1.10-1.44(5H,m),1.52-1.72(3H,m),1.79-1.90(2H,m), 2.81-2.88(4H,m),3.26-3.36(1H,m),6.41(1H,d,J=8.2 Hz), 6.49(1H,s),7.15-7.28(5H,m),7.67(1H,d,J=8.2 Hz),7.70-7.90 (1H,broad),12.21-12.48(1H,broad).

Example 86

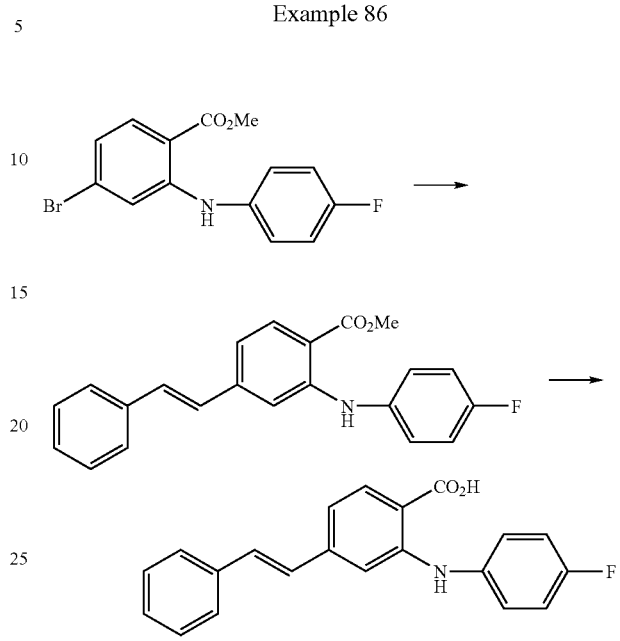

To a mixed solution of toluene 2.0 mL, ethanol 0.6 mL and water 0.2 mL of methyl 4-bromo-2-(4-fluoroanilino)benzoate 0.20 g were added (E)-2-(4,4,5,5-tetramethyl-1,3,2-dioxaborolan-2-yl)styrene 0.21 g, sodium hydrogen carbonate 0.18 g and tetrakis(triphenylphosphine)palladium(0) 40 mg, and it was heated and refluxed under nitrogen atmosphere for 2 hours. After the reaction mixture was cooled to room temperature, tetrakis(triphenylphosphine)palladium(0) 40 mg was added to it, and it was heated and refluxed under nitrogen atmosphere for 6 hours. After the reaction mixture was cooled to room temperature, ethyl acetate and water were added to it. The organic layer was separated and collected, dried over anhydrous magnesium sulfate after sequential washing with 1.0 mol/L hydrochloric acid, saturated sodium hydrogen carbonate aqueous solution and saturated sodium chloride aqueous solution, and the solvent was removed under reduced pressure. The obtained residue was refined by silica gel column chromatography [eluent; hexane:ethyl acetate=20:1] to give methyl 2-(4-fluoroanilino)-4-((E)-2-phenylvinyl)benzoate.

To a mixed solution of methanol 2 mL and tetrahydrofuran 2 mL of the obtained methyl 2-(4-fluoroanilino)-4-((E)-2-phenylvinyl)benzoate was added 2.0 mol/L sodium hydroxide aqueous solution 2.5 mL at room temperature, and it was stirred at room temperature for 4 hours. The solvent was removed under reduced pressure, water was added to it, and it was adjusted to pH4.0 with 1.0 mol/L hydrochloric acid. Solid matter was filtrated, and it was refined by silica gel column chromatography [eluent; hexane:ethyl acetate=2:1] to give 2-(4-fluoroanilino)-4-((E)-2-phenylvinyl)benzoic acid 58 mg.

$^1$H-NMR (DMSO-$d_6$) δ value:
7.11(1H,dd,J=8.4,1.3 Hz),7.18-7.38(10H,m),7.61-7.63 (2H,m),7.89(1H,d,J=8.4 Hz),9.60(1H,s),12.97-13.05(1H, broad).

Example 87

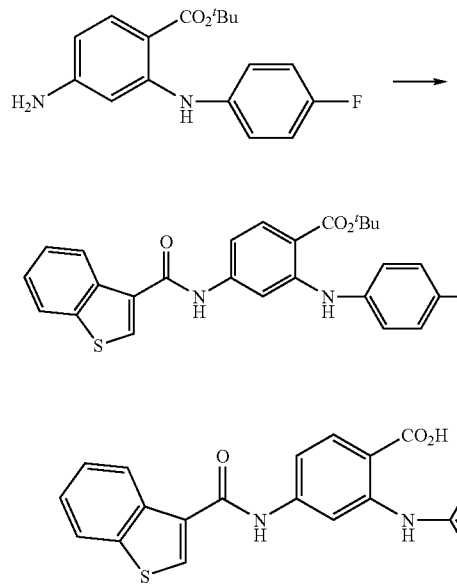

To dichloromethane 3.0 mL solution of tert-butyl 4-amino-2-(4-fluoroanilino)benzoate 40 mg were added triethylamine 0.064 mL, benzothiophene-3-carbonyl chloride 55 mg and dichloromethane 1.5 mL at room temperature, and it was stirred at same temperature for 2 hours. Aminomethylated-polystyrene 250 mg was added to the reaction mixture, and it was stirred at room temperature for 4 hours. Saturated sodium hydrogen carbonate aqueous solution was added to the reaction mixture, and insoluble matter was filtrated. The organic layer was separated and collected, and the solvent was removed under reduced pressure. The obtained residue was refined by silica gel column chromatography [Trikonex company, Flash Tube 2008, eluent; hexane:ethyl acetate=4:1] to give tert-butyl 4-(benzothiophene-3-carboxamido)-2-(4-fluoroanilino)benzoate.

Trifluoroacetic acid 5 mL was added to the obtained tert-butyl 4-(benzothiophene-3-carboxamido)-2-(4-fluoroanilino)benzoate, and it was stirred at room temperature for 1 hour. The solvent was removed under reduced pressure, diisopropyl ether was added to the obtained residue, and solid matter was filtrated to give 4-(benzothiophene-3-carboxamido)-2-(4-fluoroanilino)benzoic acid 24 mg of white solid.

$^1$H-NMR (DMSO-$d_6$) δ value:
7.21-7.36(5H,m),7.44-7.48(2H,m),7.65(1H,d,J=2.0 Hz), 7.89(1H,d,J=8.8 Hz),8.07(1H,dd,J=6.7,1.8 Hz),8.34-8.36 (1H,m),8.56(1H,s),9.66(1H,s),10.42(1H,s),12.80-12.90(1H, broad).

Example 88-91

The compounds shown in Table 17 were obtained in the same manner as in Example 87.

TABLE 17

| Example No. | R$^4$—X$^2$ |
|---|---|
| 88 | 2,3-dihydrobenzo[1,4]dioxin-6-carbonyl |
| 89 | 2,2-diphenylacetyl |
| 90 | cinnamoyl |
| 91 | benzenesulfonyl |

4-(2,3-Dihydrobenzo[1,4]dioxin-6-carboxamide)-2-(4-fluoroanilino)benzoic acid $^1$H-NMR (DMSO-$d_6$) δ value:
4.28-4.32(4H,m),6.97(1H,d,J=8.3 Hz),7.20-7.33(5H,m), 7.44-7.48(2H,m),7.69(1H,d,J=2.0 Hz),7.85(1H,d,J=8.8 Hz), 9.65(1H,s),10.12(1H,s),12.78-12.85(1H,broad).

4-(2,2-Diphenylacetamido)-2-(4-fluoroanilino)benzoic acid $^1$H-NMR (DMSO-$d_6$) δ value:
5.18(1H,s),7.08(1H,dd,J=8.8,2.0 Hz),7.20-7.35(14H,m), 7.43(1H,d,J=2.0 Hz),7.82(1H,d,J=8.8 Hz),9.61(1H,s),10.48 (1H,s),12.79-12.85(1H,broad).

4-(Cinnamamido)-2-(4-fluoroanilino)benzoic acid $^1$H-NMR (DMSO-$d_6$) δ value:
6.79(1H,d,J=15.6 Hz),7.07(1H,dd,J=8.8,2.0 Hz),7.22-7.26(2H,m),7.30-7.34(2H,m),7.39-7.47(3H,m),7.56-7.63 (4H,m),7.86(1H,d,J=8.8 Hz),9.64(1H),10.30(1H,s),12.76-12.84(1H,broad).

4-(Benzenesulfonamido)-2-(4-fluoroanilino)benzoic acid $^1$H-NMR (DMSO-$d_6$) δ value:
6.48(1H,dd,J=8.6,2.0 Hz),6.76(1H,d,J=2.0 Hz),7.07-7.11 (2H,m),7.21-7.25(2H,m),7.57-7.61(2H,m),7.64-7.68(1H, m),7.71-7.73(3H,m),10.57-10.66(1H,broad).

Example 92

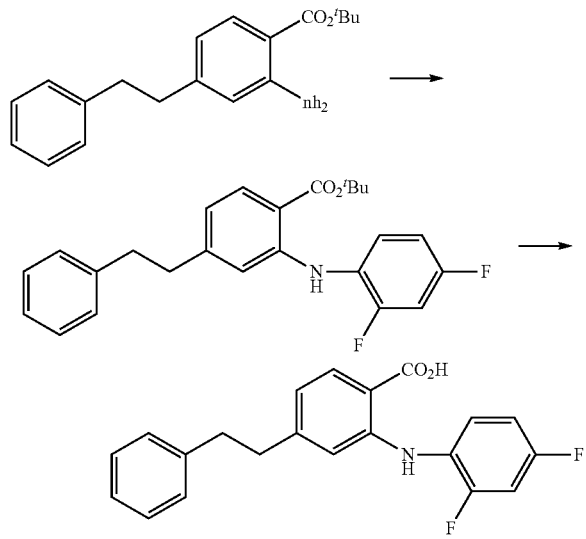

To toluene 3.0 mL solution of tert-butyl 2-amino-4-phenethyl benzoate 0.10 g were added 2,4-difluoro-1-iodobenzene 0.10 mL, cesium carbonate 0.22 g, tris(dibenzylideneacetone)dipalladium(0) 3 mg and 2-dicyclohexylphosphino-2',4',6'-triisopropyl biphenyl 8 mg, and it was stirred at 110° C. for 24 hours. After the reaction mixture was cooled to room temperature, tris(dibenzylideneacetone)dipalladium(0) 3 mg and 2-dicyclohexylphosphino-2',4',6'-triisopropylbiphenyl 8 mg were added to it, and it was stirred at 110° C. for 24 hours. After the reaction mixture was cooled to room temperature, ethyl acetate and 10% citric acid aqueous solution were added to it. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate:acetic acid=20:1:1] to give tert-butyl 2-(2,4-difluoroanilino)-4-phenethylbenzoate.

Trifluoroacetic acid 10 mL was added to the obtained tert-butyl 2-(2,4-difluoroanilino)-4-phenethylbenzoate, and it was stirred at room temperature for 2 hours. The solvent was removed under reduced pressure, methanol was added to the obtained residue, and solid matter was filtrated to give 2-(2,4-difluoroanilino)-4-phenethylbenzoic acid 59 mg of white solid.

$^1$H-NMR (DMSO-$d_6$) δ value:
2.82(4H,s),6.65(1H,s),6.70(1H,dd,J=8.1,1.5 Hz),7.05 (1H,t dd,J=8.6,2.8,1.3 Hz),7.14-7.21(3H,m),7.23-7.30(3H, m),7.37(1H,ddd,J=11.1,8.9,2.8 Hz),7.81(1H,d,J=8.1 Hz), 9.46(1H,s),12.85-13.20(1H,broad).

Example 93-100

The compounds shown in Table 18 were obtained in the same manner as in Example 92.

TABLE 18

| Example No. | R³ |
|---|---|
| 93 | 2,3-dihydro-1,4-benzodioxin-6-yl (methyl-substituted) |
| 94 | 3-fluoro-4-methylphenyl (methyl-substituted) |
| 95 | 3-nitrophenyl (methyl-substituted) |
| 96 | 2-nitrophenyl (methyl-substituted) |
| 97 | 2-methylphenyl (methyl-substituted) |
| 98 | 4-methoxyphenyl (methyl-substituted) |
| 99 | 3-methoxyphenyl (methyl-substituted) |
| 100 | phenyl (methyl-substituted) |

2-((2,3-Dihydrobenzo[1,4]dioxin-6-yl)amino)-4-phenethylbenzoic acid $^1$H-NMR (DMSO-$d_6$) δ value:
2.74-2.86(4H,m),4.21-4.28(4H,m),6.54(1H,dd,J=8.7,2.5 Hz),6.60(1H,dd,J=8.3,1.4 Hz),6.67(1H,d,J=2.5 Hz),6.78-6.83(2H,m),7.14-7.20(3H,m),7.22-7.29(2H,m),7.76(1H,d,J=8.3 Hz),9.39(1H,s),12.81(1H,s).

2-(3-Fluoro-4-methylanilino)-4-phenethylbenzoic acid $^1$H-NMR (DMSO-$d_6$) δ value:
2.19(3H,d,J=1.0 Hz),2.84(4H,s),6.71(1H,dd,J=8.2,1.2 Hz),6.79 (1H,dd,J=8.2,2.1 Hz),6.91(1H,dd,J=11.6,2.1 Hz),6.96(1H, d,J=1.2 Hz),7.14-7.22(4H,m),7.23-7.30(2H,m),7.81(1H,d,J=8.3 Hz),9.56(1H,s),12.95(1H,s).

2-(3-Nitroanilino)-4-phenethylbenzoic acid $^1$H-NMR (DMSO-$d_6$) δ value:
2.88(4H,s),6.83(1H,dd,J=8.0,1.5 Hz),7.16-7.22(4H,m),7.23-7.30(2H,m),7.45(1H,ddd,J=8.2,2.2,1.0 Hz),7.53(1H,t,J=8.1 Hz),7.79(1H,ddd,J=8.1,2.2,1.0 Hz),7.85(1H,d,J=8.0 Hz),7.99 (1H,t,J=2.2 Hz),9.69(1H,s),13.10(1H,s).

2-(2-Nitroanilino)-4-phenethylbenzoic acid $^1$H-NMR (DMSO-$d_6$) δ value:
2.89(4H,s),6.99(1H,dd,J=8.2,1.5 Hz),7.04-7.08(1H,m),7.15-7.31(7H,m),7.51-7.55(1H,m),7.89(1H,d,J=8.2 Hz),8.11(1H,dd,J=8.4,1.6 Hz),11.06 (1H,s),13.26(1H,s).

2-(2-Methylanilino)-4-phenethylbenzoic acid $^1$H-NMR (DMSO-$d_6$) δ value:
2.16(3H,s),2.74-2.86(4H,m),6.62-6.70(2H,m),7.00-7.10(2H,m),7.12-7.21(4H,m),7.22-7.30(3H,m),7.80(1H,d,J=8.0 Hz),9.48(1H,s),12.75-13.00(1H,broad).

2-(4-Methoxyanilino)-4-phenethylbenzoic acid $^1$H-NMR (DMSO-$d_6$) δ value:
2.72-2.86(4H,m),3.76(3H,s),6.59(1H,dd,J=8.2,1.3 Hz),6.69(1H,d, J=1.3 Hz),6.88-6.94(2H,m),6.99-7.05(2H,m),7.12-7.30(5H,m),7.77(1H,d,J=8.2 Hz),9.41(1H,s),12.60-13.00(1H,broad).

2-(3-Methoxyanilino)-4-phenethylbenzoic acid $^1$H-NMR (DMSO-$d_6$) δ value:
2.84(4H,s),3.74(3H,s),6.59-6.76(4H,m),7.06(1H,s),7.15-7.30(6H,m),7.81(1H,d,J=8.3 Hz),9.58(1H,s),12.93(1H,s).

2-Anilino-4-phenethylbenzoic acid $^1$H-NMR (DMSO-$d_6$) δ value:
2.78-2.89(4H,m),6.69(1H,dd,J=8.2,1.3 Hz),6.95(1H,s),7.00-7.08(3H,m),7.14-7.34(7H,m),7.81(1H,d,J=8.2 Hz),9.60(1H,s),12.80-13.05(1H,broad).

Example 101

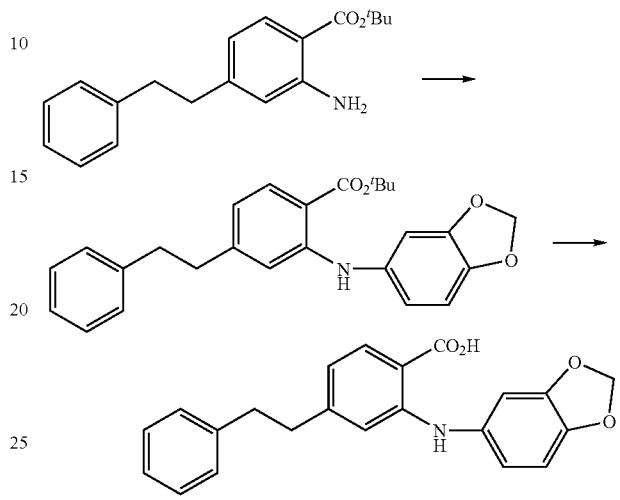

To toluene 3.0 mL solution of tert-butyl 2-amino-4-phenethylbenzoate 0.10 g were added 1-iodo-3,4-methylenedioxybenzene 0.14 g,cesium carbonate 0.22 g, tris(dibenzylideneacetone)dipalladium(0) 3 mg and 2-dicyclohexylphosphino-2',4',6'-triisopropylbiphenyl 8 mg,and it was stirred at 110° C. for 24 hours. After the reaction mixture was cooled to room temperature, tris(dibenzylideneacetone)dipalladium(0) 3 mg and 2-dicyclohexylphosphino-2',4',6'-triisopropylbiphenyl 8 mg were added to it, and it was stirred at 110° C. for 24 hours. After the reaction mixture was cooled to room temperature, ethyl acetate and 10% citric acid aqueous solution were added to it. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-((benzo-1,3-dioxol-5-yl)amino)-4-phenethylbenzoate. Trifluoroacetic acid 10 mL was added to the obtained tert-butyl 2-((benzo-1,3-dioxol-5-yl)amino)-4-phenethylbenzoate, and it was stirred at room temperature for 2 hours. The solvent was removed under reduced pressure, and the obtained residue was refined by reversed-phase silica gel column chromatography [eluent; 80-100% acetonitrile/0.1% trifluoroacetic acid aqueous solution] to give 2-((benzo-1,3-dioxol-5-yl)amino)-4-phenethylbenzoic acid 12 mg of white solid.

$^1$H-NMR (DMSO-$d_6$) δ value:
2.74-2.86(4H,m),6.03(2H,s),6.54(1H,dd,J=8.1,2.1 Hz),6.61(1H,d d,J=8.1,1.5 Hz),6.74(2H,d,J=2.1 Hz),6.86(1H,d,J=8.1 Hz),7.13-7.20(3H,m),7.22-7.29(2H,m),7.77(1H,d,J=8.1 Hz),9.40(1H,s),12.70-12.95(1H,broad).

Example 102, 103

The compounds shown in Table 19 were obtained in the same manner as in Example 101.

TABLE 19

| Example No. | R³ |
|---|---|
| 102 | 3-hydroxyphenyl |
| 103 | 4-acetylphenyl (Ac) |

2-((3-Hydroxyphenyl)amino)-4-phenethylbenzoic acid

¹H-NMR (DMSO-$d_6$) δ value:
2.78-2.89(4H,m),6.45(1H,dd,J=8.1,1.7 Hz),6.47-6.52 (1H,m),6.57-6.60(1H,m),6.66(1H,dd,J=8.3,1.2 Hz),7.06 (1H,s),7.09(1H,t, J=7.9 Hz),7.15-7.28(5H,m),7.79(1H,d, J=8.2 Hz),9.43(1H,s),9.55(1H,s),12.80-13.05(1H,broad).

2-((4-Acetylphenyl)amino)-4-phenethylbenzoic acid

¹H-NMR (DMSO-$d_6$) δ value:
2.52(3H,s),2.90(4H,s),6.86(1H,d,J=8.1 Hz),7.09(2H,d, J=8.6 Hz),7.16-7.25(4H,m),7.26-7.32(2H,m),7.82-7.90(3H, m),9.79(1H,s),12.95-13.30(1H,broad).

Example 104

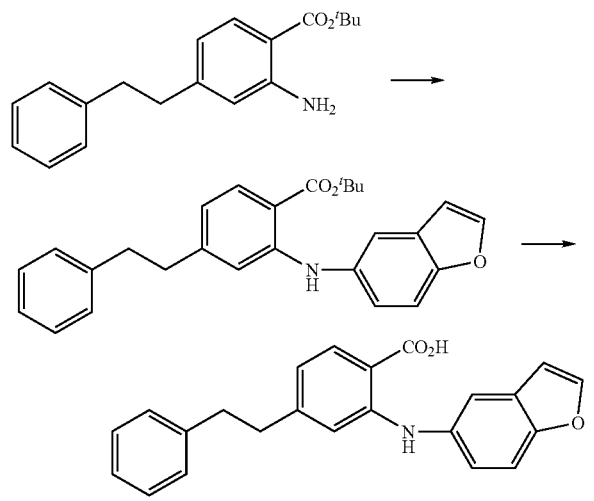

To toluene 3.0 mL suspension of tert-butyl 2-amino-4-phenethylbenzoate 0.10 g, 2-dicyclohexylphosphino-2',4',6'-triisopropylbiphenyl 8 mg, tris(dibenzylideneacetone)dipalladium(0) 3 mg and cesium carbonate 0.22 g was added 5-bromobenzofuran 0.19 g, and it was heated and refluxed for 24 hours. After the reaction mixture was cooled to room temperature, 2-dicyclohexylphosphino-2',4',6'-triisopropylbiphenyl 8 mg and tris(dibenzylideneacetone)dipalladium(0) 3 mg were added to it, and it was heated and refluxed for 24 hours. After the reaction mixture was cooled to room temperature, 2-dicyclohexylphosphino-2',4',6'-triisopropylbiphenyl 8.0 mg and tris(dibenzylideneacetone)dipalladium(0) 3 mg were added to it, and it was heated and refluxed for 24 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=20:1] to give tert-butyl 2-((benzofuran-5-yl)amino)-4-phenethylbenzoate. Trifluoroacetic acid 3.0 mL was added to the obtained tert-butyl 2-((benzofuran-5-yl)amino)-4-phenethylbenzoate, and it was stirred at room temperature for 3 hours. The solvent was removed under reduced pressure, the obtained residue was refined by silica gel column chromatography [Trikonex company, Flash Tube 2008, eluent; hexane:ethyl acetate:acetic acid=30:10:1] to give 2-((benzofuran-5-yl)amino)-4-phenethylbenzoic acid 21 mg of white solid.

¹H-NMR (DMSO-$d_6$) δ value:
2.73-2.85(4H,m),6.63(1H,dd,J=8.2,1.2 Hz),6.78(1H,s), 6.92(1H,d d,J=2.2,0.8 Hz),7.03(1H,dd,J=8.7,2.2 Hz),7.11-7.22(3H,m),7.22-7.28(2H,m),7.38(1H,d,J=2.0 Hz),7.55(1H, d,J=8.7Hz),7.80(1H,d,J=8.2 Hz),8.00(1H,d,J=2.0 Hz),9.53-9.63(1H,broad),12.76-12.92(1H,broad).

Example 105

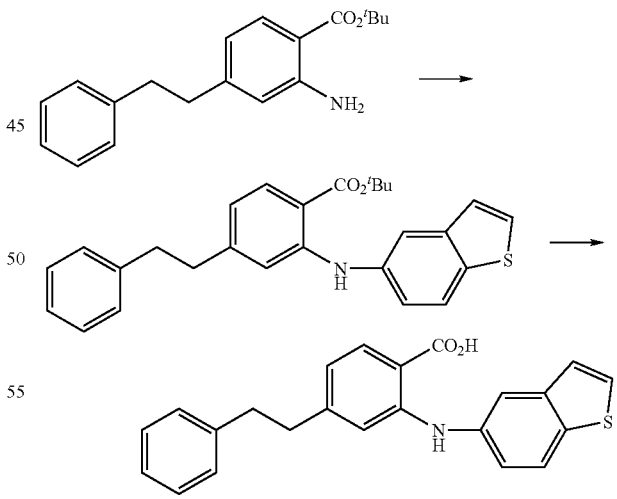

The following compound was obtained in the same manner as in Example 104.

2-((Benzothiophen-5-yl)amino)-4-phenethylbenzoic acid

¹H-NMR (DMSO-$d_6$) δ value:

2.76-2.88(4H,m),6.67(1H,d,J=7.3 Hz),6.95(1H,s),7.10 (1H,dd,J=8.7, 2.0 Hz),7.13-7.29(5H,m),7.38(1H,d,J=5.4 Hz),7.63(1H,d,J=2.0 Hz),7.77(1H,d,J=5.4 Hz),7.82(1H,d, J=8.1 Hz),7.92(1H,d,J=8.7 Hz),9.67-9.74(1H,broad).

Example 106

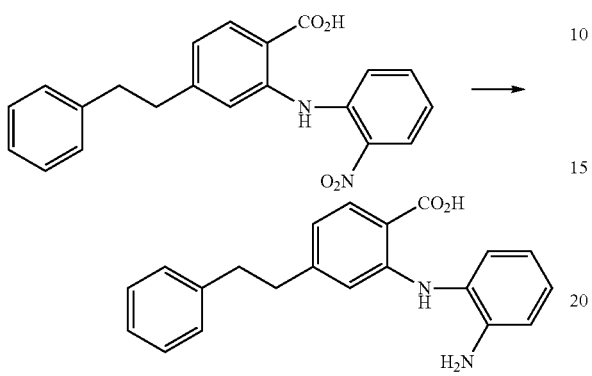

To a mixed solution of methanol 2.0 mL and ethyl acetate 1.0 mL of 2-(2-nitroanilino)-4-phenethylbenzoic acid 20 mg was added 5% palladium-carbon 8 mg, and it was stirred under hydrogen atmosphere at room temperature for 3 hours. Insoluble matter was filtrated, and the solvent was removed under reduced pressure. Methanol was added to the obtained residue, and solid matter was filtrated to give 2-((2-aminophenyl)amino)-4-phenethylbenzoic acid 13 mg of white solid.

$^1$H-NMR (DMSO-$d_6$) δ value:
2.70-2.82(4H,m),4.60-5.00(2H,broad),6.48(1H,s),6.54-6.60(2H,m),6.79(1H,dd,J=8.1,1.5 Hz),6.88-6.95(2H,m), 7.12-7.19(3H,m),7.21-7.27(2H,m),7.77(1H,d,J=8.1 Hz), 9.02(1H,s).

Example 107

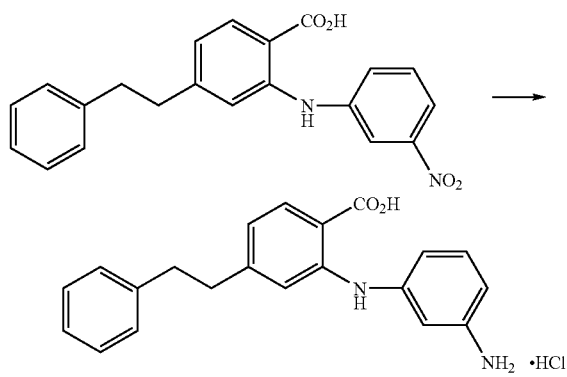

To a mixed solution of methanol 4.0 mL and ethyl acetate 2.0 mL of 2-(3-nitroanilino)-4-phenethylbenzoic acid 40 mg was added 5% palladium-carbon 20 mg, and it was stirred under hydrogen atmosphere at room temperature for 6 hours. Insoluble matter was filtrated, and the solvent was removed under reduced pressure. 4.0 mol/L hydrogen chloride dioxane solution 0.028 mL was added to ethyl acetate 5 mL solution of the obtained residue under ice cooling. Solid matter was filtrated to give 2-((3-aminophenyl)amino)-4-phenethylbenzoate acid hydrochloride 26 mg of brown solid.

$^1$H-NMR (DMSO-$d_6$) δ value:
2.87(4H,s),6.75(1H,dd,J=8.1,1.2 Hz),6.88(1H,d,J=7.6 Hz),6.95 (1H,d,J=8.1 Hz),7.10-7.35(8H,m),7.83(1H,d,J=8.1 Hz),9.68(1H,s).

Example 108

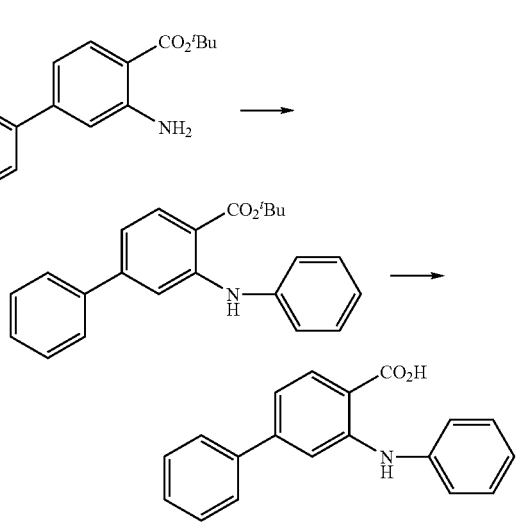

Iodobenzene 0.10 mL was added to toluene 3.0 mL suspension of tert-butyl 2-amino-4-phenylbenzoate 0.10 g, rac-2,2'-bis(diphenylphosphino)-1,1'-binaphthyl 2.3 mg, palladium acetate 0.8 mg and cesium carbonate 0.24 g, and it was heated and refluxed for 24 hours. After the reaction mixture was cooled to room temperature, rac-2,2'-bis(diphenylphosphino)-1,1'-binaphthyl 2.3 mg and palladium acetate 0.8 mg were added to it, and it was heated and refluxed for 24 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=20:1] to give tert-butyl 2-anilino-4-phenylbenzoate.

Trifluoroacetic acid 3.0 mL solution of the obtained tert-butyl 2-anilino-4-phenylbenzoate was stirred at room temperature for 3 hours. The solvent of reaction mixture was removed under reduced pressure, and the obtained residue was refined by silica gel column chromatography [Trikonex company, Flash Tube 2008, eluent; hexane:ethyl acetate:acetic acid=30:10:1] to give 2-anilino-4-phenylbenzoic acid 8 mg of pale yellow solid.

$^1$H-NMR (DMSO-$d_6$) δ value:
7.06-7.12(2H,m),7.32-7.48(8H,m),7.58-7.60(2H,m),7.99 (1H,d,J=8.3 Hz),9.71(1H,s),13.10-13.14(1H,broad).

Example 109-115

The compounds shown in Table 20 were obtained in the same manner as in Example 108.

TABLE 20

Structure: 4-phenyl-2-(NHR³)-benzoic acid (biphenyl with CO₂H and NH-R³)

| Example No. | R³ |
|---|---|
| 109 | 2,4-difluorophenyl |
| 110 | 3-fluoro-4-methylphenyl |
| 111 | 3-nitrophenyl |
| 112 | 2-nitrophenyl |
| 113 | 4-acetylphenyl |
| 114 | 2-methylphenyl |
| 115 | 3-methoxyphenyl |

2-(2,4-Difluoroanilino)-4-phenylbenzoic acid

¹H-NMR (DMSO-d₆) δ value:
7.05-7.16(3H,m),7.38-7.47(4H,m),7.56-7.66(3H,m),7.99(1H,d,J=8.1 Hz),9.56(1H,s),13.19-13.25(1H,broad).

2-(3-Fluoro-4-methylanilino)-4-phenylbenzoic acid

¹H-NMR (DMSO-d₆) δ value:
2.21(3H,s),7.08-7.15(3H,m),7.26(1H,t,J=8.5 Hz),7.38-7.48(4H,m),7.60(2H,d,J=7.3 Hz),7.99(1H,d,J=8.3 Hz),9.66(1H,s),13.11-13.19(1H,broad).

2-(3-Nitroanilino)-4-phenylbenzoic acid

¹H-NMR (DMSO-d₆) δ value:
7.25(1H,d,J=8.3 Hz),7.40-7.50(3H,m),7.59-7.67(4H,m),7.77(1H,dd,J=7.9,1.8 Hz),7.83(1H,dd,J=8.0,2.0 Hz),8.04(1H,d,J=8.3 Hz),8.11(1H,s),9.79(1H,s),13.23-13.35(1H,broad).

2-(2-Nitroanilino)-4-phenylbenzoic acid

¹H-NMR (DMSO-d₆) δ value:
7.11(1H,t,J=7.6 Hz),7.38(1H,dd,J=8.5,1.5 Hz),7.40-7.44(1H,m),7.48(2H,t,J=7.4 Hz),7.64-7.69(3H,m),7.73(1H,s),7.79(1H,d,J=8.6 Hz),8.06(1H,d,J=8.3 Hz),8.15(1H,dd,J=8.4,1.3 Hz),11.14(1H,s),13.37-13.51(1H,broad).

2-((4-Acetylphenyl)amino)-4-phenylbenzoic acid

¹H-NMR (DMSO-d₆) δ value:
2.52(3H,s),7.26(1H,dd,J=8.3,1.6 Hz),7.37-7.44(3H,m),7.49(2H,t,J=7.5 Hz),7.67-7.69(3H,m),7.94(2H,d,J=8.5 Hz),8.04(1H,d,J=8.3 Hz),9.89(1H,s),13.27-13.36(1H,broad).

2-(2-Methylanilino)-4-phenylbenzoic acid

¹H-NMR (DMSO-d₆) δ value:
2.24(3H,s),7.01-7.11(3H,m),7.25(1H,t,J=7.1 Hz),7.32-7.46(5H,m),7.52-7.54(2H,m),7.99(1H,d,J=8.3 Hz),9.59(1H,s),13.05-13.13(1H,broad).

2-(3-Methoxyanilino)-4-phenylbenzoic acid

¹H-NMR (DMSO-d₆) δ value:
3.32(3H,s),6.67(1H,dd,J=8.3,2.3 Hz),6.85-6.87(1H,m),6.91-6.93(1H,m),7.07-7.09(1H,m),7.28(1H,t,J=8.2 Hz), 7.38-7.48(4H,m),7.59(2H,d,J=7.8 Hz),7.99(1H,d,J=8.3 Hz), 9.68(1H,s),13.08-13.18(1H,broad).

Example 116

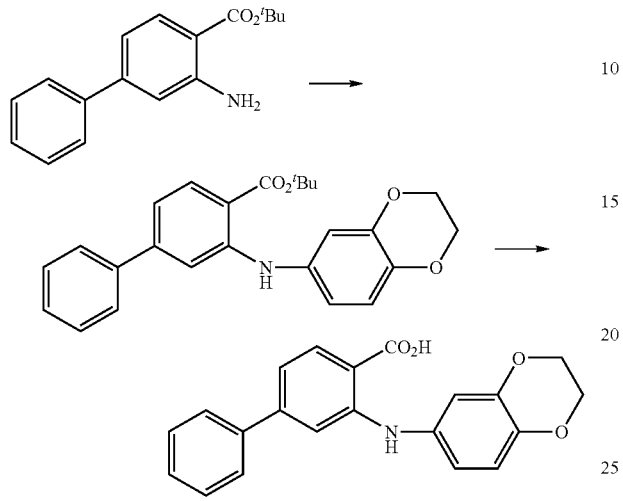

To toluene 3.0 mL suspension of tert-butyl 2-amino-4-phenylbenzoate 0.10 g, rac-2,2'-bis(diphenylphosphino)-1,1'-binaphthyl 2.3 mg, palladium acetate 0.8 mg and cesium carbonate 0.24 g was added 2,3-dihydro-6-iodobenzo[1,4]dioxin 0.24 g, and it was heated and refluxed for 24 hours. After the reaction mixture was cooled to room temperature, rac-2,2'-bis(diphenylphosphino)-1,1'-binaphthyl 2.3 mg and palladium acetate 0.8 mg were added, and it was heated and refluxed for 24 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((2,3-dihydrobenzo[1,4]dioxin-6-yl)amino)-4-phenylbenzoate.

Trifluoroacetic acid 3.0 mL solution of the obtained tert-butyl 2-((2,3-dihydrobenzo[1,4]dioxin-6-yl)amino)-4-phenylbenzoate was stirred at room temperature for 3 hours. The solvent was removed under reduced pressure, and the obtained residue was refined by reversed-phase silica gel column chromatography [eluent; 70-100% acetonitrile/0.1% trifluoroacetic acid aqueous solution] to give 2-((2,3-dihydrobenzo[1,4]dioxin-6-yl)amino)-4-phenylbenzoic acid 5 mg of a yellow solid.

$^1$H-NMR (DMSO-$d_6$) δ value:
4.24(4H,s),6.79-6.82(2H,m),6.88(1H,d,J=8.6 Hz),6.99 (1H,dd,J=8.3,1.7 Hz),7.21 (1H,s),7.37-7.41(1H,m),7.43-7.47(2H,m),7.53-7.55(2H,m),7.95(1H,d,J=8.3 Hz),9.46-9.54(1H,broad),12.94-13.07(1H,broad).

Example 117, 118

The compounds shown in Table 21 were obtained in the same manner as in Example 116.

TABLE 21

| Example No. | $R^3$ |
|---|---|
| 117 | ![4-methylphenyl-pyrazole] |
| 118 | ![benzo-1,3-dioxol-5-yl] |

4-Phenyl-2-(4-(1H-pyrazol-1-yl)anilino)benzoic acid $^1$H-NMR (DMSO-$d_6$) δ value:
6.53(1H,t,J=2.1 Hz),7.10(1H,dd,J=8.3,1.7 Hz),7.38-7.48 (6H,m),7.60-7.63(2H,m),7.73(1H,d,J=1.7 Hz),7.83-7.85 (2H,m),8.00(1H,d,J=8.3 Hz),8.46(1H,d,J=2.4 Hz),9.75(1H, s),13.12-13.20(1H,s).

2-((Benzo-1,3-dioxol-5-yl)amino)-4-phenylbenzoic acid $^1$H-NMR (DMSO-$d_6$) δ value:
6.04(2H,s),6.79(1H,dd,J=8.3,2.1 Hz),6.93(1H,d,J=8.3 Hz),6.96 (1H,d,J=2.1 Hz),6.99(1H,dd,J=8.3,1.6 Hz),7.17 (1H,s),7.37-7.40(1H,m),7.45(2H,t,J=7.3 Hz),7.53-7.55(2H, m),7.95(1H,d,J=8.3 Hz),9.48-9.56(1H,broad).

Example 119

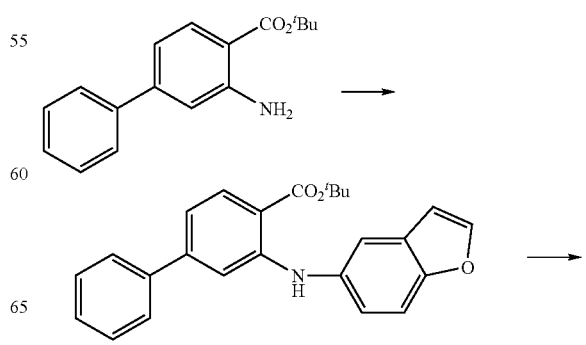

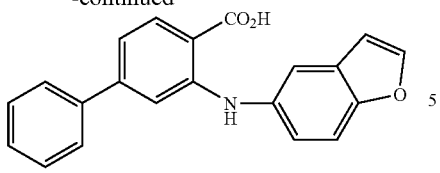

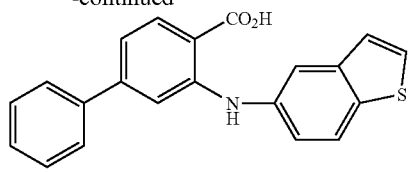

To toluene 3.0 mL suspension of tert-butyl 2-amino-4-phenylbenzoate 0.10 g, 2-dicyclohexylphosphino-2',4',6'-triisopropylbiphenyl 9 mg, tris(dibenzylideneacetone)dipalladium(0) 3 mg and cesium carbonate 0.24 g was added 5-bromobenzofuran 0.18 g, and it was heated and refluxed for 24 hours. After the reaction mixture was cooled to room temperature, 2-dicyclohexylphosphino-2',4',6'-triisopropylbiphenyl 9 mg and tris(dibenzylideneacetone)dipalladium(0) 3 mg were added to it, and it was heated and refluxed for 24 hours. After the reaction mixture was cooled to room temperature, 2-dicyclohexylphosphino-2',4',6'-triisopropylbiphenyl 9 mg and tris(dibenzylideneacetone)dipalladium(0) 3 mg were added to it, and it was heated and refluxed for 24 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=30:1] to give tert-butyl 2-((benzofuran-5-yl)amino)-4-phenylbenzoate. Trifluoroacetic acid 3.0 mL solution of the obtained tert-butyl 2-((benzofuran-5-yl)amino)-4-phenylbenzoate was stirred at room temperature for 3 hours. The solvent of reaction mixture was removed under reduced pressure, and the obtained residue was refined by silica gel column chromatography [Trikonex company, Flash Tube 2008, eluent; hexane:ethyl acetate:acetic acid=30:10:1] to give 2-((benzofuran-5-yl)amino)-4-phenylbenzoic acid 42 mg.

$^1$H-NMR (DMSO-$d_6$) δ value:
6.95(1H,dd,J=2.2,0.7 Hz),7.01(1H,dd,J=8.3,1.7 Hz),7.23 (1H, d,J=1.4 Hz),7.28(1H,dd,J=8.8,2.2 Hz),7.34-7.46(3H, m),7.52-7.54(2H,m),7.61-7.64(2H,m),7.98(1H,d,J=8.3 Hz), 8.01(1H,d,J=2.2 Hz),9.64-9.76(1H,broad),12.88-13.20(1H, broad).

Example 120

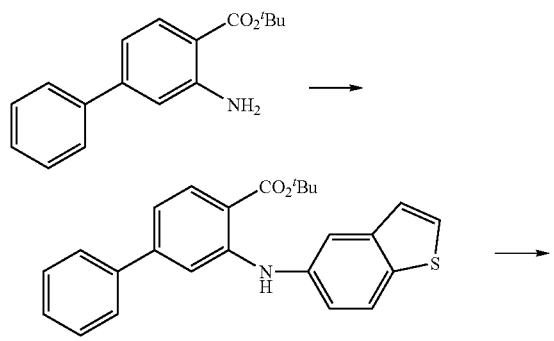

The following compound was obtained in the same manner as in Example 119.

2-((Benzothiophen-5-yl)amino)-4-phenylbenzoic acid $^1$H-NMR (DMSO-$d_6$) δ value:
7.06(1H,dd,J=8.3,1.7 Hz),7.35-7.45(6H,m),7.57(2H,d, J=7.3 Hz),7.78(1H,d,J=5.4 Hz),7.84(1H,d,J=1.9 Hz),8.00 (2H,d,J=8.3 Hz),9.77-9.95(1H,broad).

Example 121

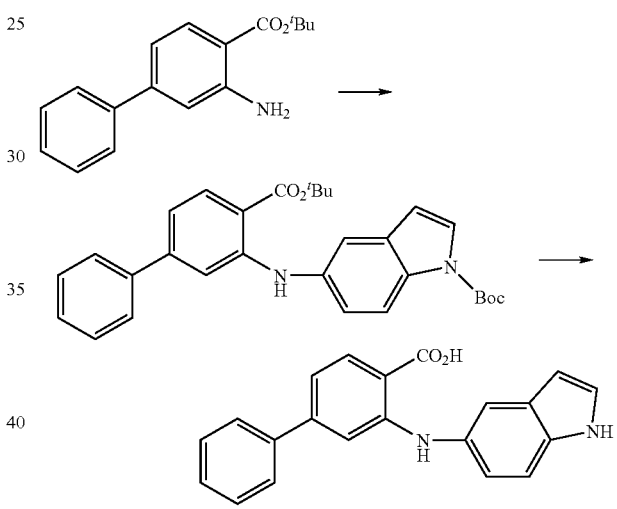

To toluene 3.0 mL suspension of tert-butyl 2-amino-4-phenylbenzoate 0.20 g, 2-dicyclohexylphosphino-2',4',6'-triisopropylbiphenyl 17 mg, tris(dibenzylideneacetone)dipalladium(0) 7 mg, palladium acetate 2 mg and cesium carbonate 0.48 g was added tert-butyl 5-bromoindol-1-carboxylate 0.55 g, and it was heated and refluxed for 8 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane: ethyl acetate=20:1] to give tert-butyl 2-((1-(tert-butoxycarbonyl)-1H-indol-5-yl)amino)-4-phenylbenzoate.

Trifluoroacetic acid 5 mL solution of the obtained tert-butyl 2-((1-(tert-butoxycarbonyl)-1H-indol-5-yl)amino)-4-phenylbenzoate was stirred at room temperature for 3 hours. The solvent was removed under reduced pressure, the obtained residue was refined by reversed-phase silica gel column chromatography [eluent; 50-100% acetonitrile/0.1% trifluoroacetic acid aqueous solution] to give 2-((1H-indol-5-yl)amino)-4-phenylbenzoic acid 8 mg of yellow solid.

$^1$H-NMR (DMSO-$d_6$) δ value:

6.42(1H,s),6.93(1H,dd,J=8.4,1.3 Hz),7.05(1H,dd,J=8.6, 1.7 Hz),7.12(1H,s),7.32-7.48(8H,m),7.95(1H,d,J=8.3 Hz), 9.60(1H,s),11.18(1H,s),12.77-13.01(1H,broad).

Example 122

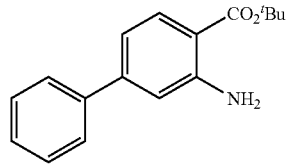

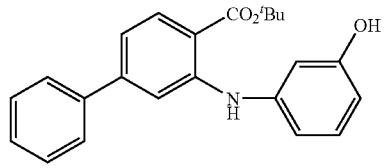

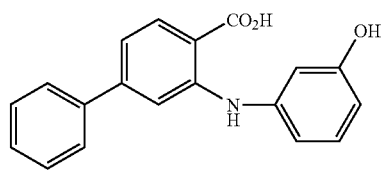

To toluene 3.0 mL suspension of tert-butyl 2-amino-4-phenylbenzoate 0.20 g, 2-dicyclohexylphosphino-2',4',6'-triisopropylbiphenyl 17 mg, tris(dibenzylideneacetone)dipalladium(0) 7 mg, palladium acetate 2 mg and cesium carbonate 0.48 g was added 3-iodophenol 0.41 g, and it was heated and refluxed for 12 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B (spherical type), eluent; hexane:ethyl acetate=6:1] to give tert-butyl 2-((3-hydroxyphenyl)amino)-4-phenylbenzoate.

Trifluoroacetic acid 5.0 mL solution of the obtained tert-butyl 2-((3-hydroxyphenyl)amino)-4-phenylbenzoate was stirred at room temperature for 3 hours. The solvent was removed under reduced pressure, hexane and diisopropyl ether were added to obtained residue, solid matter was filtrated to give 2-((3-hydroxyphenyl)amino)-4-phenylbenzoic acid 15 mg of yellow solid.

$^1$H-NMR (DMSO-$d_6$) δ value:

6.49(1H,dd,J=8.2,1.6 Hz),6.71-6.74(2H,m),7.07(1H,dd,J=8.3,1.5 Hz),7.16(1H,t,J=7.9 Hz),7.39-7.42(1H,m),7.45-7.49(3H,m),7.61(2H,d,J=7.3 Hz),7.98(1H,d,J=8.3 Hz),9.45-9.52(1H,broad),9.65(1H,s),13.05-13.17(1H,broad).

Example 123

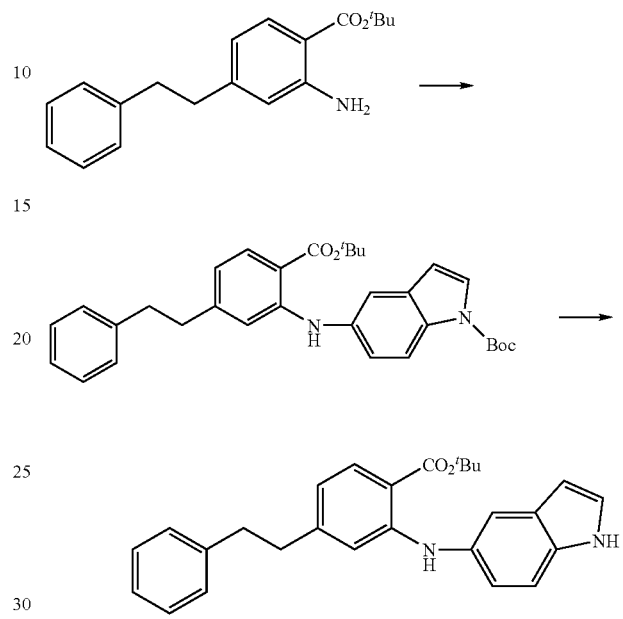

To toluene 4.0 mL solution of tert-butyl 2-amino-4-phenethylbenzoate 0.20 g were added tert-butyl 5-bromo-1H-indol-1-carboxylate 0.29 g, cesium carbonate 0.55 g, tris(dibenzylideneacetone)dipalladium(0) 6 mg, palladium acetate 3 mg and 2-dicyclohexylphosphino-2',4',6'-triisopropylbiphenyl 16 mg at room temperature, and it was heated and refluxed under nitrogen atmosphere for 8 hours. After the reaction mixture was cooled to room temperature, tris(dibenzylideneacetone)dipalladium(0) 6 mg, palladium acetate 3 mg and 2-dicyclohexylphosphino-2',4',6'-triisopropylbiphenyl 16 mg were added to it, and it was heated and refluxed under nitrogen atmosphere for 10 hours. After the reaction mixture was cooled to room temperature, water was added, and insoluble matter was filtrated. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((1-(tert-butoxycarbonyl)-1H-indol-5-yl)amino)-4-phenethylbenzoate.

Trifluoroacetic acid 3.0 mL solution of the obtained tert-butyl 2-((1-(tert-butoxycarbonyl)-1H-indol-5-yl)amino)-4-phenethylbenzoate was stirred at room temperature for 1 hour. The solvent was removed under reduced pressure, and the obtained residue was refined by reversed-phase silica gel column chromatography [eluent; 60-100% acetonitrile/0.1% trifluoroacetic acid aqueous solution] to give 2-((1H-indol-5-yl)amino)-4-phenethylbenzoic acid 25 mg of pale yellow solid.

$^1$H-NMR (DMSO-$d_6$) δ value:

2.72-2.80(4H,m),6.40(1H,s),6.55(1H,d,J=8.0 Hz),6.70(1H,s),6.85 (1H,dd,J=8.4,2.0 Hz),7.12-7.29(6H,m),7.35-

7.39(2H,m),7.77(1H,d,J=8.4 Hz),9.46-9.54(1H,broad), 11.10(1H,s),12.60-12.80(1H,broad).

Example 124

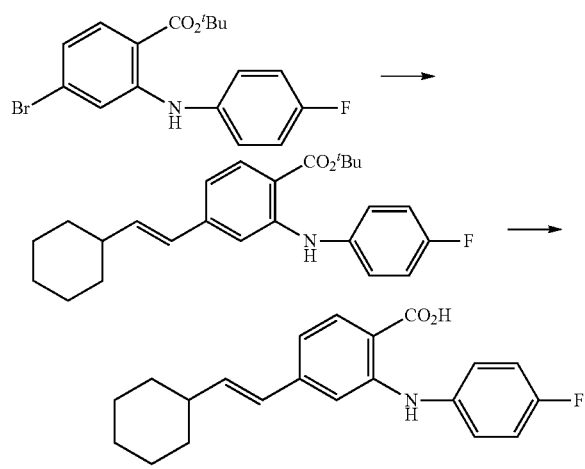

To toluene 3.0 mL solution of tert-butyl 4-bromo-2-(4-fluoroanilino)benzoate 0.20 g were added vinylcyclohexane 0.15 mL, cesium carbonate 0.36 g, tetrabutylammonium bromide 53 mg and polymer-carried bis(acetato)triphenylphosphine palladium(II) 86 mg at room temperature, and it was stirred at 110° C. for 22 hours. After the reaction mixture was cooled to room temperature, insoluble matter was filtrated, ethyl acetate and 10% citric acid aqueous solution were added to it. The organic layer was separated and collected, dried over anhydrous magnesium sulfate after sequential washing with 10% citric acid aqueous solution, saturated sodium thiosulfate aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 4-((E)-2-cyclohexylvinyl)-2-(4-fluoroanilino)benzoate.

Trifluoroacetic acid 15 mL solution of the obtained tert-butyl 4-((E)-2-cyclohexylvinyl)-2-(4-fluoroanilino)benzoate was stirred at room temperature for 2 hours. The solvent was removed under reduced pressure to give 4-((E)-2-cyclohexylvinyl)-2-(4-fluoroanilino)benzoic acid 34 mg of pale yellow solid.

$^1$H-NMR (DMSO-$d_6$) δ value:

1.08-1.31(5H,m),1.59-1.78(5H,m),2.05-2.14(1H,m),6.26 (2H,d,J=2.4 Hz),6.87(1H,dd,J=8.4,0.7 Hz),6.97 (1H,s),7.17-7.31(4H,m),7.81(1H,d,J=8.4 Hz),9.49-9.61(1H,broad), 12.86-13.02(1H,broad).

Example 125

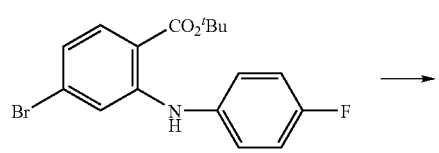

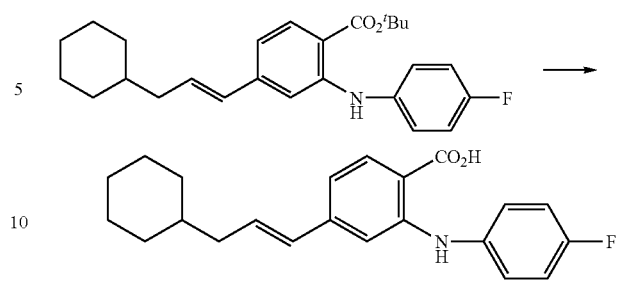

To toluene 3.0 mL solution of tert-butyl 4-bromo-2-(4-fluoroanilino)benzoate 0.20 g were added allylcyclohexane 0.17 mL, cesium carbonate 0.36 g, tetrabutylammonium bromide 53 mg and polymer-carried bis(acetato)triphenylphosphine palladium(II) 86 mg at room temperature, and it was stirred at 110° C. for 22 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after sequential washing with 10% citric acid aqueous solution, saturated sodium thiosulfate aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 4-((E)-3-cyclohexyl-1-propenyl)-2-(4-fluoroanilino) benzoate.

Trifluoroacetic acid 15 mL solution of the obtained tert-butyl 4-((E)-3-cyclohexyl-1-propenyl)-2-(4-fluoroanilino) benzoate was stirred at room temperature for 2 hours. The solvent was removed under reduced pressure, and the obtained residue was refined by reversed-phase silica gel column chromatography [eluent; 70-100% acetonitrile/0.1% trifluoroacetic acid aqueous solution] to give 4-((E)-3-cyclohexyl-1-propenyl)-2-(4-fluoroanilino)benzoic acid 23 mg of pale yellow solid.

$^1$H-NMR (DMSO-$d_6$) δ value:

0.82-0.96(2H,m),1.04-1.25(3H,m),1.30-1.41(1H,m), 1.55-1.71(5H,m),1.99-2.09(2H,m),6.22-6.35(2H,m),6.87 (1H,d,J=8.3 Hz),6.96(1H,s),7.17-7.33(4H,m),7.82(1H,d, J=8.3 Hz),9.56(1H,s),12.94(1H,s).

Example 126

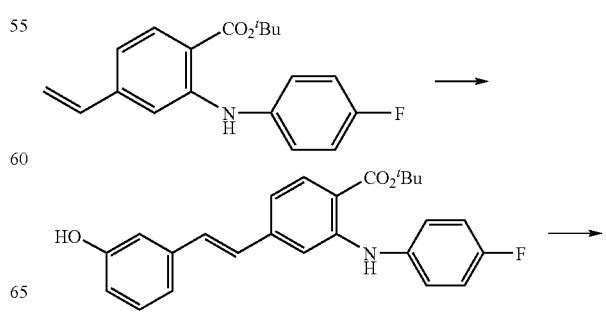

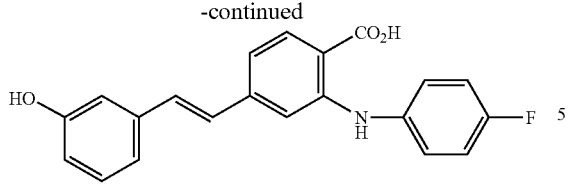

To toluene 3.0 mL solution of tert-butyl 2-(4-fluoroanilino)-4-vinylbenzoate 0.12 g were added 3-iodophenol 0.17 g, cesium carbonate 0.25 g, tetrabutylammonium bromide 37 mg and polymer-carried bis(acetato)triphenylphosphine palladium (II) 58 mg at room temperature, and it was stirred at 110° C. for 24 hours. After the reaction mixture was cooled to room temperature, insoluble matter was filtrated, ethyl acetate and 10% citric acid aqueous solution were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-(4-fluoroanilino)-4-((E)-2-(3-hydroxyphenyl)vinyl)benzoate.

Trifluoroacetic acid 10 mL solution of the obtained tert-butyl 2-(4-fluoroanilino)-4-((E)-2-(3-hydroxyphenyl)vinyl)benzoate was stirred at room temperature for 1 hour. The solvent was removed under reduced pressure, and the obtained residue was refined by reversed-phase silica gel column chromatography [eluent; 40-90% acetonitrile/0.1% trifluoroacetic acid aqueous solution] to give 2-(4-fluoroanilino)-4-((E)-2-(3-hydroxyphenyl)vinyl)benzoic acid 27 mg of pale yellow solid.

$^1$H-NMR (DMSO-$d_6$) δ value:
6.69(1H,d,J=8.0 Hz),6.97(1H,s),7.02-7.26(8H,m),7.30-7.36(2H,m),7.88(1H,d,J=8.3 Hz),9.41(1H,s),9.60(1H,s), 12.98 (1H,s).

Example 127-130

The compounds shown in Table 22 were obtained in the same manner as in Example 126.

TABLE 22

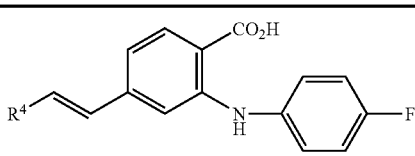

| Example No. | R$^4$ |
|---|---|
| 127 | 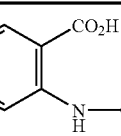 |
| 128 | 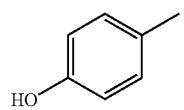 |
| 129 | 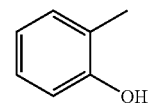 |
| 130 | 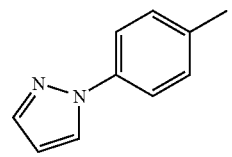 |

2-(4-Fluoroanilino)-4-((E)-2-(4-hydroxyphenyl)vinyl)benzoic acid $^1$H-NMR (DMSO-$d_6$) δ value:
6.75(2H,d,J=8.6 Hz),6.95(1H,d,J=16.1 Hz),7.04(1H,d,J=8.3 Hz),7.12-7.37(6H,m),7.44(2H,d,J=8.6 Hz),7.86(1H,d,J=8.3 Hz),9.54-9.75(2H,m).

2-(4-Fluoroanilino)-4-((E)-2-(4-methoxyphenyl)vinyl)benzoic acid $^1$H-NMR (DMSO-$d_6$) δ value:
3.77(3H,s),6.93(2H,d,J=8.8 Hz),7.01-7.10(2H,m),7.14-7.27(4H,m),7.30-7.38(2H,m),7.56(2H,d,J=8.8 Hz),7.87(1H,d,J=8.5 Hz),9.60(1H,s),12.87-13.08(1H,broad).

2-(4-Fluoroanilino)-4-((E)-2-(2-hydroxyphenyl)vinyl)benzoic acid $^1$H-NMR (DMSO-$d_6$) δ value:
6.79(1H,t,J=7.6 Hz),6.85(1H,d,J=7.8 Hz),7.03(1H,d,J=8.3 Hz), 7.07-7.17(3H,m),7.20-7.27(2H,m),7.31-7.37(2H,m),7.41(1H,d,J=16.6 Hz),7.58(1H,d,J=7.6 Hz),7.88(1H,d,J=8.5 Hz),9.58(1H,s),9.80(1H,s),12.97(1H,s).

2-(4-Fluoroanilino)-4-((E)-2-(4-(1H-pyrazol-1-yl)phenyl)vinyl)benzoic acid $^1$H-NMR (DMSO-$d_6$) δ value:
6.56(1H,t,J=2.1 Hz),7.12(1H,dd,J=8.7,1.1 Hz),7.21-7.28(5H,m),7.32-7.36(2H,m),7.73-7.76(3H,m),7.85(2H,d,J=8.8 Hz),7.90(1H,d,J=8.3 Hz),8.54(1 H,d,J=2.4 Hz),9.52-9.78 (1H,broad).

Example 131

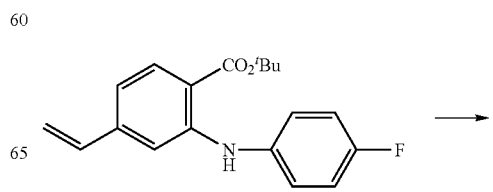

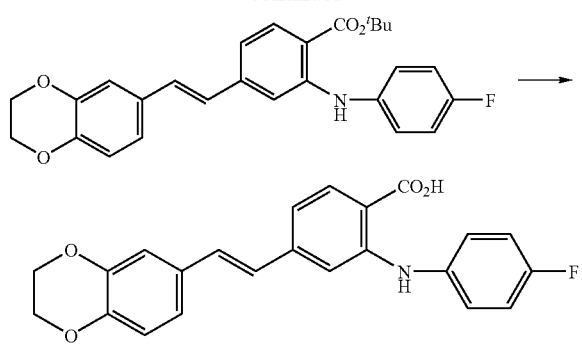

To toluene 3.0 mL solution of tert-butyl 2-(4-fluoroanilino)-4-vinylbenzoate 0.12 g were added 2,3-dihydro-6-iodobenzo[1,4]dioxin 0.20 g, cesium carbonate 0.25 g, tetrabutylammonium bromide 37 mg and polymer-carried bis(acetato)triphenylphosphine palladium(II) 58 mg at room temperature, and it was stirred at 110° C. for 24 hours. After the reaction mixture was cooled to room temperature, insoluble matter was filtrated, ethyl acetate and 10% citric acid aqueous solution were added to it. The organic layer was separated and collected, dried over anhydrous magnesium sulfate after sequential washing with 10% citric acid aqueous solution and saturated sodium chloride aqueous solution, the solvent was removed under reduced pressure. The obtained residue was refined by silica gel column chromatography [Trikonex company, Flash Tube 2008, eluent; hexane:ethyl acetate=4:1] to give tert-butyl 4-((E)-2-(2,3-dihydrobenzo[1,4]dioxin-6-yl)vinyl)-2-(4-fluoroanilino)benzoate.

Trifluoroacetic acid 10 mL solution of the obtained tert-butyl 4-((E)-2-(2,3-dihydrobenzo[1,4]dioxin-6-yl)vinyl)-2-(4-fluoroanilino)benzoate was stirred at room temperature for 1 hour. The solvent was removed under reduced pressure to give 4-((E)-2-(2,3-dihydrobenzo[1,4]dioxin-6-yl)vinyl)-2-(4-fluoroanilino)benzoic acid 17 mg of pale yellow solid.

$^1$H-NMR (DMSO-$d_6$) δ value:

4.24(4H,s),6.83(1H,d,J=8.3 Hz),7.00-7.15(6H,m),7.20-7.26(2H,m),7.29-7.36(2H,m),7.86(1H,d,J=8.3 Hz),9.60(1H,s),12.83-13.08(1H,broad).

Example 132-136

The compounds shown in Table 23 were obtained in the same manner as in Example 131.

TABLE 23

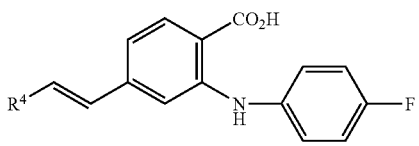

| Example No. | R$^4$ |
|---|---|
| 132 | 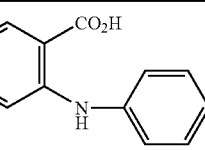 |
| 133 | 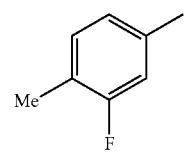 |
| 134 | 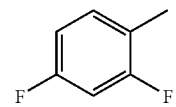 |
| 135 | 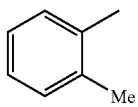 |
| 136 | 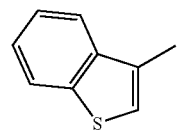 |

2-(4-Fluoroanilino)-4-((E)-2-(4-fluorophenyl)vinyl)benzoic acid $^1$H-NMR (DMSO-$d_6$) δ value:

7.10(1H,dd,J=8.4,1.3 Hz),7.13-7.28(7H,m),7.31-7.36 (2H,m),7.65-7.70(2H,m),7.89(1H,d,J=8.4 Hz),9.60(1H,s),12.88-13.14(1H,broad).

2-(4-Fluoroanilino)-4-((E)-2-(3-fluoro-4-methylphenyl)vinyl)benzoic acid $^1$H-NMR (DMSO-$d_6$) δ value:

2.23(3H,s),7.09(1H,dd,J=8.4,1.5 Hz),7.17-7.28(6H,m),7.31-7.35(3H,m),7.44(1H,d,J=11.7 Hz),7.89(1H,d,J=8.4 Hz),9.59(1H,s),12.92-13.11(1H,broad).

4-((E)-2-(2,4-Difluorophenyl)vinyl)-2-(4-fluoroanilino)benzoic acid $^1$H-NMR (DMSO-$d_6$) δ value:

7.10-7.36(10H,m),7.84-7.91(2H,m),9.60(1H,s).

2-(4-Fluoroanilino)-4-((E)-2-(2-methylphenyl)vinyl)benzoic acid $^1$H-NMR (DMSO-$d_6$) δ value:

2.38(3H,s),7.07(1H,d,J=16.1 Hz),7.14-7.26(7H,m),7.31-7.37(2H,m),7.41(1H,d,J=16.1 Hz),7.67(1H,t,J=3.0 Hz),7.89 (1H,d,J=8.3 Hz),9.61(1H,s),12.85-13.19(1H,broad).

4-((E)-2-(Benzothiophen-3-yl)vinyl)-2-(4-fluoroanilino)benzoic acid $^1$H-NMR (DMSO-$d_6$) δ value:
7.20-7.51(9H,m),7.62(1H,d,J=16.4 Hz),7.91(1H,d,J=8.3 Hz),8.03(1H,d,J=7.6 Hz),8.11(1H,s),8.23(1H,d,J=8.0 Hz),9.53-9.74(1H,broad),12.87-13.20(1H,broad).

Example 137

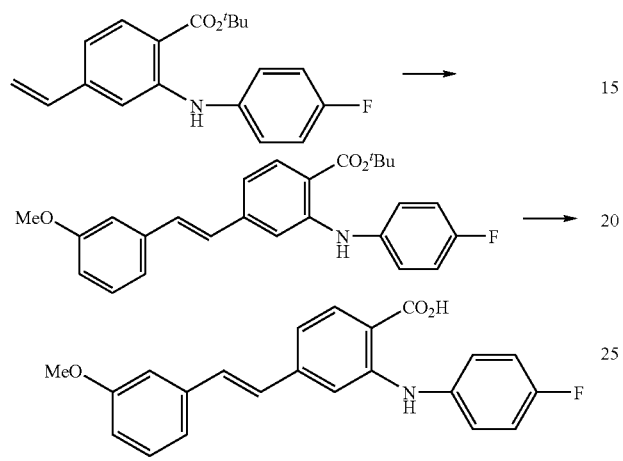

To toluene 3.0 mL solution of tert-butyl 2-(4-fluoroanilino)-4-vinylbenzoate 0.12 g were added 3-iodoanisole 0.18 g, cesium carbonate 0.25 g, tetrabutylammonium bromide 37 mg and polymer-carried bis(acetato)triphenylphosphine palladium(II) 58 mg at room temperature, and it was stirred at 110° C. for 24 hours. After the reaction mixture was cooled to room temperature, insoluble matter was filtrated, ethyl acetate and 10% citric acid aqueous solution were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-(4-fluoroanilino)-4-((E)-2-(3-methoxyphenyl)vinyl)benzoate.

Trifluoroacetic acid 10 mL solution of the obtained tert-butyl 2-(4-fluoroanilino)-4-((E)-2-(3-methoxyphenyl)vinyl)benzoate was stirred at room temperature for 1 hour. The solvent was removed under reduced pressure, and ethyl acetate and saturated sodium thiosulfate aqueous solution were added to the obtained residue. The organic layer was separated and collected, dried over anhydrous magnesium sulfate after washing with saturated sodium chloride aqueous solution, and the solvent was removed under reduced pressure to give 2-(4-fluoroanilino)-4-((E)-2-(3-methoxyphenyl)vinyl)benzoic acid 28 mg of pale yellow solid.

$^1$H-NMR (DMSO-$d_6$) δ value:
3.78(3H,s),6.85(1H,ddd,J=8.2,2.4,0.8 Hz),7.11(1H,dd,J=8.5, 1.5 Hz),7.16-7.37(10H,m),7.89(1H,d,J=8.5 Hz),9.61(1H,s),12.83-13.21(1H,broad).

Example 138-140

The compounds shown in Table 24 were obtained in the same manner as in Example 137.

TABLE 24

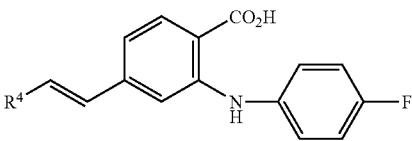

| Example No. | R$^4$ |
|---|---|
| 138 | 4-acetylphenyl |
| 139 | 3-nitrophenyl |
| 140 | benzo-1,3-dioxol-5-yl (methyl substituted) |

4-((E)-2-(4-Acetylphenyl)vinyl)-2-(4-fluoroanilino)benzoic acid $^1$H-NMR (DMSO-$d_6$) δ value:
2.58(3H,s),7.15(1H,dd,J=8.5,1.2 Hz),7.21-7.27(3H,m),7.31-7.42(4H,m),7.76(2H,d,J=8.3 Hz),7.91(1H,d,J=8.5 Hz),7.94(2H,d,J=8.3 Hz),9.61(1H,s),12.97-13.17(1H,broad).

2-(4-Fluoroanilino)-4-((E)-2-(3-nitrophenyl)vinyl)benzoic acid $^1$H-NMR (DMSO-$d_6$) δ value:
7.66(1H,t,J=7.9 Hz),7.15(1H,dd,J=8.3,1.2 Hz),7.21-7.30(3H,m),7.31-7.37(2H,m),7.42(1H,d,J=16.6 Hz),7.48(1H,d,J=16.6 Hz),7.92 (1H,d,J=8.3 Hz),8.07-8.14(2H,m),8.47(1H,s),9.54-9.79(1H,broad).

4-((E)-2-(Benzo-1,3-dioxol-5-yl)vinyl)-2-(4-fluoroanilino)benzoic acid $^1$H-NMR (DMSO-$d_6$) δ value:
6.03(2H,s),6.90(1H,d,J=8.0 Hz),7.03-7.09(3H,m),7.13-7.26(4H,m),7.30-7.36(3H,m),7.87(1H,d,J=8.3 Hz),9.44-9.76(1H,broad),12.76-13.14(1H,broad).

Example 141

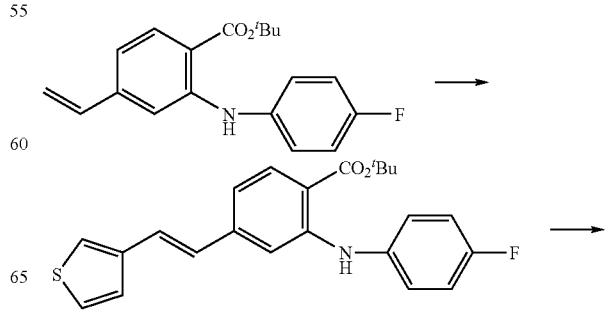

-continued

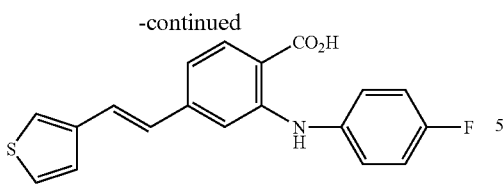

3-Bromothiophene 90 μL, cesium carbonate 0.31 g and palladium acetate 11 mg were added to N,N-dimethylacetamide 3.0 mL solution of tert-butyl 2-(4-fluoroanilino)-4-vinylbenzoate 0.15 g at room temperature, and it was stirred at 120° C. for 24 hours. After the reaction mixture was cooled to room temperature, ethyl acetate and 10% citric acid aqueous solution were added to it. The organic layer was separated and collected,dried over anhydrous magnesium sulfate after sequential washing with 10% citric acid aqueous solution, saturated sodium thiosulfate aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-(4-fluoroanilino)-4-((E)-2-(thiophen-3-yl)vinyl)benzoate.

Trifluoroacetic acid 15 mL solution of obtained tert-butyl 2-(4-fluoroanilino)-4-((E)-2-(thiophen-3-yl)vinyl)benzoate was stirred at room temperature for 2 hours. The solvent was removed under reduced pressure, and the obtained residue was refined by reversed-phase silica gel column chromatography [eluent; 70-100% acetonitrile/0.1% trifluoroacetic acid aqueous solution] to give 2-(4-fluoroanilino)-4-((E)-2-(thiophen-3-yl)vinyl)benzoic acid 9 mg of pale yellow solid.

$^1$H-NMR (DMSO-$d_6$) δ value:
7.00-7.09(2H,m),7.13(1H,s),7.20-7.36(5H,m),7.50(1H,d,J=4.9 Hz),7.56(1H,dd,J=4.9,2.8 Hz),7.64 (1H,d,J=2.8 Hz),7.87(1H,d,J=8.3 Hz),9.53-9.67(1H,broad),12.85-13.10(1H,broad).

Example 142, 143

The compounds shown in Table 25 were obtained in the same manner as in Example 141.

TABLE 25

| Example No. | R$^4$ |
|---|---|
| 142 | 4-methyl-1H-indol-4-yl |
| 143 | 5-methylbenzo[b]thiophen-5-yl |

2-(4-Fluoroanilino)-4-((E)-2-(1H-indol-4-yl)vinyl)benzoic acid $^1$H-NMR (DMSO-$d_6$) δ value:

6.85(1H,s),7.09(1H,t,J=7.7 Hz),7.20-7.28(5H,m),7.32-7.39(4H,m),7.43(1H,t,J=2.8 Hz),7.59(1H,d,J=16.6 Hz),7.90(1H,d,J=8.3 Hz),9.62(1H,s),11.23(1H,s),12.89-13.07(1H, broad).

4-((E)-2-(Benzothiophen-5-yl)vinyl)-2-(4-fluoroanilino)benzoic acid $^1$H-NMR (DMSO-$d_6$) δ value:
7.13(1H,dd,J=8.3,1.1 Hz),7.21-7.41(7H,m),7.44(1H,d,J=5.4 Hz),7.68(1H,dd,J=8.7,0.9 Hz),7.78 (1H,d,J=5.4 Hz), 7.90(1H,d,J=8.3 Hz),7.98(1H,d,J=8.7 Hz), 8.08(1H,s).

Example 144

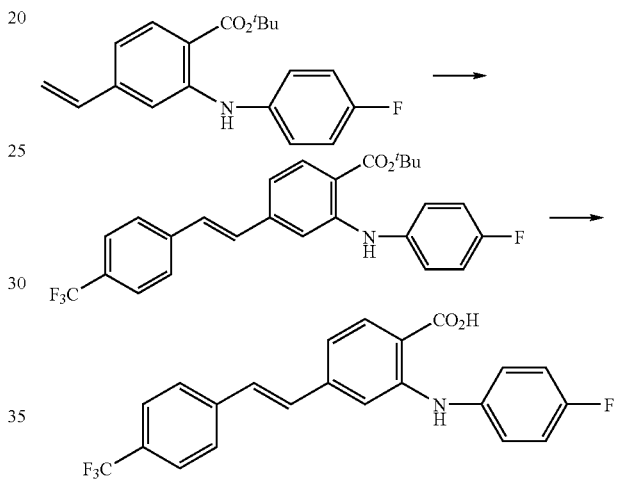

1-Bromo-4-(trifluoromethyl)benzene 0.14 mL, cesium carbonate 0.31 g and palladium acetate 11 mg were added to N,N-dimethylacetamide 3.0 mL solution of tert-butyl 2-(4-fluoroanilino)-4-vinylbenzoate 0.15 g at room temperature, and it was stirred at 120° C. for 24 hours. After the reaction mixture was cooled to room temperature, ethyl acetate and 10% citric acid aqueous solution were added to it. The organic layer was separated and collected,dried over anhydrous magnesium sulfate after sequential washing with 10% citric acid aqueous solution, saturated sodium thiosulfate aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-(4-fluoroanilino)-4-((E)-2-(4-trifluoromethylphenyl)vinyl)benzoate.

Trifluoroacetic acid 15 mL solution of the obtained tert-butyl 2-(4-fluoroanilino)-4-((E)-2-(4-trifluoromethylphenyl)vinyl)benzoate was stirred at room temperature for 2 hours. The solvent was removed under reduced pressure to give 2-(4-fluoroanilino)-4-((E)-2-(4-trifluoromethylphenyl)vinyl)benzoic acid 50 mg of pale yellow solid.

$^1$H-NMR (DMSO-$d_6$) δ value:
7.16(1H,d,J=8.4 Hz),7.21-7.27(3H,m),7.32-7.43(4H,m), 7.72(2H,d,J=8.2 Hz),7.84(2H,d,J=8.2 Hz),7.91(1H,d,J=8.4 Hz),9.61(1H,s),12.99-13.16(1H,broad).

Example 145

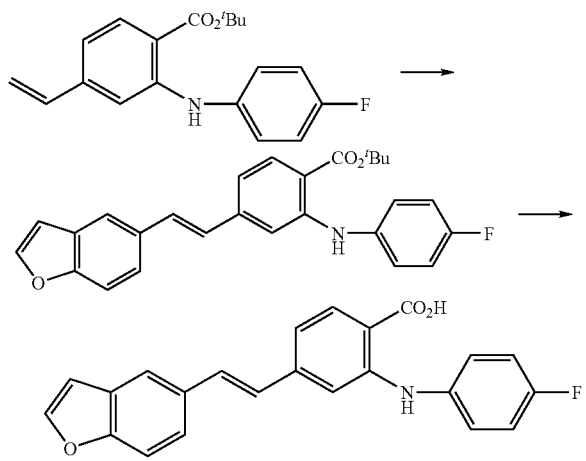

The following compound was obtained in the same manner as in Example 144.

4-((E)-2-(Benzofuran-5-yl)vinyl)-2-(4-fluoroanilino) benzoic acid $^1$H-NMR (DMSO-$d_6$) δ value:
6.95(1H,d,J=2.2 Hz),7.12(1H,d,J=8.0 Hz),7.16-7.27(4H, m),7.31-7.39(3H,m),7.57-7.64(2H,m),7.88-7.90(2H,m), 8.00(1H,d,J=2.2 Hz),9.60(1H,s),12.92-13.06(1H,broad).

Example 146

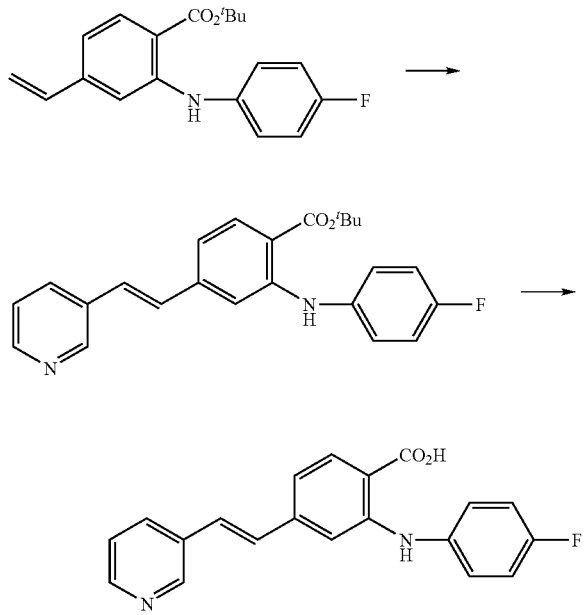

To N,N-dimethylacetamide 3.0 mL solution of tert-butyl 2-(4-fluoroanilino)-4-vinylbenzoate 0.15 g were added 3-bromopyridine 70 μL, tributylamine 0.23 mL and palladium acetate 11 mg at room temperature, and it was stirred at 110° C. for 24 hours. After the reaction mixture was cooled to room temperature, palladium acetate 11 mg was added to it, and it was stirred at 110° C. for 24 hours. After the reaction mixture was cooled to room temperature, ethyl acetate and 10% citric acid aqueous solution were added to it. The organic layer was separated and collected,dried over anhydrous magnesium sulfate after sequential washing with 10% citric acid aqueous solution, saturated sodium thiosulfate aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-(4-fluoroanilino)-4-((E)-2-(pyridin-3-yl)vinyl)benzoate.

Trifluoroacetic acid 15 ml solution of the obtained tert-butyl 2-(4-fluoroanilino)-4-((E)-2-(pyridin-3-yl)vinyl)benzoate was stirred at room temperature for 2 hours. The solvent was removed under reduced pressure, ethyl acetate and water were added to it, and it was adjusted to pH6.0 with saturated sodium hydrogen carbonate aqueous solution. The organic layer was separated and collected,dried over anhydrous magnesium sulfate, and the solvent was removed under reduced pressure to give 2-(4-fluoroanilino)-4-((E)-2-(pyridin-3-yl) vinyl)benzoic acid 46 mg of pale yellow solid.

$^1$H-NMR (DMSO-$d_6$) δ value:
7.13(1H,dd,J=8.2,1.2 Hz),7.20-7.41(8H,m),7.91(1H,d, J=8.2 Hz),8.06(1H,dt,J=8.0,1.9 Hz),8.46 (1H,dd,J=4.8,1.3 Hz),8.77(1H,d,J=2.2 Hz),9.61(1H,s),12.95-13.14(1H, broad).

Example 147

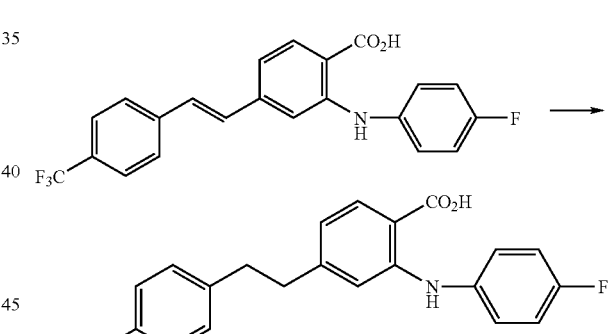

To a mixed solution of methanol 4.0 mL and ethyl acetate 4.0 mL of 2-(4-fluoroanilino)-4-((E)-2-(4-(trifluoromethyl) phenyl)vinyl)benzoic acid 15 mg was added 5% palladium-carbon 8.0 mg at room temperature, and it was stirred under hydrogen atmosphere at room temperature for 10 hours. The solvent was removed under reduced pressure after insoluble matter was filtrated to give 2-(4-fluoroanilino)-4-(2-(4-(trifluoromethyl)phenyl)ethyl)benzoic acid 14 mg of white solid.

$^1$H-NMR (DMSO-$d_6$) δ value:
2.82(2H,t,J=7.2 Hz),2.94(2H,t,J=7.2 Hz),6.61(1H,dd, J=8.0, 1.2 Hz),6.80(1H,d,J=1.2 Hz),7.00-7.12(4H,m),7.40 (2H,d,J=8.1 Hz),7.63(2H,d,J=8.1 Hz),7.81(1H,d,J=7.9 Hz).

Example 148-168

The compounds shown in Table 26 were obtained in the same manner as in Example 147.

TABLE 26
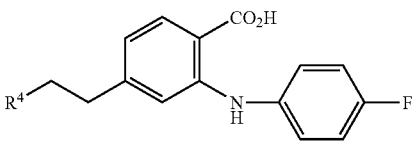
| Example No. | R⁴ |
|---|---|
| 148 | 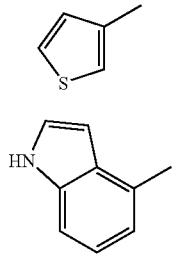 |
| 149 | 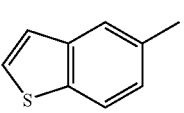 |
| 150 | 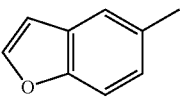 |
| 151 | 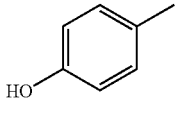 |
| 152 | 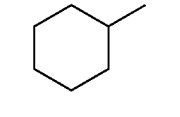 |
| 153 | 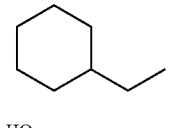 |
| 154 | 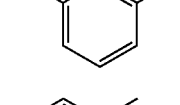 |
| 155 | 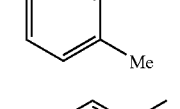 |
| 156 | 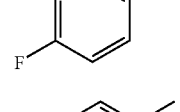 |
| 157 | 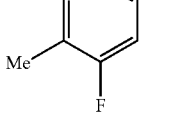 |
| 158 | 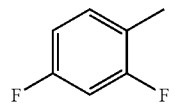 |
| 159 | 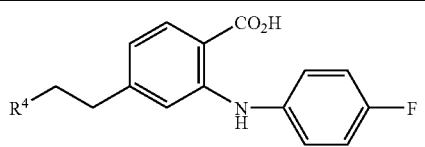 |
TABLE 26-continued
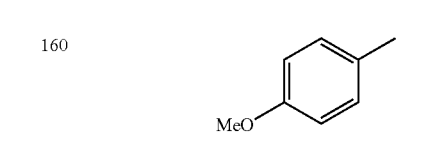
| Example No. | R⁴ |
|---|---|
| 160 | 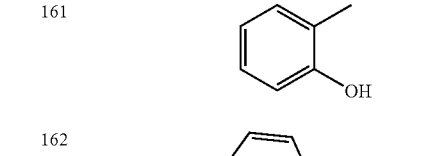 |
| 161 | 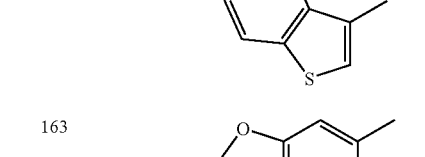 |
| 162 | 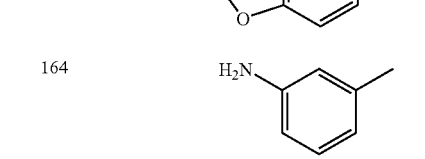 |
| 163 | 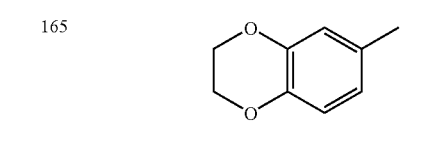 |
| 164 | 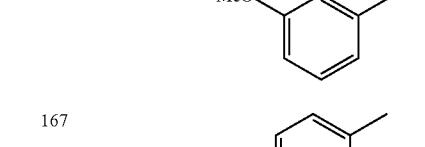 |
| 165 | 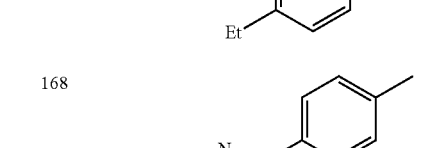 |
| 166 | 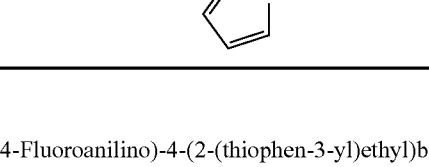 |
| 167 | 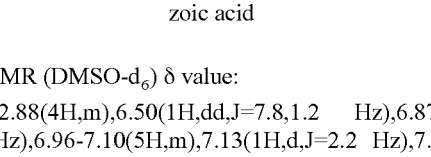 |
| 168 | 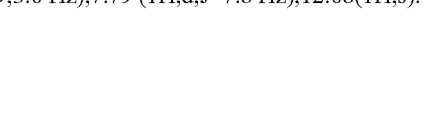 |
2-(4-Fluoroanilino)-4-(2-(thiophen-3-yl)ethyl)benzoic acid
¹H-NMR (DMSO-$d_6$) δ value:
2.74-2.88(4H,m),6.50(1H,dd,J=7.8,1.2 Hz),6.87(1H,d,J=1.2 Hz),6.96-7.10(5H,m),7.13(1H,d,J=2.2 Hz),7.45(1H,dd,J=4.9,3.0 Hz),7.79 (1H,d,J=7.8 Hz),12.08(1H,s).

2-(4-Fluoroanilino)-4-(2-(1H-indol-4-yl)ethyl)benzoic acid

¹H-NMR (DMSO-d₆) δ value:
2.84-2.91(2H,m),3.04-3.11(2H,m),6.43(1H,s),6.64(1H,d,J=8.0 Hz),6.70-6.76(2H,m),6.85-7.06(5H,m),7.26(1H,d,J=8.0 Hz),7.29(1H,t,J=2.7 Hz),7.81(1H,d,J=8.0 Hz),11.07 (1H,s).

4-(2-(Benzothiophen-5-yl)ethyl)-2-(4-fluoroanilino) benzoic acid

¹H-NMR (DMSO-d₆) δ value:
2.83(2H,t,J=7.2 Hz),2.97(2H,t,J=7.2 Hz),6.58(1H,dd,J=7.9, 1.2 Hz),6.75(1H,d,J=1.2 Hz),6.82-6.91(3H,m),6.97-7.08(1H,m),7.19(1H,dd,J=8.3,1.3 Hz),7.38(1H,d,J=5.5 Hz), 7.66 (1H,s),7.72(1H,d,J=5.5 Hz),7.81(1H,d,J=7.9 Hz),7.90 (1H, d,J=8.3 Hz).

4-(2-(Benzofuran-5-yl)ethyl)-2-(4-fluoroanilino) benzoic acid

¹H-NMR (DMSO-d₆) δ value:
2.78-2.82(2H,m),2.91-2.97(2H,m),6.51-6.56(1H,m),6.74 (1H,s),6.80-6.91(5H,m),7.12(1H,dd,J=8.3,1.7 Hz),7.41(1H,d,J=1.5 Hz),7.49 (1H,d,J=8.3 Hz),7.79(1H,d,J=7.8 Hz),7.95 (1H,d,J=2.2 Hz).

2-(4-Fluoroanilino)-4-(2-(4-hydroxyphenyl)ethyl) benzoic acid

¹H-NMR (DMSO-d₆) δ value:
2.66-2.76(4H,m),6.50(1H,dd,J=8.0,1.4 Hz),6.66(2H,d,J=8.3 Hz),6.74 (1H,d,J=1.4 Hz),6.88-6.95(4H,m),7.00-7.07 (2H,m),7.79(1H,d,J=8.0 Hz),7.95(1H,s),9.19(1H,s).

4-(2-Cyclohexylethyl)-2-(4-fluoroanilino)benzoic acid

¹H-NMR (DMSO-d₆) δ value:
0.80-0.93(2H,m),1.05-1.25(4H,m),1.35-1.43(2H,m), 1.55-1.73(5H,m),2.45-2.50(2H,m),6.57(1H,dd,J=8.1,1.3 Hz),6.88(1H,d,J=1.3 Hz),7.14-7.26(4H,m),7.79(1H,d,J=8.1 Hz).

4-(3-Cyclohexylpropyl)-2-(4-fluoroanilino)benzoic acid

¹H-NMR (DMSO-d₆) δ value:
0.75-0.87(2H,m),1.05-1.24(6H,m),1.46-1.67(7H,m), 2.42-2.48(2H,m),6.60(1H,dd,J=8.1,1.2 Hz),6.87(1H,d,J=1.2 Hz),7.16-7.22(2H,m),7.24-7.29(2H,m),7.79(1H,d,J=8.1 Hz),9.42-9.72(1H,broad).

2-(4-Fluoroanilino)-4-(2-(3-hydroxyphenyl)ethyl) benzoic acid

¹H-NMR (DMSO-d₆) δ value:
2.73-2.77(4H,m),6.53-6.62(3H,m),6.64(1H,dd,J=8.1,1.4 Hz),6.78(1H,d,J=1.4 Hz),7.01-7.15(5H,m),7.80(1H,d,J=8.1 Hz),9.04-9.43(1H,broad).

2-(4-Fluoroanilino)-4-(2-(2-methylphenyl)ethyl) benzoic acid

¹H-NMR (DMSO-d₆) δ value:
2.18(3H,s),2.71-2.85(4H,m),6.67(1H,dd,J=8.1,1.4 Hz), 6.78(1H,d,J=1.4 Hz),7.04-7.15(8H,m),7.81(1H,d,J=8.1 Hz).

2-(4-Fluoroanilino)-4-(2-(4-fluorophenyl)ethyl)benzoic acid

¹H-NMR (DMSO-d₆) δ value:
2.74-2.86(4H,m),6.64(1H,dd,J=8.1,0.9 Hz),6.78(1H,d,J=0.9 Hz),7.04-7.22(8H,m),7.80(1H,d,J=8.1 Hz).

2-(4-Fluoroanilino)-4-(2-(3-fluoro-4-methylphenyl) ethyl)benzoic acid

¹H-NMR (DMSO-d₆) δ value:
2.19(3H,s),2.77-2.83(4H,m),6.64(1H,dd,J=8.2,1.5 Hz), 6.81(1H,d,J=1.5 Hz),6.88 (1H,dd,J=7.8,1.2 Hz),6.96(1H,dd,J=11.2,1.2 Hz),7.08-7.18(5H,m),7.80(1H,d,J=8.2 Hz).

4-(2-(2,4-Difluorophenyl)ethyl)-2-(4-fluoroanilino) benzoic acid

¹H-NMR (DMSO-d₆) δ value:
2.72-2.87(4H,m),6.61(1H,dd,J=8.1,1.2 Hz),6.75(1H,d,J=1.2 Hz),6.99 (1H,td,J=8.5,2.7 Hz),7.05-7.29(6H,m),7.80 (1H,d,J=8.1 Hz).

2-(4-Fluoroanilino)-4-(2-(4-methoxyphenyl)ethyl) benzoic acid

¹H-NMR (DMSO-d₆) δ value:
2.73-2.79(4H,m),3.71(3H,s),6.63(1H,dd,J=8.0,1.1 Hz), 6.76(1H,s), 6.83(2H,d,J=8.5 Hz),7.02-7.14(6H,m),7.80(1H, d,J=8.0 Hz).

2-(4-Fluoroanilino)-4-(2-(2-hydroxyphenyl)ethyl) benzoic acid

¹H-NMR (DMSO-d₆) δ value:
2.70-2.79(4H,m),6.59(1H,dd,J=8.1,1.5 Hz),6.67(1H,td,J=7.4,1.1 Hz),6.78-6.83(2H,m),6.93(1H,dd,J=7.4,1.6 Hz), 6.99-7.13(5H,m),7.80(1H,d,J=8.1 Hz),9.29(1H,s).

4-(2-(Benzothiophen-3-yl)ethyl)-2-(4-fluoroanilino) benzoic acid

¹H-NMR (DMSO-d₆) δ value:
2.93(2H,t,J=7.4 Hz),3.09(2H,t,J=7.4 Hz),6.70(1H,d,J=8.3 Hz), 6.82(1H,s),6.99-7.08(4H,m),7.34-7.41(3H,m),7.76-7.85(2H,m),7.97-8.02(1H,m).

4-(2-(Benzo-1,3-dioxol-5-yl)ethyl)-2-(4-fluoroanilino)benzoic acid

¹H-NMR (DMSO-d₆) δ value: 2.72-2.77(4H,m),5.95(2H, s),6.59-6.65(2H,m),6.76-6.83(3H,m),7.10-7.15(4H,m),7.80 (1H,d,J=8.0 Hz).

4-(2-(3-Aminophenyl)ethyl)-2-(4-fluoroanilino)benzoic acid

¹H-NMR (DMSO-d₆) δ value:
2.62-2.76(4H,m),6.28(1H,d,J=7.7 Hz),6.37(1H,s),6.41 (1H,dd,J=7.7, 1.3 Hz),6.63(1H,dd,J=8.2,1.4 Hz),6.79(1H,d,J=1.4 Hz),6.90 (1H,t,J=7.7 Hz),7.04-7.16(4H,m),7.80(1H,d,J=8.2 Hz).

4-(2-(2,3-Dihydrobenzo[1,4]dioxin-6-yl)ethyl)-2-(4-fluoroanilino)benzoic acid $^1$H-NMR (DMSO-$d_6$) δ value:
2.67-2.78(4H,m),4.18(4H,s),6.60-6.66(3H,m),6.74(1H,d,J=8.0 Hz),6.81(1H,s),7.07-7.16(4H,m),7.79(1H,d,J=8.0 Hz).

2-(4-Fluoroanilino)-4-(2-(3-methoxyphenyl)ethyl)benzoic acid $^1$H-NMR (DMSO-$d_6$) δ value:
2.77-2.83(4H,m),3.70(3H,s),6.65(1H,dd,J=8.1,1.5 Hz),6.71-6.78(3H,m),6.81(1H,d,J=1.5 Hz),7.04-7.20(5H,m),7.80(1H,d,J=8.1 Hz).

4-(2-(4-Ethylphenyl)ethyl)-2-(4-fluoroanilino)benzoic acid $^1$H-NMR (DMSO-$d_6$) δ value:
1.15(3H,t,J=7.6 Hz),2.56(2H,q,J=7.6 Hz),2.76-2.81(4H,m),6.64(1H,dd,J=8.0,1.5 Hz),6.82(1H,d,J=1.5 Hz),7.05-7.15(8H,m),7.80(1H,d,J=8.0 Hz).

2-(4-Fluoroanilino)-4-(2-(4-(1H-pyrazol-1-yl)phenyl)ethyl)benzoic acid $^1$H-NMR (DMSO-$d_6$) δ value:
2.79(2H,t,J=7.4 Hz),2.88(2H,t,J=7.4 Hz),6.50-6.55(2H,m),6.77(1H,s),6.86-6.96(4H,m),7.27(2H,d,J=8.5 Hz),7.72(1H,d,J=2.4 Hz),7.74(2H,d,J=8.5 Hz),7.81(1H,d,J=7.8 Hz),8.46(1H,d,J=2.4 Hz),11.89-12.02(1H,broad).

Example 169

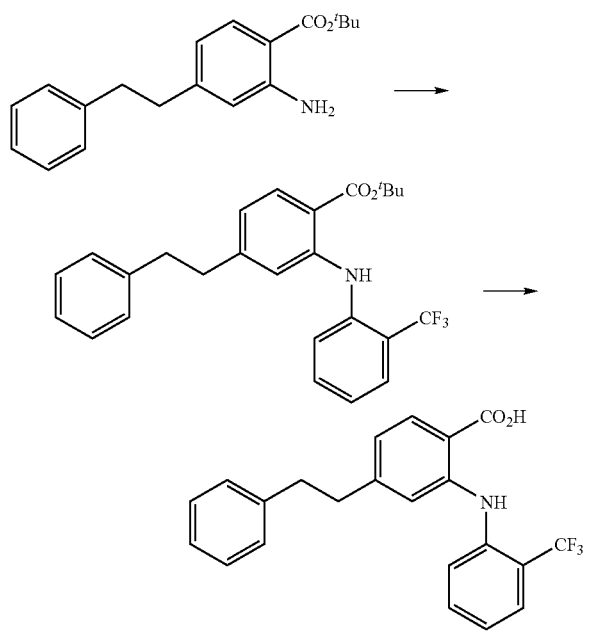

To toluene 3.0 mL solution of tert-butyl 2-amino-4-phenethylbenzoate 0.10 g were added 2-bromobenzotrifluoride 0.11 mL, cesium carbonate 0.22 g, tris(dibenzylideneacetone)dipalladium(0) 3.0 mg and 2-dicyclohexylphosphino-2',4',6'-triisopropylbiphenyl 8.0 mg at room temperature, and it was stirred at 110° C. for 24 hours. After the reaction mixture was cooled to room temperature, palladium acetate 1.5 mg, tris(dibenzylideneacetone)dipalladium(0) 3.0 mg and 2-dicyclohexylphosphino-2',4',6'-triisopropylbiphenyl 8.0 mg were added to it, and it was stirred at 110° C. for 20 hours. After the reaction mixture was cooled to room temperature, insoluble matter was filtrated, ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 4-phenethyl-2-(2-(trifluoromethyl)anilino)benzoate.

Trifluoroacetic acid 10 mL was added to the obtained tert-butyl 4-phenethyl-2-(2-(trifluoromethyl)anilino)benzoate, and it was stirred at room temperature for 2 hours. The solvent was removed under reduced pressure, diisopropyl ether was added to the obtained residue, and solid matter was filtrated to give 4-phenethyl-2-(2-(trifluoromethyl)anilino)benzoic acid 17 mg of white solid.

$^1$H-NMR (DMSO-$d_6$) δ value:
2.84(4H,s),6.79(1H,d,J=8.3 Hz),6.86-6.90(1H,m),7.13-7.32(7H,m),7.55(1H,t,J=7.7 Hz),7.71(1H,d,J=7.8 Hz),7.85(1H,d,J=8.3 Hz),9.95(1H,s),13.13(1H,s).

Example 170-175

The compounds shown in Table 27 were obtained in the same manner as in Example 169.

TABLE 27

| Example No. | R$^3$ |
|---|---|
| 170 | 4-(trifluoromethyl)phenyl |
| 171 | 2,5-difluorophenyl |
| 172 | 2,4-dimethylphenyl |

TABLE 27-continued

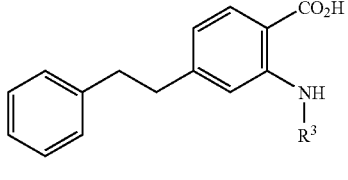

| Example No. | R³ |
|---|---|
| 173 | 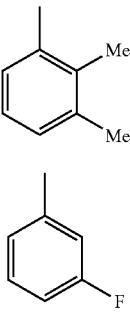 |
| 174 | (3-fluorophenyl) |
| 175 | (3,4-difluorophenyl) |

4-Phenethyl-2-(4-(trifluoromethyl)anilino)benzoic acid

¹H-NMR (DMSO-d₆) δ value:
2.89(4H,s),6.85(1H,dd,J=8.1,1.2 Hz),7.13-7.31(8H,m),7.57(2H,d,J=8.5 Hz),7.86(1H,d,J=8.3 Hz),9.72(1H,s),13.11(1H,s).

2-(2,5-Difluoroanilino)-4-phenethylbenzoic acid

¹H-NMR (DMSO-d₆) δ value:
2.88(4H,s),6.79-6.90(2H,m),7.03-7.07(1H,m),7.12-7.37(7H,m),7.85(1H,d,J=8.0 Hz),9.78(1H,s),13.17(1H,s).

2-(2,4-Dimethylanilino)-4-phenethylbenzoic acid

¹H-NMR (DMSO-d₆) δ value:
2.10(3H,s),2.27(3H,s),2.72-2.84(4H,m),6.52-6.55(1H,m),6.60(1H,dd,J=8.2,1.3 Hz),6.95-7.01(2H,m),7.08-7.27(6H,m),7.78(1H,d,J=8.3 Hz),9.36(1H,s),12.80(1H,s).

2-(2,3-Dimethylanilino)-4-phenethylbenzoic acid

¹H-NMR (DMSO-d₆) δ value:
2.05(3H,s),2.27(3H,s),2.71-2.83(4H,m),6.49(1H,dd,J=6.2,1.3 Hz),6.60(1H,dd,J=8.3,1.5 Hz),6.93(1H,d,J=7.8 Hz),6.99(1H,d,J=7.3 Hz),7.06(1H,t,J=7.7 Hz),7.11-7.20(3H,m),7.21-7.27(2H,m),7.79(1H,d,J=8.0 Hz),9.43(1H,s),12.83(1H,s).

2-(3-Fluoroanilino)-4-phenethylbenzoic acid

¹H-NMR (DMSO-d₆) δ value:
2.86(4H,s),6.74-6.89(3H,m),6.95(1H,dt,J=11.2,2.2 Hz),7.05(1H,d,J=1.4 Hz), 7.15-7.22(3H,m),7.23-7.34(3H,m),7.83(1H,d,J=8.0 Hz),9.63(1H,s),13.03(1H,s).

2-(3,4-Difluoroanilino)-4-phenethylbenzoic acid

¹H-NMR (DMSO-d₆) δ value:
2.84(4H,s),6.74(1H,d,J=8.3 Hz),6.84-6.95(2H,m),7.15-7.38(7H,m),7.82(1H,d,J=8.0 Hz),9.53(1H,s),13.00(1H,s).

Example 176

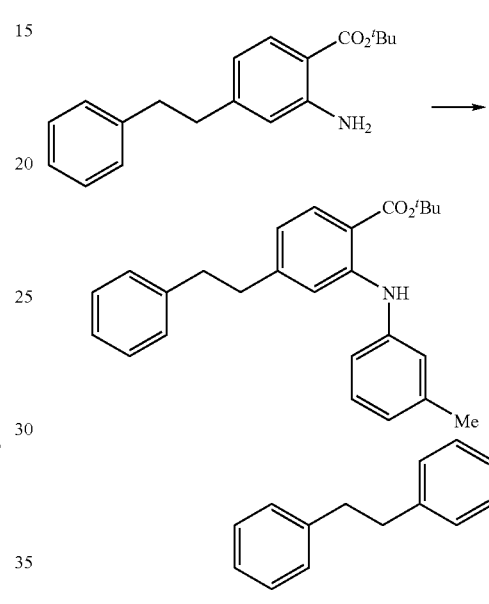

To toluene 3.0 mL solution of tert-butyl 2-amino-4-phenethylbenzoate 0.10 g were added 3-bromotoluene 0.10 mL, cesium carbonate 0.22 g, tris(dibenzylideneacetone)dipalladium(0) 3.0 mg and 2-dicyclohexylphosphino-2',4',6'-triisopropylbiphenyl 8.0 mg at room temperature, and it was stirred at 110° C. for 24 hours. After the reaction mixture was cooled to room temperature, palladium acetate 1.5 mg, tris(dibenzylideneacetone)dipalladium(0) 3.0 mg and 2-dicyclohexylphosphino-2',4',6'-triisopropylbiphenyl 8.0 mg were added, and it was stirred at 110° C. for 20 hours. After the reaction mixture was cooled to room temperature, insoluble matter was filtrated, ethyl acetate and 10% citric acid aqueous solution were added to it. The organic layer was separated and collected, dried over anhydrous magnesium sulfate after washing with saturated sodium chloride aqueous solution, the solvent was removed under reduced pressure. The obtained residue was refined by silica gel column chromatography [Trikonex company, Flash Tube 2008, eluent; hexane:ethyl acetate=4:1] to give tert-butyl 2-(3-methylanilino)-4-phenethylbenzoate.

Trifluoroacetic acid 10 mL was added to the obtained tert-butyl 2-(3-methylanilino)-4-phenethylbenzoate, and it was stirred at room temperature for 2 hours. The solvent was removed under reduced pressure, and the obtained residue was refined by reversed-phase silica gel column chromatography [eluent; 77-100% acetonitrile/0.1% trifluoroacetic acid aqueous solution] to give 2-(3-methylanilino)-4-phenethyl-benzoic acid 15 mg of white solid.

$^1$H-NMR (DMSO-$d_6$) δ value:
2.28(3H,s),2.77-2.88(4H,m),6.67(1H,dd,J=8.3,1.5 Hz),6.83-6.89(2H,m),6.93-7.00(2H,m),7.14-7.22(4H,m),7.23-7.29(2H,m),7.81(1H,d,J=8.0 Hz),9.58(1H,s),12.91(1H,s).

Example 177-181

The compounds shown in Table 28 were obtained in the same manner as in Example 176.

TABLE 28

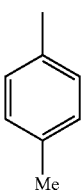

| Example No. | R$^3$ |
|---|---|
| 177 | 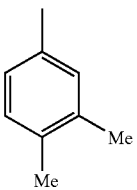 |
| 178 | 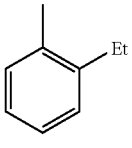 |
| 179 | 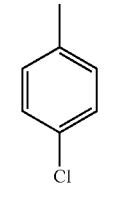 |
| 180 | 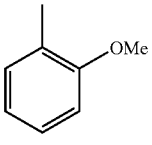 |
| 181 | 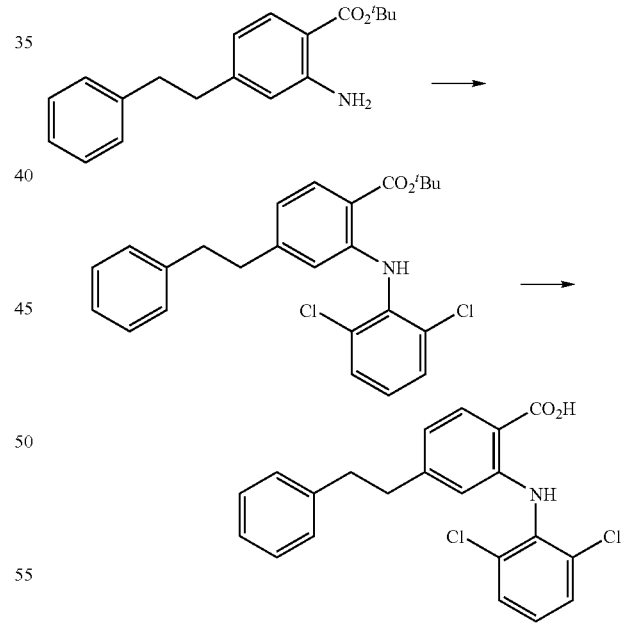 |

2-(4-Methylanilino)-4-phenethylbenzoic acid $^1$H-NMR (DMSO-$d_6$) δ value:
2.28(3H,s),2.75-2.89(4H,m),6.64(1H,d,J=7.8 Hz),6.85(1H,s),6.95(2H,d,J=8.0 Hz),7.08-7.32(7H,m),7.79(1H,d,J=8.3 Hz),9.52(1H,s),12.86(1H,s).

2-(3,4-Dimethylanilino)-4-phenethylbenzoic acid $^1$H-NMR (DMSO-$d_6$) δ value:
2.19(6H,s),2.72-2.88(4H,m),6.60-6.66(1H,m),6.80(1H,dd,J=8.0,2.2 Hz),6.86-6.95(2H,m),7.07(1H,d,J=8.1 Hz),7.12-7.30(5H,m),7.78(1H,d,J=8.0 Hz),9.50(1H,s),12.84(1H,s).

2-(2-Ethylanilino)-4-phenethylbenzoic acid $^1$H-NMR (DMSO-$d_6$) δ value:
1.12(3H,t,J=7.6 Hz),2.54(2H,q,J=7.6 Hz),2.73-2.85(4H,m),6.60-6.70(2H,m),7.04-7.31(9H,m),7.80(1H,d,J=8.0 Hz),9.54(1H,s),12.88(1H,s).

2-(4-Chloroanilino)-4-phenethylbenzoic acid $^1$H-NMR (DMSO-$d_6$) δ value:
2.82-2.87(4H,m),6.73(1H,dd,J=8.2,1.6 Hz),6.93(1H,d,J=1.2 Hz),7.03-7.09(2H,m),7.15-7.34(7H,m),7.82(1H,d,J=8.3 Hz),9.50-9.70(1H,broad),12.80-13.20(1H,broad).

2-(2-Methoxyanilino)-4-phenethylbenzoic acid $^1$H-NMR (DMSO-$d_6$) δ value:
2.78-2.89(4H,m),3.81(3H,s),6.67(1H,dd,J=8.2,1.3 Hz),6.87(1H,t d,J=7.6,1.6 Hz),6.94-7.12(4H,m),7.15-7.30(5H,m),7.80(1H,d,J=8.0 Hz),9.56(1H,s),12.70-13.00(1H,broad).

Example 182

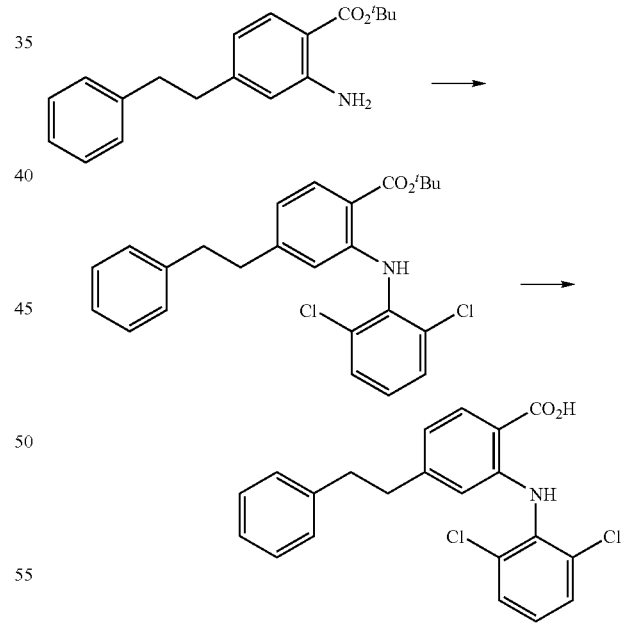

To toluene 3.0 mL solution of tert-butyl 2-amino-4-phenethylbenzoate 0.10 g were added 1,3-dichloro-2-iodobenzene 0.23 g, cesium carbonate 0.22 g, tris(dibenzylideneacetone)dipalladium(0) 3.0 mg and 2-dicyclohexylphosphino-2',4',6'-triisopropylbiphenyl 8.0 mg at room temperature, and it was stirred at 110° C. for 24 hours. After the reaction mixture was cooled to room temperature, palladium acetate 1.5 mg, tris(dibenzylideneacetone)dipalladium(0) 3.0 mg and 2-dicyclohexylphosphino-2',4',6'-triisopropylbiphenyl 8.0 mg were added, and it was stirred at 110° C. for 20 hours. After the reaction mixture was cooled to room temperature, insoluble matter was filtrated, ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-(2,6-dichloroanilino)-4-phenethylbenzoate.

Trifluoroacetic acid 10 mL was added to the obtained tert-butyl 2-(2,6-dichloroanilino)-4-phenethylbenzoate, and it was stirred at room temperature for 2 hours. The solvent was removed under reduced pressure, and the obtained residue was refined by reversed-phase silica gel column chromatography [eluent; 75-100% acetonitrile/0.1% trifluoroacetic acid aqueous solution] to give 2-(2,6-dichloroanilino)-4-phenethylbenzoic acid 9.4 mg of white solid.

$^1$H-NMR (DMSO-$d_6$) δ value:
2.76(4H,m),6.04(1H,d,J=1.2 Hz),6.66(1H,dd,J=8.1,1.2 Hz),7.08-7.24(5H,m),7.36(1H,t,J=8.2 Hz),7.61(2H,d,J=8.3 Hz),7.80(1H,d,J=8.0 Hz),9.52(1H,s),13.00(1H,s).

Example 183

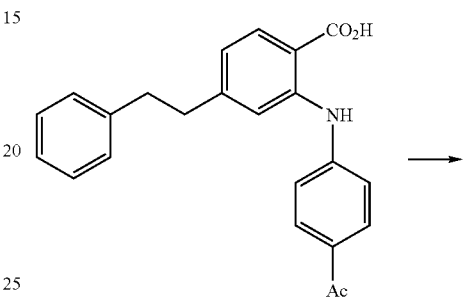

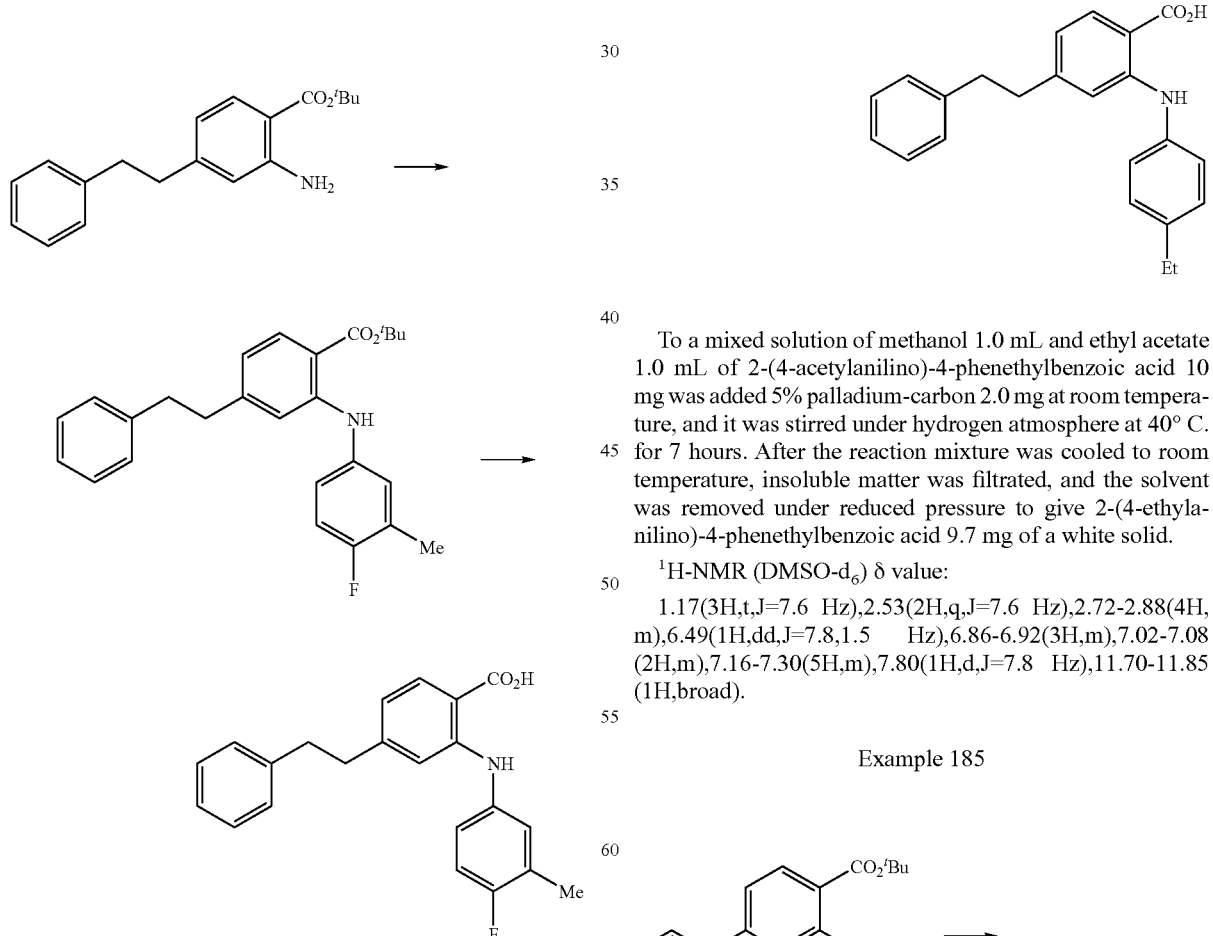

The following compound was obtained in the same manner as in Example 182.

2-(4-Fluoro-3-methylanilino)-4-phenethylbenzoic acid $^1$H-NMR (DMSO-$d_6$) δ value:
2.21(1H,d,J=1.7 Hz),2.76-2.87(4H,m),6.65(1H,dd,J=8.3, 1.5 Hz),6.82(1H,s),6.87-6.93(1H,m),7.03-7.11(2H,m),7.13-7.22(3H,m),7.23-7.29(2H,m),7.79(1H,d,J=8.0 Hz),9.48(1H, s),12.75-13.05(1H,broad).

Example 184

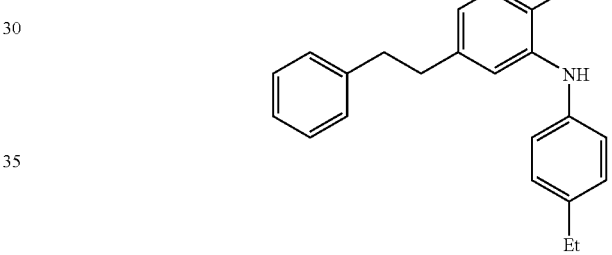

To a mixed solution of methanol 1.0 mL and ethyl acetate 1.0 mL of 2-(4-acetylanilino)-4-phenethylbenzoic acid 10 mg was added 5% palladium-carbon 2.0 mg at room temperature, and it was stirred under hydrogen atmosphere at 40° C. for 7 hours. After the reaction mixture was cooled to room temperature, insoluble matter was filtrated, and the solvent was removed under reduced pressure to give 2-(4-ethylanilino)-4-phenethylbenzoic acid 9.7 mg of a white solid.

$^1$H-NMR (DMSO-$d_6$) δ value:
1.17(3H,t,J=7.6 Hz),2.53(2H,q,J=7.6 Hz),2.72-2.88(4H, m),6.49(1H,dd,J=7.8,1.5 Hz),6.86-6.92(3H,m),7.02-7.08 (2H,m),7.16-7.30(5H,m),7.80(1H,d,J=7.8 Hz),11.70-11.85 (1H,broad).

Example 185

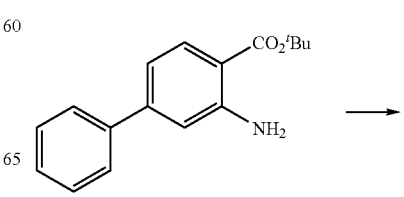

-continued

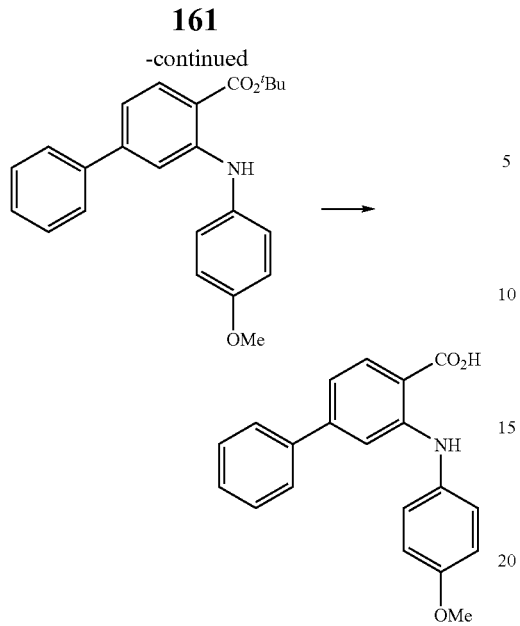

To toluene 3.0 mL solution of tert-butyl 2-amino-4-phenylbenzoate 94 mg were added 4-iodoanisole 0.20 g, cesium carbonate 0.23 g, tris(dibenzylideneacetone)dipalladium(0) 3.2 mg and 2-dicyclohexylphosphino-2',4',6'-triisopropylbiphenyl 8.3 mg at room temperature, and it was stirred at 110° C. for 6 hours. After the reaction mixture was cooled to room temperature, palladium acetate 1.6 mg, tris(dibenzylideneacetone)dipalladium(0) 3.2 mg and 2-dicyclohexylphosphino-2',4',6'-triisopropylbiphenyl 8.3 mg were added to it, and it was stirred at 110° C. for 12 hours. After the reaction mixture was cooled to room temperature, 4-iodoanisole 0.20 g, cesium carbonate 0.23 g, palladium acetate 1.6 mg, tris(dibenzylideneacetone)dipalladium(0) 3.2 mg and 2-dicyclohexylphosphino-2',4',6'-triisopropylbiphenyl 8.3 mg were added to it, and it was stirred at 110° C. for 4 hours. After the reaction mixture was cooled to room temperature, insoluble matter was filtrated, ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane: ethyl acetate=10:1] to give tert-butyl 2-(4-methoxyanilino)-4-phenylbenzoate.

Trifluoroacetic acid 10 mL was added to the obtained tert-butyl 2-(4-methoxyanilino)-4-phenylbenzoate, and it was stirred at room temperature for 2 hours. The solvent was removed under reduced pressure, diisopropyl ether was added to the obtained residue, and solid matter was filtrated to give 2-(4-methoxyanilino)-4-phenylbenzoic acid 44 mg of yellow solid.

$^1$H-NMR (DMSO-$d_6$) δ value:
3.77(3H,s),6.95-7.01(3H,m),7.14(1H,d,J=1.7 Hz),7.24-7.30(2H,m),7.35-7.48(3H,m),7.50-7.55(2H,m),7.95(1H,d, J=8.3 Hz),9.51(1H,s),13.00(1H,s).

Example 186, 187

The compounds shown in Table 29 were obtained in the same manner as in Example 185.

TABLE 29

| Example No. | $R^3$ |
|---|---|
| 186 | 2-methoxyphenyl |
| 187 | 3-chlorophenyl |

2-(2-Methoxyanilino)-4-phenylbenzoic acid $^1$H-NMR (DMSO-$d_6$) δ value:
3.84(3H,s),6.95-7.20(4H,m),7.36-7.53(5H,m),7.56-7.63 (2H,m),7.98(1H,d,J=8.3 Hz),9.65(1H,s),12.85-13.15(1H, broad).

2-(3-Chloroanilino)-4-phenylbenzoic acid $^1$H-NMR (DMSO-$d_6$) δ value:
7.07-7.11(1H,m),7.16(1H,dd,J=8.3,1.7 Hz),7.31-7.51 (7H,m),7.59-7.64(2H,m),8.00(1H,d,J=8.3 Hz),9.68(1H,s), 13.21(1H,s).

Example 188

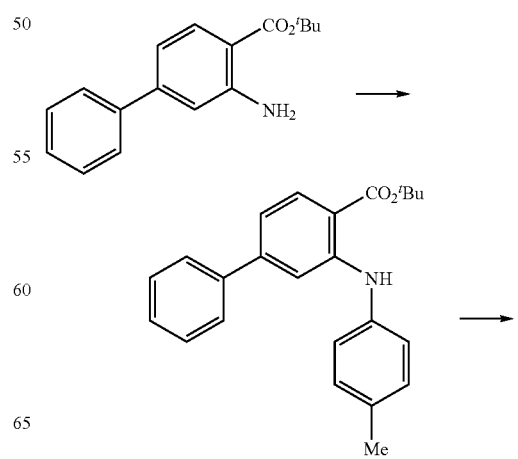

-continued

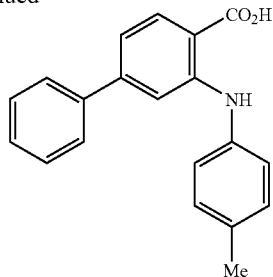

To toluene 3.0 mL solution of tert-butyl 2-amino-4-phenylbenzoate 94 mg were added 4-bromotoluene 0.11 mL, cesium carbonate 0.23 g, tris(dibenzylideneacetone)dipalladium(0) 3.2 mg and 2-dicyclohexylphosphino-2',4',6'-triisopropylbiphenyl 8.3 mg at room temperature, and it was stirred at 110° C. for 6 hours. After the reaction mixture was cooled to room temperature, palladium acetate 1.6 mg, tris(dibenzylideneacetone)dipalladium(0) 3.2 mg and 2-dicyclohexylphosphino-2',4',6'-triisopropylbiphenyl 8.3 mg were added to it, and it was stirred at 110° C. for 12 hours. After the reaction mixture was cooled to room temperature, insoluble matter was filtrated, and ethyl acetate and 10% citric acid aqueous solution were added to it. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-(4-methylanilino)-4-phenylbenzoate.

Trifluoroacetic acid 10 mL was added to the obtained tert-butyl 2-(4-methylanilino)-4-phenylbenzoate, and it was stirred at room temperature for 2 hours. The solvent was removed under reduced pressure,diisopropyl ether was added to the obtained residue, and solid matter was filtrated to give 2-(4-methylanilino)-4-phenylbenzoic acid 8.7 mg of white solid.

$^1$H-NMR (DMSO-$d_6$) δ value:
2.30(3H,s),7.02(1H,dd,J=8.3,1.7 Hz),7.12-7.28(4H,m),7.31-7.34(1H,m),7.36-7.48(3H,m),7.53-7.58(2H,m),7.97(1H,d,J=8.3 Hz),9.62(1H,s),13.06(1H,s).

Example 189-194

The compounds shown in Table 30 were obtained in the same manner as in Example 188.

TABLE 30

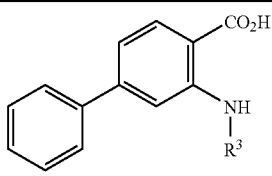

| Example No. | R³ |
|---|---|
| 189 | 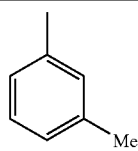 |

TABLE 30-continued

| Example No. | R³ |
|---|---|
| 190 | 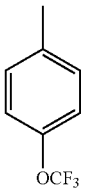 |
| 191 | 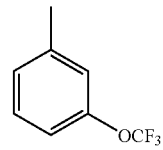 |
| 192 | 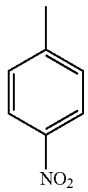 |
| 193 | 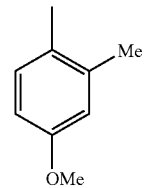 |
| 194 | 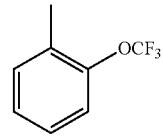 |

2-(3-Methylanilino)-4-phenylbenzoic acid $^1$H-NMR (DMSO-$d_6$) δ value:
2.31(3H,s),6.92(1H,d,J=7.6 Hz),7.06(1H,dd,J=8.3,1.7 Hz),7.11 (1H,s),7.15(1H,d,J=8.0 Hz),7.27(1H,t,J=7.8 Hz),7.37-7.49(4H,m),7.55-7.61(2H,m),7.98(1H,d,J=8.3 Hz),9.67(1H,s),13.10(1H,s).

4-Phenyl-2-(4-(trifluoromethoxy)anilino)benzoic acid $^1$H-NMR (DMSO-$d_6$) δ value:
7.13(1H,dd,J=8.3,1.7 Hz),7.33-7.50(8H,m),7.60-7.65(2H,m),8.01(1H,d,J=8.3 Hz),9.74(1H,s),13.20(1H,s).

4-Phenyl-2-(3-(trifluoromethoxy)anilino)benzoic acid $^1$H-NMR (DMSO-$d_6$) δ value:
7.01(1H,d,J=8.3 Hz),7.18(1H,dd,J=8.3,1.5 Hz),7.31-7.54 (7H,m),7.60-7.65(2H,m),8.02(1H,d,J=8.3 Hz),9.74(1H,s), 13.24(1H,s).

2-(4-Nitroanilino)-4-phenylbenzoic acid $^1$H-NMR (DMSO-$d_6$) δ value:
7.35-7.53(6H,m),7.70-7.76(3H,m),8.05(1H,d,J=8.3 Hz), 8.17(2H,d,J=9.0 Hz),9.92(1H,s),13.37(1H,s).

2-(4-Methoxy-2-methylanilino)-4-phenylbenzoic acid $^1$H-NMR (DMSO-$d_6$) δ value:
2.18(3H,s),3.76(3H,s),6.71-6.75(1H,m),6.84(1H,dd, J=8.5,2.9 Hz),6.91-6.96(2H,m),7.25(1H,d,J=8.5 Hz),7.34-7.50(5H,m),7.94(1H,d,J=8.3 Hz),9.34(1H,s),12.95(1H,s).

4-Phenyl-2-(2-(trifluoromethoxy)anilino)benzoic acid $^1$H-NMR (DMSO-$d_6$) δ value:
7.14-7.22(2H,m),7.38-7.51(6H,m),7.61-7.66(2H,m),7.78 (1H,dd,J=8.0,1.5 Hz),8.03(1H,d,J=8.3 Hz),10.07 (1H,s), 13.33(1H,s).

Example 195

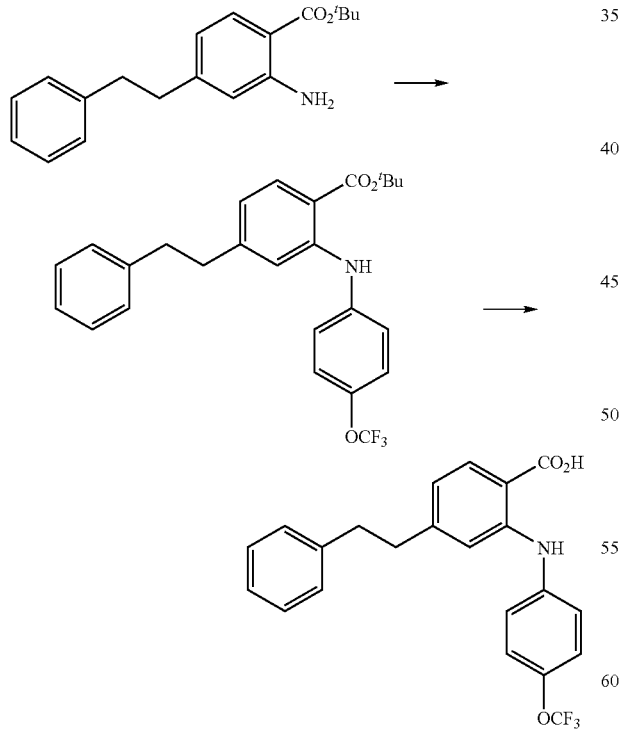

To toluene 3.0 mL solution of tert-butyl 2-amino-4-phenethylbenzoate 0.10 g were added 1-bromo-4-(trifluoromethoxy)benzene 0.13 mL, cesium carbonate 0.23 g, tris(dibenzylideneacetone)dipalladium(0) 3.2 mg and 2-dicyclohexylphosphino-2',4',6'-triisopropylbiphenyl 8.3 mg at room temperature, and it was stirred at 110° C. for 6 hours. After the reaction mixture was cooled to room temperature, palladium acetate 1.6 mg, tris(dibenzylideneacetone)dipalladium(0) 3.2 mg and 2-dicyclohexylphosphino-2',4',6'-triisopropylbiphenyl 8.3 mg were added at room temperature, and it was stirred at 110° C. for 12 hours. After the reaction mixture was cooled to room temperature, insoluble matter was filtrated, ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 4-phenethyl-2-(4-(trifluoromethoxy)anilino)benzoate.

Trifluoroacetic acid 10 mL was added to the obtained tert-butyl 4-phenethyl-2-(4-(trifluoromethoxy)anilino)benzoate, and it was stirred at room temperature for 2 hours. The solvent was removed under reduced pressure, diisopropyl ether was added to the obtained residue, and solid matter was filtrated to give 4-phenethyl-2-(4-(trifluoromethoxy)anilino)benzoic acid 20 mg of white solid.

$^1$H-NMR (DMSO-$d_6$) δ value:
2.85(4H,s),6.72-6.78(1H,m),6.97(1H,s),7.11-7.30(9H, m),7.83(1H,d,J=8.0 Hz),9.62(1H,s),13.00(1H,s).

Example 196-199

The compounds shown in Table 31 were obtained in the same manner as in Example 195.

TABLE 31

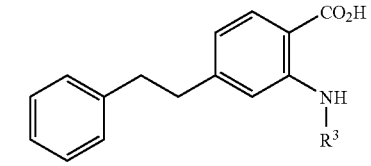

| Example No. | R$^3$ |
|---|---|
| 196 | 4-nitrophenyl |
| 197 | 3-(trifluoromethoxy)phenyl |
| 198 | 2-methyl-4-methoxyphenyl |

TABLE 31-continued

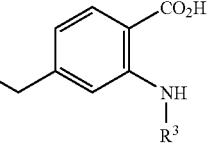

| Example No. | R³ |
|---|---|
| 199 | (2-OCF₃-phenyl) |

2-(4-Nitroanilino)-4-phenethylbenzoic acid

¹H-NMR (DMSO-d₆) δ value:
2.92(4H,s),7.00(1H,dd,J=8.1,1.5 Hz),7.06-7.12(2H,m),7.18-7.32(6H,m),7.88(1H,d,J=8.0 Hz),8.05-8.11(2H,m),9.82(1H,s),13.10-13.35(1H,broad).

4-Phenethyl-2-(3-(trifluoromethoxy)anilino)benzoic acid

¹H-NMR (DMSO-d₆) δ value:
2.86(4H,s),6.79(1H,dd,J=8.2,1.3 Hz),6.93-6.98(1H,m),7.03-7.09(2H,m),7.12(1H,s),7.15-7.21(3H,m),7.23-7.30(2H,m),7.38(1H,t,J=8.2 Hz),7.84(1H,d,J=8.1 Hz),9.62(1H,s),13.05(1H,s).

2-(4-Methoxy-2-methylanilino)-4-phenethylbenzoic acid

¹H-NMR (DMSO-d₆) δ value:
2.09(3H,s),2.69-2.81(4H,m),3.76(3H,s),6.33(1H,d,J=1.2 Hz),6.55(1H,dd,J=8.3, 1.5 Hz),6.77(1H,dd,J=8.5,2.9 Hz),6.89(1H,d,J=3.0 Hz),7.00 (1H,d,J=8.6 Hz),7.09-7.27(5H,m),7.76(1H,d,J=8.0 Hz),9.22(1H,s),12.74(1H,s).

4-Phenethyl-2-(2-(trifluoromethoxy)anilino)benzoic acid

¹H-NMR (DMSO-d₆) δ value:
2.87(4H,m),6.76-6.81(1H,m),6.98-7.02(1H,m),7.08-7.15(1H,m),7.15-7.23(3H,m),7.24-7.34(4H,m),7.40-7.44(1H,m),7.85(1H,d,J=8.3 Hz),9.98(1H,s),13.14(1H,s).

Example 200

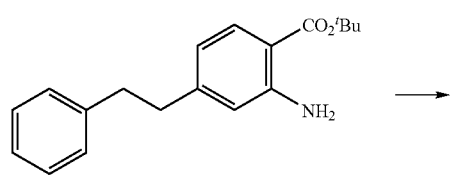

-continued

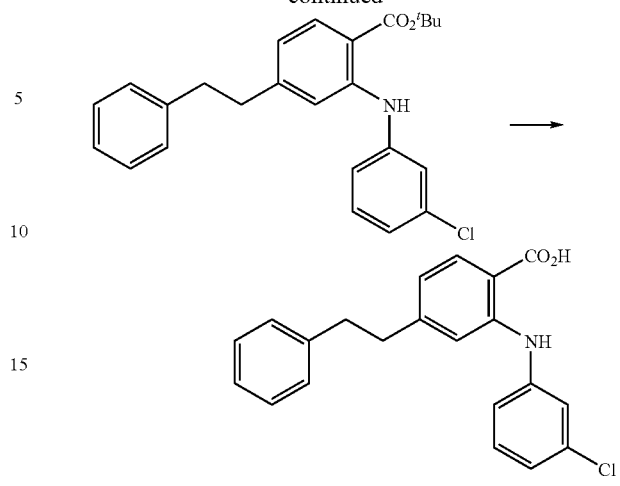

To toluene 3.0 mL solution of tert-butyl 2-amino-4-phenethylbenzoate 0.10 g were added 1-chloro-3-iodobenzene 0.11 mL, cesium carbonate 0.23 g, tris(dibenzylideneacetone)dipalladium(0) 3.2 mg and 2-dicyclohexylphosphino-2',4',6'-triisopropylbiphenyl 8.3 mg at room temperature, and it was stirred at 110° C. for 6 hours. After the reaction mixture was cooled to room temperature, palladium acetate 1.6 mg, tris(dibenzylideneacetone)dipalladium(0) 3.2 mg and 2-dicyclohexylphosphino-2',4',6'-triisopropylbiphenyl 8.3 mg were added, and it was stirred at 110° C. for 12 hours. After the reaction mixture was cooled to room temperature, insoluble matter was filtrated, ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-(3-chloroanilino)-4-phenethylbenzoate.

Trifluoroacetic acid 10 mL was added to the obtained tert-butyl 2-(3-chloroanilino)-4-phenethylbenzoate, and it was stirred at room temperature for 2 hours. The solvent was removed under reduced pressure, diisopropyl ether was added to the obtained residue, and solid matter was filtrated to give 2-(3-chloroanilino)-4-phenethylbenzoic acid 21 mg of white solid.

¹H-NMR (DMSO-d₆) δ value:
2.86(4H,s),6.76(1H,dd,J=8.2,1.3 Hz),6.97-7.06(3H,m),7.15-7.21(4H,m),7.24-7.32(3H,m),7.83(1H,d,J=8.1 Hz),9.58(1H,s),13.02(1H,s).

Example 201

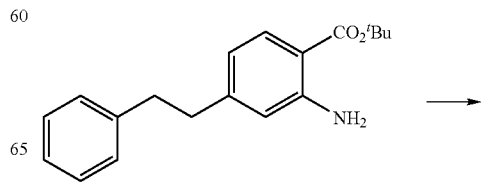

-continued

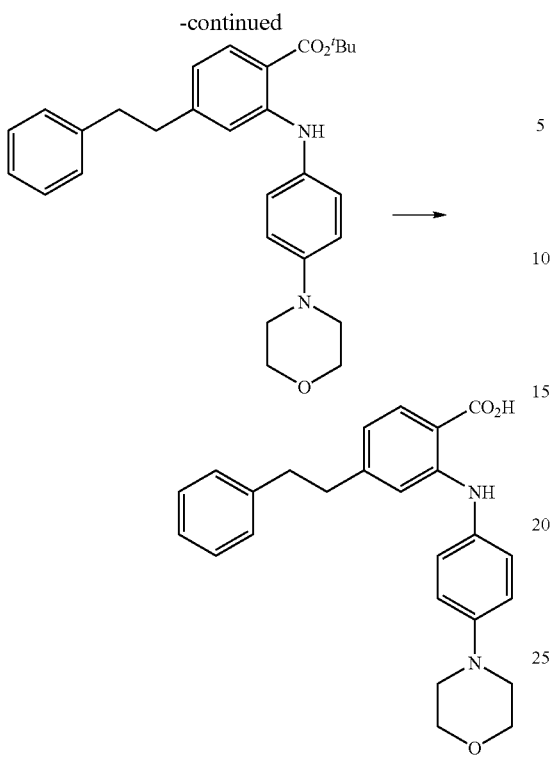

To toluene 3.0 mL solution of tert-butyl 2-amino-4-phenethylbenzoate 0.10 g were added 4-(4-bromophenyl)morpholine 0.21 g, cesium carbonate 0.23 g, tris(dibenzylideneacetone)dipalladium(0) 3.2 mg and 2-dicyclohexylphosphino-2',4',6'-triisopropylbiphenyl 8.3 mg at room temperature, and it was stirred at 110° C. for 6 hours. After the reaction mixture was cooled to room temperature, palladium acetate 1.6 mg, tris(dibenzylideneacetone)dipalladium(0) 3.2 mg and 2-dicyclohexylphosphino-2',4',6'-triisopropylbiphenyl 8.3 mg were added, and it was stirred at 110° C. for 12 hours. After the reaction mixture was cooled to room temperature, 4-(4-bromophenyl)morpholine 0.21 g, cesium carbonate 0.23 g, palladium acetate 1.6 mg, tris(dibenzylideneacetone)dipalladium(0) 3.2 mg and 2-dicyclohexylphosphino-2',4',6'-triisopropylbiphenyl 8.3 mg were added, and it was stirred at 110° C. for 4 hours. After the reaction mixture was cooled to room temperature, insoluble matter was filtrated, ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-(4-morpholinoanilino)-4-phenethylbenzoate.

Trifluoroacetic acid 10 mL was added to the obtained tert-butyl 2-(4-morpholinoanilino)-4-phenethylbenzoate, and it was stirred at room temperature for 2 hours. The solvent was removed under reduced pressure, and the obtained residue was refined by reversed-phase silica gel column chromatography [eluent; 45-80% acetonitrile/0.1% trifluoroacetic acid aqueous solution] to give 2-(4-morpholinoanilino)-4-phenethylbenzoic acid 11 mg of a white solid.

$^1$H-NMR (DMSO-$d_6$) δ value:
2.72-2.85(4H,m),3.09(4H,t,J=4.8 Hz),3.75(4H,t,J=4.8 Hz),6.58(1H,d,J=8.3 Hz),6.72(1H,s),6.92(2H,d,J=9.0 Hz), 6.97(2H,d,J=9.0 Hz),7.12-7.22(3H,m),7.22-7.30(2H,m),7.76(1H,d,J=8.0 Hz),9.40(1H,s),12.76(1H,s).

Example 202

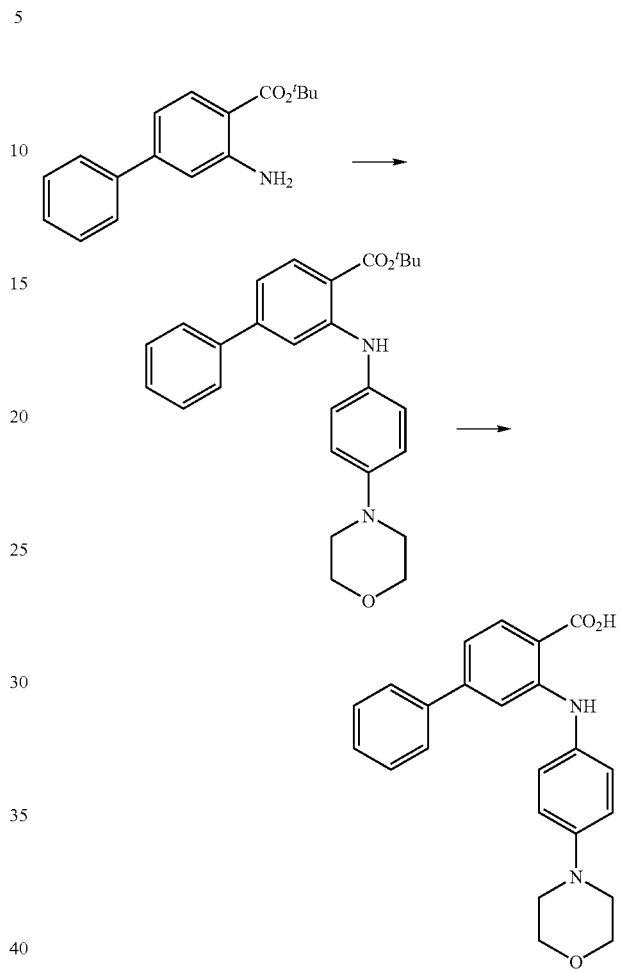

To toluene 3.0 mL solution of tert-butyl 2-amino-4-phenylbenzoate 94 mg were added 4-(4-bromophenyl)morpholine 0.21 g, cesium carbonate 0.23 g, tris(dibenzylideneacetone)dipalladium(0) 3.2 mg and 2-dicyclohexylphosphino-2',4',6'-triisopropylbiphenyl 8.3 mg at room temperature, and it was stirred at 110° C. for 6 hours. After the reaction mixture was cooled to room temperature, palladium acetate 1.6 mg, tris(dibenzylideneacetone)dipalladium(0) 3.2 mg and 2-dicyclohexylphosphino-2',4',6'-triisopropylbiphenyl 8.3 mg were added, and it was stirred at 110° C. for 12 hours. After the reaction mixture was cooled to room temperature, 4-(4-bromophenyl)morpholine 0.21 g, cesium carbonate 0.23 g, palladium acetate 1.6 mg, tris(dibenzylideneacetone)dipalladium(0) 3.2 mg and 2-dicyclohexylphosphino-2',4',6'-triisopropylbiphenyl 8.3 mg were added, and it was stirred at 110° C. for 4 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-(4-morpholinoanilino)-4-phenylbenzoate.

Trifluoroacetic acid 10 mL was added to the obtained tert-butyl 2-(4-morpholinoanilino)-4-phenylbenzoate, and it was stirred at room temperature for 2 hours. The solvent was removed under reduced pressure, the obtained residue was refined by reversed-phase silica gel column chromatography [eluent; 50-80% acetonitrile/0.1% trifluoroacetic acid aqueous solution] to give 2-(4-morpholinoanilino)-4-phenylbenzoic acid 31 mg of a yellow solid.

$^1$H-NMR (DMSO-$d_6$) δ value:
3.10(4H,t,J=4.8 Hz),3.74(4H,t,J=4.8 Hz),6.93-6.99(1H,m),6.99(2H,d,J=8.8 Hz),7.15-7.19(1H,m),7.21(2H,d,J=8.8 Hz),7.35-7.47(3H,m),7.50-7.55(2H,m),7.94(1H,d,J=8.3 Hz),9.50(1H,s),12.96(1H,s).

Example 203

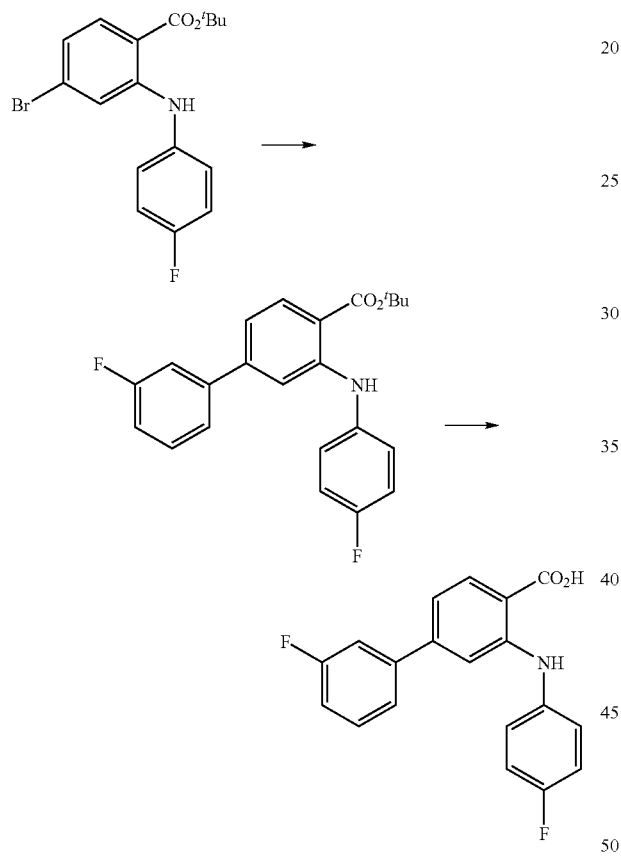

To toluene 2.1 mL solution of tert-butyl 4-bromo-2-(4-fluoroanilino)benzoate 0.10 g were added ethanol 0.6 mL, water 0.3 mL, 3-fluorophenylboronic acid 46 mg, sodium hydrogen carbonate 69 mg and tetrakis(triphenylphosphine)palladium(0) 16 mg at room temperature, and it was heated and refluxed for 2 hours. After the reaction mixture was cooled to room temperature, tetrakis(triphenylphosphine)palladium(0) 16 mg were added, and it was heated and refluxed for 2 hours. After the reaction mixture was cooled to room temperature, toluene and saturated sodium hydrogen carbonate aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 200S, eluent; hexane:ethyl acetate=10:1] to give tert-butyl 2-(4-fluoroanilino)-4-(3-fluorophenyl)benzoate.

Trifluoroacetic acid 10 mL was added to the obtained tert-butyl 2-(4-fluoroanilino)-4-(3-fluorophenyl)benzoate, and it was stirred at room temperature for 2 hours. The solvent was removed under reduced pressure, hexane was added to the obtained residue, and solid matter was filtrated to give 2-(4-fluoroanilino)-4-(3-fluorophenyl)benzoic acid 56 mg of a yellow solid.

$^1$H-NMR (DMSO-$d_6$) δ value:
7.07(1H,dd,J=8.3,1.7 Hz),7.19-7.29(4H,m),7.35-7.45(4H,m),7.49(1H,td,J=8.1,6.2 Hz),7.98(1H,d,J=8.3 Hz),9.63(1H,s),13.12-13.21(1H,broad).

Example 204-223

The compounds shown in Table 32 were obtained in the same manner as in Example 203.

TABLE 32

| Example No. | $R^4$ |
|---|---|
| 204 | 2-fluorophenyl |
| 205 | 2-methyl-4-fluoro-phenyl (Me, F substituents) |
| 206 | 4-fluoro-2-methylphenyl |
| 207 | 4-chlorophenyl |
| 208 | 2-chlorophenyl |
| 209 | 3,4-dimethoxyphenyl |
| 210 | 4-(isopropoxy)phenyl |

TABLE 32-continued

[Structure: benzoic acid with CO₂H, NH-linked 4-fluorophenyl, and R⁴ substituent]

| Example No. | R⁴ |
|---|---|
| 211 | 3-nitrophenyl (O₂N-phenyl, meta) |
| 212 | 4-nitrophenyl (O₂N-phenyl, para) |
| 213 | 2,3-dimethylphenyl |
| 214 | 2,4-dimethylphenyl (Me, Me) |
| 215 | 2,6-dimethylphenyl |
| 216 | 2-hydroxyphenyl |
| 217 | 4-hydroxy-3,5-dimethylphenyl |
| 218 | 3-chloro-4-methoxyphenyl |
| 219 | 3-methylphenyl |
| 220 | 2-(trifluoromethoxy)phenyl |

TABLE 32-continued

[Structure: benzoic acid with CO₂H, NH-linked 4-fluorophenyl, and R⁴ substituent]

| Example No. | R⁴ |
|---|---|
| 221 | 3-(trifluoromethoxy)phenyl (F₃CO, meta) |
| 222 | 4-(trifluoromethoxy)phenyl (F₃CO, para) |
| 223 | 5-methyl-2-oxoindolin-yl |

2-(4-Fluoroanilino)-4-(2-fluorophenyl)benzoic acid

¹H-NMR (DMSO-d₆) δ value:
6.95(1H,d,J=8.3 Hz),7.17-7.38(7H,m),7.40-7.47(1H,m),7.50(1H,td,J=7.9,1.5 Hz),7.99(1H,d,J=8.3 Hz),9.60 (1H,s),13.18(1H,s).

2-(4-Fluoroanilino)-4-(3-fluoro-4-methylphenyl)benzoic acid

¹H-NMR (DMSO-d₆) δ value:
2.25(3H,s),7.05(1H,dd,J=8.3,1.7 Hz),7.18-7.27(3H,m),7.29-7.40(5H,m),7.96(1H,d,J=8.3 Hz),9.58-9.70(1H,broad).

2-(4-Fluoroanilino)-4-(4-fluoro-2-methylphenyl)benzoic acid

¹H-NMR (DMSO-d₆) δ value:
2.21(3H,s),6.72(1H,dd,J=8.3,1.5 Hz),6.80-6.90(1H,m),7.05(1H,td,J=8.6,2.6 Hz),7.14(1H,dd,J=10.2,2.4 Hz),7.16-7.24(3H,m),7.28-7.35(2H,m),7.94(1H,d,J=8.0 Hz),9.59(1H,s),13.00-13.20(1H,broad).

4-(4-Chlorophenyl)-2-(4-fluoroanilino)benzoic acid

¹H-NMR (DMSO-d₆) δ value:
7.05(1H,dd,J=8.3,1.7 Hz),7.18-7.26(3H,m),7.34-7.40(2H,m),7.48-7.53(2H,m),7.57-7.63(2H,m),7.98(1H,d,J=8.3 Hz),9.50-9.70(1H,broad),13.00-13.30(1H,broad).

4-(2-Chlorophenyl)-2-(4-fluoroanilino)benzoic acid

¹H-NMR (DMSO-d₆) δ value:
6.81(1H,dd,J=8.3,1.7 Hz),7.04(1H,d,J=1.5 Hz),7.17-7.23(2H,m),7.30-7.35(2H,m),7.38-7.42(3H,m),7.52-7.57(1H,m),7.97(1H,d,J=8.3 Hz),9.60(1H,s).

4-(3,4-Dimethoxyphenyl)-2-(4-fluoroanilino)benzoic acid

¹H-NMR (DMSO-d₆) δ value:
3.78(3H,s),3.80(3H,s),6.99-7.27(7H,m),7.33-7.40(2H,m),7.94(1H,d,J=8.3 Hz),9.61(1H,s),13.04(1H,s).

2-(4-Fluoroanilino)-4-(4-isopropoxyphenyl)benzoic acid

¹H-NMR (DMSO-d₆) δ value:
1.27(6H,d,J=6.1 Hz),4.64(1H,sep,J=6.1 Hz),6.95-7.00(2H,m),7.01(1H,dd,J=8.3,1.7 Hz),7.19-7.26(3H,m),7.34-7.39(2H,m),7.46-7.51(2H,m),7.94(1H,d,J=8.6 Hz),9.60(1H,s),13.01(1H,s).

2-(4-Fluoroanilino)-4-(3-nitrophenyl)benzoic acid

¹H-NMR (DMSO-d₆) δ value:
7.15(1H,dd,J=8.3,1.7 Hz),7.19-7.26(2H,m),7.33(1H,d,J=1.4 Hz),7.35-7.42(2H,m),7.75(1H,t,J=8.0 Hz),8.00-8.07(2H,m),8.21-8.26(1H,m),8.33(1H,t,J=1.9 Hz),9.60-9.80(1H,broad),13.00-13.04(1H,broad).

2-(4-Fluoroanilino)-4-(4-nitrophenyl)benzoic acid

¹H-NMR (DMSO-d₆) δ value:
7.14(1H,dd,J=8.2,1.6 Hz),7.19-7.26(2H,m),7.33(1H,d,J=1.4 Hz),7.36-7.42(2H,m),7.86(2H,d,J=9.0 Hz),8.03(1H,d,J=8.3 Hz),8.28(2H,d,J=9.0 Hz),9.65(1H,s),13.10-13.40(1H,broad).

4-(2,3-Dimethylphenyl)-2-(4-fluoroanilino)benzoic acid

¹H-NMR (DMSO-d₆) δ value:
2.09(3H,s),2.26(3H,s),6.68(1H,dd,J=8.1,1.5 Hz),6.86(1H,d,J=1.5H),6.99(1H,d,J=6.8 Hz),7.10(1H,t,J=7.6 Hz),7.12-7.22(3H,m),7.27-7.34(2H,m),7.94(1H,d,J=8.3 Hz),9.59(1H,s),13.07(1H,s).

4-(3,4-Dimethylphenyl)-2-(4-fluoroanilino)benzoic acid

¹H-NMR (DMSO-d₆) δ value:
2.23(3H,s),2.26(3H,s),7.02(1H,d,J=8.3 Hz),7.17-7.29(5H,m),7.32-7.39(3H,m),7.95(1H,d,J=8.3 Hz),9.57-9.65(1H,broad),12.90-13.20(1H,broad).

4-(2,6-Dimethylphenyl)-2-(4-fluoroanilino)benzoic acid

¹H-NMR (DMSO-d₆) δ value:
1.99(6H,s),6.54(1H,dd,J=8.0,1.5 Hz),6.71(1H,d,J=1.2 Hz),7.05-7.10(2H,m),7.11-7.22(3H,m),7.23-7.29(2H,m),7.97(1H,d,J=8.1 Hz),9.59(1H,s),13.08(1H,s).

2-(4-Fluoroanilino)-4-(2-hydroxyphenyl)benzoic acid

¹H-NMR (DMSO-d₆) δ value:
6.85(1H,t,J=7.4 Hz),6.91(1H,d,J=7.8 Hz),6.94(1H,dd,J=8.3,1.5 Hz),7.14-7.21(3H,m),7.24(1H,dd,J=7.6,1.4 Hz),7.29-7.37(3H,m),7.91(1H,d,J=8.3 Hz),9.56(1H,s),9.63(1H,s),12.99 (1H,s).

4-(3,5-Dimethyl-4-hydroxyphenyl)-2-(4-fluoroanilino)benzoic acid

¹H-NMR (DMSO-d₆) δ value:
2.19(6H,s),6.97(1H,dd,J=8.3,1.7 Hz),7.13(2H,s),7.19-7.25(3H,m),7.31-7.37(2H,m),7.91(1H,d,J=8.3 Hz),8.48(1H,s),9.59(1H,s),12.96 96(1H,s).

4-(3-Chloro-4-methoxyphenyl)-2-(4-fluoroanilino)benzoic acid

¹H-NMR (DMSO-d₆) δ value:
3.88(3H,s),7.04(1H,dd,J=8.3, 1.7 Hz),7.19-7.25(4H,m),7.34-7.40(2H,m),7.52(1H,dd,J=8.6, 2.3 Hz),7.64(1H,d,J=2.2 Hz),7.95 (1H,d,J=8.3 Hz),9.62(1H,s),13.09(1H,s).

2-(4-Fluoroanilino)-4-(3-methylphenyl)benzoic acid

¹H-NMR (DMSO-d₆) δ value:
2.35(3H,s),7.03(1H,dd,J=8.3, 1.7 Hz),7.18-7.26(4H,m),7.31-7.40(5H,m),7.97(1H,d,J=8.3 Hz),9.50-9.70(1H,broad),12.90-13.20(1H,broad).

2-(4-Fluoroanilino)-4-(2-(trifluoromethoxy)phenyl)benzoic acid

¹H-NMR (DMSO-d₆) δ value:
6.85(1H,dd,J=8.2, 1.5 Hz),7.06-7.11(1H,m),7.16-7.24(2H,m),7.27-7.35(2H,m),7.42-7.56(4H,m),7.98(1H,d,J=8.2 Hz),9.57(1H,s),13.10-13.30(1H,broad).

2-(4-Fluoroanilino)-4-(3-(trifluoromethoxy)phenyl)benzoic acid

¹H-NMR (DMSO-d₆) δ value:
7.08(1H,dd,J=8.4, 1.6 Hz),7.18-7.30(3H,m),7.34-7.44(3H,m),7.52-7.64(3H,m),7.99(1H,d,J=8.4 Hz),9.66(1H,s),12.90-13.30(1H,broad).

2-(4-Fluoroanilino)-4-(4-(trifluoromethoxy)phenyl)benzoic acid

¹H-NMR (DMSO-d₆) δ value:
7.06(1H,dd,J=8.3, 1.7 Hz),7.18-7.28(3H,m),7.33-7.47(4H,m),7.67-7.74(2H,m),7.99(1H,d,J=8.3 Hz),9.63(1H,s),13.15(1H,s).

2-(4-Fluoroanilino)-4-(2-oxo-2,3-dihydro-1H-indol-5-yl)benzoic acid

¹H-NMR (DMSO-d₆) δ value:
3.51(2H,s),6.87(1H,d,J=8.0 Hz),6.99(1H,dd,J=8.5, 1.6 Hz),7.18-7.26(3H,m),7.32-7.44(4H,m),7.94(1H,d,J=8.5 Hz),9.60(1H,s),10.48(1H,s),13.01(1H,s).

Example 224

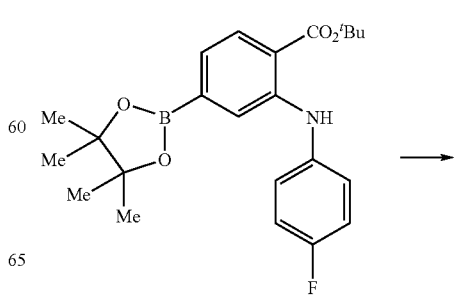

-continued

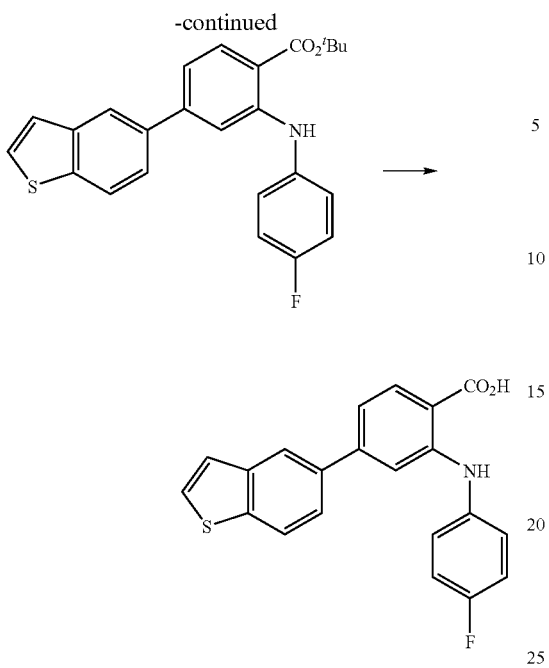

To toluene 1.6 mL solution of tert-butyl 2-(4-fluoroanilino)-4-(4,4,5,5-tetramethyl-1,3,2-dioxaborolan-2-yl)benzoate 79 mg were added ethanol 0.60 mL, water 0.30 mL, 5-bromobenzothiophene 61 mg, sodium hydrogen carbonate 48 mg and tetrakis(triphenylphosphine)palladium(0) 11 mg at room temperature, and it was heated and refluxed for 6 hours. After the reaction mixture was cooled to room temperature, and ethyl acetate and water were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=5:1] to give tert-butyl 4-(benzothiophen-5-yl)-2-(4-fluoroanilino) benzoate. Trifluoroacetic acid 5.0 mL was added to the obtained tert-butyl 4-(benzothiophen-5-yl)-2-(4-fluoroanilino)benzoate, and it was stirred at room temperature for 3 hours. The solvent was removed under reduced pressure, the obtained residue was refined by reversed-phase silica gel column chromatography [eluent; 80-100% acetonitrile/0.1% trifluoroacetic acid aqueous solution] to give 4-(benzothiophen-5-yl)-2-(4-fluoroanilino)benzoic acid 16 mg of a yellow solid.

$^1$H-NMR (DMSO-$d_6$) δ value:

7.13(1H,dd,J=8.3, 1.7 Hz),7.19-7.27(2H,m),7.34-7.43 (3H,m),7.52(1H,d,J=5.6 Hz),7.56(1H,dd,J=8.5, 1.6 Hz),7.81 (1H,d,J=5.6 Hz),8.00(1H,d,J=8.3 Hz),8.07(1H,d,J=8.5 Hz), 8.10(1H,d,J=1.6 Hz),9.66(1H,s),13.10(1H,s).

Example 225-231

The compounds shown in Table 33 were obtained in the same manner as in Example 224.

TABLE 33

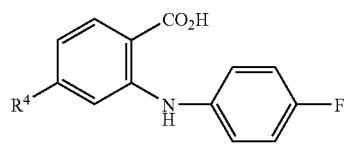

| Example No. | R$^4$ |
|---|---|
| 225 | 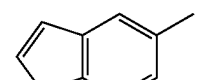 |
| 226 | 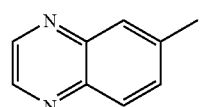 |
| 227 | 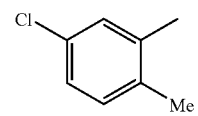 |
| 228 | 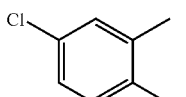 |
| 229 | 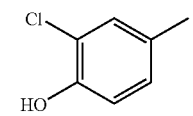 |
| 230 | 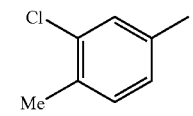 |
| 231 | 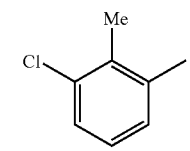 |

4-(Benzofuran-5-yl)-2-(4-fluoroanilino)benzoic acid $^1$H-NMR (DMSO-$d_6$) δ value:

7.00(1H,dd,J=2.2, 0.7 Hz),7.09(1H,dd,J=8.3, 1.7 Hz), 7.19-7.27(2H,m),7.28-7.32(1H,m),7.35-7.42(2H,m),7.51 (1H,dd,J=8.7, 1.8 Hz),7.66(1H,d,J=8.7 Hz),7.86(1H,d,J=1.4 Hz),7.98(1H,d,J=8.3 Hz),8.04(1H,d,J=2.2 Hz), 9.64(1H,s), 12.95-13.20(1H,broad).

2-(4-Fluoroanilino)-4-(quinoxalin-6-yl)benzoic acid $^1$H-NMR (DMSO-$d_6$) δ value:

7.21-7.30(3H,m),7.39-7.47(3H,m),8.06(1H,d,J=8.0 Hz), 8.09(1H,dd,J=8.8, 2.0 Hz),8.18(1H,d,J=8.8 Hz),8.26(1H,d, J=2.0 Hz),8.94-9.01(2H,m),9.67(1H,s).

4-(5-Chloro-2-methylphenyl)-2-(4-fluoroanilino)benzoic acid $^1$H-NMR (DMSO-$d_6$) δ value:
2.17(3H,s),6.73(1H,dd,J=8.1, 1.6 Hz),6.86-6.90(1H,m),7.16-7.24(3H,m),7.28-7.36(4H,m),7.95(1H,d,J=8.1 Hz),9.60(1H,s),13.14(1H,s).

4-(5-Chloro-2-methoxyphenyl)-2-(4-fluoroanilino)benzoic acid $^1$H-NMR (DMSO-$d_6$) δ value:
3.78(3H,s),6.87(1H,dd,J=8.2, 1.7 Hz),7.13(1H,d,J=8.8 Hz),7.17-7.26(3H,m),7.29-7.36(3H,m),7.40(1H,dd,J=8.8, 2.7 Hz),7.92(1H,d,J=8.2 Hz),9.54(1H,s),13.10(1H,s).

4-(3-Chloro-4-hydroxyphenyl)-2-(4-fluoroanilino)benzoic acid $^1$H-NMR (DMSO-$d_6$) δ value:
6.98-7.06(2H,m),7.17-7.27(3H,m),7.32-7.41(3H,m),7.54(1H,d,J=2.2 Hz),7.93(1H,d,J=8.3 Hz),9.60(1H,s),10.44(1H,s),13.05(1H,s).

4-(3-Chloro-4-methylphenyl)-2-(4-fluoroanilino)benzoic acid $^1$H-NMR (DMSO-$d_6$) δ value:
2.35(3H,s),7.05(1H,dd,J=8.3, 1.7 Hz),7.18-7.26(3H,m),7.33-7.47(4H,m),7.60(1H,s),7.97(1H,d,J=8.3 Hz),9.62(1H,s),13.14(1H,s).

4-(3-Chloro-2-methylphenyl)-2-(4-fluoroanilino)benzoic acid $^1$H-NMR (DMSO-$d_6$) δ value:
2.22(3H,s),6.72(1H,dd,J=8.3, 1.6 Hz),6.86-6.91(1H,m),7.13-7.36(6H,m),7.45(1H,dd,J=8.1, 1.0 Hz),7.96(1H,d,J=8.3 Hz),9.62(1H,s),13.05-13.25(1H,broad).

Example 232

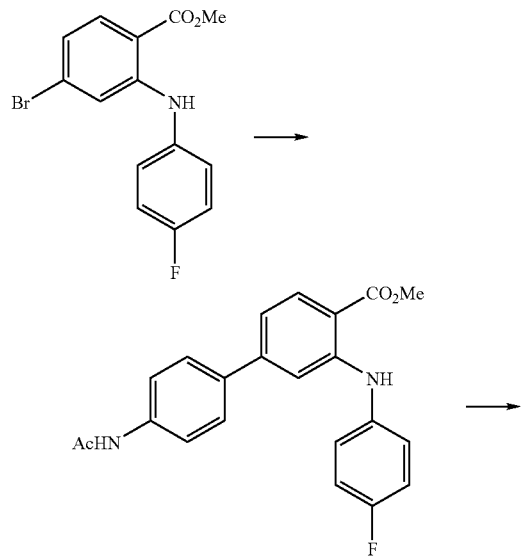

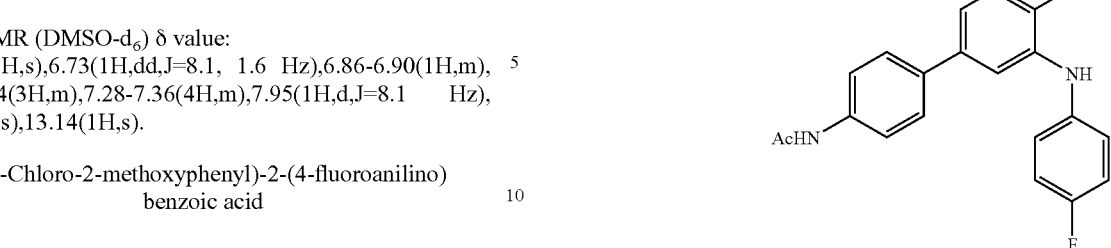

To N,N-dimethylacetamide 2.5 mL solution of methyl 4-bromo-2-(4-fluoroanilino)benzoate 70 mg were added 4-(acetamido)phenylboronic acid 77 mg, sodium carbonate 69 mg and polymer-carried di(acetato)dicyclohexylphenylphosphine palladium(II) 31 mg, and it was stirred at 90° C. for 12 hours. After the reaction mixture was cooled to room temperature, 4-(acetamido)phenylboronic acid 39 mg and sodium carbonate 22 mg were added, and it was stirred at 95° C. for 14 hours. After the reaction mixture was cooled to room temperature, insoluble matter was filtrated, and ethyl acetate and 1.0 mol/L hydrochloric acid were added to it. The organic layer was separated and collected, dried over anhydrous magnesium sulfate after sequential washing with 1.0 mol/L hydrochloric acid and saturated sodium chloride aqueous solution, and the solvent was removed under reduced pressure. Ethanol 2.0 mL and 2.0 mol/L sodium hydroxide aqueous solution 1.0 mL were added to the obtained residue, and it was stirred at room temperature for 1 hour. 6.0 mol/L hydrochloric acid 0.50 mL, water 3.0 mL and ethyl acetate 4.0 mL were added to the reaction mixture. The organic layer was separated and collected, and the solvent was removed under reduced pressure. The obtained residue was refined by reversed-phase silica gel column chromatography [eluent; 40-100% acetonitrile/0.1% trifluoroacetic acid aqueous solution] to give 4-(4-(acetamido)phenyl)-2-(4-fluoroanilino)benzoic acid 14 mg of a pale yellow solid.

$^1$H-NMR (DMSO-$d_6$) δ value:
2.05(3H,s),7.04(1H,d,J=8.1 Hz),7.18-7.28(3H,m),7.33-7.41(2H,m),7.49-7.56(2H,m),7.61-7.70(2H,m),7.95(1H,d,J=8.3 Hz),9.62(1H,s),10.07(1H,s).

Example 233

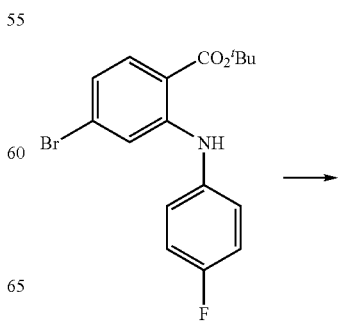

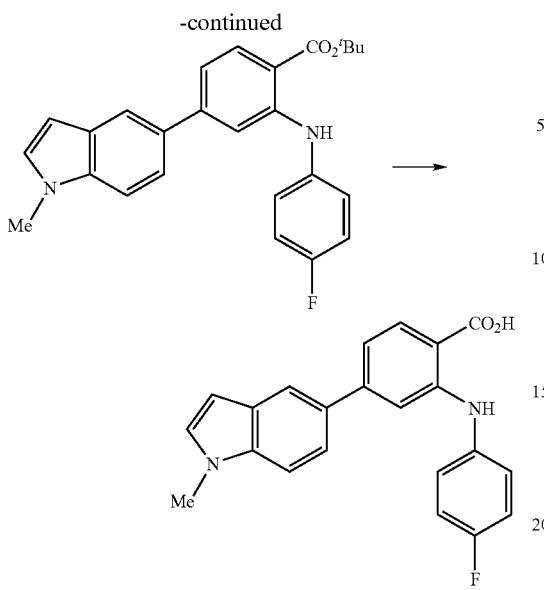

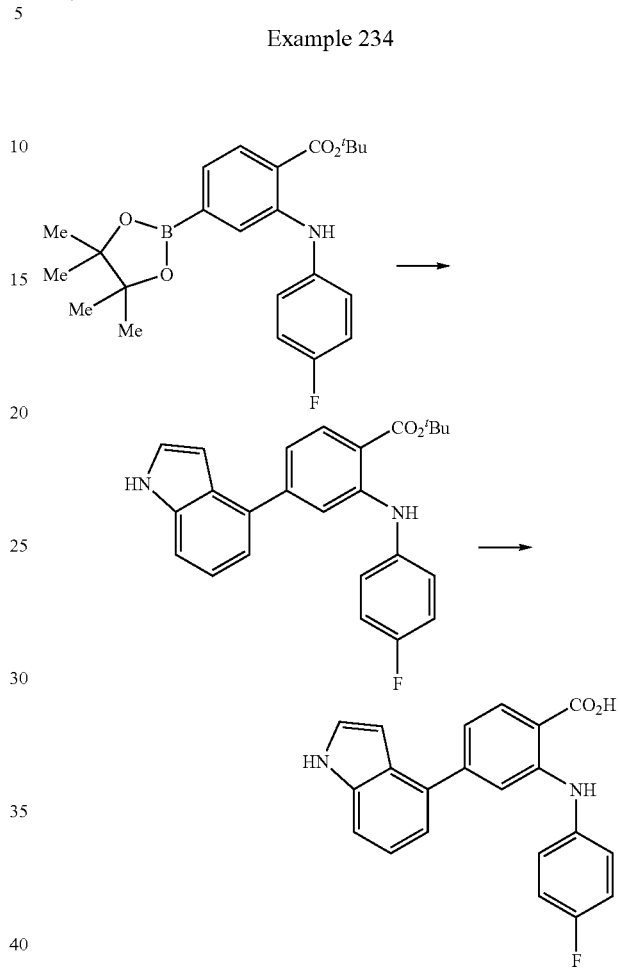

To toluene 2.1 mL solution of tert-butyl 4-bromo-2-(4-fluoroanilino)benzoate 0.1 g were added ethanol 0.60 mL, water 0.30 mL, 1-methyl-5-(4,4,5,5-tetramethyl-1,3,2-dioxaborolan-2-yl)-1H-indole 84 mg, sodium hydrogen carbonate 69 mg and tetrakis(triphenylphosphine)palladium(0) 16 mg at room temperature, and it was heated and refluxed for 4 hours. After the reaction mixture was cooled to room temperature, toluene and saturated sodium hydrogen carbonate aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-(4-fluoroanilino)-4-(1-methyl-1H-indol-5-yl)benzoate.

To the obtained tert-butyl 2-(4-fluoroanilino)-4-(1-methyl-1H-indol-5-yl)benzoate were added dioxane 1.5 mL, methanol 1.5 mL and 2.0 mol/L sodium hydroxide aqueous solution 0.29 mL, and it was stirred at 50° C. for 2 hours. After the reaction mixture was cooled to room temperature, 2.0 mol/L sodium hydroxide aqueous solution 0.20 mL was added to it, and it was stirred at 55° C. for 1 hour and 30 minutes. Subsequently, 2.0 mol/L sodium hydroxide aqueous solution 0.29 mL was added, it was stirred at 55° C. for 1 hour and 20 minutes, 2.0 mol/L sodium hydroxide aqueous solution 0.29 mL was added, it was stirred at 55° C. for 1 hour, 2.0 mol/L sodium hydroxide aqueous solution 0.29 mL was added, and it was stirred at 55° C. for 1 hour. After the reaction mixture was cooled to room temperature, toluene and water were added to it. The water layer was separated and collected, it was adjusted to pH3.4 with 1.0 mol/L hydrochloric acid after washing with toluene, and ethyl acetate was added to it. The organic layer was separated and collected, dried over anhydrous magnesium sulfate after washing with saturated sodium chloride aqueous solution, and the solvent was removed under reduced pressure. Diisopropyl ether was added to the obtained residue, solid matter was filtrated to give 2-(4-fluoroanilino)-4-(1-methyl-1H-indol-5-yl)benzoic acid 37 mg of a pale yellow solid.

$^1$H-NMR (DMSO-$d_6$) δ value:
3.80(3H,m),6.46-6.49(1H,m),7.08(1H,dd,J=8.3, 1.7 Hz), 7.18-7.25(2H,m),7.32(1H,d,J=1.4 Hz),7.33-7.40(4H,m), 7.49(1H,d,J=8.6 Hz),7.75(1H,d,J=1.2 Hz),7.96(1H,d,J=8.3 Hz).

Example 234

To toluene 1.6 mL solution of tert-butyl 2-(4-fluoroanilino)-4-(4,4,5,5-tetramethyl-1,3,2-dioxaborolan-2-yl)benzoate 60 mg were added ethanol 0.60 mL, water 0.30 mL, 4-bromoindole 0.034 mL, sodium hydrogen carbonate 30 mg and tetrakis(triphenylphosphine)palladium(0) 8.4 mg at room temperature, and it was heated and refluxed under nitrogen atmosphere for 5 hours. After the reaction mixture was cooled to room temperature, ethyl acetate and water were added, and insoluble matter was filtrated. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=5:1] to give tert-butyl 2-(4-fluoroanilino)-4-(1H-indol-4-yl)benzoate.

To the obtained tert-butyl 2-(4-fluoroanilino)-4-(1H-indol-4-yl)benzoate were added methanol 1.0 mL, dioxane 1.0 mL and 2.0 mol/L sodium hydroxide aqueous solution 0.23 mL, it was stirred at 50° C. for 2 hours and 30 minutes, subsequently 2.0 mol/L sodium hydroxide aqueous solution 0.23 mL was added, it was stirred at 50° C. for 4 hours, furthermore 2.0 mol/L sodium hydroxide aqueous solution 0.23 mL was added, and it was heated and refluxed for 2 hours. After the reaction mixture was cooled to room temperature, toluene and water were added to it. The water layer was separated and collected, it was adjusted to pH3.0 with 1.0 mol/L hydrochloric acid after washing with toluene, and ethyl acetate was added to it. The organic layer was separated and collected, dried over anhydrous magnesium sulfate after washing with saturated sodium chloride aqueous solution, and the solvent was removed under reduced pressure. Diisopropyl ether was added to the obtained residue, and solid matter was filtrated to give 2-(4-fluoroanilino)-4-(1H-indol-4-yl)benzoic acid 23 mg of a yellow solid.

$^1$H-NMR (DMSO-$d_6$) δ value:
6.44-6.48(1H,m),7.03-7.09(2H,m),7.12-7.26(3H,m),7.28(1H,d,J=1.2 Hz),7.34-7.44(4H,m),8.00(1H,d,J=8.3 Hz),9.59(1H,s),11.29(1H,s),12.90-13.15(1H,broad).

Example 235

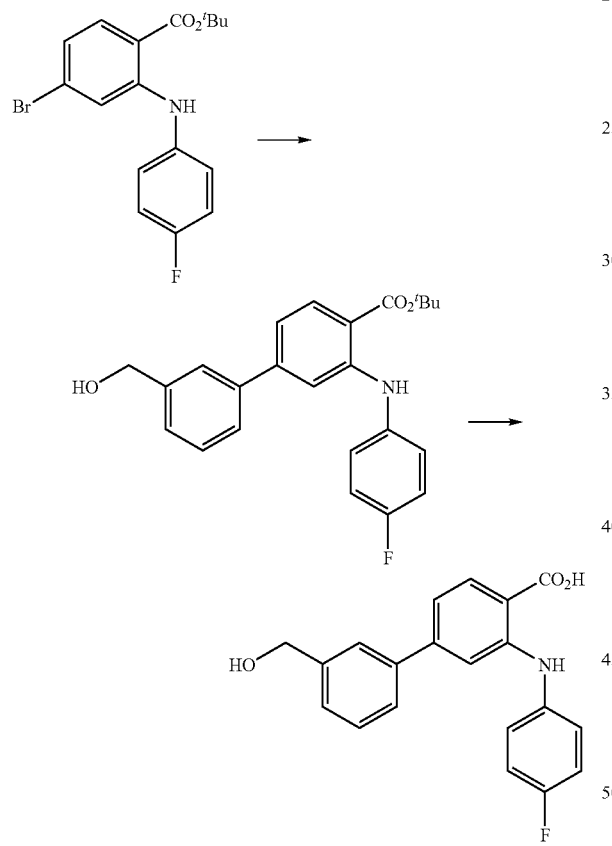

To N,N-dimethylacetamide 2.5 mL solution of tert-butyl 4-bromo-2-(4-fluoroanilino)benzoate 80 mg were added 3-(hydroxymethyl)phenylboronic acid 50 mg, sodium carbonate 58 mg and polymer-carried di(acetato)dicyclohexylphenylphosphine palladium(II) 7.0 mg, and it was stirred at 110° C. for 19 hours. After the reaction mixture was cooled to room temperature, polymer-carried di(acetato)dicyclohexylphenylphosphine palladium (II) 7.0 mg were added to it, and it was stirred at 110° C. for 30 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-(4-fluoroanilino)-4-(3-(hydroxymethyl)phenyl)benzoate.

Trifluoroacetic acid 10 mL was added to the obtained tert-butyl 2-(4-fluoroanilino)-4-(3-(hydroxymethyl)phenyl)benzoate, and it was stirred at room temperature for 1 hour. The solvent was removed under reduced pressure, and the obtained residue was refined by reversed-phase silica gel column chromatography [eluent; 70-100% acetonitrile/0.1% trifluoroacetic acid aqueous solution] to give 2-(4-fluoroanilino)-4-(3-(hydroxymethyl)phenyl)benzoic acid 7.7 mg of a pale yellow solid.

$^1$H-NMR (DMSO-$d_6$) δ value:
4.53(2H,d,J=5.6 Hz),5.23(1H,t,j=5.6 Hz),7.04(1H,dd,J=8.3, 1.6 Hz),7.19-7.28(3H,m),7.31-7.45(5H,m),7.51(1H,s),7.98(1H,d,J=8.3 Hz),9.62(1H,s).

Example 236

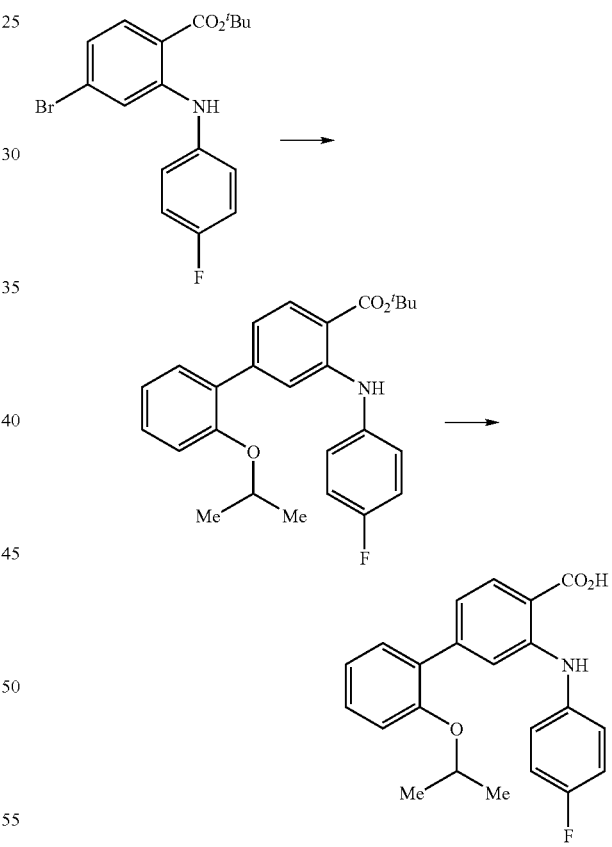

To toluene 1.6 mL solution of tert-butyl 4-bromo-2-(4-fluoroanilino)benzoate 70 mg were added ethanol 0.60 mL, water 0.30 mL, 2-isopropoxyphenylboronic acid 0.048 mL, sodium hydrogen carbonate 48 mg and tetrakis(triphenylphosphine)palladium(0) 11 mg at room temperature, and it was heated and refluxed for 6 hours. After the reaction mixture was cooled to room temperature, ethyl acetate and water were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=5:1] to give tert-butyl 2-(4-fluoroanilino)-4-(2-isopropoxyphenyl)benzoate.

Trifluoroacetic acid 5.0 mL was added to the obtained tert-butyl 2-(4-fluoroanilino)-4-(2-isopropoxyphenyl)benzoate, and it was stirred at room temperature for 3 hours. The solvent was removed under reduced pressure, and the obtained residue was refined by reversed-phase silica gel column chromatography [eluent; 80-100% acetonitrile/0.1% trifluoroacetic acid aqueous solution] to give 2-(4-fluoroanilino)-4-(2-isopropoxyphenyl)benzoic acid 16 mg of a white solid.

$^1$H-NMR (DMSO-$d_6$) δ value:
1.11(6H,d,J=6.0 Hz),4.57(1H, sep,J=6.0 Hz),6.86(1H,dd, J=8.3, 1.6 Hz),6.94-7.01(1H,m),7.07(1H,d,J=8.0 Hz),7.16-7.36(7H,m),7.91(1H,d,J=8.3 Hz),9.53(1H,s),13.00(1H,s).

Example 237

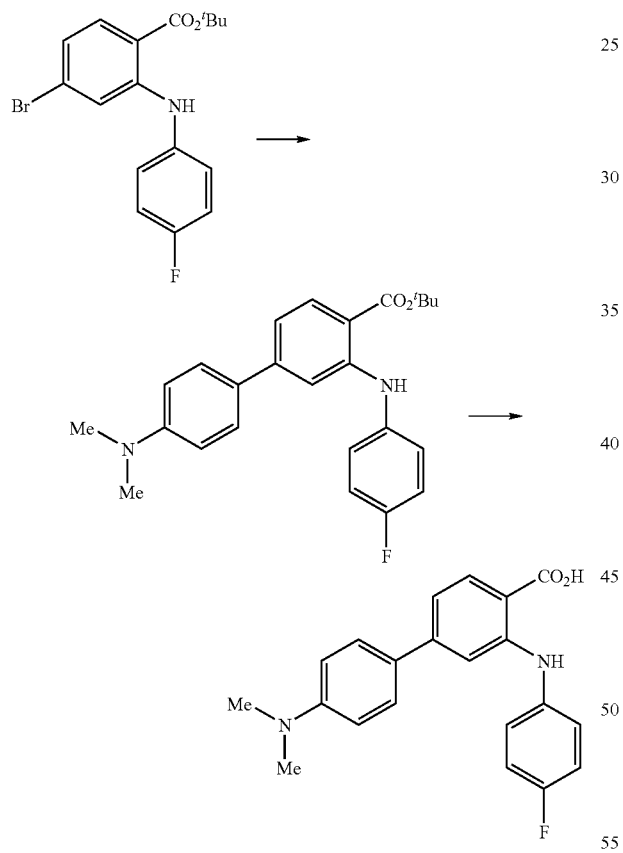

To toluene 1.6 mL solution of tert-butyl 4-bromo-2-(4-fluoroanilino)benzoate 70 mg were added ethanol 0.60 mL, water 0.30 mL, 4-(dimethylamino)phenylboronic acid 47 mg, sodium hydrogen carbonate 48 mg and tetrakis(triphenylphosphine)palladium(0) 11 mg at room temperature, and it was heated and refluxed for 6 hours. After the reaction mixture was cooled to room temperature, ethyl acetate and water were added to it. The organic layer was separated and collected,dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=10:1] to give tert-butyl 4-(4-(dimethylamino)phenyl)-2-(4-fluoroanilino)benzoate.

Trifluoroacetic acid 5.0 mL was added to the obtained tert-butyl 4-(4-(dimethylamino)phenyl)-2-(4-fluoroanilino) benzoate, and it was stirred at room temperature for 3 hours. The solvent was removed under reduced pressure, ethyl acetate and water were added, and it was adjusted to pH6.5 with saturated sodium hydrogen carbonate aqueous solution. The organic layer was separated and collected,dried over anhydrous magnesium sulfate after washing with saturated sodium chloride aqueous solution, and the solvent was removed under reduced pressure. Diisopropyl ether was added to the obtained residue, and solid matter was filtrated to give 4-(4-(dimethylamino)phenyl)-2-(4-fluoroanilino)benzoic acid 33 mg of a yellow solid.

$^1$H-NMR (DMSO-$d_6$) δ value:
2.93(6H,s),6.73-6.80(2H,m),7.00(1H,dd,J=8.4, 1.7 Hz), 7.18-7.26(3H,m),7.32-7.39(2H,m),7.40-7.46(2H,m),7.90 (1H,d,J=8.4 Hz),9.59(1H,s),12.92(1H,s).

Example 238

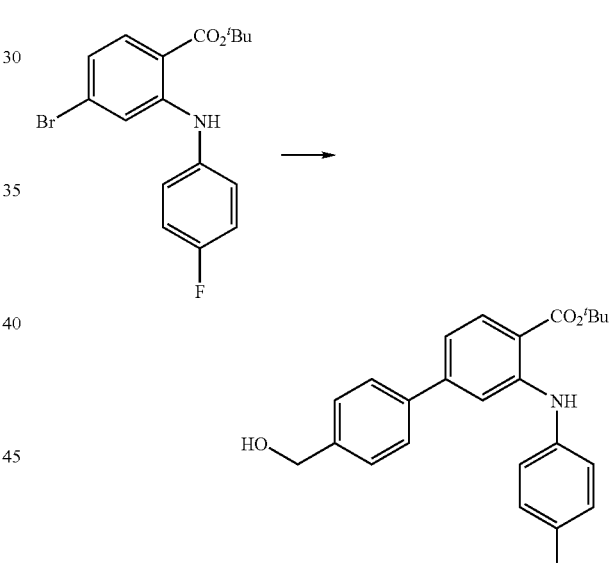

To toluene 4.0 mL solution of tert-butyl 4-bromo-2-(4-fluoroanilino)benzoate 0.20 g were added ethanol 1.2 mL, water 0.60 mL, 4-(hydroxymethyl)phenylboronic acid 91 mg, sodium hydrogen carbonate 0.12 g and tetrakis(triphenylphosphine)palladium(0) 35 mg at room temperature, and it was heated and refluxed under nitrogen atmosphere for 6 hours. After the reaction mixture was cooled to room temperature, water was added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B (spherical type), eluent; hexane:ethyl acetate=2:1] to give tert-butyl 2-(4-fluoroanilino)-4-(4-(hydroxymethyl)phenyl) benzoate 64 mg of a pale yellow solid.

¹H-NMR (DMSO-d₆) δ value:

1.58(9H,s),4.50-4.54(2H,m),5.22(1H,t,J=5.6 Hz),7.06(1H,dd,J=8.3, 1.7 Hz),7.18-7.25(2H,m),7.26(1H,d,J=1.7 Hz),7.34-7.41(4H,m),7.50-7.54(2H,m),7.92(1H,d,J=8.3 Hz),9.37(1H,s).

Example 239

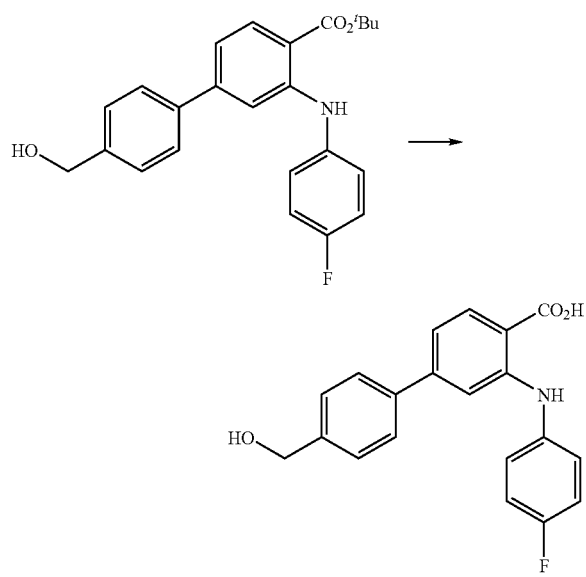

Trifluoroacetic acid 5.0 mL solution of tert-butyl 2-(4-fluoroanilino)-4-(4-(hydroxymethyl)phenyl)benzoate 64 mg was stirred at room temperature for 1 hour. The solvent was removed under reduced pressure, diisopropyl ether and hexane were added to the obtained residue, solid matter was filtrated to give 2-(4-fluoroanilino)-4-(4-(hydroxymethyl)phenyl)benzoic acid 2.0 mg of a pale yellow solid.

¹H-NMR (DMSO-d₆) δ value:

4.52(2H,d,J=4.4 Hz),5.20-5.26(1H,m),7.05(1H,d,J=8.3 Hz),7.15-7.30(3H,m),7.32-7.42(4H,m),7.53(2H,d,J=7.8 Hz),7.97(1H,d,J=8.3 Hz),9.56-9.74(1H,broad).

Example 240

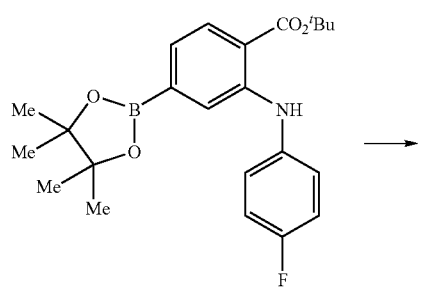

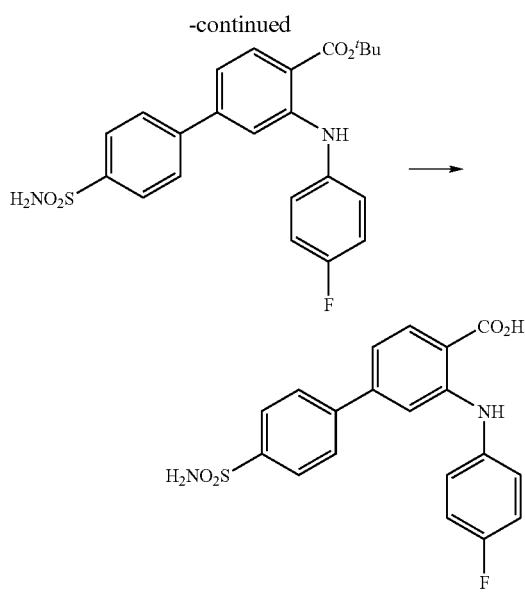

To toluene 3.0 mL solution of tert-butyl 2-(4-fluoroanilino)-4-(4,4,5,5-tetramethyl-1,3,2-dioxaborolan-2-yl)benzoate 0.15 g were added ethanol 0.90 mL, water 0.45 mL, 4-bromobenzenesulfonamide 85 mg, sodium hydrogen carbonate 0.10 g and tetrakis(triphenylphosphine)palladium(0) 21 mg at room temperature, and it was heated and refluxed under nitrogen atmosphere for 2 hours. After the reaction mixture was cooled to room temperature, and ethyl acetate and water were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=2:1] to give tert-butyl 4-(4-(aminosulfonyl)phenyl)-2-(4-fluoroanilino)benzoate.

Trifluoroacetic acid 3.0 mL solution of the obtained tert-butyl 4-(4-(aminosulfonyl)phenyl)-2-(4-fluoroanilino)benzoate was stirred at room temperature for 30 minutes. The solvent was removed under reduced pressure, diisopropyl ether was added to the obtained residue, and solid matter was filtrated to give 4-(4-(aminosulfonyl)phenyl)-2-(4-fluoroanilino)benzoic acid 20 mg of a pale yellow solid.

¹H-NMR (DMSO-d₆) δ value:

7.10(1H,d,J=7.8 Hz),7.18-7.26(2H,m),7.30-7.40(5H,m),7.74-7.81(2H,m),7.84-7.90(2H,m),8.01(1H,d,J=8.0 Hz), 9.63-9.68(1H,broad),13.16-13.24(1H,broad).

Example 241

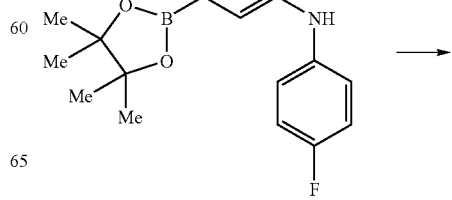

-continued

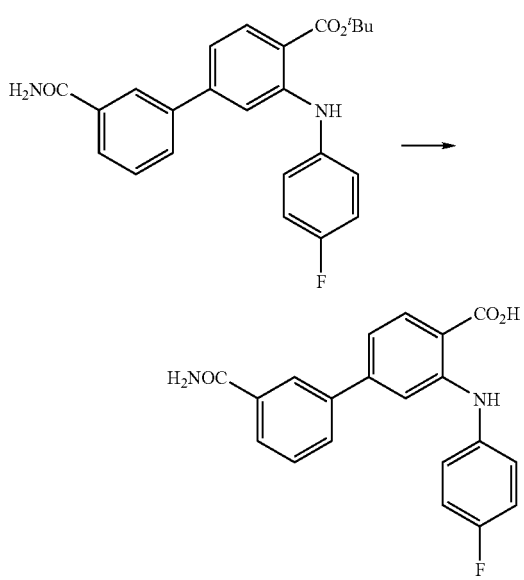

The following compound was obtained in the same manner as in Example 240.

4-(3-(Aminocarbonyl)phenyl)-2-(4-fluoroanilino) benzoic acid $^1$H-NMR (DMSO-$d_6$) δ value:
7.12(1H,dd,J=8.3, 1.7 Hz),7.18-7.25(2H,m),7.32(1H,d, J=1.7 Hz),7.34-7.46(3H,m),7.53(1H,t,j=7.7 Hz),7.68-7.74 (1H,m),7.85-7.90(1H,m),8.00(1H,d,J=8.3 Hz),8.04-8.12 (2H,m),9.64(1H,s),13.12-13.17(1H,broad).

Example 242

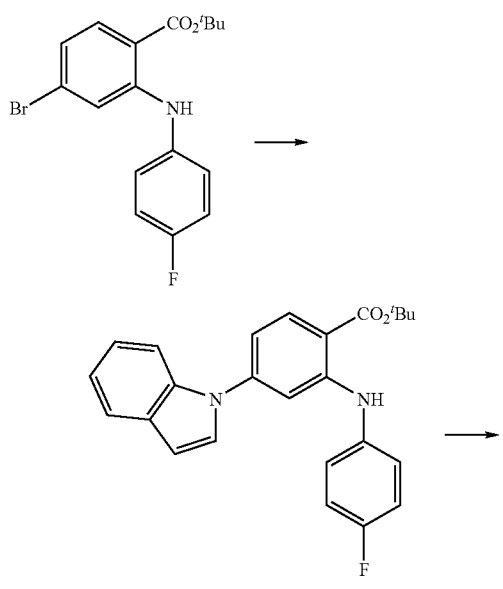

-continued

To toluene 3.0 mL solution of tert-butyl 4-bromo-2-(4-fluoroanilino)benzoate 0.10 g were added 1H-indole 48 mq, tripotassium phosphate 0.12 g, tris(dibenzylideneacetone)dipalladium(0) 8.0 mg, tri-tert-butylphosphine tetrafluoroborate 2.0 mg and 2-dicyclohexylphosphino-2',4',6'-triisopropylbiphenyl 7.0 mg at room temperature, and it was heated and refluxed for 2 hours. After the reaction mixture was cooled to room temperature, tris(dibenzylideneacetone)dipalladium(0) 8.0 mg, tri-tert-butylphosphine tetrafluoroborate 2.0 mg and 2-dicyclohexylphosphino-2',4',6'-triisopropylbiphenyl 7.0 mg were added to it, and it was heated and refluxed for 3 hours. After the reaction mixture was cooled to room temperature, tris(dibenzylideneacetone)dipalladium(0) 8.0 mg, tri-tert-butylphosphine tetrafluoroborate 2.0 mg and 2-dicyclohexylphosphino-2',4',6'-triisopropylbiphenyl 7.0 mg were added to it, and it was heated and refluxed for 7 hours. After the reaction mixture was cooled to room temperature, toluene and 10% citric acid aqueous solution were added. The organic layer was separated and collected,dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=5:1] to give tert-butyl 2-(4-fluoroanilino)-4-(1H-indol-1-yl)benzoate.

To the obtained tert-butyl 2-(4-fluoroanilino)-4-(1H-indol-1-yl)benzoate were added dioxane 1.5 mL, methanol 1.5 mL and 2.0 mol/L sodium hydroxide aqueous solution 0.41 mL, and it was stirred at 40° C. for 5 hours. After the reaction mixture was cooled to room temperature, 2.0 mol/L sodium hydroxide aqueous solution 0.41 mL was added to it, and it was stirred at 50° C. for 3 hours. After the reaction mixture was cooled to room temperature, water was added to it, it was adjusted to pH3.6 with 1.0 mol/L hydrochloric acid, and ethyl acetate was added to it. The organic layer was separated and collected,dried over anhydrous magnesium sulfate after sequential washing with water and saturated sodium chloride aqueous solution, and the solvent was removed under reduced pressure. The obtained residue was refined by reversed-phase silica gel column chromatography [eluent; 60-100% acetonitrile/0.1% trifluoroacetic acid aqueous solution] to give 2-(4-fluoroanilino)-4-(1H-indol-1-yl)benzoic acid 6.0 mg of a white solid.

$^1$H-NMR (DMSO-$d_6$) δ value:
6.70(1H,d,J=3.2 Hz),7.00(1H,dd,J=8.6, 2.2 Hz),7.08(1H, d,J=2.2 Hz),7.10-7.16(1H,m),7.18-7.27(3H,m),7.40-7.46 (2H,m),7.57(1H,d,J=8.3 Hz),7.61-7.66(2H,m),8.07(1H,d, J=8.6 Hz),9.73(1H,s).

Example 243

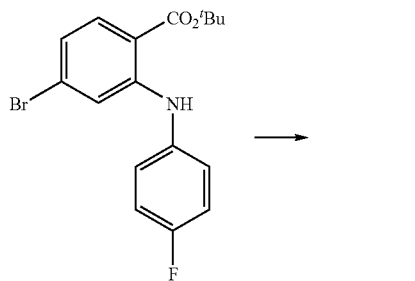

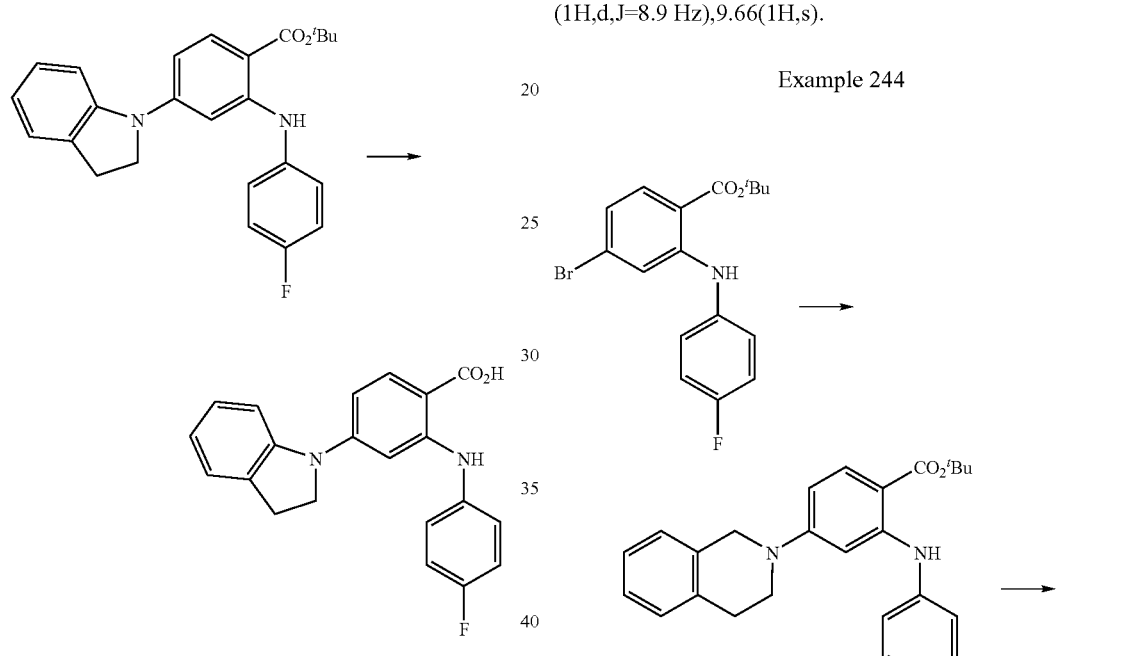

To toluene 3.0 mL solution of tert-butyl 4-bromo-2-(4-fluoroanilino)benzoate 0.10 g were added indoline 0.046 mL, cesium carbonate 0.18 g, tris(dibenzylideneacetone)dipalladium(0) 3.0 mg, 2-dicyclohexylphosphino-2',4',6'-triisopropylbiphenyl 7.0 mg and palladium acetate 1.0 mg, and it was heated and refluxed for 2 hours. Tris(dibenzylideneacetone)dipalladium(0) 3.0 mg, 2-dicyclohexylphosphino-2',4',6'-triisopropylbiphenyl 7.0 mg and palladium acetate 1.0 mg were added to it, and it was heated and refluxed for 3 hours. Tris(dibenzylideneacetone)dipalladium(0) 3.0 mg, 2-dicyclohexylphosphino-2',4',6'-triisopropylbiphenyl 7.0 mg and palladium acetate 1.0 mg were added to it, and it was heated and refluxed for 7 hours. After the reaction mixture was cooled to room temperature, and toluene and 10% citric acid aqueous solution were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-(4-fluoroanilino)-4-(indolin-1-yl)benzoate.

Trifluoroacetic acid 10 mL was added to the obtained tert-butyl 2-(4-fluoroanilino)-4-(indolin-1-yl)benzoate, and it was stirred at room temperature for 2 hours and 10 minutes. The solvent was removed under reduced pressure, ethyl acetate and water were added to the obtained residue, and it was adjusted to pH6.5 with saturated sodium hydrogen carbonate aqueous solution. The organic layer was separated and collected, dried over anhydrous magnesium sulfate after sequential washing with water and saturated sodium chloride aqueous solution, and the solvent was removed under reduced pressure. Diisopropyl ether was added to the obtained residue, solid matter was filtrated to give 2-(4-fluoroanilino)-4-(indolin-1-yl)benzoic acid 22 mg of a white solid.

$^1$H-NMR (DMSO-$d_6$) δ value:
3.06(2H,t,j=8.4 Hz),3.91(2H,t,j=8.4 Hz),6.62(1H,dd,J=8.9, 2.0 Hz),6.73(1H,d,J=2.0 Hz),6.78(1H,t,j=7.1 Hz),7.03-7.13(2H,m),7.17-7.27(3H,m),7.32-7.40(2H,m),7.85(1H,d,J=8.9 Hz),9.66(1H,s).

Example 244

The following compound was obtained in the same manner as in Example 243.

2-(4-Fluoroanilino)-4-(1,2,3,4-tetrahydroisoquinolin-2-yl)benzoic acid $^1$H-NMR (DMSO-$d_6$) δ value:
2.88(2H,t,j=6.0 Hz),3.51(2H,t,j=6.0 Hz),4.42(2H,s),6.45(1H,dd,J=9.0, 2.2 Hz),6.48(1H,d,J=2.2 Hz),7.16-7.23(6H,m),7.27-7.33(2H,m),7.75(1H,d,J=9.0 Hz),9.70(1H,s).

Example 245

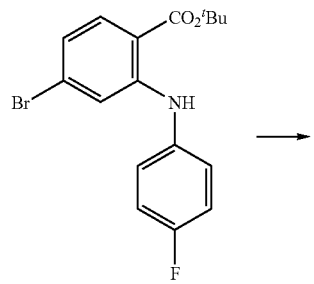

→

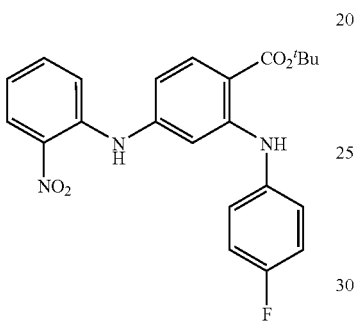

To toluene 3.0 mL solution of tert-butyl 4-bromo-2-(4-fluoroanilino)benzoate 0.30 g were added 2-nitroaniline 0.17 g, cesium carbonate 0.53 g, tris(dibenzylideneacetone)dipalladium(0) 8.0 mg, palladium acetate 4.0 mg and 2-dicyclohexylphosphino-2',4',6'-triisopropylbiphenyl 20 mg at room temperature, and it was heated and refluxed under nitrogen atmosphere for 2 hours. Tris(dibenzylideneacetone)dipalladium(0) 8.0 mg, palladium acetate 4.0 mg and 2-dicyclohexylphosphino-2',4',6'-triisopropylbiphenyl 20 mg were added to it, and it was heated and refluxed for 3 hours. Tris(dibenzylideneacetone)dipalladium(0) 8.0 mg, palladium acetate 4.0 mg and 2-dicyclohexylphosphino-2',4',6'-triisopropylbiphenyl 20 mg were added to it, and it was heated and refluxed for 7 hours. After the reaction mixture was cooled to room temperature, toluene, ethyl acetate and 10% citric acid aqueous solution were added to it, and insoluble matter was filtrated. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=10:1] to give tert-butyl 2-(4-fluoroanilino)-4-(2-nitroanilino)benzoate 0.35 g of a yellow solid.

$^1$H-NMR (CDCl$_3$) δ value:
1.62(9H,s),6.57(1H,dd,J=8.8, 2.2 Hz),6.80(1H,d,J=2.2 Hz),6.81-6.87(1H,m),7.02-7.08(2H,m),7.17-7.24(2H,m), 7.37-7.41(2H,m),7.91(1H,d,J=8.8 Hz),8.14-8.19(1H,m), 9.29(1H,s),9.57(1H,s).

Example 246

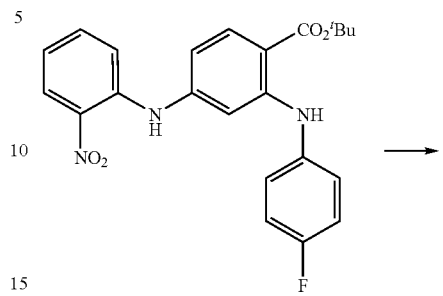

→

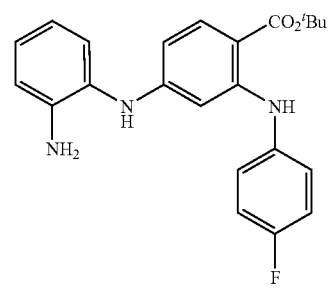

To a mixed solution of tetrahydrofuran 10 mL and ethyl acetate 5.0 mL of tert-butyl 2-(4-fluoroanilino)-4-(2-nitroanilino)benzoate 0.35 g was added 10% palladium-carbon 74 mg, it was stirred under hydrogen atmosphere at room temperature for 4 hours and 30 minutes, and subsequently it was stirred at 34° C. for 4 hours. After the reaction mixture was cooled to room temperature, insoluble matter was filtrated, and the solvent was removed under reduced pressure. Hexane was added to the obtained residue, and solid matter was filtrated to give tert-butyl 4-((2-aminophenyl)amino)-2-(4-fluoroanilino)benzoate 0.15 g of a white solid.

$^1$H-NMR (CDCl$_3$) δ value:
1.57(9H,s),5.34(1H,s),6.06(1H,dd,J=8.8, 2.3 Hz),6.31 (1H,d, J=2.3 Hz),6.70-6.79(2H,m),6.94-7.10(4H,m),7.14-7.20(2H,m),7.77(1H,d,J=8.8 Hz),9.57(1H,s).

Example 247

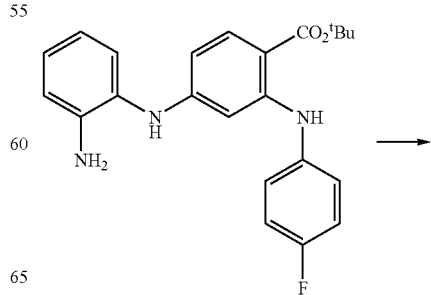

→

-continued

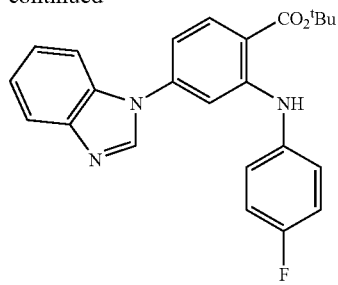

Formamidine acetate 0.10 g was added to ethylene glycol monomethyl ether 3.0 mL solution of tert-butyl 4-((2-aminophenyl)amino)-2-(4-fluoroanilino)benzoate 0.15 g at room temperature, and it was stirred at 80° C. for 6 hours. After the reaction mixture was cooled to room temperature, and ethyl acetate and water were added to it. The organic layer was separated and collected, dried over anhydrous magnesium sulfate after sequential washing with saturated sodium hydrogen carbonate aqueous solution and saturated sodium chloride aqueous solution, the solvent was removed under reduced pressure. The obtained residue was refined by silica gel column chromatography [Fuji SILYSIA Chemical Ltd., PSQ100B(spherical type), eluent; hexane:ethyl acetate=2:1] to give tert-butyl 4-(1H-benzimidazol-1-yl)-2-(4-fluoroanilino)benzoate 0.16 g of a pale red solid.

$^1$H-NMR (CDCl$_3$) δ value:
1.65(9H,s),6.83(1H,dd,J=8.6, 2.2 Hz),7.04-7.11(3H,m),7.23-7.28(2H,m),7.30-7.34(2H,m),7.47-7.51(1H,m),7.82-7.86(1H,m),8.05(1H,s),8.10(1H,d,J=8.6 Hz),9.68(1H,s).

Example 248

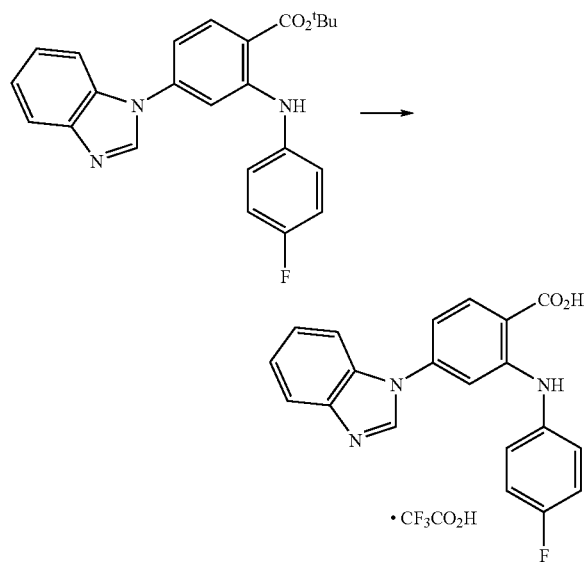

Trifluoroacetic acid 7.5 mL solution of tert-butyl 4-(1H-benzimidazol-1-yl)-2-(4-fluoroanilino)benzoate 0.16 g was stirred at room temperature for 1 hour and 30 minutes. The solvent was removed under reduced pressure, ethyl acetate was added to the obtained residue, and solid matter was filtrated to give 4-(1H-benzimidazol-1-yl)-2-(4-fluoroanilino)benzoic acid trifluoroacetate 99 mg of a yellow solid.

$^1$H-NMR (DMSO-d$_6$) δ value:
7.10(1H,dd,J=8.5, 2.2 Hz),7.20-7.26(3H,m),7.36-7.48(4H,m),7.63-7.68(1H,m),7.78-7.83(1H,m),8.14(1H,d,J=8.5 Hz),8.91(1H,s),9.79(1H,s).

Example 249

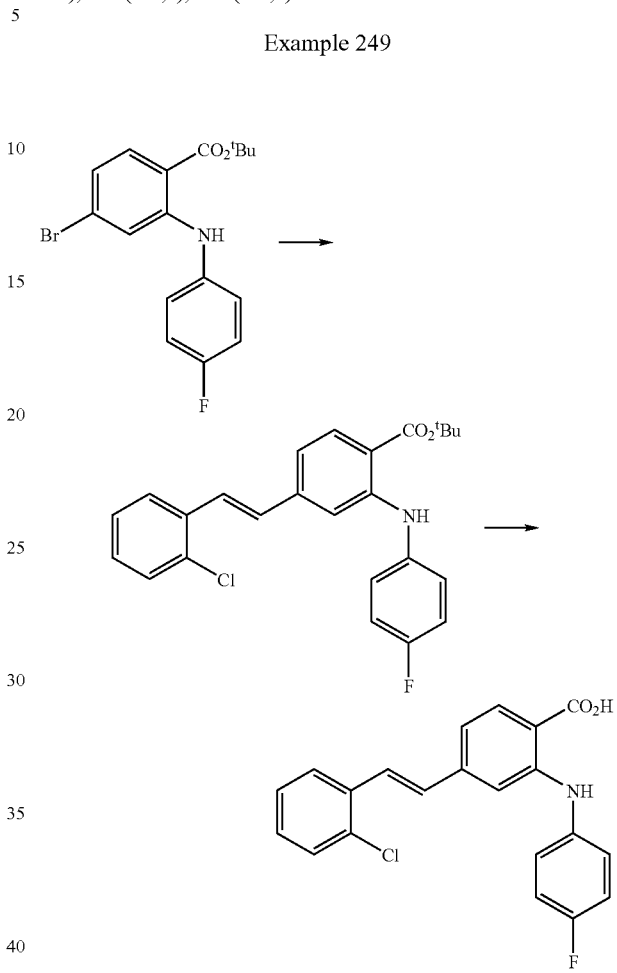

To N,N-dimethylacetamide 3.0 mL solution of tert-butyl 4-bromo-2-(4-fluoroanilino)benzoate 0.15 g were added 2-chlorostyrene 0.15 mL, N,N-dicyclohexylmethylamine 0.35 mL and palladium acetate 4.6 mg at room temperature, and it was stirred at 130° C. for 4 hours. 2-Chlorostyrene 0.052 mL, N,N-dicyclohexylmethylamine 0.087 mL and palladium acetate 9.2 mg were added, and it was stirred at 130° C. for 2 hours. Palladium acetate 4.6 mg and tri-tert-butylphosphine tetrafluoroborate 5.9 mg were added, and it was stirred at 130° C. for 8 hours. After the reaction mixture was cooled to room temperature, ethyl acetate and 10% citric acid aqueous solution were added to it.

The organic layer was separated and collected, the solvent was removed under reduced pressure after sequential washing with 10% citric acid aqueous solution, saturated sodium thiosulfate aqueous solution and saturated sodium chloride aqueous solution. The obtained residue was refined by silica gel column chromatography [Trikonex company, Flash Tube 2008, eluent; hexane:ethyl acetate=4:1] to give tert-butyl 4-((E)-2-(2-chlorophenyl)vinyl)-2-(4-fluoroanilino)benzoate.

Trifluoroacetic acid 10 mL solution of the obtained tert-butyl 4-((E)-2-(2-chlorophenyl)vinyl)-2-(4-fluoroanilino) benzoate was stirred at room temperature for 2 hours. The solvent was removed under reduced pressure, the obtained residue was refined by reversed-phase silica gel column chromatography [eluent; 85-100% acetonitrile/0.1% trifluoroacetic acid aqueous solution] to give 4-((E)-2-(2-chlorophenyl)vinyl)-2-(4-fluoroanilino)benzoic acid 4.6 mg of a yellow solid.

$^1$H-NMR (DMSO-$d_6$) δ value:
7.08-7.14(1H,m),7.20-7.51(10H,m),7.86-7.95(2H,m),9.59(1H,s),13.06(1H,s).

Example 250

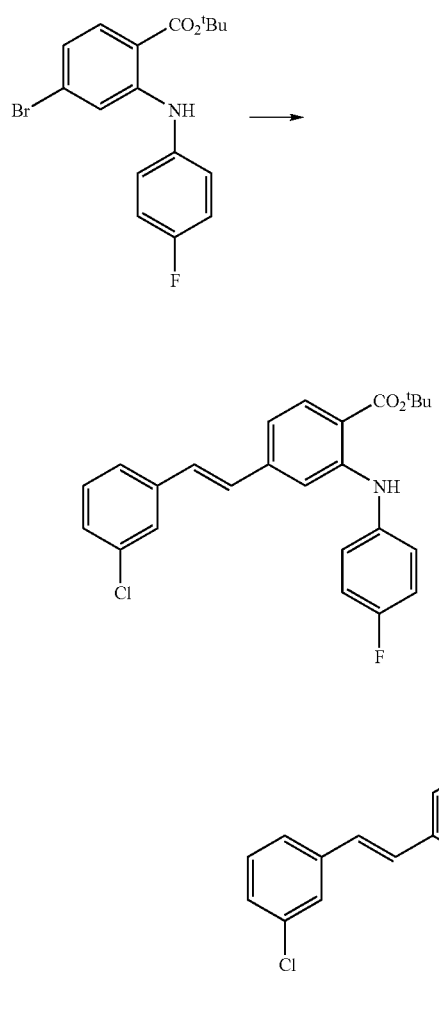

The following compound was obtained in the same manner as in Example 249.

4-((E)-2-(3-Chlorophenyl)vinyl)-2-(4-fluoroanilino)benzoic acid $^1$H-NMR (DMSO-$d_6$) δ value:
7.11(1H,dd,J=8.4, 1.2 Hz),7.18-7.42(9H,m),7.57(1H,d,J=7.8 Hz),7.74(1H,s),7.90(1H,d,J=8.4 Hz),9.60(1H,s),13.03(1H,s).

Example 251

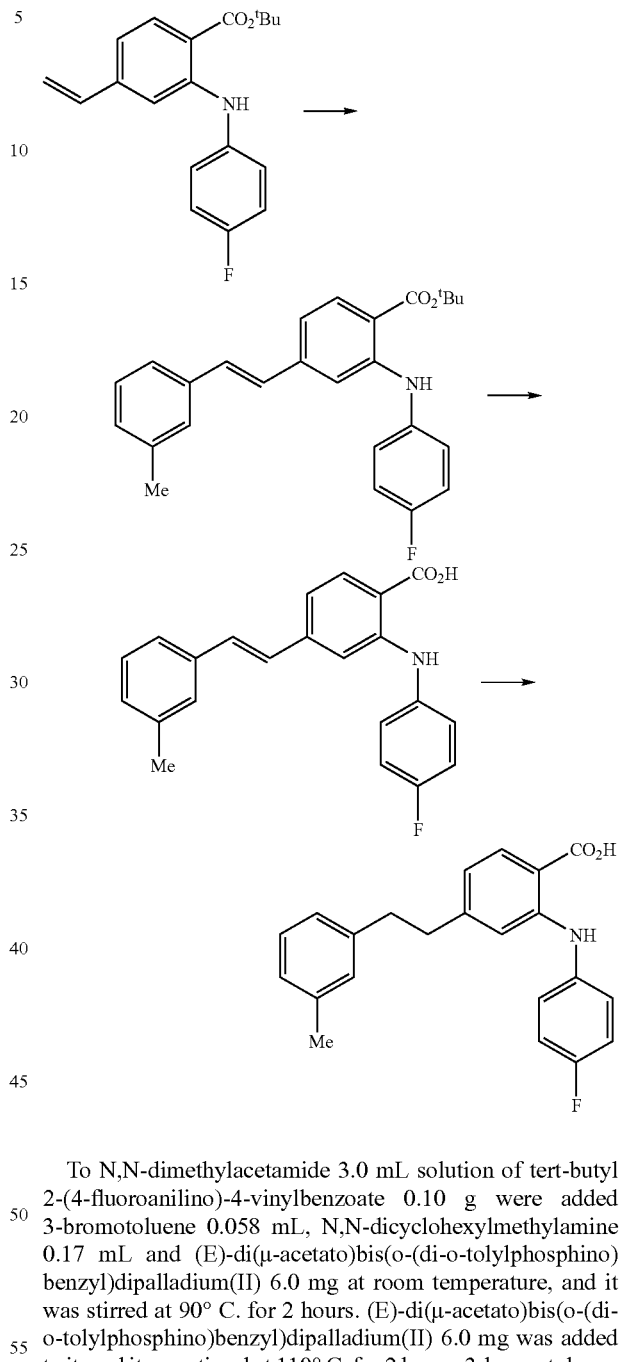

To N,N-dimethylacetamide 3.0 mL solution of tert-butyl 2-(4-fluoroanilino)-4-vinylbenzoate 0.10 g were added 3-bromotoluene 0.058 mL, N,N-dicyclohexylmethylamine 0.17 mL and (E)-di(μ-acetato)bis(o-(di-o-tolylphosphino)benzyl)dipalladium(II) 6.0 mg at room temperature, and it was stirred at 90° C. for 2 hours. (E)-di(μ-acetato)bis(o-(di-o-tolylphosphino)benzyl)dipalladium(II) 6.0 mg was added to it, and it was stirred at 110° C. for 2 hours. 3-bromotoluene 0.040 mL, N,N-dicyclohexylmethylamine 0.068 mL and (E)-di(μ-acetato)bis(o-(di-o-tolylphosphino)benzyl)dipalladium (II) 6.0 mg were added to it, and it was stirred at 110° C. for 4 hours. After the reaction mixture was cooled to room temperature, and ethyl acetate and 10% citric acid aqueous solution were added to it. The organic layer was separated and collected, the solvent was removed under reduced pressure after sequential washing with 10% citric acid aqueous solution, saturated sodium thiosulfate aqueous solution and saturated sodium chloride aqueous solution. The obtained residue was refined by silica gel column chromatography [Trikonex company, Flash Tube 2008, eluent; hexane:ethyl acetate=10:1] to tert-butyl 2-(4-fluoroanilino)-4-((E)-2-(3-methylphenyl)vinyl)benzoate.

Trifluoroacetic acid 10 mL solution of the obtained tert-butyl 2-(4-fluoroanilino)-4-((E)-2-(3-methylphenyl)vinyl)benzoate was stirred at room temperature for 2 hours. The solvent was removed under reduced pressure, the obtained residue was refined by reversed-phase silica gel column chromatography [eluent; 60-100% acetonitrile/0.1% trifluoroacetic acid aqueous solution] to give 2-(4-fluoroanilino)-4-((E)-2-(3-methylphenyl)vinyl)benzoic acid.

To the obtained 2-(4-fluoroanilino)-4-((E)-2-(3-methylphenyl)vinyl)benzoic acid, ethyl acetate 1.0 mL, methanol 1.0 mL and 10% palladium-carbon 2.0 mg were added sequentially, and it was stirred under hydrogen atmosphere at room temperature for 3 hours and 30 minutes. The solvent was removed under reduced pressure after insoluble matter was filtrated to give 2-(4-fluoroanilino)-4-(2-(3-methylphenyl)ethyl)benzoic acid 3.0 mg of a white solid.

$^1$H-NMR (DMSO-$d_6$) δ value:
2.26(3H,s),2.70-2.84(4H,m),6.56(1H,d,J=7.6 Hz),6.83(1H,s),6.93-7.10(7H,m),7.12-7.18(1H,m),7.81(1H,d,J=8.0 Hz).

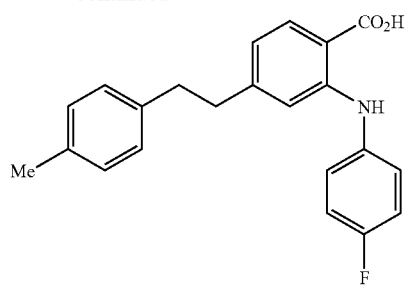

The following compound was obtained in the same manner as in Example 251.

2-(4-Fluoroanilino)-4-(2-(4-methylphenyl)ethyl)benzoic acid $^1$H-NMR (DMSO-$d_6$) δ value:
2.26(3H,s),2.69-2.83(4H,m),6.49(1H,dd,J=7.8, 1.5 Hz),6.81(1H,d,J=1.2 Hz),6.91-7.11(8H,m),7.78(1H,d,J=7.8 Hz),12.04(1H,s).

Example 252

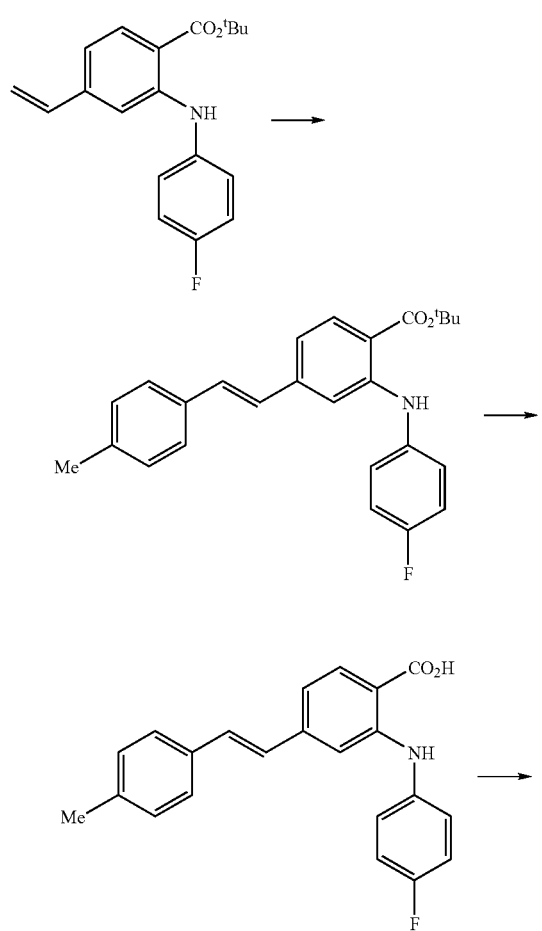

Example 253

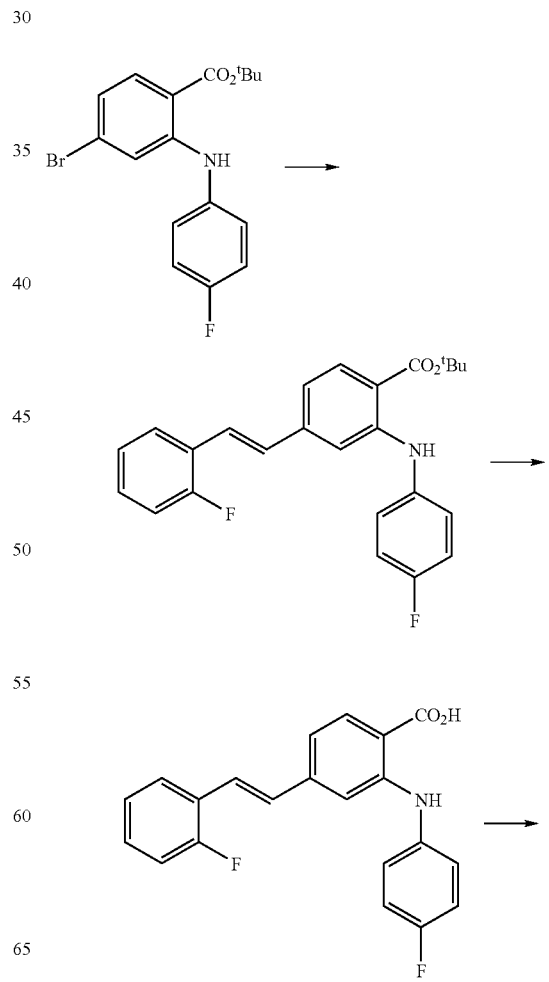

-continued

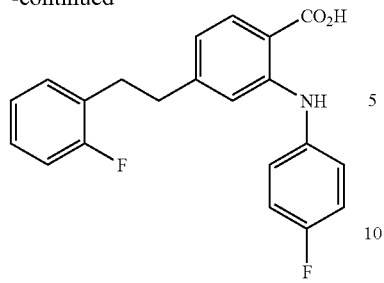

To N,N-dimethylacetamide 3.0 mL solution of tert-butyl 4-bromo-2-(4-fluoroanilino)benzoate 0.15 g were added 2-fluorostyrene 0.15 g, N,N-dicyclohexylmethylamine 0.35 mL and palladium acetate 4.6 mg at room temperature, and it was stirred at 130° C. for 4 hours. 2-Fluorostyrene 0.05 g, N,N-dicyclohexylmethylamine 0.087 mL and (E)-di(μ-acetato)bis(o-(di-o-tolylphosphino)benzyl)dipalladium(II) 4.8 mg were added to it, and it was stirred at 130° C. for 2 hours. (E)-di(μ-acetato)bis(o-(di-o-tolylphosphino)benzyl)dipalladium(II) 9.6 mg and tri-tert-butylphosphine tetrafluoroborate 5.9 mg were added to it, and it was stirred at 130° C. for 8 hours. After the reaction mixture was cooled to room temperature, ethyl acetate and 10% citric acid aqueous solution were added to it. The organic layer was separated and collected, the solvent was removed under reduced pressure after sequential washing with 10% citric acid aqueous solution, saturated sodium thiosulfate aqueous solution and saturated sodium chloride aqueous solution. The obtained residue was refined by silica gel column chromatography [Trikonex company, Flash Tube 2008, eluent; hexane:ethyl acetate=4:1] to give tert-butyl 2-(4-fluoroanilino)-4-((E)-2-(2-fluorophenyl)vinyl)benzoate.

Trifluoroacetic acid 10 mL solution of the obtained tert-butyl 2-(4-fluoroanilino)-4-((E)-2-(2-fluorophenyl)vinyl)benzoate was stirred at room temperature for 2 hours. The solvent was removed under reduced pressure, acetic acid 2.0 mL, dioxane 2.0 mL and 10% palladium-carbon 22 mg were added to the obtained residue sequentially, and it was stirred under hydrogen atmosphere at room temperature for 2 hours and 30 minutes. The solvent was removed under reduced pressure after insoluble matter was filtrated.

Diisopropyl ether and hexane were added to the obtained residue, and solid matter was filtrated to give 2-(4-fluoroanilino)-4-(2-(2-fluorophenyl)ethyl)benzoic acid 44 mg of a white solid.

$^1$H-NMR (DMSO-$d_6$) δ value:
2.73-2.91(4H,m),6.57-6.63(1H,m),6.75-6.78(1H,m), 7.01-7.30(8H,m),7.80(1H,d,J=8.0 Hz).

Example 254

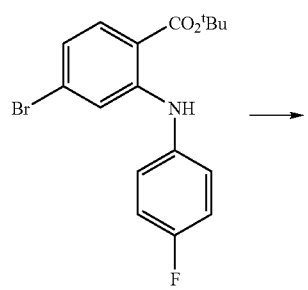

-continued

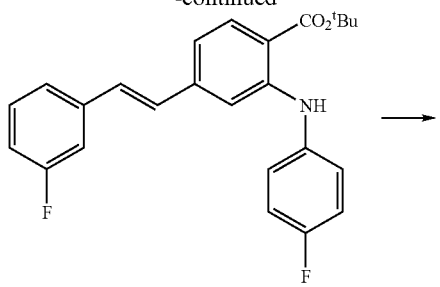

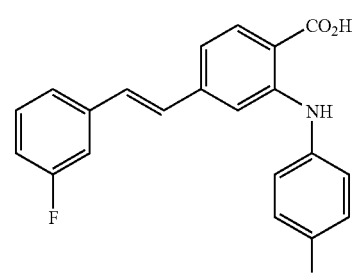

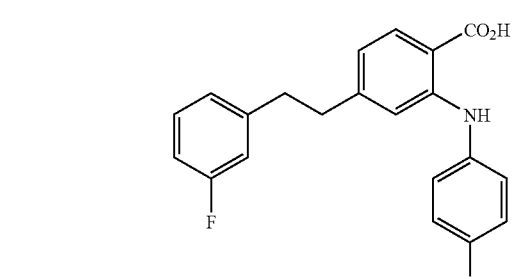

The following compound was obtained in the same manner as in Example 253.

2-(4-Fluoroanilino)-4-(2-(3-fluorophenyl)ethyl)benzoic acid $^1$H-NMR (DMSO-$d_6$) δ value:
2.76-2.89(4H,m),6.65(1H,dd,J=8.3, 1.5 Hz),6.81(1H,d,J=1.2 Hz),6.97-7.20(7H,m),7.26-7.34(1H,m),7.80(1H,d,J=8.3 Hz).

Example 255

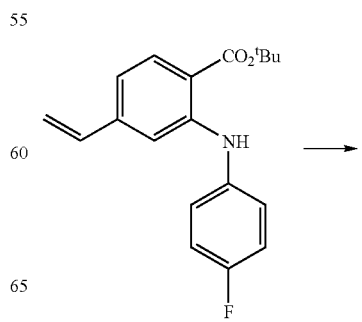

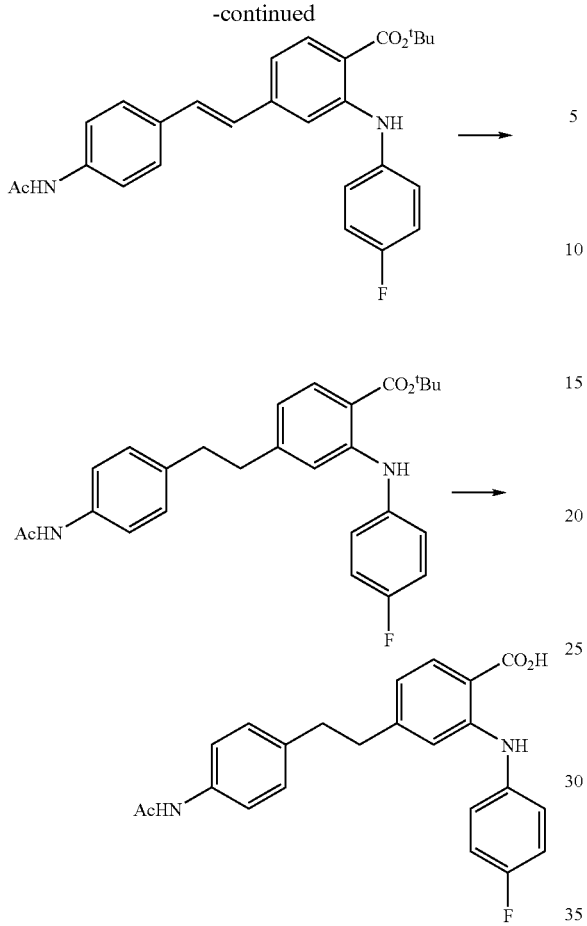

To N,N-dimethylacetamide 3.0 mL solution of tert-butyl 2-(4-fluoroanilino)-4-vinylbenzoate 0.15 g were added N-(4-iodophenyl)acetamide 0.37 g, N,N-dicyclohexylmethylamine 0.41 mL and palladium acetate 5.4 mg at room temperature, and it was stirred at 130° C. for 4 hours. After the reaction mixture was cooled to room temperature, ethyl acetate and 10% citric acid aqueous solution were added to it. The organic layer was separated and collected, and the solvent was removed under reduced pressure after sequential washing with 10% citric acid aqueous solution, saturated sodium thiosulfate aqueous solution and saturated sodium chloride aqueous solution. The obtained residue was refined by silica gel column chromatography [Trikonex company, Flash Tube 2008, eluent; hexane:ethyl acetate=1:1] to give tert-butyl 4-((E)-2-(4-(acetamido)phenyl)vinyl)-2-(4-fluoroanilino)benzoate.

To the obtained tert-butyl 4-((E)-2-(4-(acetamido)phenyl) vinyl)-2-(4-fluoroanilino)benzoate were added acetic acid 2.0 mL, dioxane 2.0 mL and 10% palladium-carbon 30 mg sequentially, and it was stirred under hydrogen atmosphere at room temperature for 3 hours. The solvent was removed under reduced pressure after insoluble matter was filtrated. Trifluoroacetic acid 10 mL was added to the obtained residue, and it was stirred at room temperature for 2 hours. The solvent was removed under reduced pressure, diisopropyl ether was added to the obtained residue, and solid matter was filtrated to give 4-(2-(4-(acetamido)phenyl)ethyl)-2-(4-fluoroanilino) benzoic acid 60 mg of a white solid.

$^1$H-NMR (DMSO-$d_6$) δ value:

2.02(3H,s),2.77(4H,s),6.65(1H,d,J=8.3 Hz),6.71-6.75 (1H,m),7.01-7.07(4H,m),7.09-7.16(2H,m),7.47(2H,d,J=8.3 Hz),7.79(1H,d,J=8.1 Hz),9.48(1H,s),9.87(1H,s),12.89(1H, s).

Example 256

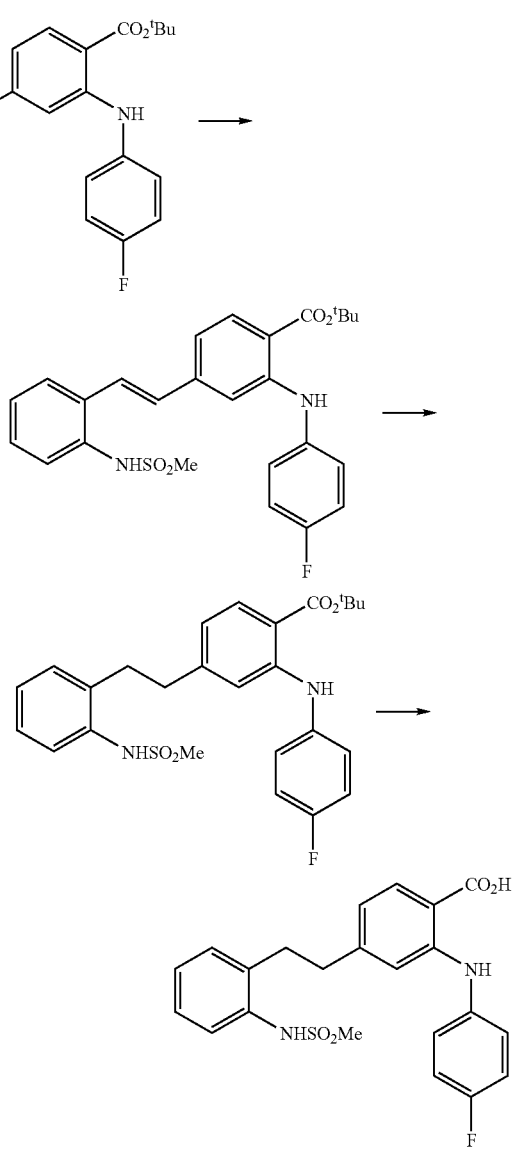

The following compound was obtained in the same manner as in Example 255.

2-(4-Fluoroanilino)-4-(2-(2-(methanesulfonamido) phenyl)ethyl)benzoic acid $^1$H-NMR (DMSO-$d_6$) δ value:

2.76-2.82(2H,m),2.91-3.00(5H,m),6.71(1H,d,J=8.3 Hz), 6.91-6.96(1H,m),7.13-7.26(7H,m),7.29-7.33(1H,m),7.82 (1H,d,J=8.0 Hz),9.07(1H,s),9.55(1H,s),12.80-13.00(1H, broad).

Example 257

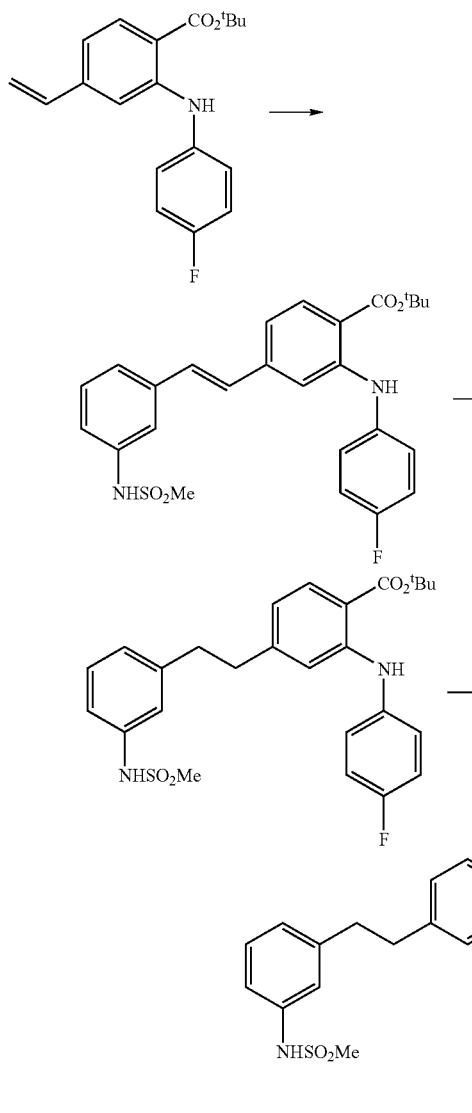

N-(3-Bromophenyl)methanesulfonamide 0.36 g, N,N-dicyclohexylmethylamine 0.41 mL and palladium acetate 5.4 mg were added to N,N-dimethylacetamide 3.0 mL solution of tert-butyl 2-(4-fluoroanilino)-4-vinylbenzoate 0.15 g at room temperature, and it was stirred at 130° C. for 4 hours. N-(3-bromophenyl)methanesulfonamide 0.12 g, N,N-dicyclohexylmethylamine 0.10 mL and (E)-di(μ-acetato)bis(o-(di-o-tolylphosphino)benzyl)dipalladium(II) 5.4 mg were added to it, and it was stirred at 130° C. for 2 hours. (E)-di(μ-acetato)bis(o-(di-o-tolylphosphino)benzyl)dipalladium(II) 11 mg and tri-tert-butylphosphine tetrafluoroborate 6.9 mg were added to it, and it was stirred at 130° C. for 8 hours. After the reaction mixture was cooled to room temperature, ethyl acetate and 10% citric acid aqueous solution were added to it. The organic layer was separated and collected, and the solvent was removed under reduced pressure after sequential washing with 10% citric acid aqueous solution, saturated sodium thiosulfate aqueous solution and saturated sodium chloride aqueous solution. The obtained residue was refined by silica gel column chromatography [Trikonex company, Flash Tube 2008, eluent; hexane:ethyl acetate=1:1] to give tert-butyl 2-(4-fluoroanilino)-4-((E)-2-(3-(methanesulfonamido)phenyl)vinyl)benzoate.

Acetic acid 2.0 mL, dioxane 2.0 mL and 10% palladium-carbon 37 mg were added to the obtained tert-butyl 2-(4-fluoroanilino)-4-((E)-2-(3-(methanesulfonamido)phenyl)vinyl)benzoate sequentially, and it was stirred under hydrogen atmosphere at room temperature for 5 hours and 30 minutes. The solvent was removed under reduced pressure after insoluble matter was filtrated. Trifluoroacetic acid 10 mL was added to the obtained residue, and it was stirred at room temperature for 2 hours. The solvent was removed under reduced pressure, diisopropyl ether was added to the obtained residue, and solid matter was filtrated to give 2-(4-fluoroanilino)-4-(2-(3-(methanesulfonamido)phenyl)ethyl)benzoic acid 75 mg of a white solid.

$^1$H-NMR (DMSO-$d_6$) δ value:
2.75-2.84(4H,m),2.88(3H,s),6.63-6.68(1H,m),6.75-6.79(1H,m),6.91(1H,d,J=7.8 Hz),6.96(1H,s),7.02-7.18(5H,m),7.23(1H,t,j=7.8 Hz),7.80(1H,d,J=8.3 Hz),9.50(1H,s),9.63(1H,s),12.90(1H,s).

Example 258

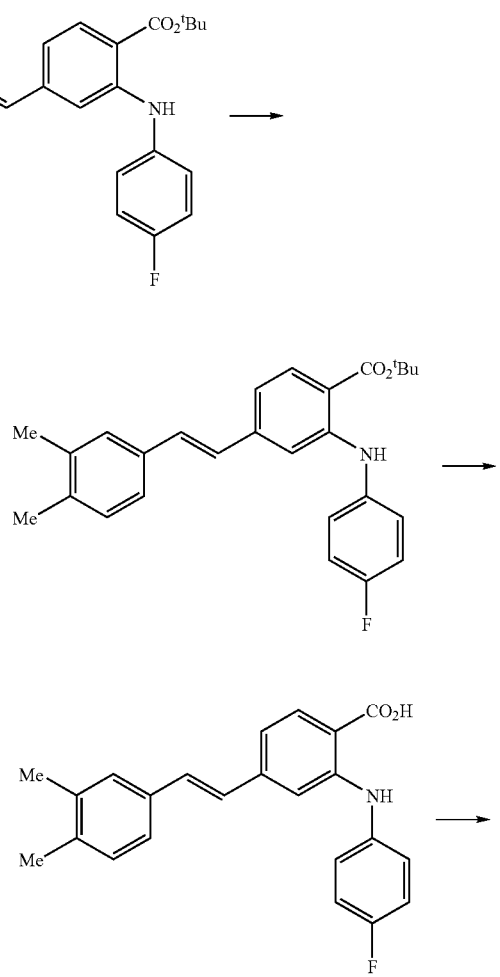

-continued

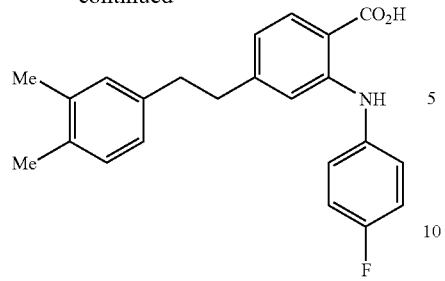

To N,N-dimethylacetamide 3.0 mL solution of tert-butyl 2-(4-fluoroanilino)-4-vinylbenzoate 0.15 g were added 4-bromo-o-xylene 0.19 mL, N,N-dicyclohexylmethylamine 0.41 mL and palladium acetate 5.4 mg at room temperature, and it was stirred at 130° C. for 4 hours. 4-bromo-o-xylene 0.063 mL, N,N-dicyclohexylmethylamine 0.10 mL and (E)-di(μ-acetato)bis(o-(di-o-tolylphosphino)benzyl)dipalladium (II) 5.4 mg were added to it, and it was stirred at 130° C. for 2 hours. (E)-di(μ-acetato)bis(o-(di-o-tolylphosphino)benzyl) dipalladium(II) 11 mg and tri-tert-butylphosphine tetrafluoroborate 6.9 mg were added to it, and it was stirred at 130° C. for 8 hours. After the reaction mixture was cooled to room temperature, ethyl acetate and 10% citric acid aqueous solution were added to it. The organic layer was separated and collected, and the solvent was removed under reduced pressure after sequential washing with 10% citric acid aqueous solution, saturated sodium thiosulfate aqueous solution and saturated sodium chloride aqueous solution. The obtained residue was refined by silica gel column chromatography [Trikonex company, Flash Tube 2008, eluent; hexane:ethyl acetate=4:1] to give tert-butyl 4-((E)-2-(3,4-dimethylphenyl)vinyl)-2-(4-fluoroanilino)benzoate.

Trifluoroacetic acid 10 mL solution of tert-butyl 4-((E)-2-(3,4-dimethylphenyl)vinyl)-2-(4-fluoroanilino)benzoate was stirred at room temperature for 2 hours. The solvent was removed under reduced pressure, and the obtained residue was refined by reversed-phase silica gel column chromatography [eluent; 85-100% acetonitrile/0.1% trifluoroacetic acid aqueous solution] to give 4-((E)-2-(3,4-dimethylphenyl)vinyl)-2-(4-fluoroanilino)benzoic acid.

To the obtained 4-((E)-2-(3,4-dimethylphenyl)vinyl)-2-(4-fluoroanilino)benzoic acid were added ethyl acetate 1.0 mL, methanol 1.0 mL and 10% palladium-carbon 10 mg sequentially, and it was stirred under hydrogen atmosphere at room temperature for 2 hours. The solvent was removed under reduced pressure after insoluble matter was filtrated to give 4-(2-(3,4-dimethylphenyl)ethyl)-2-(4-fluoroanilino)benzoic acid 2.5 mg of a white solid.

$^1$H-NMR (DMSO-$d_6$) δ value:
2.16(3H,s),2.17(3H,s),2.68-2.81(4H,m),6.66(1H,d,J=8.1 Hz),6.80-7.04(4H,m),7.08-7.17(4H,m),7.80(1H,d,J=7.8 Hz),9.51(1H,s),12.90(1H,s).

Example 259

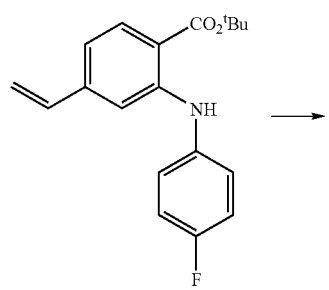

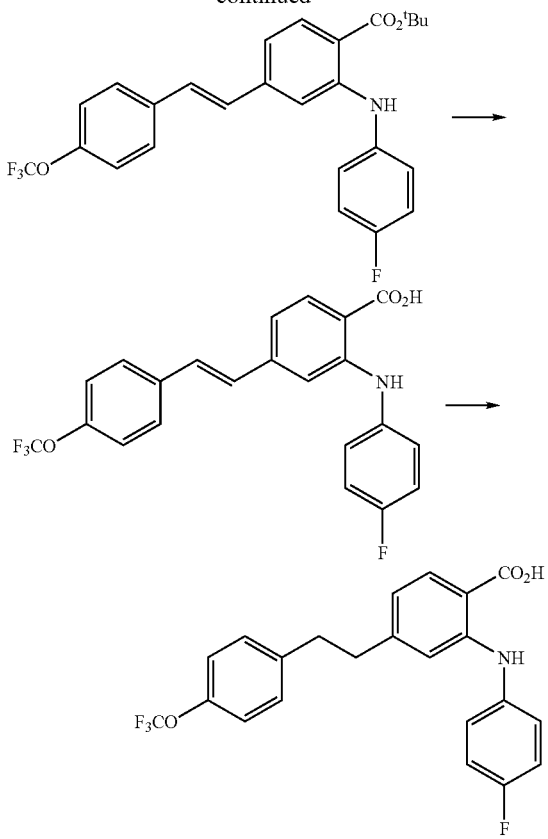

To N,N-dimethylacetamide 3.0 mL solution of tert-butyl 2-(4-fluoroanilino)-4-vinylbenzoate 0.10 g were added 1-bromo-4-(trifluoromethoxy)benzene 0.12 g, tributylamine 0.15 mL and palladium acetate 3.6 mg at room temperature, and it was stirred at 110° C. for 6 hours. Palladium acetate 3.6 mg was added to it, and it was stirred at 130° C. for 6 hours. 1-bromo-4-(trifluoromethoxy)benzene 0.12 g, tributylamine 0.076 mL and (E)-di(μ-acetato)bis(o-(di-o-tolylphosphino)benzyl)dipalladium(II) 6.3 mg were added to it, and it was stirred at 80° C. for 2 hours. After the reaction mixture was cooled to room temperature, ethyl acetate and 10% citric acid aqueous solution were added to it. The organic layer was separated and collected, and the solvent was removed under reduced pressure after sequential washing with 10% citric acid aqueous solution, saturated sodium thiosulfate aqueous solution and saturated sodium chloride aqueous solution. The obtained residue was refined by silica gel column chromatography [Trikonex company, Flash Tube 2008, eluent; hexane:ethyl acetate=10:1] to give tert-butyl 2-(4-fluoroanilino)-4-((E)-2-(4-(trifluoromethoxy)phenyl)vinyl)benzoate.

Trifluoroacetic acid 10 mL solution of the obtained tert-butyl 2-(4-fluoroanilino)-4-((E)-2-(4-(trifluoromethoxy)phenyl)vinyl)benzoate was stirred at room temperature for 2 hours. The solvent was removed under reduced pressure, and the obtained residue was refined by reversed-phase silica gel column chromatography [eluent; 60-100% acetonitrile/0.1% trifluoroacetic acid aqueous solution] to give 2-(4-fluoroanilino)-4-((E)-2-(4-(trifluoromethoxy)phenyl)vinyl)benzoic acid.

To the obtained 2-(4-fluoroanilino)-4-((E)-2-(4-(trifluoromethoxy)phenyl)vinyl)benzoic acid were added ethyl acetate 1.0 mL, methanol 1.0 mL and 10% palladium-carbon 2.0 mg sequentially, and it was stirred under hydrogen atmosphere at room temperature for 2 hours and 30 minutes. The solvent was removed under reduced pressure after insoluble matter was filtrated to give 2-(4-fluoroanilino)-4-(2-(4-(trifluoromethoxy)phenyl)ethyl)benzoic acid 3.4 mg of a white solid.

$^1$H-NMR (DMSO-$d_6$) δ value:
2.74-2.82(2H,m),2.84-2.93(2H,m),6.52(1H,d,J=8.0 Hz), 6.83(1H,s),6.95-7.08(4H,m),7.25(2H,d,J=8.7 Hz),7.31(2H, d,J=8.7 Hz),7.80(1H,d,J=7.8 Hz).

Example 260

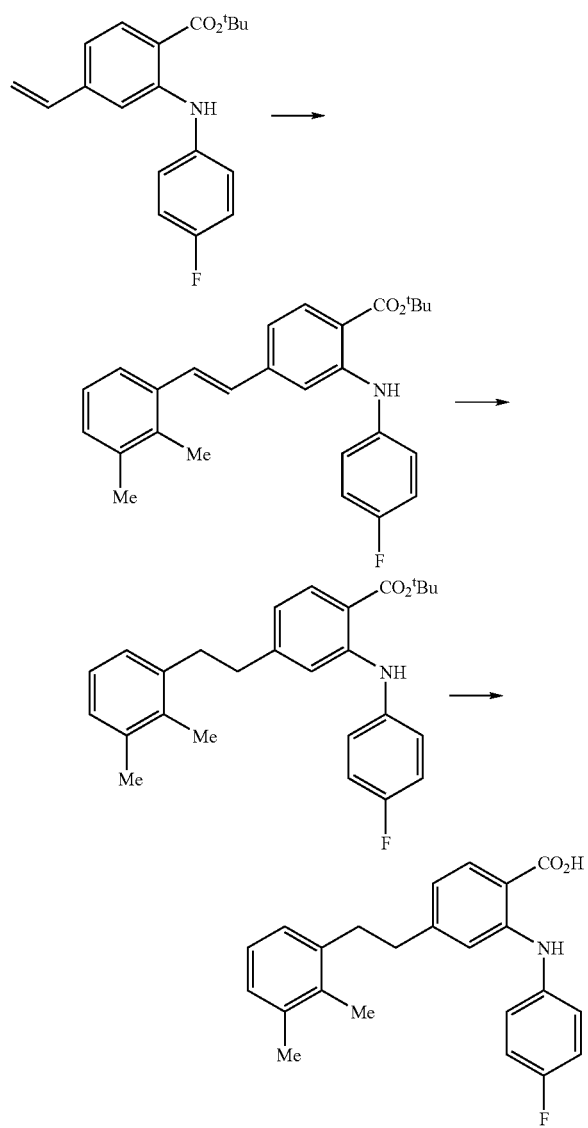

To N,N-dimethylacetamide 2.0 mL solution of tert-butyl 2-(4-fluoroanilino)-4-vinylbenzoate 0.10 g were added 3-bromo-o-xylene 0.064 mL, tributylamine 0.15 mL, palladium acetate 4.0 mg and tri-tert-butylphosphine tetrafluoroborate 3.0 mg at room temperature, and it was stirred under nitrogen atmosphere at 120° C. for 2 hours. Palladium acetate 4.0 mg and tri-tert-butylphosphine tetrafluoroborate 3.0 mg were added to it, and it was stirred under nitrogen atmosphere at 120° C. for 2 hours. 3-Bromo-o-xylene 0.064 mL, tributylamine 0.11 mL, palladium acetate 4.0 mg and tri-tert-butylphosphine tetrafluoroborate 3.0 mg were added to it, and it was stirred under nitrogen atmosphere at 120° C. for 5 hours. After the reaction mixture was cooled to room temperature, ethyl acetate and 10% citric acid aqueous solution were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=10:1] to give tert-butyl 4-((E)-2-(2,3-dimethylphenyl)vinyl)-2-(4-fluoroanilino)benzoate.

To the obtained tert-butyl 4-((E)-2-(2,3-dimethylphenyl)vinyl)-2-(4-fluoroanilino)benzoate were added ethyl acetate 1.5 mL, methanol 1.5 mL and 10% palladium-carbon 27 mg sequentially, and it was stirred under hydrogen atmosphere at room temperature for 3 hours and 20 minutes. The solvent was removed under reduced pressure after insoluble matter was filtrated. Dichloromethane 1.0 mL and trifluoroacetic acid 7.5 mL were added to the obtained residue, and it was stirred at room temperature for 2 hours. The solvent was removed under reduced pressure, diisopropyl ether was added to the obtained residue, and solid matter was filtrated to give 4-(2-(2,3-dimethylphenyl)ethyl)-2-(4-fluoroanilino)benzoic acid 17 mg of a white solid.

$^1$H-NMR (DMSO-$d_6$) δ value:
2.09(3H,s),2.22(3H,s),2.70(2H,t,j=7.5 Hz),2.83(2H,t, j=7.5 Hz),6.68(1H,d,J=8.3 Hz),6.77(1H,s),6.87-6.92(1H,m), 6.96(1H,t,J=7.3 Hz),7.01(1H,d,J=7.3 Hz),7.07-7.15(4H,m), 7.81(1H,d,J=8.0 Hz),9.47-9.57(1H,broad),12.85-12.96(1H, broad).

Example 261-262

The compounds shown in table 34 were obtained in the same manner as in Example 260.

TABLE 34

| Example No. | $R^4$ |
|---|---|
| 261 | F$_3$CO-(3-methylphenyl) |
| 262 | AcHN-(3-methylphenyl) |

2-(4-Fluoroanilino)-4-(2-(3-(trifluoromethoxy)phenyl)ethyl)benzoic acid $^1$H-NMR (DMSO-$d_6$) δ value:
2.78-2.92(4H,m),6.66(1H,d,J=8.0 Hz),6.80(1H,s),7.07-7.23(7H,m),7.40(1H,t,j=7.9 Hz),7.80(1H,d,J=8.1 Hz),9.47-9.55(1H,broad),12.85-12.96(1H,broad).

4-(2-(3-Acetamidophenyl)ethyl)-2-(4-fluoroanilino)benzoic acid $^1$H-NMR (DMSO-$d_6$) δ value:
2.01(3H,s),2.78(4H,s),6.66(1H,d,J=8.3 Hz),6.75(1H,s), 6.81 (1H,d,J=7.8 Hz),7.04-7.20(5H,m),7.36(1H,s),7.45(1H,d,J=8.0 Hz),7.80(1H,d,J=8.3 Hz),9.50(1H,s),9.85(1H,s),12.84-12.94(1H,broad).

Example 263

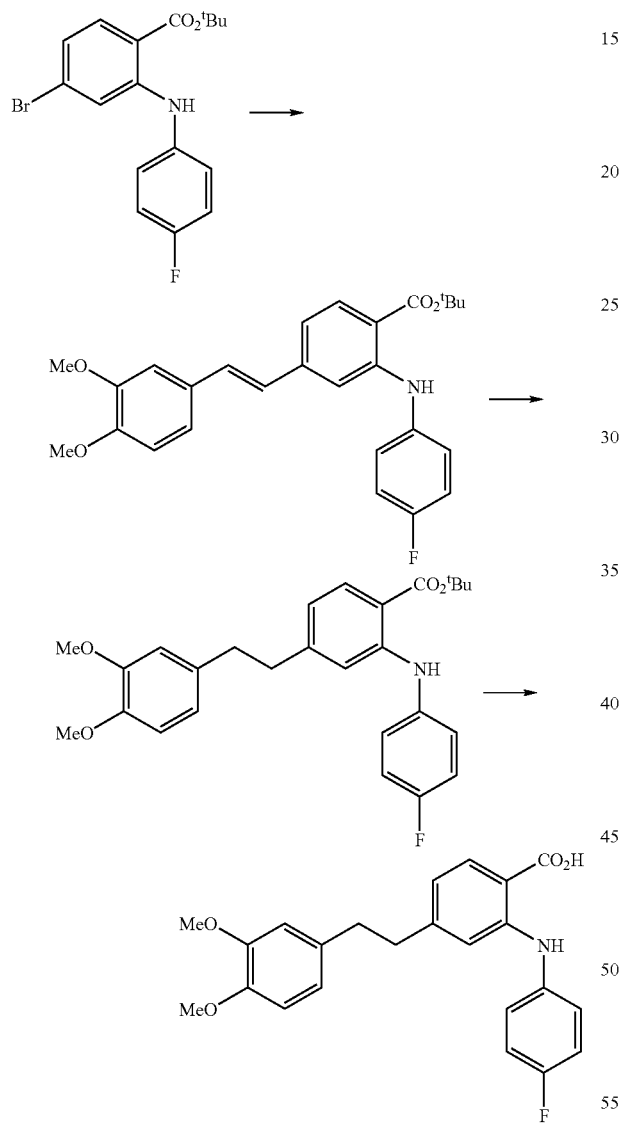

To N,N-dimethylacetamide 2.0 mL solution of tert-butyl 4-bromo-2-(4-fluoroanilino)benzoate 0.10 g were added 3,4-dimethoxystyrene 0.081 mL, tributylamine 0.13 mL, palladium acetate 3.0 mg and tri-tert-butylphosphine tetrafluoroborate 2.0 mg at room temperature, and it was stirred under nitrogen atmosphere at 120° C. for 2 hours. Palladium acetate 3.0 mg and tri-tert-butylphosphine tetrafluoroborate 2.0 mg were added to it, and it was stirred at 120° C. for 2 hours. After the reaction mixture was cooled to room temperature, ethyl acetate and 10% citric acid aqueous solution were added to it. The organic layer was separated and collected, dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 4-((E)-2-(3,4-dimethoxyphenyl)vinyl)-2-(4-fluoroanilino) benzoate.

To the obtained tert-butyl 4-((E)-2-(3,4-dimethoxyphenyl)vinyl)-2-(4-fluoroanilino)benzoate were added ethyl acetate 1.5 mL, methanol 1.5 mL and 10% palladium-carbon 28 mg sequentially, and it was stirred under hydrogen atmosphere at room temperature for 3 hours and 30 minutes. The solvent was removed under reduced pressure after insoluble matter was filtrated. Trifluoroacetic acid 7.5 mL was added to the obtained residue, and it was stirred at room temperature for 2 hours. The solvent was removed under reduced pressure, diisopropyl ether was added to obtained residue, and solid matter was filtrated to give 4-(2-(3,4-dimethoxyphenyl)ethyl)-2-(4-fluoroanilino)benzoic acid 56 mg of a yellow solid.

$^1$H-NMR (DMSO-$d_6$) δ value:
2.73-2.81(4H,m),3.68(3H,s),3.71(3H,s),6.61(1H,dd, J=8.0, 2.0 Hz), 6.67(1H,dd,J=8.0, 1.2 Hz),6.77(2H,s),6.82 (1H,d,J=8.3 Hz), 7.02-7.15(4H,m),7.80(1H,d,J=8.0 Hz),9.49 (1H,s),12.89(1H,s).

Example 264

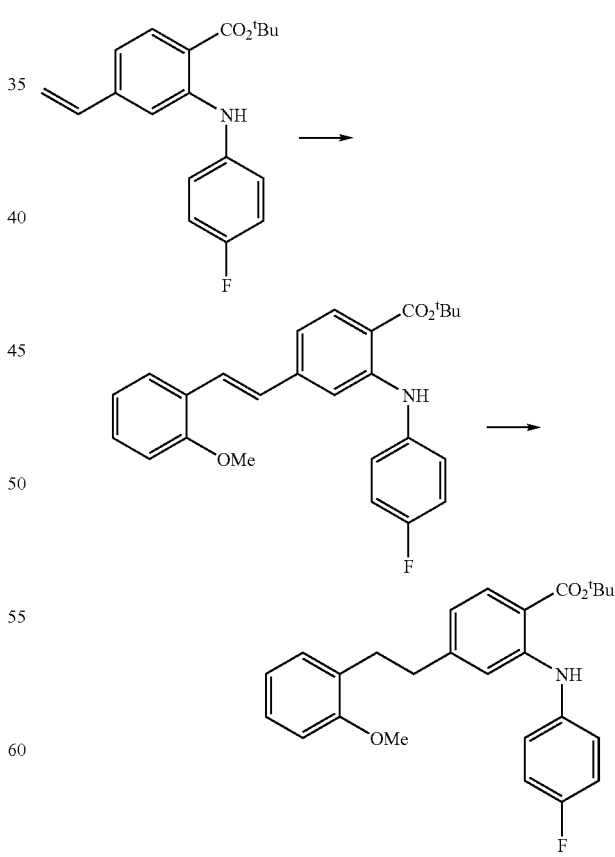

To N,N-dimethylacetamide 2.0 mL solution of tert-butyl 2-(4-fluoroanilino)-4-vinylbenzoate 0.10 g were added 2-iodoanisole 0.046 mL, tributylamine 0.15 mL, palladium acetate 4.0 mg and tri-tert-butylphosphine tetrafluoroborate 3.0 mg at room temperature, and it was stirred under nitrogen atmosphere at 110° C. for 1 hour and 30 minutes. After the reaction mixture was cooled to room temperature, ethyl acetate and 10% citric acid aqueous solution were added to it. The organic layer was separated and collected,dried over anhydrous magnesium sulfate after sequential washing with 10% citric acid aqueous solution and saturated sodium chloride aqueous solution, and the solvent was removed under reduced pressure. The obtained residue was refined by silica gel column chromatography [Trikonex company, Flash Tube 2008, eluent; hexane:ethyl acetate=20:1] to give tert-butyl 2-(4-fluoroanilino)-4-((E)-2-(2-methoxyphenyl)vinyl)benzoate.

To the obtained tert-butyl 2-(4-fluoroanilino)-4-((E)-2-(2-methoxyphenyl)vinyl)benzoate were added acetic acid 4.0 mL and 10% palladium-carbon 26 mg sequentially, and it was stirred under hydrogen atmosphere at room temperature for 7 hours. Subsequently, 10% palladium-carbon 39 mg was added to it, it was stirred under hydrogen atmosphere at the same temperature for 3 hours, subsequently it was stirred at 40° C. for 2 hours. After the reaction mixture was cooled to room temperature, insoluble matter was filtrated, 10% palladium-carbon 64 mg was added to it, and it was stirred under hydrogen atmosphere at 40° C. for 3 hours and 30 minutes. After the reaction mixture was cooled to room temperature, insoluble matter was filtrated, and the solvent was removed under reduced pressure. To the obtained residue were added water, ethyl acetate and saturated sodium hydrogen carbonate aqueous solution. The organic layer was separated and collected,dried over anhydrous magnesium sulfate after washing with saturated sodium chloride aqueous solution, and the solvent was removed under reduced pressure to give tert-butyl 2-(4-fluoroanilino)-4-(2-(2-methoxyphenyl)ethyl)benzoate 0.11 g of a pale red oil.

$^1$H-NMR (DMSO-$d_6$) δ value:
1.55(9H,s),2.69-2.82(4H,m),3.73(3H,s),6.64(1H,dd, J=8.3, 1.2 Hz),6.75(1H,s), 6.81(1H,t,j=7.4 Hz),6.94-7.00 (2H,m),7.05-7.23(5H,m),7.75(1H,d,J=8.3 Hz),9.25(1H,s).

Example 265

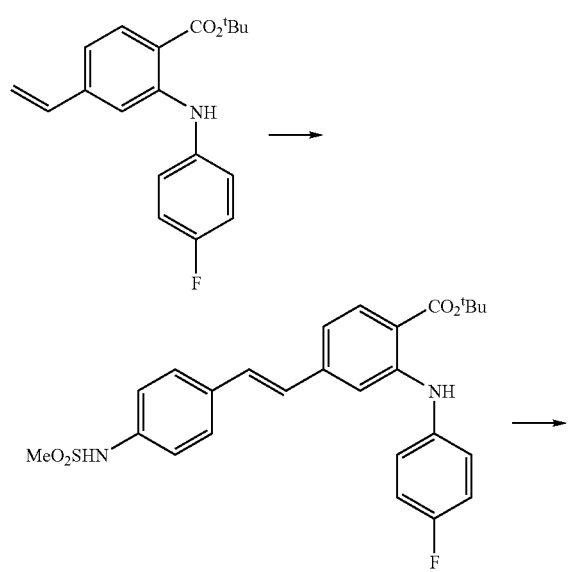

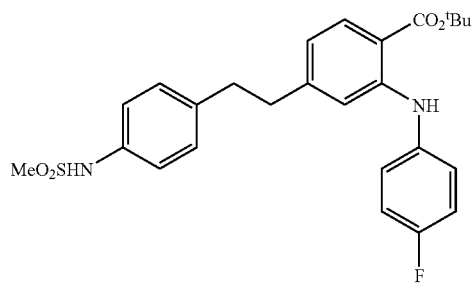

The following compound was obtained in the same manner as in Example 264.

tert-Butyl 2-(4-fluoroanilino)-4-(2-(4-(methanesulfonamido)phenyl)ethyl)benzoate $^1$H-NMR (DMSO-$d_6$) δ value:
1.55(9H,s),2.78(4H,s),2.92(3H,s),6.66(1H,dd,J=8.3, 1.5 Hz), 6.77(1H,d,J=1.5 Hz),7.05-7.18(8H,m),7.75(1H,d,J=8.0 Hz),9.25(1H,s),9.60-9.70(1H,broad).

Example 266

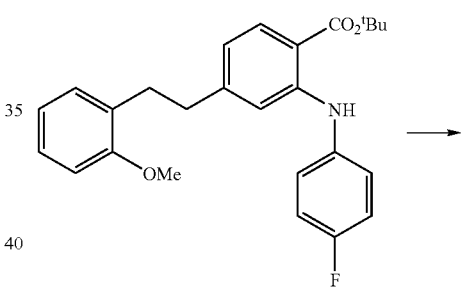

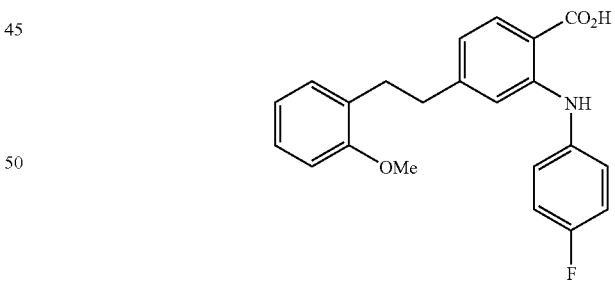

Trifluoroacetic acid 7.5 mL solution of tert-butyl 2-(4-fluoroanilino)-4-(2-(2-methoxyphenyl)ethyl)benzoate 0.11 g was stirred at room temperature for 2 hours. The solvent was removed under reduced pressure,diisopropyl ether was added to the obtained residue, and solid matter was filtrated to give 2-(4-fluoroanilino)-4-(2-(2-methoxyphenyl)ethyl)benzoic acid 12 mg of a white solid.

$^1$H-NMR (DMSO-$d_6$) δ value:
2.70-2.82(4H,m),3.73(3H,s),6.64(1H,dd,J=8.3, 1.3 Hz), 6.76(1H,s), 6.82(1H,td,J=7.4, 0.9 Hz),6.96(1H,d,J=8.3 Hz), 7.00(1H,dd, J=7.3, 1.7 Hz),7.07-7.23(5H,m),7.80(1H,d, J=8.3 Hz),9.51(1H,s),12.82-12.93(1H,broad).

Example 267

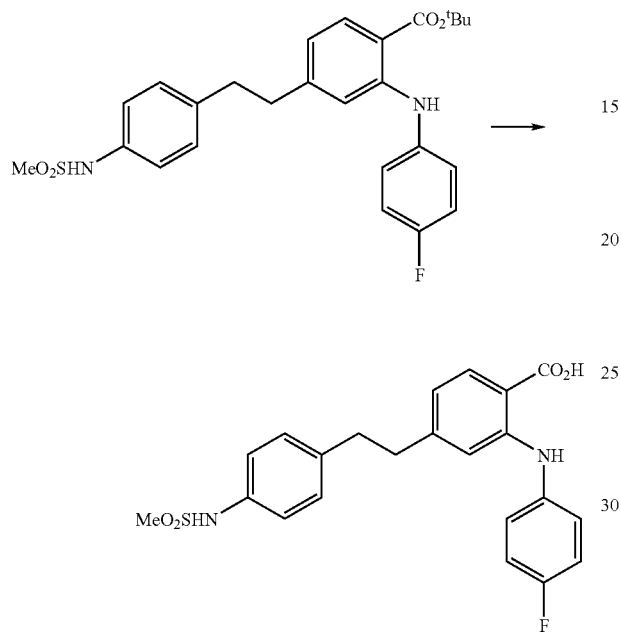

The following compound was obtained in the same manner as in Example 266.

2-(4-Fluoroanilino)-4-(2-(4-(methanesulfonamido)phenyl)ethyl)benzoic acid $^1$H-NMR (DMSO-$d_6$) δ value:

2.78(4H,s),2.92(3H,s),6.66(1H,dd,J=8.2, 1.2 Hz),6.78(1H,s),7.05-7.19(8H,m),7.80(1H,d,J=8.2 Hz),9.40-9.60(1H,broad),9.62(1H,s),12.70-13.00(1H,broad).

Example 268

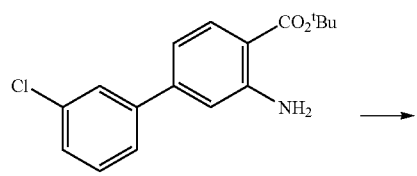

-continued

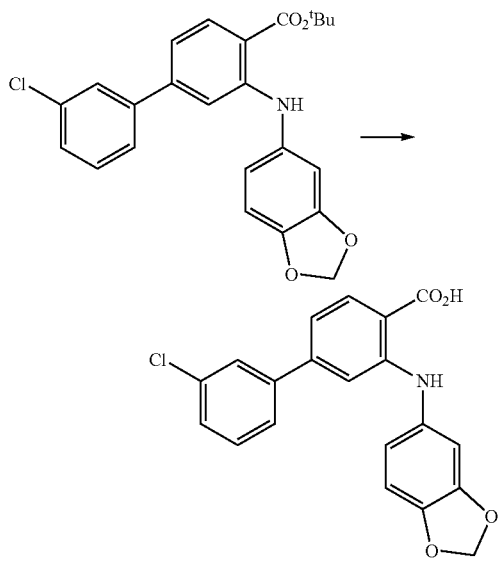

To toluene 3.0 mL suspension of tert-butyl 2-amino-4-(3-chlorophenyl)benzoate 0.12 g and cesium carbonate 0.32 g were added 1-iodo-3,4-methylenedioxybenzene 0.20 g, 2-dicyclohexylphosphino-2',4',6'-triisopropylbiphenyl 9.4 mg, tris(dibenzylideneacetone)dipalladium(0) 3.6 mg and palladium acetate 1.8 mg at room temperature, and it was stirred at 110° C. for 24 hours. After the reaction mixture was cooled to room temperature, 2-dicyclohexylphosphino-2',4',6'-triisopropylbiphenyl 9.4 mg, tris(dibenzylideneacetone)dipalladium(0) 3.6 mg and palladium acetate 1.8 mg were added to it, and it was stirred at 110° C. for 21 hours. After the reaction mixture was cooled to room temperature, ethyl acetate and 10% citric acid aqueous solution were added to it, and insoluble matter was filtrated. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((benzo-1,3-dioxol-5-yl)amino)-4-(3-chlorophenyl)benzoate.

Trifluoroacetic acid 5.0 mL was added to the obtained tert-butyl 2-((benzo-1,3-dioxol-5-yl)amino)-4-(3-chlorophenyl)benzoate, and it was stirred at room temperature for 3 hours. The solvent was removed under reduced pressure, diisopropyl ether was added to the obtained residue, and solid matter was filtrated to give 2-((benzo-1,3-dioxol-5-yl)amino)-4-(3-chlorophenyl)benzoic acid 52 mg of a yellow solid.

$^1$H-NMR (DMSO-$d_6$) δ value:

6.04(2H,s),6.79(1H,dd,J=8.2, 2.1 Hz),6.93(1H,d,J=8.2 Hz),6.98(1H,d,J=2.1 Hz),7.01(1H,dd,J=8.3, 1.7 Hz),7.14-7.19(1H,m),7.43-7.53(3H,m),7.60(1H,s),7.95(1H,d,J=8.3 Hz),9.51(1H,s),13.00-13.15(1H,broad).

Example 269, 270

The compounds shown in Table 35 were obtained in the same manner as in Example 268.

TABLE 35

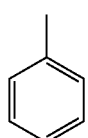

| Example No. | R³ |
|---|---|
| 269 | 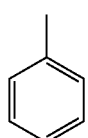 |
| 270 | 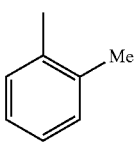 |

2-Anilino-4-(3-chlorophenyl)benzoic acid

¹H-NMR (DMSO-$d_6$) δ value:
7.06-7.14(2H,m),7.30-7.58(8H,m),7.64(1H,s),7.99(1H,d, J=8.3 Hz),9.71(1H,s),13.10-13.30(1H,broad).

4-(3-Chlorophenyl)-2-(2-methylanilino)benzoic acid

¹H-NMR (DMSO-$d_6$) δ value:
2.24(3H,s),7.01-7.13(3H,m),7.22-7.29(1H,m),7.33(1H,d, J=7.3 Hz),7.40-7.51(4H,m),7.57(1H,d,J=1.5 Hz),7.99(1H,d, J=8.3 Hz),9.60(1H,s),13.05-13.25(1H,broad).

Example 271

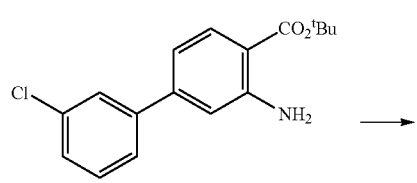

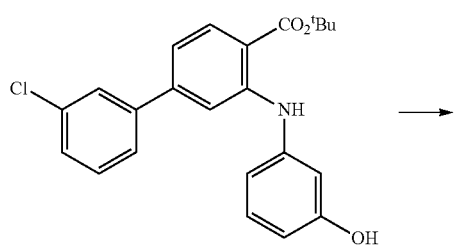

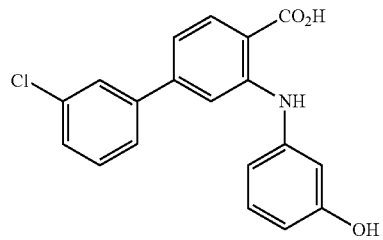

To toluene 3.0 mL suspension of tert-butyl 2-amino-4-(3-chlorophenyl)benzoate 0.12 g and cesium carbonate 0.32 g were added 3-iodophenol 0.17 g, 2-dicyclohexylphosphino-2',4',6'-triisopropylbiphenyl 9.4 mg, tris(dibenzylideneacetone)dipalladium(0) 3.6 mg and palladium acetate 1.8 mg at room temperature, and it was stirred at 110° C. for 24 hours. 2-Dicyclohexylphosphino-2',4',6'-triisopropylbiphenyl 9.4 mg, tris(dibenzylideneacetone)dipalladium(0) 3.6 mg and palladium acetate 1.8 mg were added to it, and it was stirred at 110° C. for 21 hours. Cesium carbonate 64 mg, 3-iodophenol 43 mg, 2-dicyclohexylphosphino-2',4',6'-triisopropylbiphenyl 9.4 mg, tris(dibenzylideneacetone)dipalladium(0) 3.6 mg and palladium acetate 1.8 mg were added to it, and it was stirred at 110° C. for 24 hours. After the reaction mixture was cooled to room temperature, ethyl acetate and 10% citric acid aqueous solution were added to it, and insoluble matter was filtrated. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=5:1] to give tert-butyl 4-(3-chlorophenyl)-2-((3-hydroxyphenyl)amino)benzoate.

Trifluoroacetic acid 5.0 mL was added to the obtained tert-butyl 4-(3-chlorophenyl)-2-((3-hydroxyphenyl)amino)benzoate, and it was stirred at room temperature for 3 hours. The solvent was removed under reduced pressure, and the obtained residue was refined by reversed-phase silica gel column chromatography [eluent; 80-100% acetonitrile/0.1% trifluoroacetic acid aqueous solution] to give 4-(3-chlorophenyl)-2-((3-hydroxyphenyl)amino)benzoic acid 22 mg of a yellow solid.

¹H-NMR (DMSO-$d_6$) δ value:
6.46-6.52(1H,m),6.69-6.76(2H,m),7.08(1H,dd,J=8.3, 1.5 Hz),7.16(1H,t,j=7.9 Hz),7.44-7.53(3H,m),7.54-7.60(1H,m), 7.65(1H,s),7.98(1H,d,J=8.3 Hz),9.49(1H,s),9.66 (1H,s), 13.05-13.30(1H,broad).

Example 272

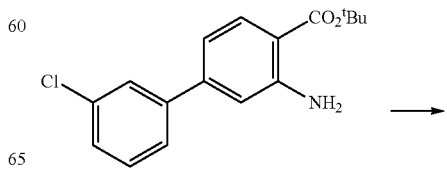

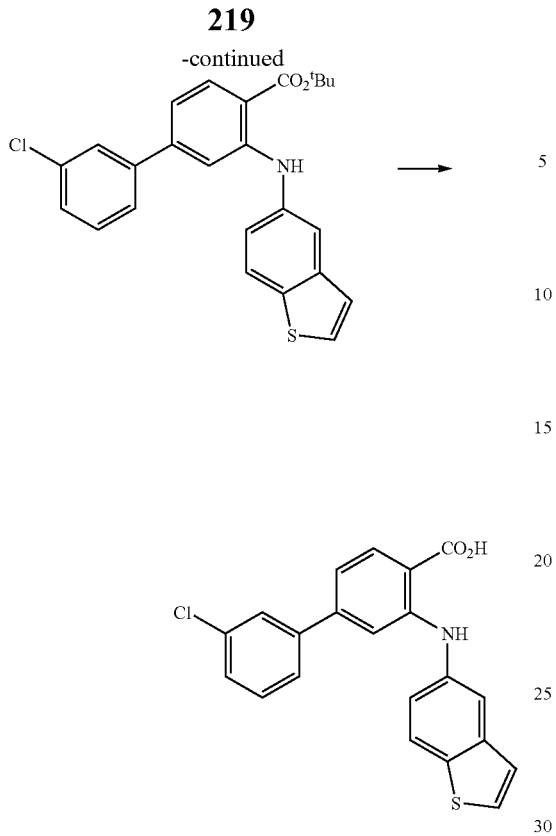

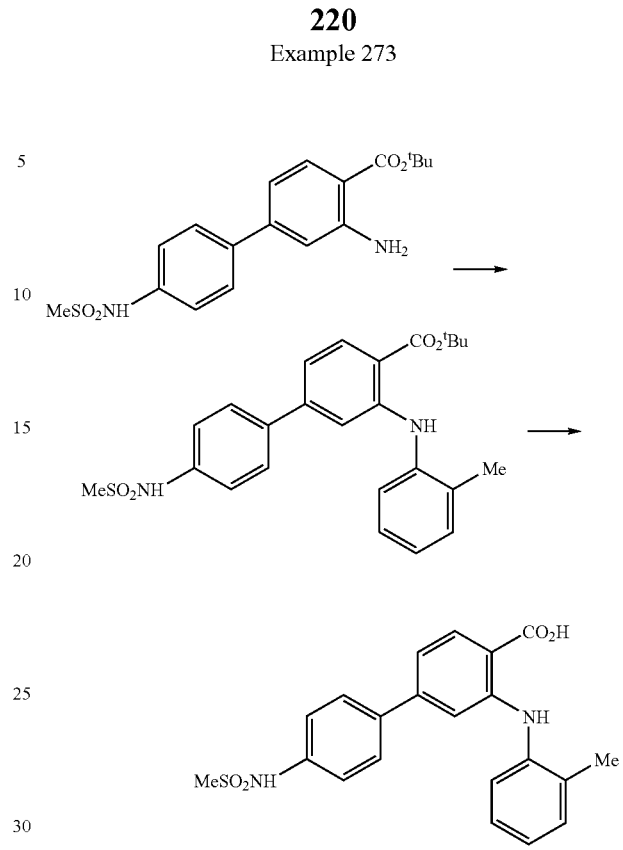

Example 273

To toluene 3.0 mL suspension of tert-butyl 2-amino-4-(3-chlorophenyl)benzoate 0.12 g and cesium carbonate 0.32 g were added 5-bromobenzothiophene 0.17 g, 2-dicyclohexylphosphino-2',4',6'-triisopropylbiphenyl 9.4 mg, tris(dibenzylideneacetone)dipalladium(0) 3.6 mg and palladium acetate 1.8 mg at room temperature, and it was stirred at 110° C. for 24 hours. After the reaction mixture was cooled to room temperature, 2-dicyclohexylphosphino-2',4',6'-triisopropylbiphenyl 9.4 mg, tris(dibenzylideneacetone)dipalladium(0) 3.6 mg and palladium acetate 1.8 mg were added to it, and it was stirred at 110° C. for 21 hours. After the reaction mixture was cooled to room temperature, ethyl acetate and 10% citric acid aqueous solution were added to it, and insoluble matter was filtrated. The organic layer was separated and collected, dried over anhydrous magnesium sulfate after washing with saturated sodium chloride aqueous solution, the solvent was removed under reduced pressure. The obtained residue was refined by silica gel column chromatography [Trikonex company, Flash Tube 2008, eluent; hexane:ethyl acetate=10:1] to give tert-butyl 2-((benzothiophen-5-yl)amino)-4-(3-chlorophenyl)benzoate.

Trifluoroacetic acid 5.0 mL was added to the obtained tert-butyl 2-((benzothiophen-5-yl)amino)-4-(3-chlorophenyl)benzoate, and it was stirred at room temperature for 3 hours. The solvent was removed under reduced pressure, and the obtained residue was refined by reversed-phase silica gel column chromatography [eluent; 80-100% acetonitrile/0.1% trifluoroacetic acid aqueous solution] to give 2-((benzothiophen-5-yl)amino)-4-(3-chlorophenyl)benzoic acid 10 mg of a yellow solid.

$^1$H-NMR (DMSO-$d_6$) δ value:
7.08(1H,dd,J=8.3, 1.7 Hz),7.37(1H,dd,J=8.5, 2.1 Hz), 7.37-7.56(5H,m),7.63(1H,s),7.78(1H,d,J=5.4 Hz),7.86(1H, d,J=2.1 Hz),8.00(2H,d,J=8.3 Hz),9.79(1H,s),13.10-13.25 (1H,broad).

To toluene 3.0 mL suspension of tert-butyl 2-amino-4-(4-(methanesulfonamido)phenyl)benzoate 0.12 g and cesium carbonate 0.27 g were added 2-iodotoluene 0.084 mL, 2-dicyclohexylphosphino-2',4',6'-triisopropylbiphenyl 7.9 mg, tris(dibenzylideneacetone)dipalladium(0) 3.0 mg and palladium acetate 1.5 mg at room temperature, and it was stirred at 110° C. for 24 hours. 2-Dicyclohexylphosphino-2',4',6'-triisopropylbiphenyl 7.9 mg, tris(dibenzylideneacetone)dipalladium(0) 3.0 mg and palladium acetate 1.5 mg were added to it, and it was stirred at 110° C. for 21 hours. After the reaction mixture was cooled to room temperature, ethyl acetate and 10% citric acid aqueous solution were added to it, and insoluble matter was filtrated. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=2:1] to give tert-butyl 4-(4-(methanesulfonamido)phenyl)-2-(2-methylanilino)benzoate.

Trifluoroacetic acid 5.0 mL was added to the obtained tert-butyl 4-(4-(methanesulfonamido)phenyl)-2-(2-methylanilino)benzoate, and it was stirred at room temperature for 3 hours. The solvent was removed under reduced pressure, diisopropyl ether was added to the obtained residue, solid matter was filtrated to give 4-(4-(methanesulfonamido)phenyl)-2-(2-methylanilino)benzoic acid 52 mg of a yellow solid.

$^1$H-NMR (DMSO-$d_6$) δ value:
2.24(3H,s),3.01(3H,s),7.00(1H,dd,J=8.3, 1.7 Hz),7.04-7.12(2H,m),7.22-7.29(3H,m),7.33(1H,d,J=7.0 Hz),7.39-7.44(1H,m),7.48-7.54(2H,m),7.96(1H,d,J=8.3 Hz),9.59(1H, s),9.90(1H,s),12.95-13.15(1H,broad).

Example 274

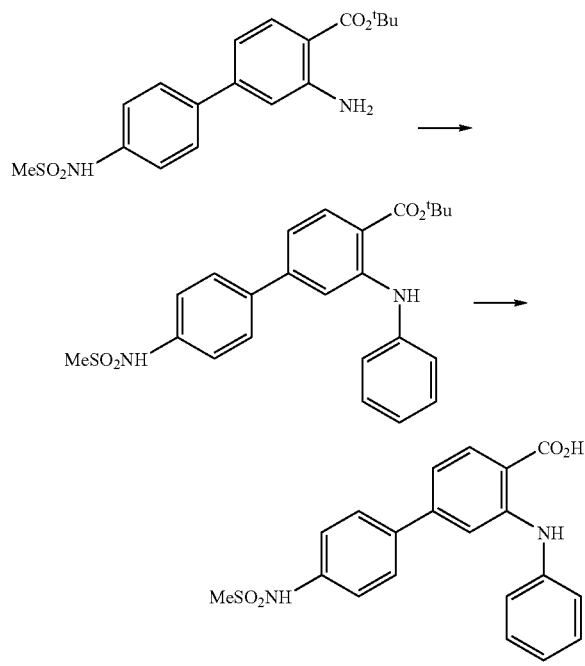

The following compound was obtained in the same manner as in Example 273.

2-Anilino-4-(4-(methanesulfonamido)phenyl)benzoic acid $^1$H-NMR (DMSO-$d_6$) δ value:
3.02(3H,s),7.05(1H,dd,J=8.3, 1.7 Hz),7.06-7.13(1H,m), 7.25-7.43(7H,m),7.54-7.61(2H,m),7.97(1H,d,J=8.3 Hz), 9.71(1H,s),9.92(1H,s),13.00-13.20(1H,broad).

Example 275

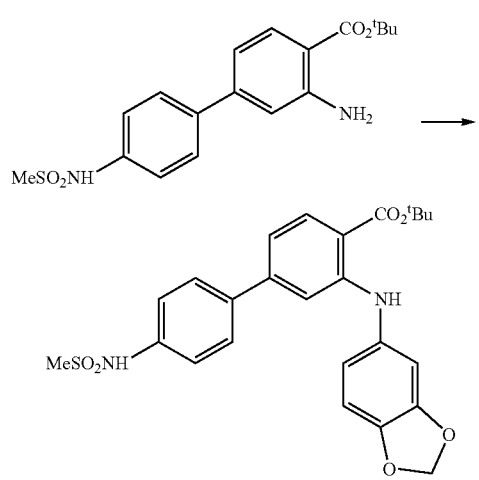

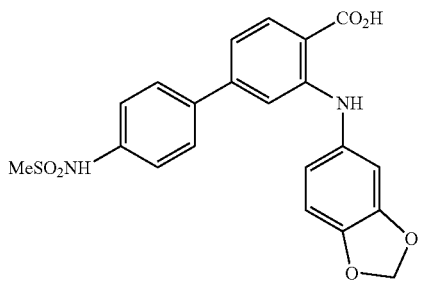

To toluene 3.0 mL suspension of tert-butyl 2-amino-4-(4-(methanesulfonamido)phenyl)benzoate 0.12 g and cesium carbonate 0.27 g were added 1-iodo-3,4-methylenedioxybenzene 0.16 g, 2-dicyclohexylphosphino-2',4',6'-triisopropylbiphenyl 7.9 mg, tris(dibenzylideneacetone)dipalladium(0) 3.0 mg and palladium acetate 1.5 mg at room temperature, and it was stirred at 110° C. for 24 hours. 2-Dicyclohexylphosphino-2',4',6'-triisopropylbiphenyl 7.9 mg, tris(dibenzylideneacetone)dipalladium(0) 3.0 mg and palladium acetate 1.5 mg were added to it, and it was stirred at 110° C. for 21 hours. After the reaction mixture was cooled to room temperature, ethyl acetate and 10% citric acid aqueous solution were added to it, and insoluble matter was filtrated. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=2:1] to give tert-butyl 2-((benzo-1,3-dioxol-5-yl)amino)-4-(4-(methanesulfonamido)phenyl)benzoate.

Trifluoroacetic acid 5.0 mL was added to the obtained tert-butyl 2-((benzo-1,3-dioxol-5-yl)amino)-4-(4-(methanesulfonamido)phenyl)benzoate, and it was stirred at room temperature for 3 hours. The solvent was removed under reduced pressure, the obtained residue was refined by reversed-phase silica gel column chromatography [eluent; 50-90% acetonitrile/0.1% trifluoroacetic acid aqueous solution] to give 2-((benzo-1,3-dioxol-5-yl)amino)-4-(4-(methanesulfonamido)phenyl)benzoic acid 2.8 mg of a yellow solid.

$^1$H-NMR (DMSO-$d_6$) δ value:
3.02(3H,s),6.04(2H,s),6.74-6.83(1H,m),6.90-7.01(3H, m),7.13-7.18(1H,m),7.24-7.31(2H,m),7.50-7.57(2H,m), 7.93(1H,d,J=8.3 Hz),9.51(1H,s),9.91(1H,s).

Example 276

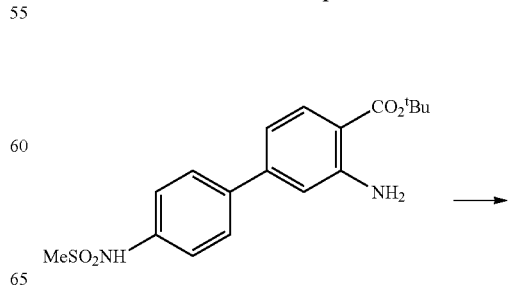

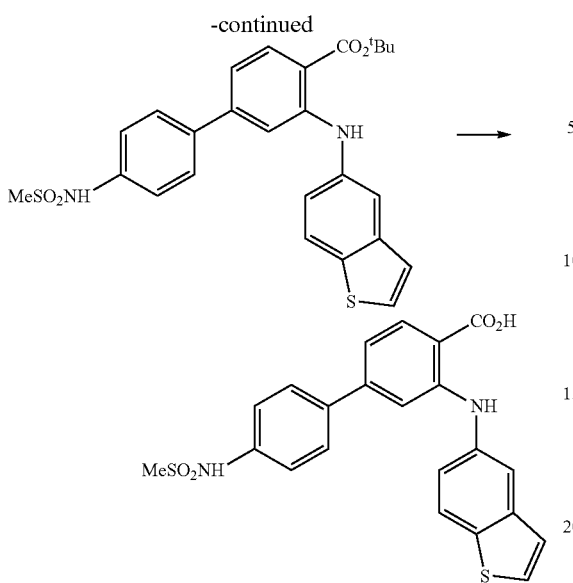

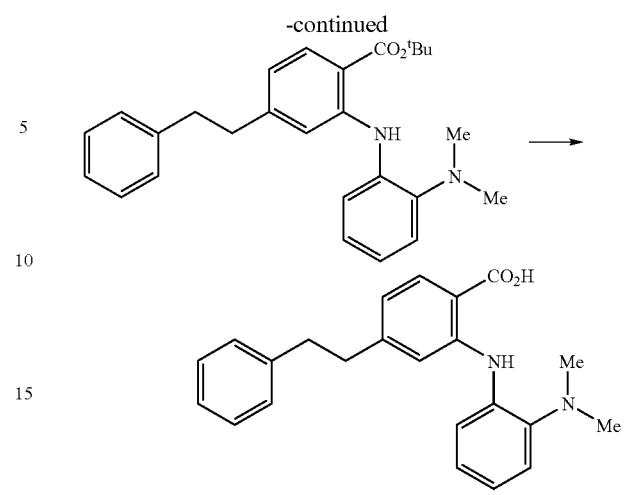

To toluene 3.0 mL suspension of tert-butyl 2-amino-4-(4-(methanesulfonamido)phenyl)benzoate 0.12 g and cesium carbonate 0.27 g were added 5-bromobenzothiophene 0.14 g, 2-dicyclohexylphosphino-2',4',6'-triisopropylbiphenyl 7.9 mg, tris(dibenzylideneacetone)dipalladium(0) 3.0 mg and palladium acetate 1.5 mg at room temperature, and it was stirred at 110° C. for 24 hours. After the reaction mixture was cooled to room temperature, ethyl acetate and 10% citric acid aqueous solution were added to it, and insoluble matter was filtrated. The organic layer was separated and collected, dried over anhydrous magnesium sulfate after washing with saturated sodium chloride aqueous solution, the solvent was removed under reduced pressure. The obtained residue was refined by silica gel column chromatography [Trikonex company, Flash Tube 2008, eluent; hexane:ethyl acetate=2:1] to give tert-butyl 2-((benzothiophen-5-yl)amino)-4-(4-(methanesulfonamido)phenyl)benzoate.

Trifluoroacetic acid 5.0 mL was added to the obtained tert-butyl 2-((benzothiophen-5-yl)amino)-4-(4-(methanesulfonamido)phenyl)benzoate, and it was stirred at room temperature for 3 hours. The solvent was removed under reduced pressure, diisopropyl ether was added to the obtained residue, and solid matter was filtrated to give 2-((benzothiophen-5-yl)amino)-4-(4-(methanesulfonamido)phenyl)benzoic acid 52 mg of a yellow solid.

$^1$H-NMR (DMSO-$d_6$) δ value:
3.01(3H,s),7.04(1H,dd,J=8.3, 1.5 Hz),7.26(2H,d,J=8.6 Hz),7.36 (1H,dd,J=8.6, 2.1 Hz),7.36-7.41(1H,m),7.44(1H,d, J=5.4 Hz),7.56(2H,d,J=8.6 Hz),7.78(1H,d,J=5.4 Hz),7.84 (1H,d,J=2.1 Hz),7.95-8.02(2H,m),9.78(1H,s),9.90(1H,s), 13.00-13.15(1H,broad).

Example 277

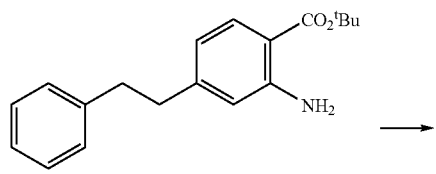

To toluene 3.0 mL suspension of tert-butyl 2-amino-4-phenethylbenzoate 0.12 g and cesium carbonate 0.33 g were added 2-bromo-N,N-dimethylaniline 0.16 g, 2-dicyclohexylphosphino-2',4',6'-triisopropylbiphenyl 9.6 mg, tris(dibenzylideneacetone)dipalladium(0) 3.7 mg and palladium acetate 1.8 mg at room temperature, and it was stirred at 110° C. for 24 hours. 2-Dicyclohexylphosphino-2',4',6'-triisopropylbiphenyl 9.6 mg, tris(dibenzylideneacetone)dipalladium (0) 3.7 mg and palladium acetate 1.8 mg were added to it, and it was stirred at 110° C. for 21 hours. Cesium carbonate 66 mg, 2-bromo-N,N-dimethylaniline 40 mg, 2-dicyclohexylphosphino-2',4',6'-triisopropylbiphenyl 9.6 mg, tris(dibenzylideneacetone)dipalladium(0) 3.7 mg and palladium acetate 1.8 mg were added to it, and it was stirred at 110° C. for 24 hours. After the reaction mixture was cooled to room temperature, ethyl acetate and 10% citric acid aqueous solution were added to it, and insoluble matter was filtrated. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((2-(dimethylamino)phenyl)amino)-4-phenethylbenzoate.

Trifluoroacetic acid 5.0 mL was added to the obtained tert-butyl 2-((2-(dimethylamino)phenyl)amino)-4-phenethylbenzoate, and it was stirred at room temperature for 3 hours. The solvent was removed under reduced pressure, the obtained residue was refined by reversed-phase silica gel column chromatography [eluent; 50-85% acetonitrile/0.1% trifluoroacetic acid aqueous solution], and ethyl acetate, water and saturated sodium hydrogen carbonate aqueous solution were added to it, and it was adjusted to pH6.5. The organic layer was separated and collected, dried over anhydrous magnesium sulfate after washing with saturated sodium chloride aqueous solution, and the solvent was removed under reduced pressure. Hexane was added to the obtained residue, and solid matter was filtrated to give 2-((2-(dimethylamino)phenyl)amino)-4-phenethylbenzoic acid 7.0 mg of a yellow solid.

$^1$H-NMR (DMSO-$d_6$) δ value:
2.59(6H,s),2.78-2.90(4H,m),6.67(1H,dd,J=8.1, 1.2 Hz), 6.89-7.12(5H,m),7.13-7.30(5H,m),7.80(1H,d,J=8.1 Hz), 9.56(1H,s),12.73(1H,s).

Example 278

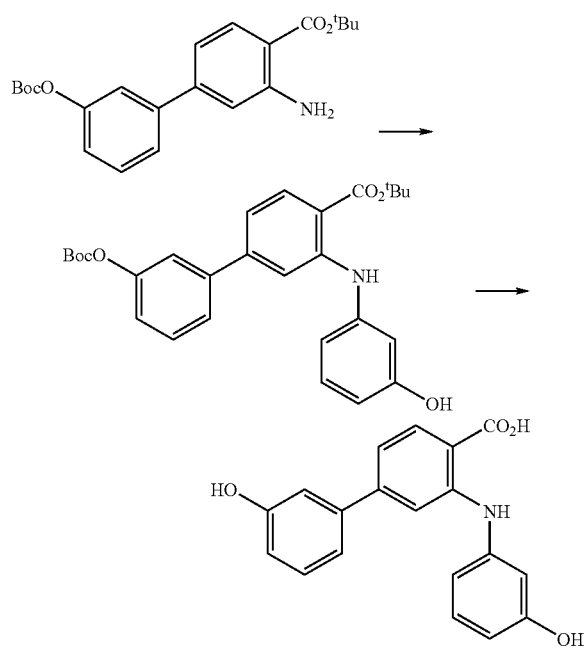

To toluene 3.0 mL suspension of tert-butyl 2-amino-4-(3-(tert-butoxycarbonyloxy)phenyl)benzoate 0.12 g and cesium carbonate 0.25 g were added 3-iodophenol 0.14 g, 2-dicyclohexylphosphino-2',4',6'-triisopropylbiphenyl 7.4 mg, tris(dibenzylideneacetone)dipalladium(0) 2.9 mg and palladium acetate 1.4 mg at room temperature, and it was stirred at 110° C. for 24 hours. 2-Dicyclohexylphosphino-2',4',6'-triisopropylbiphenyl 7.4 mg, tris(dibenzylideneacetone)dipalladium (0) 2.9 mg and palladium acetate 1.4 mg were added to it, and it was stirred at 110° C. for 21 hours. After the reaction mixture was cooled to room temperature, ethyl acetate and 10% citric acid aqueous solution were added to it, and insoluble matter was filtrated. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=3:1] to give tert-butyl 4-(3-(tert-butoxycarbonyl)oxyphenyl)-2-((3-hydroxyphenyl)amino)benzoate.

Trifluoroacetic acid 5.0 mL was added to the obtained tert-butyl 4-(3-(tert-butoxycarbonyl)oxyphenyl)-2-((3-hydroxyphenyl)amino)benzoate, and it was stirred at room temperature for 3 hours. The solvent was removed under reduced pressure, hexane and diisopropyl ether were added to the obtained residue, and solid matter was filtrated to give 4-(3-hydroxyphenyl)-2-((3-hydroxyphenyl)amino)benzoic acid 10 mg of a yellow solid.

$^1$H-NMR (DMSO-$d_6$) δ value:
6.50(1H,d,J=7.6 Hz),6.68-6.74(2H,m),6.76-6.82(1H,m),6.92-7.06(3H,m),7.12-7.20(1H,m),7.22-7.29(1H,m),7.39-7.44(1H,m),7.95(1H,d,J=8.3 Hz),9.49(1H,s),9.58(1H,s),9.62 (1H,s),13.08(1H,s).

Example 279, 280

The compounds shown in Table 36 were obtained in the same manner as in Example 278.

TABLE 36

| Example No. | R³ |
|---|---|
| 279 | phenyl |
| 280 | 2-methylphenyl (o-tolyl) |

2-Anilino-4-(3-hydroxyphenyl)benzoic acid $^1$H-NMR (DMSO-$d_6$) δ value:
6.75-6.81(1H,m),6.91-6.96(1H,m),6.97-7.04(2H,m),7.11 (1H,t,j=7.3 Hz),7.24(1H,t,j=7.9 Hz),7.29-7.43(5H,m),7.97 (1H,d,J=8.3 Hz),9.57(1H,s),9.68(1H,s),13.09 (1H,s).

4-(3-Hydroxyphenyl)-2-(2-methylanilino)benzoic acid $^1$H-NMR (DMSO-$d_6$) δ value:
2.24(3H,s),6.74-6.79(1H,m),6.86-6.90(1H,m),6.91-7.03 (3H,m),7.07-7.14(1H,m),7.18-7.29(2H,m),7.34(1H,d,J=7.6 Hz),7.37-7.42(1H,m),7.96(1H,d,J=8.3 Hz),9.56(2H,s),13.05 (1H,s).

Example 281

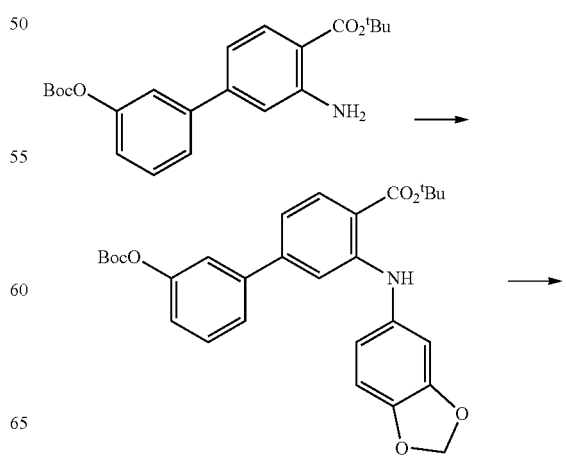

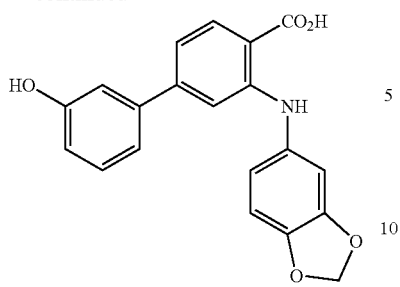

To toluene 3.0 mL suspension of tert-butyl 2-amino-4-(3-(tert-butoxycarbonyloxy)phenyl)benzoate 0.12 g and cesium carbonate 0.25 g were added 1-iodo-3,4-methylenedioxybenzene 0.15 g, 2-dicyclohexylphosphino-2',4',6'-triisopropylbiphenyl 7.4 mg, tris(dibenzylideneacetone)dipalladium(0) 2.9 mg and palladium acetate 1.4 mg at room temperature, and it was stirred at 110° C. for 24 hours. 2-Dicyclohexylphosphino-2',4',6'-triisopropylbiphenyl 7.4 mg, tris(dibenzylideneacetone)dipalladium(0) 2.9 mg and palladium acetate 1.4 mg were added to it, and it was stirred at 110° C. for 21 hours. After the reaction mixture was cooled to room temperature, ethyl acetate and 10% citric acid aqueous solution were added to it, and insoluble matter was filtrated. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((benzo-1,3-dioxol-5-yl)amino)-4-(3-(tert-butoxycarbonyloxy)phenyl)benzoate.

Trifluoroacetic acid 5.0 mL was added to the obtained tert-butyl 2-((benzo-1,3-dioxol-5-yl)amino)-4-(3-(tert-butoxycarbonyloxy)phenyl)benzoate, and it was stirred at room temperature for 3 hours. The solvent was removed under reduced pressure, and the obtained residue was refined by reversed-phase silica gel column chromatography [eluent; 50-90% acetonitrile/0.1% trifluoroacetic acid aqueous solution] to give 2-((benzo-1,3-dioxol-5-yl)amino)-4-(3-hydroxyphenyl)benzoic acid 17 mg of a yellow solid.

$^1$H-NMR (DMSO-$d_6$) δ value:
6.04(2H,s),6.75-6.80(2H,m),6.88-6.98(5H,m),7.11(1H,d,J=1.7 Hz),7.23(1H,t,j=7.9 Hz),7.92(1H,d,J=8.3 Hz),9.47(1H,s),9.56(1H,s),12.99(1H,s).

Example 282

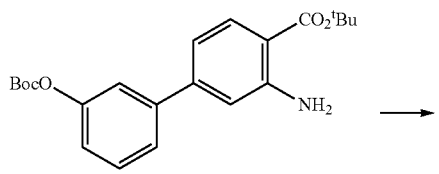

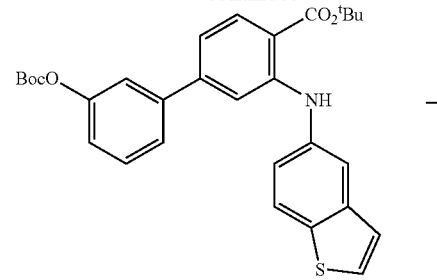

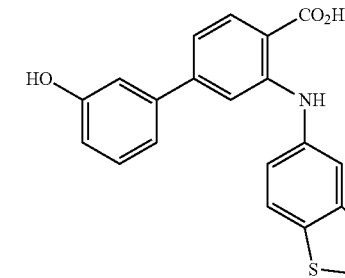

To toluene 3.0 mL suspension of tert-butyl 2-amino-4-(3-(tert-butoxycarbonyloxy)phenyl)benzoate 0.12 g and cesium carbonate 0.25 g were added 5-bromobenzothiophene 0.13 g, 2-dicyclohexylphosphino-2',4',6'-triisopropylbiphenyl 7.4 mg, tris(dibenzylideneacetone)dipalladium(0) 2.9 mg and palladium acetate 1.4 mg at room temperature, and it was stirred at 110° C. for 24 hours. 2-Dicyclohexylphosphino-2',4',6'-triisopropylbiphenyl 7.4 mg, tris(dibenzylideneacetone) dipalladium(0) 2.9 mg and palladium acetate 1.4 mg were added to it, and it was stirred at 110° C. for 21 hours. Cesium carbonate 51 mg, 5-bromobenzothiophene 33 mg, 2-dicyclohexylphosphino-2',4',6'-triisopropylbiphenyl 7.4 mg, tris(dibenzylideneacetone)dipalladium(0) 2.9 mg and palladium acetate 1.4 mg were added to it, and it was stirred at 110° C. for 24 hours. After the reaction mixture was cooled to room temperature, ethyl acetate and 10% citric acid aqueous solution were added to it, and insoluble matter was filtrated. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((benzothiophen-5-yl)amino)-4-(3-(tert-butoxycarbonyloxy)phenyl)benzoate.

Trifluoroacetic acid 5.0 mL was added to the obtained tert-butyl 2-((benzothiophen-5-yl)amino)-4-(3-(tert-butoxycarbonyloxy)phenyl)benzoate, and it was stirred at room temperature for 3 hours. The solvent was removed under reduced pressure,diisopropyl ether was added to the obtained residue, and solid matter was filtrated to give 2-((benzothiophen-5-yl)amino)-4-(3-hydroxyphenyl)benzoic acid 30 mg of a yellow solid.

$^1$H-NMR (DMSO-$d_6$) δ value:
6.76(1H,dd,J=8.1, 1.9 Hz),6.91(1H,s),6.95-7.03(2H,m),7.22(1H,t,j=7.8 Hz),7.32-7.38(2H,m),7.44(1H,d,J=5.4 Hz),7.79(1H,d,J=5.4 Hz),7.83(1H,d,J=2.0 Hz),7.98(1H,d,J=8.3 Hz),8.01(1H,d,J=8.8 Hz),9.54 (1H,s),9.75(1H,s),13.00-13.15(1H,broad).

Example 283

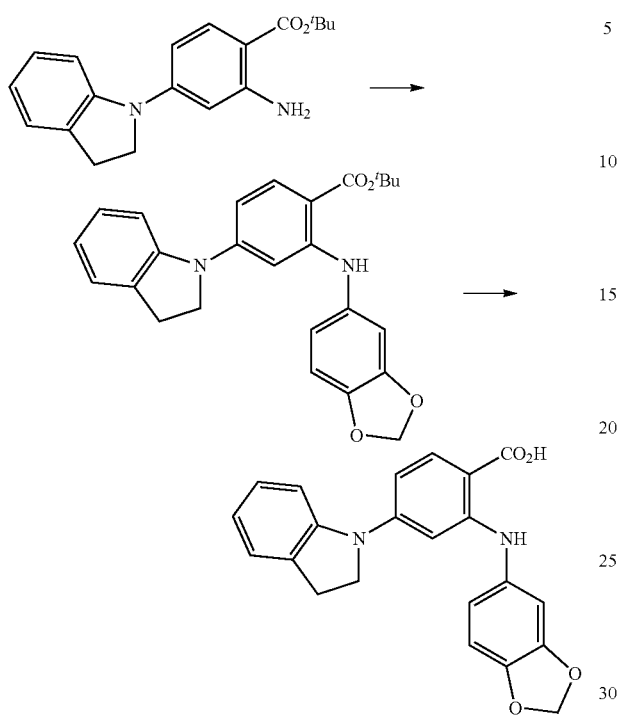

To toluene 3.0 mL solution of tert-butyl 2-amino-4-(indolin-1-yl)benzoate 0.12 g were added 1-bromo-3,4-methylenedioxybenzene 0.12 mL, cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg at room temperature, and it was stirred at 110° C. for 6 hours. Tris(dibenzylideneacetone)dipalladium(0) 3.7 mg, palladium acetate 1.8 mg and 2-dicyclohexylphosphino-2',4',6'-triisopropylbiphenyl 9.5 mg were added at room temperature, and it was stirred at 110° C. for 18 hours 30 minutes. 1-Bromo-3,4-methylenedioxybenzene 0.12 mL, cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 110° C. for 22 hours. After the reaction mixture was cooled to room temperature, tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 110° C. for 20 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((benzo-1,3-dioxol-5-yl)amino)-4-(indolin-1-yl)benzoate.

Trifluoroacetic acid 10 mL was added to the obtained tert-butyl 2-((benzo-1,3-dioxol-5-yl)amino)-4-(indolin-1-yl)benzoate, and it was stirred at room temperature for 2 hours. The solvent was removed under reduced pressure, methanol was added to the obtained residue, and solid matter was filtrated to give 2-((benzo-1,3-dioxol-5-yl)amino)-4-(indolin-1-yl)benzoic acid 31 mg of a white solid.

$^1$H-NMR (DMSO-$d_6$) δ value:
3.06(2H,t,j=8.5 Hz),3.90(2H,t,j=8.5 Hz),6.04(2H,s),6.55-6.60(1H,m),6.67-6.71(1H,m),6.75-6.81(2H,m),6.92-6.97(2H,m),7.02-7.12(2H,m),7.19(1H,d,J=7.3 Hz),7.82(1H,d,J=8.8 Hz),9.51(1H,s),12.45-12.55(1H,broad).

Example 284, 285

The compounds shown in Table 37 were obtained in the same manner as in Example 283.

TABLE 37

| Example No. | R³ |
|---|---|
| 284 | phenyl |
| 285 | 2-methylphenyl (o-tolyl) |

2-Anilino-4-(indolin-1-yl)benzoic acid $^1$H-NMR (DMSO-$d_6$) δ value:
3.07(2H,t,j=8.4 Hz),3.93(2H,t,j=8.4 Hz),6.65(1H,dd,J=8.9, 2.3 Hz),6.79(1H,t,j=7.3 Hz),6.90(1H,d,J=2.2 Hz),7.04-7.17(3H,m),7.19(1H,d,J=7.0 Hz),7.30-7.36(2H,m),7.36-7.44(2H,m),7.86(1H,d,J=9.0 Hz),9.76(1H,s),12.40-12.70(1H,broad).

4-(Indolin-1-yl)-2-(2-methylanilino)benzoic acid $^1$H-NMR (DMSO-$d_6$) δ value:
2.23(3H,s),3.05(2H,t,j=8.4 Hz),3.88(2H,t,j=8.4 Hz),6.56-6.63(2H,m),6.77(1H,t,j=7.1 Hz),6.99-7.12(3H,m),7.18(1H,d,J=7.3 Hz),7.27(1H,t,j=7.4 Hz),7.32(1H,d,J=7.6 Hz),7.43(1H,d,J=7.8 Hz),7.85(1H,d,J=9.5 Hz),9.61 (1H,s),12.52(1H,s).

Example 286

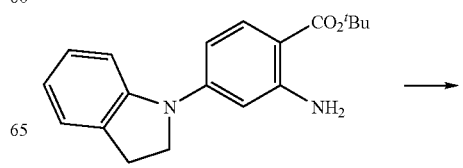

-continued

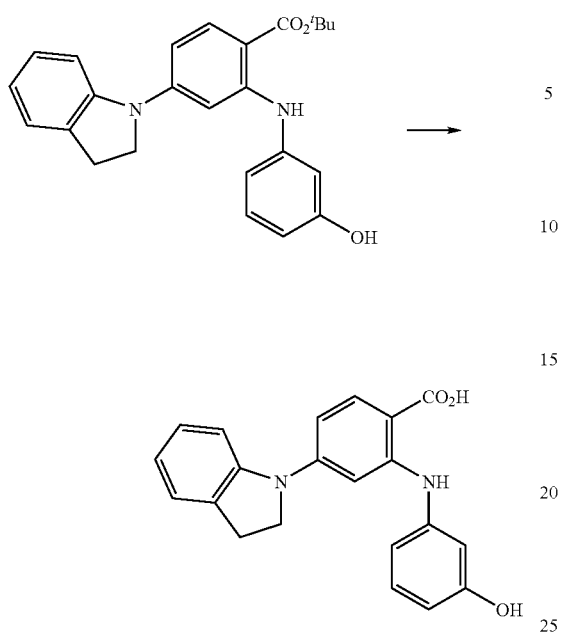

To 2-methyl-2-propanol 3.0 mL solution of tert-butyl 2-amino-4-(indolin-1-yl)benzoate 0.12 g were added 3-iodophenol 0.22 g, cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg at room temperature, and it was stirred at 70° C. for 12 hours. Tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 70° C. for 7 hours. Cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 70° C. for 12 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2,008, eluent; hexane:ethyl acetate=4:1] to give tert-butyl 2-((3-hydroxyphenyl)amino)-4-(indolin-1-yl)benzoate.

Trifluoroacetic acid 10 mL was added to the obtained tert-butyl 2-((3-hydroxyphenyl)amino)-4-(indolin-1-yl)benzoate, and it was stirred at room temperature for 2 hours. The solvent was removed under reduced pressure, and the obtained residue was refined by reversed-phase silica gel column chromatography [eluent; 50-90% acetonitrile/0.1% trifluoroacetic acid aqueous solution] to give 2-((3-hydroxyphenyl)amino)-4-(indolin-1-yl)benzoic acid 13 mg of a white solid.

$^1$H-NMR (DMSO-$d_6$) δ value:
3.08(2H,t,j=8.4 Hz),3.94(2H,t,j=8.4 Hz),6.46-6.52(1H,m),6.64(1H,dd,J=8.9, 2.1 Hz),6.69-6.74(2H,m),6.79(1H,t,j=7.3 Hz),6.93-6.97(1H,m),7.07(1H,t,j=7.7 Hz),7.13-7.23(3H,m),7.85(1H,d,J=9.0 Hz),9.47(1H,s),9.68(1H,s),12.55(1H,s).

Example 287

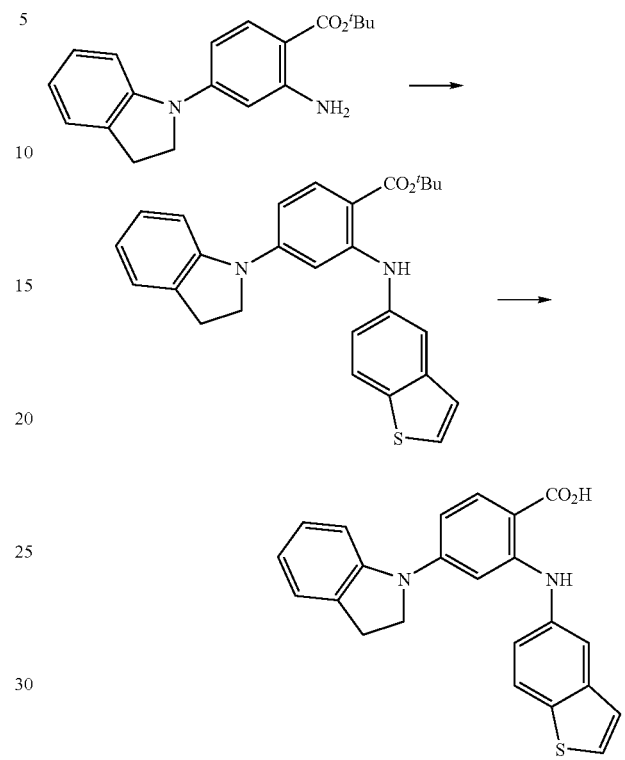

To toluene 3.0 mL solution of tert-butyl 2-amino-4-(indolin-1-yl)benzoate 0.12 g were added 5-bromobenzothiophene 0.21 g, cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg at room temperature, and it was stirred at 110° C. for 12 hours. Tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 110° C. for 6 hours. 5-Bromobenzothiophene 0.21 g, cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg were added at room temperature, and it was stirred at 110° C. for 12 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((benzothiophen-5-yl)amino)-4-(indolin-1-yl)benzoate.

Trifluoroacetic acid 10 mL was added to the obtained tert-butyl 2-((benzothiophen-5-yl)amino)-4-(indolin-1-yl)benzoate, and it was stirred at room temperature for 2 hours. The solvent was removed under reduced pressure, methanol was added to the obtained residue, and solid matter was filtrated to give 2-((benzothiophen-5-yl)amino)-4-(indolin-1-yl)benzoic acid 67 mg of a brown solid.

¹H-NMR (DMSO-d₆) δ value:
3.05(2H,t,j=8.4 Hz),3.91(2H,t,j=8.4 Hz),6.62(1H,dd,J=9.0, 2.2 Hz),6.76(1H,t,j=7.4 Hz),6.91(1H,d,J=2.2 Hz),7.02 (1H, t, J=7.8 Hz),7.13-7.20(2H,m),7.34(1H,dd,J=8.5, 1.9 Hz),7.45(1H,d,J=5.4 Hz),7.79 (1H,d,J=5.4 Hz),7.84-7.91 (2H,m),8.00(1H,d,J=8.5 Hz),9.83(1H,s),12.56(1H,s).

Example 288

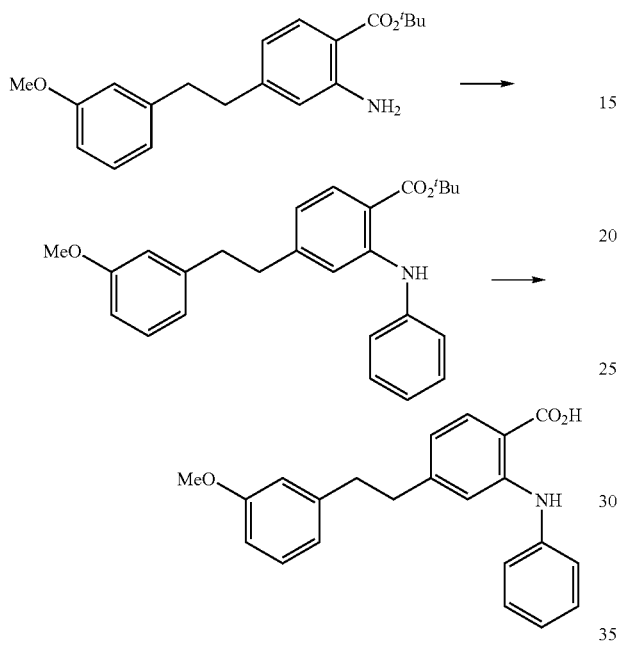

To toluene 3.0 mL solution of tert-butyl 2-amino-4-(2-(3-methoxyphenyl)ethyl)benzoate 0.13 g were added iodobenzene 0.11 mL, cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg, and it was stirred at 110° C. for 6 hours. Tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 110° C. for 18 hours 30 minutes. Iodobenzene 0.11 mL, cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 110° C. for 22 hours. Tris(dibenzylideneacetone) dipalladium(0) 3.7 mg, palladium acetate 1.8 mg and 2-dicyclohexylphosphino-2',4',6'-triisopropylbiphenyl 9.5 mg were added to it, and it was stirred at 110° C. for 20 hours. After the reaction mixture was cooled to room temperature, insoluble matter was filtrated, and ethyl acetate and 10% citric acid aqueous solution were added to it. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-anilino-4-(2-(3-methoxyphenyl)ethyl)benzoate.

Trifluoroacetic acid 10 mL was added to the obtained tert-butyl 2-anilino-4-(2-(3-methoxyphenyl)ethyl)benzoate, and it was stirred at room temperature for 2 hours. The solvent was removed under reduced pressure, and the obtained residue was refined in reversed-phase silica gel column chromatography [eluent; 65-100% acetonitrile/0.1% trifluoroacetic acid aqueous solution] to give 2-anilino-4-(2-(3-methoxyphenyl)ethyl)benzoic acid 4.2 mg of a white solid.

¹H-NMR (DMSO-d₆) δ value:
2.82(4H,s),3.70(3H,s),6.66-6.80(4H,m),6.97(1H,s),7.00-7.10(3H,m),7.17(1H,t,j=7.9 Hz),7.31(2H,t,j=7.7 Hz),7.81 (1H,d,J=8.0 Hz),9.61(1H,s),12.85-13.05(1H,broad).

Example 289, 290

The compounds shown in Table 38 were obtained in the same manner as in Example 288.

TABLE 38

| Example No. | R³ |
|---|---|
| 289 | ![benzo-1,3-dioxol-5-yl] |
| 290 | ![2-methylphenyl] |

2-((Benzo-1,3-dioxol-5-yl)amino)-4-(2-(3-methoxyphenyl)ethyl)benzoic acid

¹H-NMR (DMSO-d₆) δ value:
2.78(4H,s),3.70(3H,s),6.03(2H,s),6.56(1H,dd,J=8.3, 2.2 Hz), 6.62(1H,d,J=8.0 Hz),6.71-6.78(5H,m),6.86(1H,d,J=8.3 Hz),7.16(1H,t,j=7.7 Hz),7.77(1H,d,J=8.0 Hz),9.40(1H,s), 12.82(1H,s).

4-(2-(3-Methoxyphenyl)ethyl)-2-(2-methylanilino)benzoic acid

¹H-NMR (DMSO-d₆) δ value:
2.16(3H,s),2.78(4H,s),3.69(3H,s),6.63-6.77(5H,m),7.00-7.07(1H,m),7.07-7.20(3H,m),7.27(1H,d,J=7.3 Hz),7.81(1H, d,J=8.1 Hz),9.49(1H,s),12.88(1H,s).

Example 291

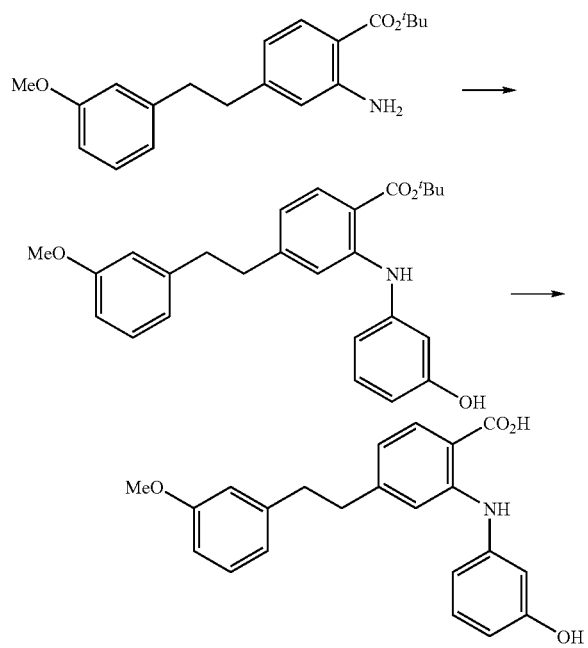

To 2-methyl-2-propanol 3.0 mL solution of tert-butyl 2-amino-4-(2-(3-methoxyphenyl)ethyl)benzoate 0.13 g were added 3-iodophenol 0.22 g, cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg at room temperature, and it was stirred at 70° C. for 12 hours. Tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 70° C. for 7 hours. Cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 70° C. for 12 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 2-((3-hydroxyphenyl)amino)-4-(2-(3-methoxyphenyl)ethyl)benzoate.

Trifluoroacetic acid 10 mL was added to the obtained tert-butyl 2-((3-hydroxyphenyl)amino)-4-(2-(3-methoxyphenyl)ethyl)benzoate, and it was stirred at room temperature for 2 hours. The solvent was removed under reduced pressure, and the obtained residue was refined by reversed-phase silica gel column chromatography [eluent; 50-90% acetonitrile/0.1% trifluoroacetic acid aqueous solution] to give 2-((3-hydroxyphenyl)amino)-4-(2-(3-methoxyphenyl)ethyl)benzoic acid 17 mg of a white solid.

$^1$H-NMR (DMSO-$d_6$) δ value:
2.82(4H,s),3.70(3H,s),6.45(1H,dd,J=7.9, 1.8 Hz),6.49-6.54(1H,m),6.57-6.61(1H,m),6.65-6.70(1H,m),6.72-6.79 (3H,m),7.05-7.12(2H,m),7.17(1H,t,j=8.0 Hz),7.80(1H,d,J=8.3 Hz),9.42(1H,s),9.55(1H,s),12.90(1H,s).

Example 292

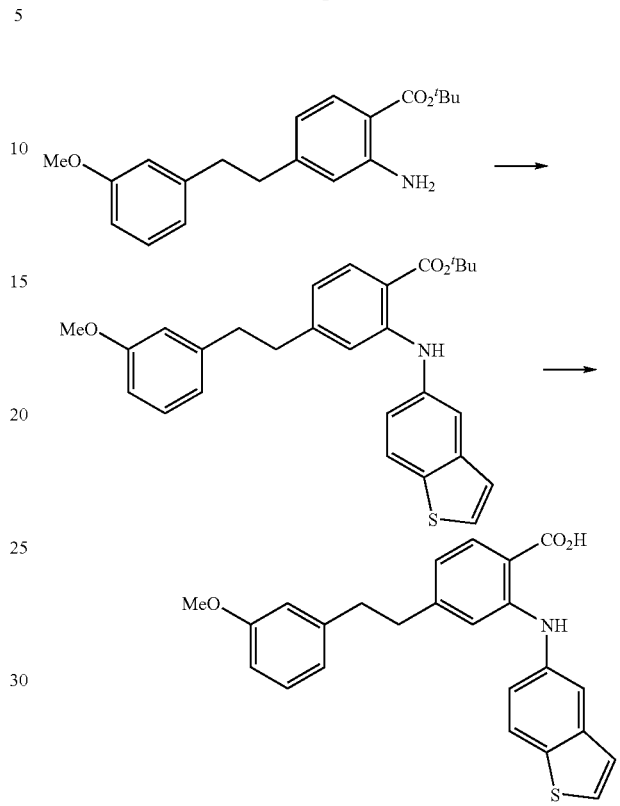

To toluene 3.0 mL solution of tert-butyl 2-amino-4-(2-(3-methoxyphenyl)ethyl)benzoate 0.13 g were added 5-bromobenzothiophene 0.21 g, cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg at room temperature, and it was stirred at 110° C. for 12 hours. Tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 110° C. for 6 hours. 5-Bromobenzothiophene 0.21 g, cesium carbonate 0.26 g, tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 110° C. for 12 hours. After the reaction mixture was cooled to room temperature, insoluble matter was filtrated, and ethyl acetate and 10% citric acid aqueous solution were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((benzothiophen-5-yl)amino)-4-(2-(3-methoxyphenyl)ethyl)benzoate.

Trifluoroacetic acid 10 mL was added to the obtained tert-butyl 2-((benzothiophen-5-yl)amino)-4-(2-(3-methoxyphenyl)ethyl)benzoate, and it was stirred at room temperature for 2 hours. The solvent was removed under reduced pressure, diisopropyl ether was added to the obtained residue, and solid matter was filtrated to give 2-((benzothiophen-5-yl)amino)-4-(2-(3-methoxyphenyl)ethyl)benzoic acid 61 mg of a brown solid.

$^1$H-NMR (DMSO-d$_6$) δ value:
2.80(4H,s),3.69(3H,s),6.66-6.82(4H,m),6.97(1H,s),7.10-7.20(2H,m),7.39(1H,d,J=5.5 Hz),7.65(1H,d,J=1.9 Hz),7.78 (1H,d,J=5.5 Hz),7.82(1H,d,J=8.3 Hz),7.93(1H,d,J=8.8 Hz), 9.68 (1H,s),12.80-13.00(1H,broad).

Example 293

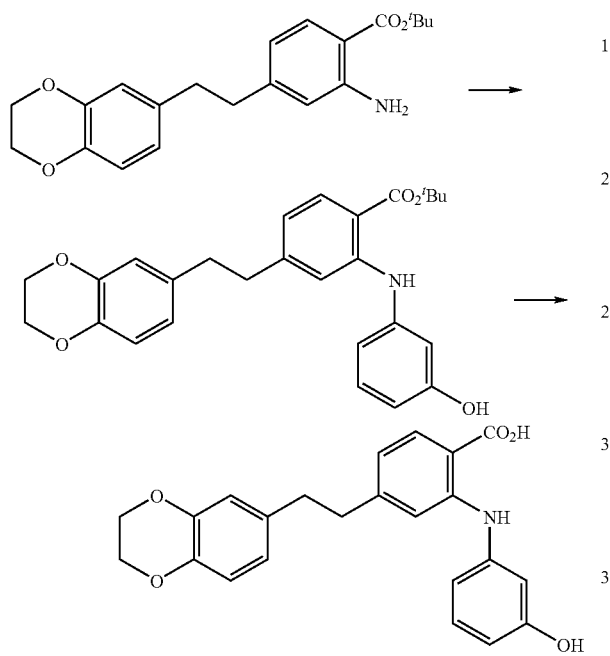

To toluene 3.0 mL solution of tert-butyl 2-amino-4-(2-(2,3-dihydro[1,4]benzodioxin-6-yl)ethyl)benzoate 0.14 g were added 3-iodophenol 0.22 g, cesium carbonate 0.52 g, tris (dibenzylideneacetone)dipalladium(0) 3.7 mg, palladium acetate 1.8 mg and 2-dicyclohexylphosphino-2',4',6'-triisopropylbiphenyl 9.5 mg at room temperature, and it was stirred at 110° C. for 6 hours. Tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 110° C. for 18 hours and 30 minutes. 3-iodophenol 0.22 g, cesium carbonate 0.52 g, tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 110° C. for 22 hours. Tris(dibenzylideneacetone)dipalladium(0) 3.7 mg, palladium acetate 1.8 mg and 2-dicyclohexylphosphino-2',4',6'-triisopropylbiphenyl 9.5 mg were added to it, and it was stirred at 110° C. for 20 hours. After the reaction mixture was cooled to room temperature, insoluble matter was filtrated, and ethyl acetate and 10% citric acid aqueous solution were added to it. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=4:1] to give tert-butyl 4-(2-(2,3-dihydro[1,4]benzodioxin-6-yl)ethyl)-2-((3-hydroxyphenyl)amino)benzoate.

Trifluoroacetic acid 10 mL was added to the obtained tert-butyl 4-(2-(2,3-dihydro[1,4]benzodioxin-6-yl)ethyl)-2-((3-hydroxyphenyl)amino)benzoate, and it was stirred at room temperature for 2 hours. The solvent was removed under reduced pressure, and the obtained residue was refined by reversed-phase silica gel column chromatography [eluent; 55-75% acetonitrile/0.1% trifluoroacetic acid aqueous solution] to give 4-(2-(2,3-dihydro[1,4]benzodioxin-6-yl)ethyl)-2-((3-hydroxyphenyl)amino)benzoic acid 8.1 mg of a white solid.

$^1$H-NMR (DMSO-d$_6$) δ value:
2.69-2.81(4H,m),4.18(4H,s),6.43-6.69(6H,m),6.73(1H,d, J=8.1 Hz),7.05(1H,s),7.10(1H,t,j=7.9 Hz),7.79(1H,d,J=8.1 Hz),9.43(1H,s),9.55(1H,s),12.91(1H, s).

Example 294-296

The compounds shown in Table 39 were obtained in the same manner as in Example 293.

TABLE 39

| Example No. | R$^3$ |
|---|---|
| 294 | ![o-methylphenyl] |
| 295 | ![benzo-1,3-dioxol-5-yl] |
| 296 | ![phenyl] |

4-(2-(2,3-Dihydro[1,4]benzodioxin-6-yl)ethyl)-2-(2-methylanilino)benzoic acid $^1$H-NMR (DMSO-d$_6$) δ value:
2.17(3H,s),2.66-2.76(4H,m),4.18(4H,s),6.57-6.69(4H, m),6.72(1H,d,J=8.0 Hz),7.00-7.07(1H,m),7.10-7.20(2H,m), 7.27(1H,d,J=7.6 Hz),7.80(1H,d,J=8.1 Hz),9.49(1H,s),12.88 (1H,s).

2-((Benzo-1,3-dioxol-5-yl)amino)-4-(2-(2,3-dihydro [1,4]benzodioxin-6-yl)ethyl)benzoic acid $^1$H-NMR (DMSO-d$_6$) δ value:
2.66-2.77(4H,m),4.18(4H,s),6.03(2H,s),6.55-6.66(4H, m),6.72(1H,d,J=8.3 Hz),6.74-6.81(2H,m),6.87(1H,d,J=8.0 Hz),7.77(1H,d,J=8.3 Hz),9.40(1H,s),12.81(1H,s).

2-Anilino-4-(2-(2,3-dihydro[1,4]benzodioxin-6-yl)ethyl)benzoic acid $^1$H-NMR (DMSO-d$_6$) δ value:
2.69-2.80(4H,m),4.18(4H,s),6.60-6.71(3H,m),6.74(1H,d,J=7.8 Hz),6.96(1H,s),7.02-7.12(3H,m),7.27-7.37(2H,m),7.81(1H,d,J=8.0 Hz),9.61(1H,s),12.91(1H,s).

Example 297

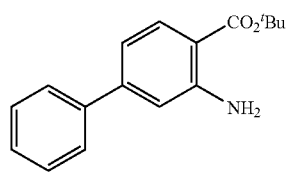
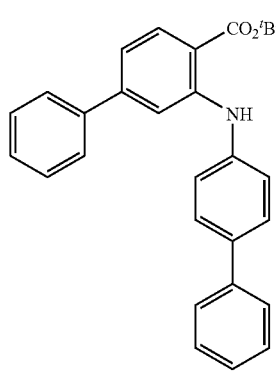

To toluene 3.0 mL solution of 4-bromobiphenyl 0.43 g were added 2-dicyclohexylphosphino-2',4',6'-triisopropylbiphenyl 17 mg, tert-butyl 2-amino-4-phenylbenzoate 0.20 g, cesium carbonate 0.48 g, palladium acetate 1.7 mg and tris(dibenzylideneacetone)dipalladium(0) 6.8 mg at room temperature, and it was heated and refluxed for 5 hours and 40 minutes. 2-Dicyclohexylphosphino-2',4',6'-triisopropylbiphenyl 17 mg, tris(dibenzylideneacetone)dipalladium(0) 6.8 mg and palladium acetate 1.7 mg were added to it, and it was heated and refluxed for 2 hours and 20 minutes. After the reaction mixture was cooled to room temperature, ethyl acetate and 1.0 mol/L hydrochloric acid were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=50:1] to give tert-butyl 2-((biphenyl-4-yl)amino)-4-phenylbenzoate 0.24 g of a pale yellow solid.

$^1$H-NMR (CDCl$_3$) δ value:
1.63(9H,s),6.98(1H,dd,J=8.4, 1.8 Hz),7.28-7.47(8H,m),7.53-7.64(7H,m),8.00(1H,d,J=8.3 Hz),9.69(1H,s).

Example 298-306

The compounds shown in Table 40 were obtained in the same manner as in Example 297.

TABLE 40

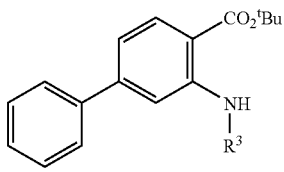

| Example | R$^3$ |
|---|---|
| 298 | 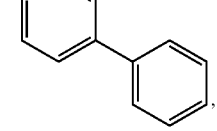 |
| 299 | 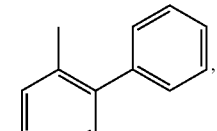 |
| 300 | 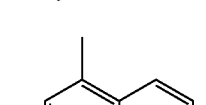 |
| 301 | 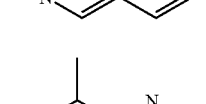 |
| 302 | 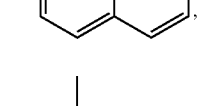 |
| 303 | 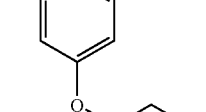 |
| 304 | 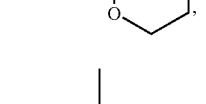 |

TABLE 40-continued

[Structure: biphenyl with CO₂ᵗBu and NH-R³ substituents]

| Example | R³ |
|---|---|
| 305 | [2-methylphenyl linked via O to tetrahydropyran-2-yl] |
| 306 | [3-(1H-pyrazol-1-yl)phenyl with methyl] | tert-Butyl 2-((biphenyl-3-yl)amino)-4-phenylbenzoate

¹H-NMR (CDCl₃) δ value:
1.63(9H,s),6.97(1H,dd,J=8.3, 1.7 Hz),7.26-7.64(15H,m), 8.00(1H,d,J=8.3 Hz),9.71(1H,s).

tert-Butyl 2-((biphenyl-2-yl)amino)-4-phenylbenzoate

¹H-NMR (CDCl₃) δ value:
1.47(9H,s),6.90(1H,dd,J=8.3, 1.7 Hz),7.19(1H,td,J=7.6, 1.2 Hz),7.26-7.60(14H,m),7.92(1H,d,J=8.3 Hz),9.19(1H,s).

tert-Butyl 2-((isoquinolin-4-yl)amino)-4-phenylbenzoate

¹H-NMR (CDCl₃) δ value:
1.66(9H,s),7.26-7.30(1H,m),7.37-7.50(3H,m),7.50-7.58(2H,m),7.62-7.66(1H,m),7.97(1H,t,j=7.4 Hz),8.10-8.18(2H,m),8.25(1H,d,J=8.3 Hz),8.44(1H,d,J=8.6 Hz),8.63(1H,s),9.04(1H,s),10.82(1H,s).

tert-Butyl 4-phenyl-2-((quinolin-8-yl)amino)benzoate

¹H-NMR (CDCl₃) δ value:
1.66(9H,s),7.10(1H,dd,J=8.3, 1.7 Hz),7.33-7.40(2H,m),7.42-7.48(4H,m),7.58-7.62(2H,m),7.78-7.83(1H,m),8.01(1H,d,J=1.7 Hz),8.06(1H,d,J=8.3 Hz),8.14(1H,dd,J=8.3, 1.7 Hz),8.93(1H,dd,J=4.1, 1.7 Hz),10.72(1H,s).

tert-Butyl 4-phenyl-2-(4-((tetrahydro-2H-pyran-2-yl)oxy)phenylamino)benzoate ¹H-NMR (DMSO-d₆) δ value:
1.46-1.94(6H,m),1.59(9H,s),3.52-3.60(1H,m),3.76-3.84(1H,m),5.43(1H,t,j=3.3 Hz),7.00(1H,dd,J=8.3, 1.7 Hz),7.02-7.08(2H,m),7.19(1H,d,J=1.7 Hz),7.22-7.28(2H,m),7.36-7.48(3H,m),7.50-7.56(2H,m),7.91(1H,d,J=8.3 Hz),9.33(1H,s).

tert-Butyl 4-phenyl-2-((quinolin-3-yl)amino)benzoate

¹H-NMR (CDCl₃) δ value:
1.65(9H,s),7.06(1H,dd,J=8.3, 1.7 Hz),7.32-7.44(3H,m),7.48-7.58(4H,m),7.58-7.64(1H,m),7.73(1H,dd,J=8.0, 1.2 Hz),7.99(1H,d,J=2.4 Hz),8.02-8.08(2H,m),8.94(1H,d,J=2.4 Hz),9.91(1H,s).

tert-Butyl 2-((isoquinolin-5-yl)amino)-4-phenylbenzoate

¹H-NMR (CDCl₃) δ value:
1.66(9H,s),7.00(1H,dd,J=8.4, 1.8 Hz),7.24-7.27(1H,m),7.30-7.40(3H,m),7.40-7.46(2H,m),7.59(1H,t,j=7.8 Hz),7.78(2H,t,j=7.8 Hz),7.94(1H,d,J=6.1 Hz),8.05(1H,d,J=8.3 Hz),8.56(1H,d,J=5.8 Hz),9.28 (1H,s),10.07(1H,s).

tert-Butyl 4-phenyl-2-(2-((tetrahydro-2H-pyran-2-yl)oxy)phenylamino)benzoate ¹H-NMR (CDCl₃) δ value:
1.51-2.17(6H,m),1.60(9H,s),3.55-3.62(1H,m),3.93(1H,td,J=11.1, 2.8 Hz),5.51(1H,t,j=2.8 Hz), 6.93-7.01(3H,m),7.17-7.24(1H,m),7.32-7.45(3H,m),7.50-7.60(4H,m),7.99(1H,d,J=8.3 Hz),9.89(1H,s).

tert-Butyl 4-phenyl-2-(3-(1H-pyrazol-1-yl)phenylamino)benzoate

¹H-NMR (CDCl₃) δ value:
1.63(9H,s),6.46(1H,dd,J=2.4, 2.0 Hz),7.00(1H,dd,J=8.3, 1.7 Hz),7.22-7.28(1H,m),7.32-7.45(5H,m),7.52-7.60(3H,m),7.65-7.69(1H,m),7.70-7.73(1H,m),7.91(1H,d,J=2.4 Hz),8.00(1H,d,J=8.3 Hz),9.75(1H,s).

Example 307

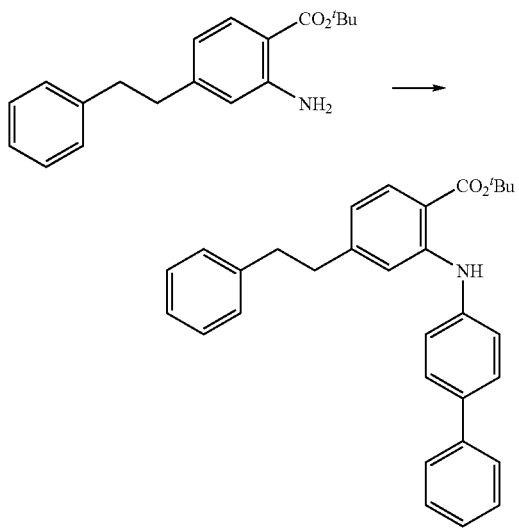

To toluene 1.0 mL solution of 4-bromobiphenyl 0.12 g were added 2-dicyclohexylphosphino-2',4',6'-triisopropylbiphenyl 4.8 mg, tert-butyl 2-amino-4-phenethylbenzoate 60 mg, cesium carbonate 0.13 g, palladium acetate 0.50 mg and tris(dibenzylideneacetone)dipalladium(0) 1.8 mg at room temperature, and it was heated and refluxed for 5 hours and 30 minutes. 2-Dicyclohexylphosphino-2',4',6'-triisopropylbiphenyl 4.8 mg, palladium acetate 0.50 mg and tris(dibenzylideneacetone)dipalladium(0) 1.8 mg were added to it, and it was heated and refluxed for 7 hours. After the reaction mixture was cooled to room temperature, ethyl acetate and 1.0 mol/L hydrochloric acid were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=200:1] to give tert-butyl 2-((biphenyl-4-yl)amino)-4-phenethylbenzoate 50 mg of a yellow oil.

$^1$H-NMR (CDCl$_3$) δ value:
1.60(9H,s),2.80-2.94(4H,m),6.58(1H,dd,J=8.2, 1.6 Hz), 7.06(1H,d,J=1.2 Hz),7.11-7.36(8H,m),7.40-7.47(2H,m), 7.49-7.55(2H,m),7.56-7.63(2H,m),7.85(1H,d,J=8.3 Hz), 9.58(1H,s).

Example 308-318

The compounds shown in Table 41 were obtained in the same manner as in Example 307.

TABLE 41

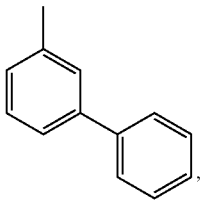

| Example | R$^3$ |
|---|---|
| 308 | 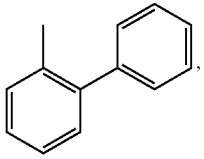 |
| 309 | 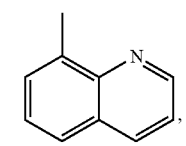 |
| 310 | 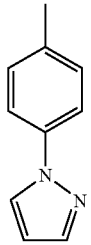 |

TABLE 41-continued

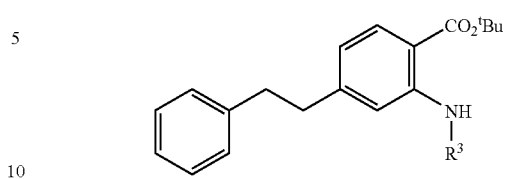

| Example | R$^3$ |
|---|---|
| 311 | 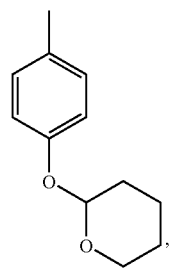 |
| 312 | 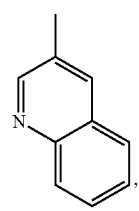 |
| 313 | 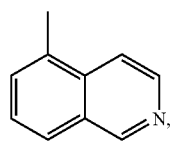 |
| 314 | 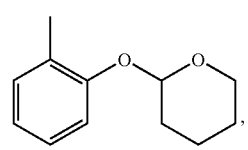 |
| 315 | 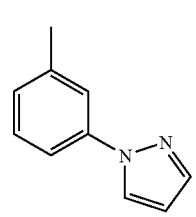 |
| 316 | 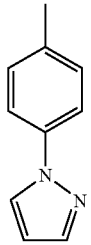 |

TABLE 41-continued

[Structure: benzoate with CO₂ᵗBu, phenethyl, and NH-R³ substituents]

| Example | R³ |
|---|---|
| 317 | [3-(1H-pyrrol-1-yl)phenyl group] |
| 318 | [4-(1H-pyrrol-1-yl)phenyl group] | tert-Butyl 2-((biphenyl-3-yl)amino)-4-phenethylbenzoate

¹H-NMR (CDCl₃) δ value:
1.60(9H,s),2.78-2.92(4H,m),6.58(1H,dd,J=8.3, 1.6 Hz),7.08-7.21(5H,m),7.23-7.62(10H,m),7.84(1H,d,J=8.3 Hz),9.61(1H,s).

tert-Butyl 2-((biphenyl-2-yl)amino)-4-phenethylbenzoate

¹H-NMR (CDCl₃) δ value:
1.44(9H,s),2.74-2.88(4H,m),6.52(1H,dd,J=8.3, 1.5 Hz),6.89(1H,d,J=1.5 Hz),7.10-7.23(4H,m),7.24-7.43(10H,m),7.77(1H,d,J=8.3 Hz),9.08(1H,s).

tert-Butyl 2-((quinolin-8-yl)amino)-4-phenethylbenzoate

¹H-NMR (CDCl₃) δ value:
1.63(9H,s),2.86-3.00(4H,m),6.71(1H,dd,J=8.2, 1.6 Hz),7.14-7.46(10H,m),7.90(1H,d,J=8.3 Hz),8.10(1H,dd,J=8.3, 1.7 Hz), 8.89(1H,dd,J=4.3, 1.8 Hz),10.61(1H,s).

tert-Butyl 4-phenethyl-2-(4-((tetrahydro-2H-pyran-2-yl)oxy)phenylamino)benzoate ¹H-NMR (CDCl₃) δ value:
1.54-1.76(3H,m),1.59(9H,s),1.82-1.94(2H,m),1.94-2.08(1H,m),2.74-2.88(4H,m),3.60-3.65(1H,m),3.93-4.01(1H,m),5.38(1H,t,J=3.3 Hz),6.50(1H,dd,J=8.2, 1.5 Hz),6.79 (1H,d,J=1.5 Hz),6.96-7.06(4H,m),7.10-7.30(5H,m),7.81(1H,d,J=8.0 Hz),9.34(1H,s).

tert-Butyl 4-phenethyl-2-((quinolin-3-yl)amino)benzoate

¹H-NMR (DMSO-d₆) δ value:
1.56(9H,s),2.87(4H,s),6.80(1H,d,J=8.3 Hz),7.12-7.28(6H,m),7.54-7.64(2H,m),7.82(1H,d,J=8.0 Hz),7.85(1H,d,J=8.3 Hz),7.93-8.00(2H,m),8.79(1H,d,J=2.4 Hz),9.58(1H,s).

tert-Butyl 2-((isoquinolin-5-yl)amino)-4-phenethylbenzoate

¹H-NMR (CDCl₃) δ value:
1.63(9H,s),2.74-2.88(4H,m),6.63(1H,dd,J=8.2, 1.5 Hz), 6.80(1H,d,J=1.5 Hz),7.06-7.12(2H,m),7.15-7.29(3H,m),7.45-7.55(2H,m),7.72(1H,d,J=7.6 Hz),7.86-7.92(2H,m),8.53(1H,d,J=5.9 Hz),9.26(1H,d,J=0.8 Hz),9.99(1H,s).

tert-Butyl 4-phenethyl-2-(2-((tetrahydro-2H-pyran-2-yl)oxy)phenylamino)benzoate ¹H-NMR (CDCl₃) δ value:
1.52-2.22(6H,m),1.58(9H,s),2.80-2.92(4H,m),3.55-3.63(1H,m),3.94(1H,td,J=11.2, 2.6 Hz),5.49(1H,t,j=2.8 Hz), 6.57(1H,dd,J=8.3, 1.5 Hz),6.86-6.98(2H,m),7.10-7.32(8H,m),7.84(1H,d,J=8.3 Hz),9.81(1H,s).

tert-Butyl 4-phenethyl-2-(3-(1H-pyrazol-1-yl)phenylamino)benzoate

¹H-NMR (CDCl₃) δ value:
1.60(9H,s),2.80-2.94(4H,m),6.45(1H,dd,J=2.3, 1.8 Hz), 6.61(1H,dd,J=8.2, 1.6 Hz),6.98-7.04(1H,m),7.08-7.38(8H,m),7.52-7.56(1H,m),7.71(1H,d,J=1.7 Hz),7.84(1H,d,J=8.2 Hz),7.88(1H,d,J=2.4 Hz),9.66(1H,s).

tert-Butyl 4-phenethyl-2-(4-(1H-pyrazol-1-yl)phenylamino)benzoate

¹H-NMR (CDCl₃) δ value:
1.60(9H,s),2.79-2.92(4H,m),6.45-6.48(1H,m),6.59(1H,dd,J=8.3, 1.4 Hz),6.95(1H,d,J=1.4 Hz),7.10-7.32(7H,m),7.56-7.62(2H,m),7.72(1H,d,J=1.5 Hz),7.84(1H,d,J=8.3 Hz),7.88(1H,d,J=2.4 Hz),9.57(1H,s).

tert-Butyl 4-phenethyl-2-(3-(1H-pyrrol-1-yl)phenylamino)benzoate

¹H-NMR (CDCl₃) δ value:
1.60(9H,s),2.80-2.94(4H,m),6.33(2H,t,j=2.2 Hz),6.61(1H,dd,J=8.3, 1.6 Hz),6.96 (1H,dd,J=7.8, 1.7 Hz),7.02-7.10(4H,m),7.12-7.34(7H,m),7.85(1H,d,J=8.3 Hz),9.62(1H,s).

tert-Butyl 4-phenethyl-2-(4-(1H-pyrrol-1-yl)phenylamino)benzoate

¹H-NMR (CDCl₃) δ value:
1.60(9H,s),2.80-2.92(4H,m),6.35(2H,t,j=2.1 Hz),6.59(1H,dd,J=8.2, 1.6 Hz),6.93 (1H,d,J=1.6 Hz),7.04-7.34(11H,m),7.84(1H,d,J=8.2 Hz),9.53(1H,s).

Example 319

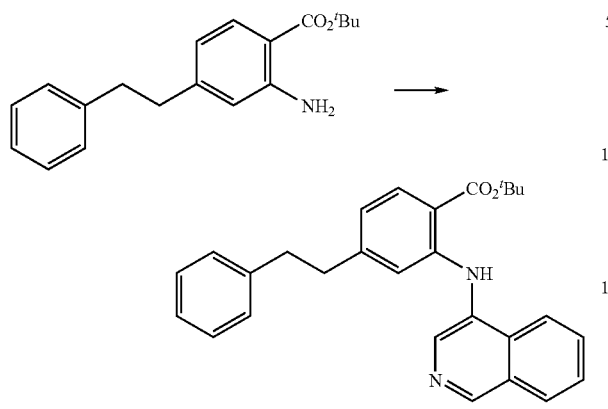

To toluene 1.0 mL solution of 4-bromoisoquinoline 0.12 g were added 2-dicyclohexylphosphino-2',4',6'-triisopropylbiphenyl 9.5 mg, tert-butyl 2-amino-4-phenethylbenzoate 59 mg, cesium carbonate 0.13 g, palladium acetate 0.90 mg and tris(dibenzylideneacetone)dipalladium(0) 3.7 mg at room temperature, and it was heated and refluxed for 7 hours. After the reaction mixture was cooled to room temperature, ethyl acetate and 1.0 mol/L hydrochloric acid were added to it. The organic layer was separated and collected, dried over anhydrous magnesium sulfate after washing with 1.0 mol/L hydrochloric acid and saturated sodium chloride aqueous solution sequentially, and the solvent was removed under reduced pressure. Ethyl acetate and hexane were added to the obtained residue, and solid matter was filtrated to give tert-butyl 2-((isoquinolin-4-yl)amino)-4-phenethylbenzoate 34 mg of a yellow solid.

$^1$H-NMR (CDCl$_3$) δ value:
1.63(9H,s),2.88-3.02(4H,m),6.88(1H,d,J=8.0 Hz),7.12-7.36(6H,m),7.94-8.00(2H,m),8.11-8.17(1H,m),8.25(1H,d,J=8.5 Hz),8.33(1H,s),8.39(1H,d,J=8.6 Hz),9.04(1H,s),10.82(1H,s).

Example 320

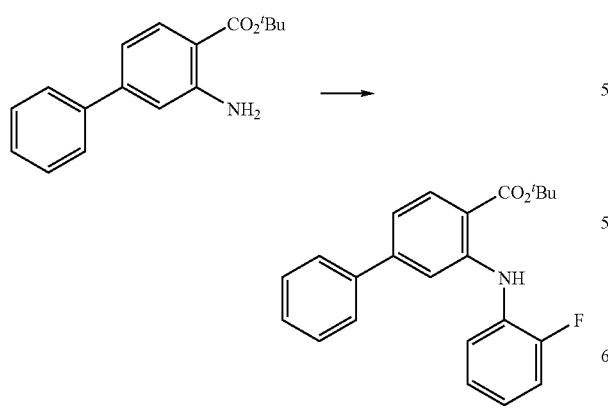

To 1-fluoro-2-iodobenzene 0.11 g were added 2-dicyclohexylphosphino-2',4',6'-triisopropylbiphenyl 9.5 mg, tris(dibenzylideneacetone)dipalladium(0) 3.7 mg, palladium acetate 0.90 mg, tert-butyl 2-amino-4-phenylbenzoate 54 mg, cesium carbonate 0.13 g and toluene 1.0 mL at room temperature, and it was heated and refluxed for 9 hours and 30 minutes. After the reaction mixture was cooled to room temperature, ethyl acetate and 1.0 mol/L hydrochloric acid were added to it. The organic layer was separated and collected, dried over anhydrous magnesium sulfate after washing with saturated sodium chloride aqueous solution, the solvent was removed under reduced pressure. The obtained residue was refined by silica gel column chromatography [Fuji SILYSIA Chemical Ltd., PSQ100B(spherical type), eluent];hexane:ethyl acetate=200:1] to give tert-butyl 2-(2-fluoroanilino)-4-phenylbenzoate 42 mg of a white solid.

$^1$H-NMR (CDCl$_3$) δ value:
1.63(9H,s),6.99(1H,dd,J=8.3, 1.7 Hz),7.00-7.20(3H,m),7.32-7.56(7H,m),8.00(1H,d,J=8.3 Hz),9.51(1H,s).

Example 321

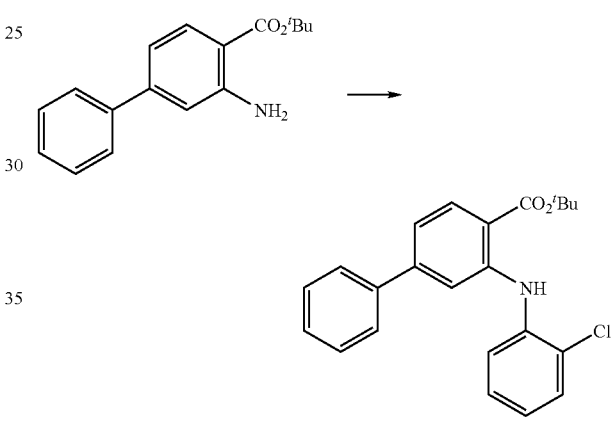

The following compound was obtained in the same manner as in Example 320.

tert-Butyl 2-(2-chloroanilino)-4-phenylbenzoate $^1$H-NMR (CDCl$_3$) δ value:
1.63(9H,s),6.98(1H,td,J=7.7, 1.5 Hz),7.02(1H,dd,J=8.3, 1.7 Hz),7.18-7.24(1H,m),7.32-7.48(5H,m),7.50-7.58(3H,m),8.00(1H,d,J=8.3 Hz),9.63(1H,s).

Example 322

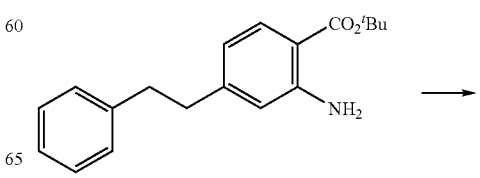

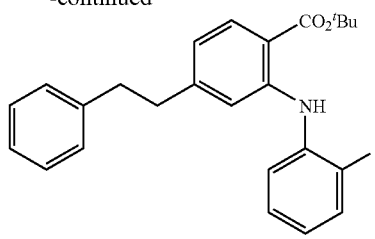

To 1-fluoro-2-iodobenzene 0.11 g were added 2-dicyclohexylphosphino-2',4',6'-triisopropylbiphenyl 9.5 mg, tris(dibenzylideneacetone)dipalladium(0) 3.7 mg, palladium acetate 0.90 mg, tert-butyl 2-amino-4-phenethylbenzoate 59 mg, cesium carbonate 0.13 g and toluene 1.0 mL at room temperature, and it was heated and refluxed for 9 hours and 30 minutes. After the reaction mixture was cooled to room temperature, ethyl acetate and 1.0 mol/L hydrochloric acid were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=200:1] to give tert-butyl 2-(2-fluoroanilino)-4-phenethylbenzoate 62 mg of a colorless oil.

$^1$H-NMR (CDCl$_3$) δ value:
1.60(9H,s),2.80-2.92(4H,m),6.61(1H,dd,J=8.1, 1.7 Hz), 6.88(1H,s),6.95-7.06(2H,m),7.06-7.30(7H,m),7.84(1H,d, J=8.1 Hz),9.40(1H,s).

Example 323

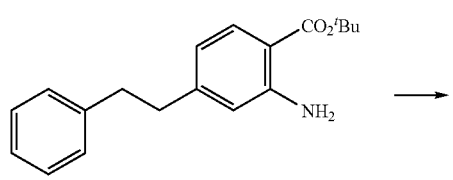

The following compound was obtained in the same manner as in Example 322.

tert-Butyl 2-(2-chloroanilino)-4-phenethylbenzoate $^1$H-NMR (CDCl$_3$) δ value:
1.60(9H,s),2.80-2.92(4H,m),6.64(1H,dd,J=8.1,1.6 Hz), 6.90-6.96(2H,m),7.08-7.30(7H,m),7.40(1H,dd,J=7.9,1.3 Hz),7.85(1H,d,J=8.1 Hz),9.52 (1H,s).

Example 324

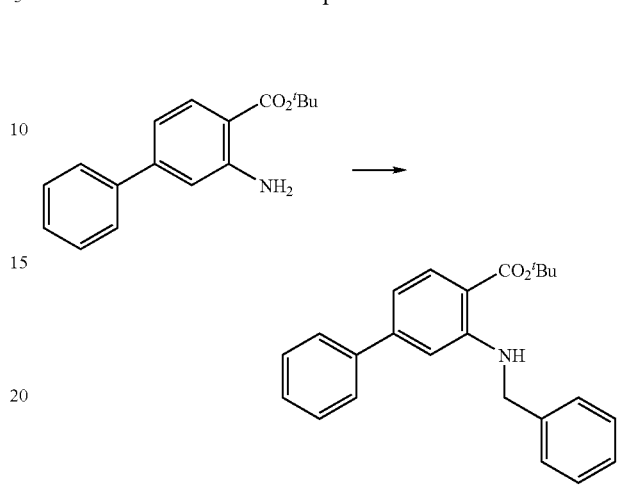

To N,N-dimethylformamide 0.5 mL solution of benzyl bromide 41 mg were added tert-butyl 2-amino-4-phenylbenzoate 54 mg and potassium carbonate 55 mg at room temperature, and it was stirred at 80° C. for 9 hours. After the reaction mixture was cooled to room temperature, ethyl acetate and 1.0 mol/L hydrochloric acid were added to it. The organic layer was separated and collected,dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane:ethyl acetate=100:1] to give tert-butyl 2-benzylamino-4-phenylbenzoate 45 mg of a white solid.

$^1$H-NMR(CDCl$_3$) δ value:
1.59(9H,s),4.51(2H,d,J=5.9 Hz),6.78-6.83(2H,m),7.24-7.30(1H,m),7.30-7.43(7H,m),7.45-7.50(2H,m),7.91-7.96 (1H,m),8.26(1H,t,J=5.9 Hz).

Example 325

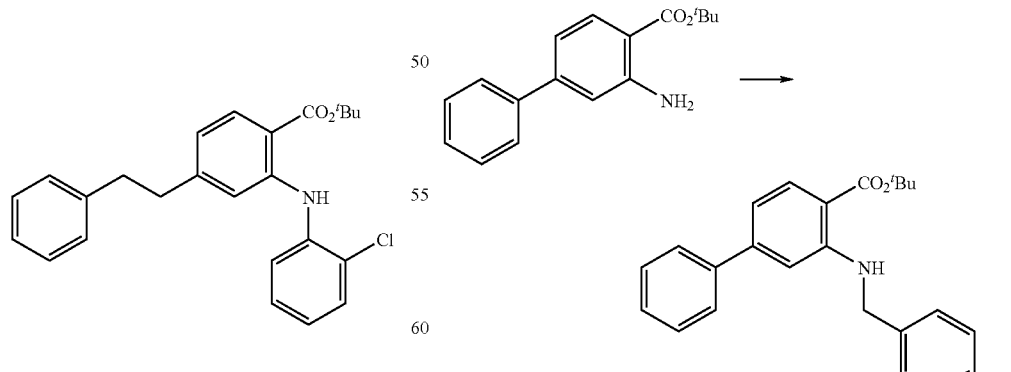

To N,N-dimethylformamide 0.5 mL solution of 4-fluorobenzyl chloride 35 mg were added tert-butyl 2-amino-4-phenylbenzoate 54 mg and potassium carbonate 55 mg at room temperature, and it was stirred at 80° C. for 11 hours. After the reaction mixture was cooled to room temperature, sodium iodide 30 mg was added to it at room temperature, and it was stirred at 80° C. for 4 hours and 40 minutes. After the reaction mixture was cooled to room temperature, ethyl acetate and 1.0 mol/L hydrochloric acid were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; hexane: ethyl acetate=100:1] to give tert-butyl 2-(4-fluorobenzylamino)-4-phenylbenzoate 26 mg of a white solid.

$^1$H-NMR(CDCl$_3$) δ value:

1.59(9H,s),4.47(2H,d,J=5.6 Hz),6.77(1H,d,J=1.5 Hz), 6.82(1H,dd,J=8.3,1.6 Hz),6.98-7.08(2H,m),7.32-7.44(5H, m),7.44-7.52(2H,m),7.94(1H,d,J=8.3 Hz),8.25(1H,t,J=5.6 Hz).

Example 326

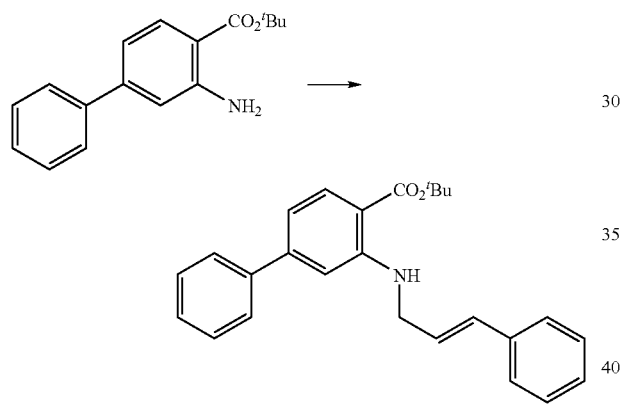

The following compound was obtained in the same manner as in Example 325.

tert-Butyl 2-(cinnamylamino)-4-phenylbenzoate $^1$H-NMR(CDCl$_3$) δ value:

1.60(9H,s),4.07-4.13(2H,m),6.35(1H,dt,J=15.9,5.6 Hz), 6.67(1H,d,J=15.9 Hz), 6.81(1H,dd,J=8.3,1.7 Hz),6.91(1H,d, J=1.7 Hz),7.18-7.45(8H,m),7.54-7.60(2H,m),7.94(1H,d, J=8.3 Hz),8.02-8.08(1H,m).

Example 327

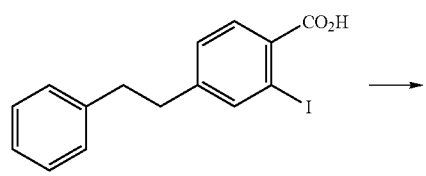

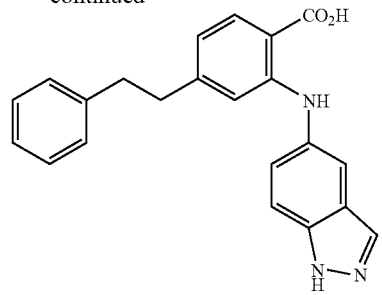

To 2-iodo-4-phenethylbenzoic acid 40 mg were added 5-aminoindazole 23 mg, copper(I) iodide 2.2 mg, proline 2.6 mg, potassium carbonate 19 mg and dimethyl sulfoxide 0.40 mL at room temperature, and it was stirred at 70° C. for 3 hours. After the reaction mixture was cooled to room temperature, ethyl acetate and 1.0 mol/L hydrochloric acid were added to it. The organic layer was separated and collected, dried over anhydrous magnesium sulfate after sequential washing with water and saturated sodium chloride aqueous solution, and the solvent was removed under reduced pressure. The obtained residue was refined by silica gel column chromatography [Fuji SILYSIA Chemical Ltd., PSQ100B (spherical type), eluent; chloroform:methanol=100:1] to give 2-((1H-indazol-5-yl)amino)-4-phenethylbenzoic acid 4.0 mg of a white solid.

$^1$H-NMR(DMSO-d$_6$) δ value:

2.70-2.84(4H,m),6.61(1H,dd,J=8.3,1.4 Hz),6.72(1H, J=1.4 Hz),7.08-7.28(6H,m),7.46(1H,d,J=1.7 Hz),7.52(1H,d, J=8.8 Hz),7.80(1H,d,J=8.3 Hz),8.01(1H,s),9.56(1H,s), 12.70-13.20(2H,broad).

Example 328-334

The compounds shown in Table 42 were obtained in the same manner as in Example 327.

TABLE 42

| Example No. | R$^3$ |
|---|---|
| 328 | ![5-methyl-1-phenyl-1H-pyrazol-3-yl] |
| 329 | ![3-methyl-5-phenyl-1H-pyrazol-4-yl] |

TABLE 42-continued

[Structure: 4-phenethyl-2-(NHR³)benzoic acid core with CO₂H]

| Example No. | R³ |
|---|---|
| 330 | 6-methylbenzothiazol-2-yl (methyl-substituted benzothiazole) |
| 331 | 5-methyl-1H-indol-2-yl (methyl-substituted indole) |
| 332 | 2-methyl-4-phenylthiazol-5-yl |
| 333 | 5-methyl-2-phenyl-1,3,4-thiadiazol-? (methyl/phenyl thiadiazole) |
| 334 | 5-methyl-3-phenyl-4,5-dihydroisoxazol-? |

4-Phenethyl-2-((1-phenyl-1H-pyrazol-5-yl)amino) benzoic acid

¹H-NMR(DMSO-d₆) δ value:
2.74-2.88(4H,m),6.24(1H,d,J=1.7 Hz),6.69(1H,dd,J=8.1,1.2 Hz),6.80(1H,d,J=1.2 Hz),7.14-7.22(3H,m),7.22-7.28(2H,m),7.35-7.42(1H,m),7.44-7.55(4H,m),7.68(1H,d,J=2.0 Hz),7.76(1H,d,J=8.1 Hz),9.89(1H,s),13.07(1H,s).

4-Phenethyl-2-((3-phenyl-1H-pyrazol-5-yl)amino) benzoic acid

¹H-NMR(DMSO-d₆) δ value:
2.80-2.95(4H,m),6.47(1H,s),6.68(1H,dd,J=8.3,1.2 Hz),7.14-7.20(1H,m),7.20-7.31(4H,m),7.32-7.40(1H,m),7.43-7.50(2H,m),7.74-7.85(4H,m),10.15(1H,s),12.70-13.20(2H,broad).

2-((Benzothiazol-6-yl)amino)-4-phenethylbenzoic acid

¹H-NMR(DMSO-d₆) δ value:
2.78-2.90(4H,m),6.73(1H,dd,J=8.2,1.4 Hz),7.01(1H,s),7.14-7.30(6H,m),7.81-7.87(2H,m),7.98(1H,d,J=8.5 Hz),9.25(1H,s),9.78(1H,s),12.85-13.10(1H,broad).

2-((1H-Indol-5-yl)amino)-4-phenethylbenzoic acid

¹H-NMR(DMSO-d₆) δ value:
2.66-2.82(4H,m),6.37-6.42(1H,m),6.52-6.58(1H,m),6.70(1H,s),6.85(1H,dd,J=8.4,2.0 Hz),7.10-7.32(6H,m),7.34-7.40(2H,m),7.77(1H,d,J=8.4 Hz),9.49(1H,s),11.10(1H,s),12.70 (1H,s).

4-Phenethyl-2-((4-phenylthiazol-2-yl)amino)benzoic acid

¹H-NMR(DMSO-d₆) δ value:
3.01(4H,s),6.95(1H,dd,J=8.1,1.5 Hz),7.14-7.22(1H,m),7.25-7.38(5H,m),7.42-7.48(2H,m),7.54(1H,s),7.92(1H,d,J=8.1 Hz),7.94-7.99(2H,m),8.54(1H,s),11.40-11.50(1H,broad),13.40-13.60(1H,broad).

4-Phenethyl-2-((5-phenyl-1,3,4-thiadiazol-2-yl)amino)benzoic acid

¹H-NMR(DMSO-d₆) δ value:
2.90-3.04(4H,m),7.00(1H,dd,J=8.1,1.5 Hz),7.14-7.22(1H,m),7.24-7.32(4H,m),7.50-7.60(3H,m),7.86-7.96(3H,m),8.20(1H,s),11.50(1H,s),13.50-13.70(1H,broad).

4-Phenethyl-2-((3-phenylisoxazol-5-yl)amino)benzoic acid

¹H-NMR(DMSO-d₆) δ value:
2.90-3.06(4H,m),6.49-6.52(1H,m),6.96(1H,dd,J=8.1,1.2 Hz),7.14-7.20(1H,m),7.22-7.32(4H,m),7.37(1H,s),7.50-7.58(3H,m),7.88-7.95(3H,m),11.05-11.25(1H,broad),13.40-13.70(1H,broad).

Example 335

[Structure: tert-butyl 2-amino-4-phenethylbenzoate with CO₂ᵗBu and NH₂ groups] →

-continued

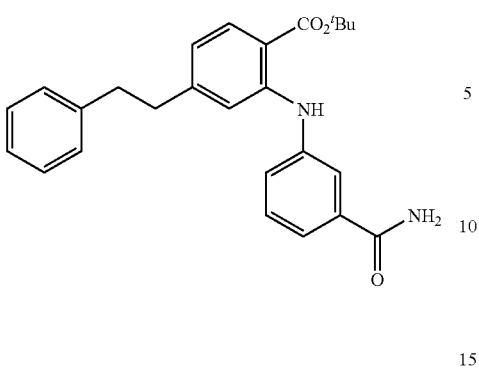

To toluene 1.0 mL solution of tert-butyl 2-amino-4-phenethylbenzoate 59 mg were added 2-dicyclohexylphosphino-2',4',6'-triisopropylbiphenyl 9.5 mg, tris(dibenzylideneacetone)dipalladium(0) 3.7 mg, palladium acetate 0.90 mg, cesium carbonate 0.13 g and 3-bromobenzamide 0.10 g at room temperature, and it was heated and refluxed for 4 hours. After the reaction mixture was cooled to room temperature, ethyl acetate and 1.0 mol/L hydrochloric acid were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Fuji SILYSIA Chemical Ltd., PSQ100B(spherical type), eluent; chloroform:methanol=100:1] to give tert-butyl 2-((benzamide-3-yl)amino)-4-phenethylbenzoate 15 mg of a yellow solid.

$^1$H-NMR(CDCl$_3$) δ value:
1.60(9H,s),2.80-2.92(4H,m),5.42-5.78(1H,broad),5.78-6.18(1H,broad),6.62(1H,dd,J=8.3,1.3 Hz),7.00(1H,d,J=1.3H z),7.10-7.30(6H,m),7.34(1H,t,J=7.8 Hz),7.42-7.46(1H,m),7.60(1H,t,J=1.8 Hz),7.84(1H,d,J=8.3 Hz),9.64(1H,s).

Example 336

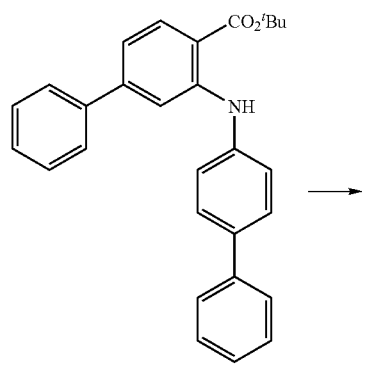

-continued

Trifluoroacetic acid 2.5 mL was added to dichloromethane 2.5 mL solution of tert-butyl 2-((biphenyl-4-yl)amino)-4-phenylbenzoate 84 mg, and it was stirred at room temperature for 2 hours. The solvent was removed under reduced pressure, diisopropyl ether was added to the obtained residue, and solid matter was filtrated to give 2-((biphenyl-4-yl)amino)-4-phenylbenzoic acid 52 mg of a yellow solid.

$^1$H-NMR(DMSO-d$_6$) δ value:
7.11(1H,dd,J=8.3,1.7 Hz),7.31-7.36(1H,m),7.37-7.56 (8H,m),7.60-7.74(6H,m),8.01(1H,d,J=8.3 Hz),9.79(1H,s), 13.05-13.30(1H,broad).

Example 337-350

The compounds shown in Table 43 were obtained in the same manner as in Example 336.

TABLE 43

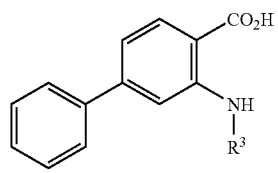

| Example No. | R$^3$ |
|---|---|
| 337 | 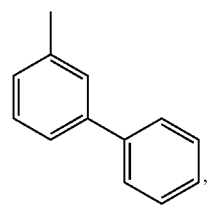 |
| 338 | 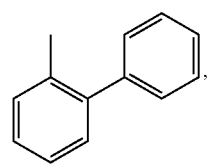 |
| 339 |  CF$_3$CO$_2$H |

TABLE 43-continued

[Structure: biphenyl-benzoic acid with NH-R³ substituent]

| Example No. | R³ |
|---|---|
| 340 | 8-methylquinolin-yl |
| 341 | 4-hydroxy-2-methylphenyl |
| 342 | 2-fluoro-6-methylphenyl |
| 343 | 2-chloro-6-methylphenyl |
| 344 | 3-methylquinolin-yl, CF₃CO₂H |
| 345 | 5-methylisoquinolin-yl, CF₃CO₂H |
| 346 | 2-hydroxy-6-methylphenyl |
| 347 | 3-(1H-pyrazol-1-yl)-methylphenyl |
| 348 | ethylphenyl |
| 349 | 4-fluoro-ethylphenyl |
| 350 | cinnamyl-propyl |

2-((Biphenyl-3-yl)amino)-4-phenylbenzoic acid $^1$H-NMR(DMSO-$d_6$) δ value: δ 7.10(1H,dd,J=8.3,1.7 Hz), 7.36-7.43(4H,m),7.43-7.53(6H,m),7.54-7.57(1H,m),7.58-7.64(2H,m),7.66-7.72(2H,m),8.01(1H,d,J=8.3 Hz),9.79(1H, s),13.00-13.30(1H,broad).

2-((Biphenyl-2-yl)amino)-4-phenylbenzoic acid $^1$H-NMR(DMSO-$d_6$) δ value:
6.99(1H,dd,J=8.2,1.7 Hz),7.22-7.49(12H,m),7.52-7.62 (3H,m),7.89(1H,d,J=8.2 Hz),9.54(1H,s),12.80-13.05(1H, broad).

2-((Isoquinolin-4-yl)amino)-4-phenylbenzoic acid trifluoroacetate $^1$H-NMR(DMSO-$d_6$) δ value:
7.24(1H,dd,J=8.3,1.7 Hz),7.32-7.46(4H,m),7.53-7.59 (2H,m),7.88-7.94(1H,m),8.00-8.06(1H,m),8.08(1H,d,J=8.3 Hz),8.18(1H,d,J=8.3 Hz),8.38(1H,d,J=8.3 Hz),8.68-8.72 (1H,m),9.34(1H,s),10.22(1H,s).

4-Phenyl-2-((quinolin-8-yl)amino)benzoic acid $^1$H-NMR(DMSO-$d_6$) δ value:
7.23(1H,dd,J=8.3,1.5 Hz),7.40-7.46(1H,m),7.46-7.64 (5H,m),7.69-7.74(2H,m),7.89(1H,dd,J=7.6,1.2 Hz),7.96

(1H,d,J=1.4 Hz),8.08 (1H,d,J=8.3 Hz),8.38(1H,dd,J=8.4,1.6 Hz),8.92(1H,dd,J=4.2,1.7 Hz),11.02(1H,s),13.00-13.25(1H, broad).

2-(4-Hydroxyphenylamino)-4-phenylbenzoic acid $^1$H-NMR(DMSO-d$_6$) δ value:
6.78-6.84(2H,m),6.94(1H,dd,J=8.3,1.6 Hz),7.06(1H,d, J=1.6 Hz),7.10-7.16(2H,m),7.34-7.40(1H,m),7.40-7.47(2H, m),7.48-7.54(2H,m),7.93(1H,d,J=8.3 Hz),9.20-9.50(2H, broad),12.80-13.10(1H,broad).

2-(2-Fluoroanilino)-4-phenylbenzoic acid $^1$H-NMR(DMSO-d$_6$) δ value:
7.12(1H,dd,J=8.3,1.7 Hz),7.13-7.20(1H,m),7.20-7.29 (2H,m),7.30-7.50(4H,m),7.56-7.66(3H,m),8.01(1H,d,J=8.3 Hz),9.73(1H,s),13.10-13.40(1H,broad).

2-(2-Chloroanilino)-4-phenylbenzoic acid $^1$H-NMR(DMSO-d$_6$) δ value:
7.11(1H,td,J=7.7,1.5 Hz),7.16(1H,dd,J=8.3,1.7 Hz),7.34-7.44(3H,m),7.44-7.50(2H,m), 7.57(1H,dd,J=8.1,1.5 Hz), 7.59-7.65(2H,m),7.65-7.70(1H,m),8.02(1H,d,J=8.3 Hz), 9.91(1H,s),13.10-13.40(1H,broad).

4-Phenyl-2-((quinolin-3-yl)amino)benzoic acid trifluoroacetate $^1$H-NMR(DMSO-d$_6$) δ value:
7.21(1H,dd,J=8.3,1.7 Hz),7.36-7.43(1H,m),7.43-7.49 (2H,m),7.56-7.63(2H,m),7.63-7.70(3H,m),7.96-8.02(2H, m),8.05(1H,d,J=8.3 Hz),8.35(1H,d,J=2.4 Hz),8.98(1H,d, J=2.7 Hz),9.96(1H,s),13.20-13.50(1H,broad).

2-((Isoquinolin-5-yl)amino)-4-phenylbenzoic acid trifluoroacetate $^1$H-NMR(DMSO-d$_6$) δ value:
7.16(1H,dd,J=8.3,1.7 Hz),7.23-7.28(1H,m),7.34-7.46 (3H,m),7.50-7.56(2H,m),7.82(1H,t,J=7.9 Hz),8.01-8.10(4H, m),8.61(1H,d,J=6.1 Hz),9.56(1H,s),10.23(1H,s),13.20-13.50(1H,broad).

2-(2-Hydroxyphenylamino)-4-phenylbenzoic acid $^1$H-NMR(DMSO-d$_6$) δ value:
6.80-6.88(1H,m),6.90-6.96(2H,m),7.01(1H,dd,J=8.3,1.7 Hz),7.30(1H,d,J=1.7 Hz),7.36-7.49(4H,m),7.54-7.60(2H, m),7.96(1H,d,J=8.3 Hz),9.53(1H,s),9.71(1H,s),12.80-13.10 (1H,broad).

4-Phenyl-2-(3-(1H-pyrazol-1-yl)phenylamino)benzoic acid $^1$H-NMR(DMSO-d$_6$) δ value:
6.53-6.57(1H,m),7.15(1H,dd,J=8.3,1.5 Hz),7.26-7.32 (1H,m),7.36-7.58(6H,m),7.62-7.67(2H,m),7.75(1H,d,J=1.7 Hz),7.84(1H,t,J=2.0 Hz), 8.02(1H,d,J=8.3 Hz),8.55(1H,d, J=2.7 Hz),9.81(1H,s),13.10-13.40(1H,broad).

2-(Benzylamino)-4-phenylbenzoic acid $^1$H-NMR(DMSO-d$_6$) δ value:
4.57(2H,s),6.85(1H,dd,J=8.3,1.6 Hz),6.88-6.92(1H,m), 7.22-7.29(1H,m),7.32-7.48(7H,m),7.55-7.60(2H,m),7.88 (1H,d,J=8.3 Hz).

2-(4-Fluorobenzylamino)-4-phenylbenzoic acid $^1$H-NMR(DMSO-d$_6$) δ value:
4.56(2H,s),6.84-6.90(2H,m),7.14-7.22(2H,m),7.35-7.48 (5H,m),7.55-7.60(2H,m),7.88(1H,d,J=8.3 Hz).

2-(Cinnamylamino)-4-phenylbenzoic acid $^1$H-NMR(DMSO-d$_6$) δ value:
4.16(2H,d,J=5.5 Hz),6.44(1H,dt,J=16.0,5.5 Hz),6.67(1H, d,J=16.0 Hz),6.87(1H,dd,J=8.3,1.6 Hz),7.00(1H,d,J=1.6 Hz),7.20-7.26(1H,m),7.29-7.50(7H,m),7.65-7.70(2H,m), 7.88(1H,d,J=8.3 Hz).

Example 351

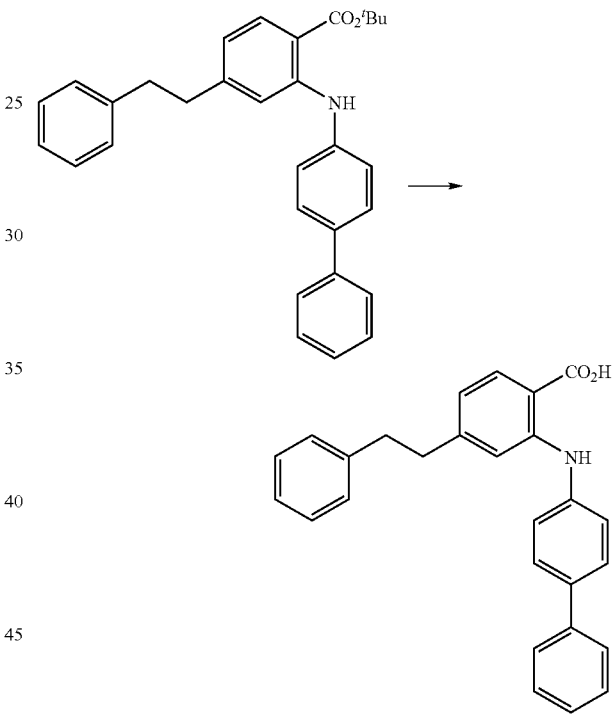

Trifluoroacetic acid 2.0 mL was added to dichloromethane 2.0 mL solution of tert-butyl 2-((biphenyl-4-yl)amino)-4-phenethylbenzoate 50 mg, and it was stirred at room temperature for 4 hours and 30 minutes. The solvent was removed under reduced pressure,diisopropyl ether was added to the obtained residue, and solid matter was filtrated to give 2-((biphenyl-4-yl)amino)-4-phenethylbenzoic acid 27 mg of a yellow solid.

$^1$H-NMR(DMSO-d$_6$) δ value:
2.80-2.92(4H,m),6.72(1H,d,J=8.6 Hz),7.05(1H,s),7.12-7.25(5H,m),7.25-7.38(3H,m),7.46(2H,t,J=7.7 Hz),7.61(2H, d,J=8.6 Hz),7.66(2 H,d,J=7.3 Hz),7.83(1H,d,J=8.3 Hz),9.68 (1H,s),12.80-13.15(1H,broad).

Example 352-364

The compounds shown in Table 44 were obtained in the same manner as in Example 351.

TABLE 44
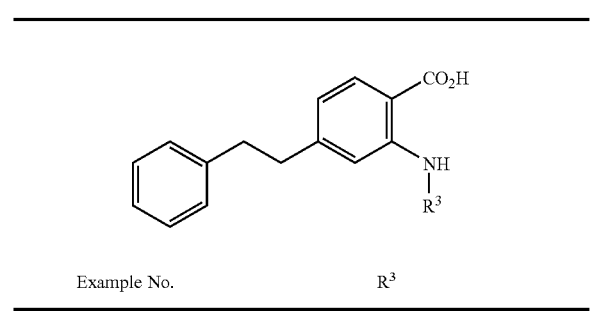
| Example No. | R³ |
|---|---|
| 352 | 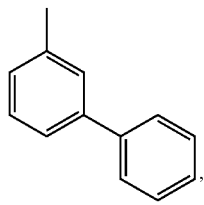 |
| 353 | 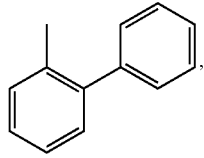 |
| 354 | <br>CF₃CO₂H |
| 355 | 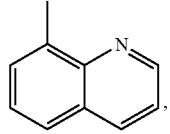 |
| 356 | 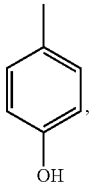 |
| 357 | 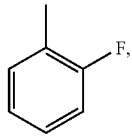 |
| 358 | 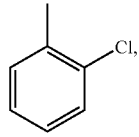 |
TABLE 44-continued
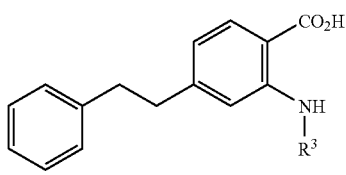
| Example No. | R³ |
|---|---|
| 359 | 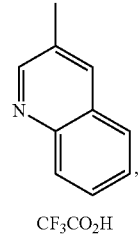<br>CF₃CO₂H |
| 360 | 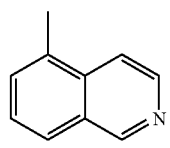<br>CF₃CO₂H |
| 361 | 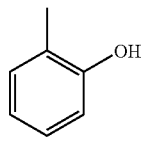 |
| 362 | 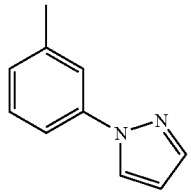 |
| 363 | 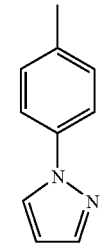 |
| 364 | 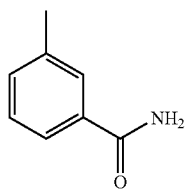 |

2-((Biphenyl-3-yl)amino)-4-phenethylbenzoic acid $^1$H-NMR(DMSO-d$_6$) δ value:
2.78-2.90(4H,m),6.71(1H,dd,J=8.2,1.2 Hz),7.04-7.11(2H,m),7.13-7.20(3H,m),7.21-7.28(2H,m),7.30-7.50(6H,m),7.64-7.70(2H,m),7.82(1H,d,J=8.2 Hz),9.67(1H,s),12.80-13.10(1H,broad).

2-((Biphenyl-2-yl)amino)-4-phenethylbenzoic acid $^1$H-NMR(DMSO-d$_6$) δ value:
2.74-2.88(4H,m),6.61(1H,dd,J=8.1,1.5 Hz),6.81-6.85(1H,m),7.12-7.23(5H,m),7.23-7.42(9H,m),7.72(1H,d,J=8.1 Hz),9.42(1H,s),12.60-12.80(1H,broad).

2-((Isoquinolin-4-yl)amino)-4-phenethylbenzoic acid trifluoroacetate $^1$H-NMR(DMSO-d$_6$) δ value:
2.80(4H,s),6.81(1H,d,J=7.3 Hz),6.98(1H,s),7.10-7.16(3H,m),7.18-7.26(2H,m),7.84-7.92(2H,m),7.96-8.02(1H,m),8.08-8.14(1H,m),8.34(1H,d,J=8.3 Hz),8.48(1H,s),9.28(1H,s),10.12 (1H,s),13.10-13.30(1H,broad).

4-Phenethyl-2-((quinolin-8-yl)amino)benzoic acid $^1$H-NMR(DMSO-d$_6$) δ value:
2.93(4H,s),6.83(1H,dd,J=8.2,1.2 Hz),7.18-7.26(3H,m),7.27-7.38(3H,m),7.41-7.48(3H,m),7.59(1H,dd,J=8.3,4.2 Hz),7.89(1H,d,J=8.2 Hz),8.34 (1H,dd,J=8.2,1.6 Hz),8.88(1H,dd,J=4.2,1.7 Hz),10.90(1H, s),12.91(1H,s).

2-(4-Hydroxyphenylamino)-4-phenethylbenzoic acid $^1$H-NMR(DMSO-d$_6$) δ value:
2.72-2.84(4H,m),6.56(1H,dd,J=8.2,1.5 Hz),6.63(1H,s),6.71-6.77(2H,m),6.86-6.92(2H,m),7.12-7.28(5H,m),7.75(1H,d,J=8.2 Hz),9.32(2H,s),12.60-12.90(1H,broad).

2-(2-Fluoroanilino)-4-phenethylbenzoic acid $^1$H-NMR(DMSO-d$_6$) δ value:
2.85(4H,s),6.74(1H,dd,J=8.1,1.5 Hz),6.87(1H,s),7.04-7.32(9H,m),7.83(1H,d,J=8.1 Hz),9.63(1H,s),12.90-13.20(1H,broad).

2-(2-Chloroanilino)-4-phenethylbenzoic acid $^1$H-NMR(DMSO-d$_6$) δ value:
2.86(4H,s),6.78(1H,dd,J=8.2,1.3 Hz),6.94(1H,d,J=1.3 Hz),7.01-7.06(1H,m),7.15-7.30(7H,m),7.51(1H,dd,J=8.0,1.5 Hz),7.85(1H,d,J=8.2 Hz),9.80 (1H,s),12.90-13.20(1H,broad).

4-Phenethyl-2-((quinolin-3-yl)amino)benzoic acid trifluoroacetate $^1$H-NMR(DMSO-d$_6$) δ value:
2.88(4H,s),6.82(1H,dd,J=8.2,1.5 Hz),7.12-7.28(6H,m),7.58-7.70(2H,m),7.88(1H,d,J=8.2 Hz),7.92(1H,dd,J=7.9,1.4 Hz),7.99 (1H,d,J=7.8 Hz),8.14(1H,d,J=2.4 Hz),8.87(1H,d,J=2.7 Hz), 9.90(1H,s),13.00-13.20(1H,broad).

2-((Isoquinolin-5-yl)amino)-4-phenethylbenzoic acid trifluoroacetate $^1$H-NMR(DMSO-d$_6$) δ value:
2.81(4H,s),6.79(1H,dd,J=8.1,1.5 Hz),6.84-6.88(1H,m),7.10-7.27(5H,m),7.63(1H,d,J=7.6 Hz),7.74(1H,t,J=7.9 Hz),7.90(1H,d,J=8.1 Hz),7.98-8.04(2H,m),8.59(1H,d,J=6.1 Hz),9.56(1H,s),10.16(1H,s),13.00-13.30(1H,broad).

2-(2-Hydroxyphenylamino)-4-phenethylbenzoic acid $^1$H-NMR(DMSO-d$_6$) δ value:
2.76-2.90(4H,m),6.63(1H,dd,J=8.1,1.3 Hz),6.70-6.76(1H,m),6.82-6.95(3H,m),7.02(1H,dd,J=7.8,1.0 Hz),7.14-7.23(3H,m),7.23-7.30(2H,m),7.79(1H,d,J=8.1 Hz),9.44(1H,s),9.63(1H,s),12.73 (1H,s).

4-Phenethyl-2-(3-(1H-pyrazol-1-yl)phenylamino)benzoic acid $^1$H-NMR(DMSO-d$_6$) δ value:
2.80-2.92(4H,m),6.52-6.56(1H,m),6.74(1H,dd,J=8.0,1.5 Hz),6.98(1H,dd,J=7.9,1.3 Hz),7.12(1H,d,J=1.2 Hz),7.14-7.30(5H,m),7.39(1H,t,J=8.1 Hz),7.47-7.52(1H,m),7.68(1H,t,J=2.1 Hz),7.73(1H,d,J=1.7 Hz),7.84(1H,d,J=8.0 Hz),8.51(1H,d,J=2.4 Hz),9.70(1H,s),13.01(1H,s).

4-Phenethyl-2-(4-(1H-pyrazol-1-yl)phenylamino)benzoic acid $^1$H-NMR(DMSO-d$_6$) δ value:
2.80-2.90(4H,m),6.53(1H,dd,J=2.4,2.0 Hz),6.71(1H,dd,J=8.3,1.5 Hz),6.96(1H,d,J=1.5 Hz),7.14-7.31(7H,m),7.72-7.78(3H,m),7.83(1H,d,J=8.3 Hz),8.45(1H,d,J=2.4 Hz),9.64(1H,s),12.96(1H,s).

2-((Benzamide-3-yl)amino)-4-phenethylbenzoic acid $^1$H-NMR(DMSO-d$_6$) δ value:
2.80-2.90(4H,m),6.71(1H,d,J=8.0 Hz),7.03(1H,s),7.14-7.30(6H,m),7.34-7.40(2H,m),7.53(1H,d,J=7.3 Hz),7.67(1H,s),7.82(1H,d,J=8.0 Hz),7.97(1H,s),9.68(1H,s),12.99(1H,s).

Example 365

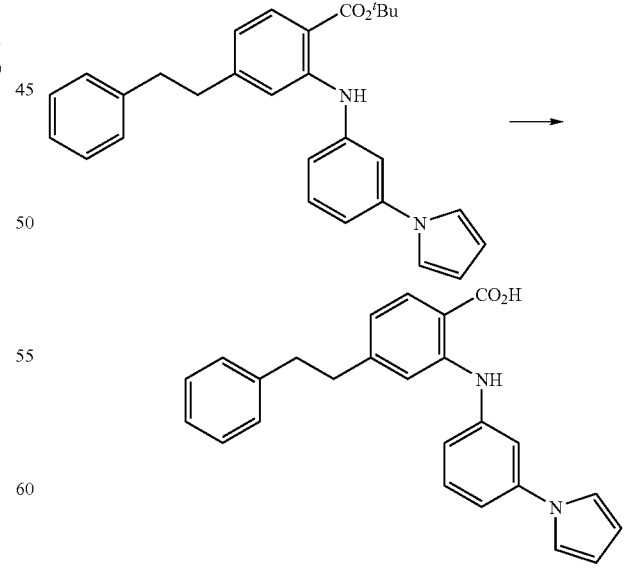

To dioxane 2.0 mL solution of tert-butyl 4-phenethyl-2-(3-(1H-pyrrol-1-yl)phenylamino)benzoate 83 mg were added methanol 2.0 mL and 2.0 mol/L sodium hydroxide aqueous solution 1.0 mL, and it was heated and refluxed for 3 hours. After the reaction mixture was cooled to room temperature, ethyl acetate and 1.0 mol/L hydrochloric acid were added to it. The organic layer was separated and collected, dried over anhydrous magnesium sulfate after washing with saturated sodium chloride aqueous solution, and the solvent was removed under reduced pressure. Diisopropyl ether was added to the obtained residue, and solid matter was filtrated to give 4-phenethyl-2-(3-(1H-pyrrol-1-yl)phenylamino)benzoic acid 36 mg of a white solid.

$^1$H-NMR(DMSO-$d_6$) δ value:
2.86(4H,s),6.23-6.28(2H,m),6.73(1H,dd,J=8.3,1.2 Hz), 6.90-6.94(1H,m),7.09(1H,s),7.14-7.28(6H,m),7.32-7.40 (4H,m),7.83(1H,d,J=8.3 Hz),9.65(1H,s),12.85-13.10(1H, broad).

Example 366

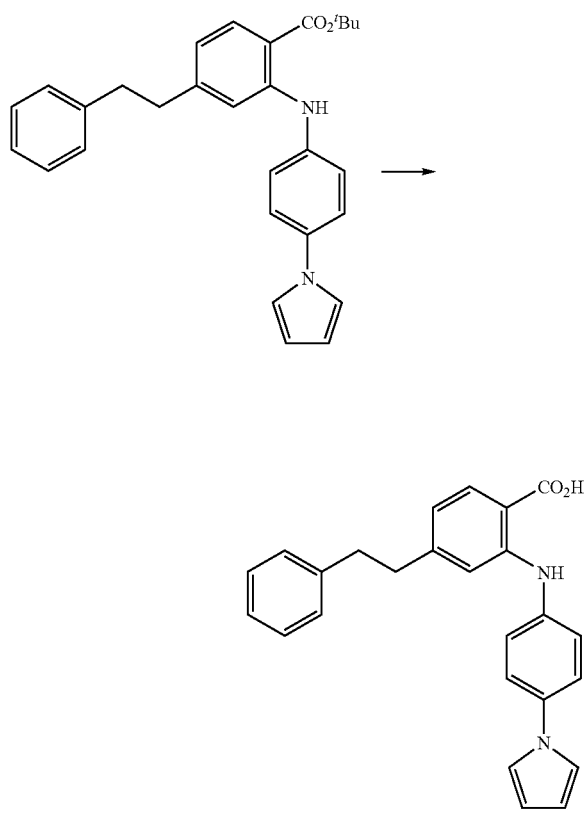

The following compound was obtained in the same manner as in Example 365.

4-Phenethyl-2-(4-(1H-pyrrol-1-yl)phenylamino)benzoic acid $^1$H-NMR(DMSO-$d_6$) δ value:
2.78-2.90(4H,m),6.26(2H,t,J=2.2 Hz),6.69(1H,dd,J=8.2, 1.2 Hz),6.94 (1H,s),7.12-7.24(5H,m),7.24-7.31(2H,m),7.33 (2H,t,J=2.2 Hz),7.46-7.52(2H,m),7.82(1H,d,J=8.2),9.60 (1H,s),12.92(1H,s).

Example 367

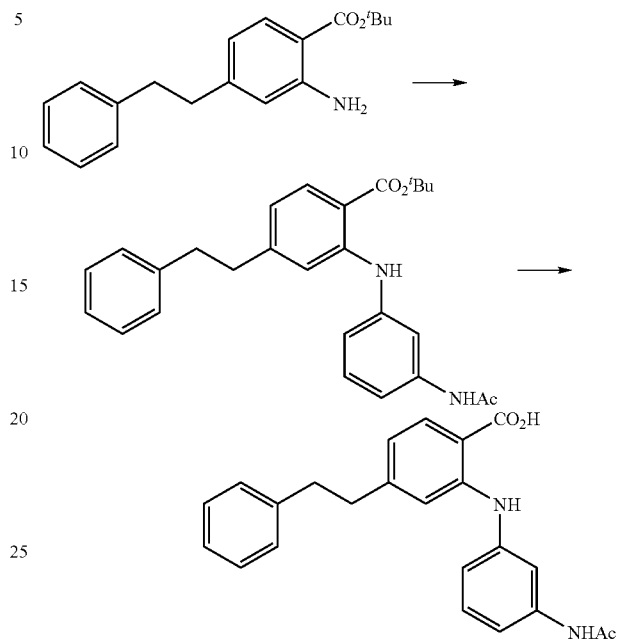

To 2-methyl-2-propanol 2.5 mL solution of tert-butyl 2-amino-4-phenethylbenzoate 0.12 g were added cesium carbonate 0.26 g, N-(3-bromophenyl)acetamide 0.13 g, 2-dicyclohexylphosphino-2',4',6'-triisopropylbiphenyl 10 mg, tris (dibenzylideneacetone)dipalladium(0) 4.0 mg and palladium acetate 2.0 mg at room temperature, and it was stirred at 80° C. for 4 hours. Tris(dibenzylideneacetone)dipalladium(0) 4.0 mg, palladium acetate 2.0 mg and 2-dicyclohexylphosphino-2',4',6'-triisopropylbiphenyl 10 mg were added to it, and it was stirred at 80° C. for 12 hours. Cesium carbonate 0.26 g, N-(3-bromophenyl)acetamide 0.13 g, 2-dicyclohexylphosphino-2',4',6'-triisopropylbiphenyl 10 mg, tris(dibenzylideneacetone)dipalladium(0) 4.0 mg and palladium acetate 2.0 mg were added to it, and it was stirred at 80° C. for 5 hours and 30 minutes. After the reaction mixture was cooled to room temperature, ethyl acetate and water were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=2:1] to give tert-butyl 2-((3-(acetamido)phenyl)amino)-4-phenethylbenzoate.

Trifluoroacetic acid 7.5 mL was added to the obtained tert-butyl 2-((3-(acetamido)phenyl)amino)-4-phenethylbenzoate, and it was stirred at room temperature for 2 hours. The solvent was removed under reduced pressure, diisopropyl ether was added to the obtained residue, and solid matter was filtrated to give 2-((3-(acetamido)phenyl)amino)-4-phenethylbenzoic acid 0.12 g of a white solid.

$^1$H-NMR(DMSO-$d_6$) δ value:
2.04(3H,s),2.78-2.90(4H,m),6.68(1H,d,J=8.2 Hz),6.73 (1H,d,J=7.8 Hz),7.10-7.29(8H,m),7.62(1H,s),7.81(1H,d, J=8.2 Hz),9.64(1H,s),9.92 (1H,s),12.95(1H,s).

Example 368

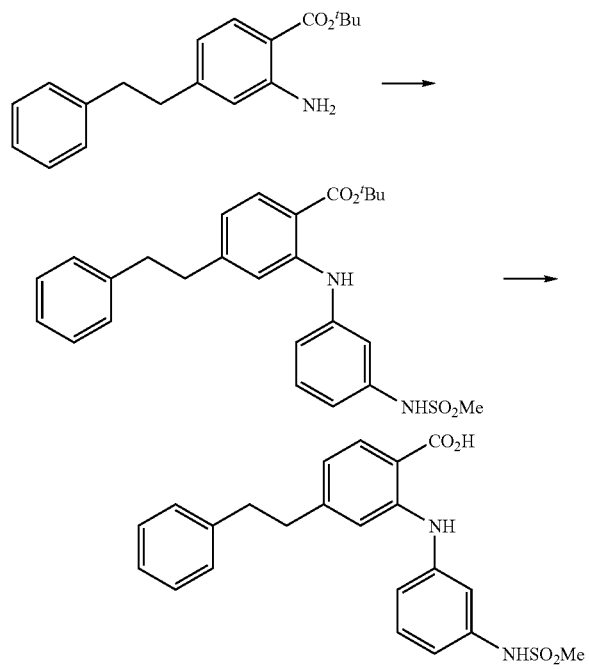

The following compound was obtained in the same manner as in Example 367.

2-((3-(Methanesulfonamido)phenyl)amino)-4-phenethylbenzoic acid $^1$H-NMR(DMSO-$d_6$) δ value:
2.79-2.90(4H,m),3.02(3H,s),6.70(1H,d,J=8.3 Hz),6.80 (1H,dd,J=8.1, 1.0 Hz),6.87(1H,dd,J=8.1,1.0 Hz),7.10-7.30 (8H,m),7.82(1H,d,J=8.3 Hz),9.66(1H,s),9.75(1H,s),12.80-13.20(1H,broad).

Example 369

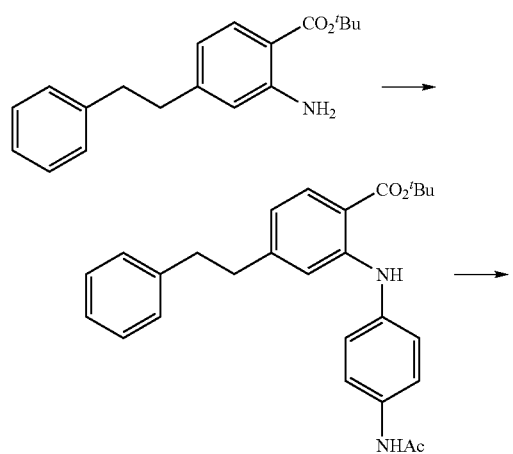

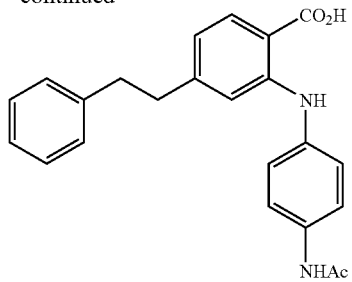

To 2-methyl-2-propanol 2.5 mL solution of tert-butyl 2-amino-4-phenethylbenzoate 0.12 g were added cesium carbonate 0.26 g, N-(4-iodophenyl)acetamide 0.16 g, 2-dicyclohexylphosphino-2',4',6'-triisopropylbiphenyl 10 mg, tris(dibenzylideneacetone)dipalladium(0) 4.0 mg and palladium acetate 2.0 mg at room temperature, and it was stirred at 80° C. for 4 hours. Tris(dibenzylideneacetone)dipalladium(0) 4.0 mg, palladium acetate 2.0 mg and 2-dicyclohexylphosphino-2',4',6'-triisopropylbiphenyl 10 mg were added to it, and it was stirred at 80° C. for 12 hours. Cesium carbonate 0.26 g, N-(4-iodophenyl)acetamide 0.16 g, 2-dicyclohexylphosphino-2',4',6'-triisopropylbiphenyl 1 mg, tris(dibenzylideneacetone)dipalladium(0) 4.0 mg and palladium acetate 2.0 mg were added to it, and it was stirred at 80° C. for 5 hours and 30 minutes. 2-Dicyclohexylphosphino-2',4',6'-triisopropylbiphenyl 10 mg, tris(dibenzylideneacetone)dipalladium(0) 4.0 mg and palladium acetate 2.0 mg were added to it, and it was stirred at 80° C. for 12 hours. After the reaction mixture was cooled to room temperature, ethyl acetate and water were added to it. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=1:1] to give tert-butyl 2-((4-(acetamido)phenyl)amino)-4-phenethylbenzoate.

Trifluoroacetic acid 7.5 mL was added to the obtained tert-butyl 2-((4-(acetamido)phenyl)amino)-4-phenethylbenzoate, and it was stirred at room temperature for 2 hours. The solvent was removed under reduced pressure, methanol was added to the obtained residue, and solid matter was filtrated to give 2-((4-(acetamido)phenyl)amino)-4-phenethylbenzoic acid 23 mg of a white solid.

$^1$H-NMR(DMSO-$d_6$) δ value:
2.04(3H,s),2.76-2.87(4H,m),6.64(1H,d,J=8.2 Hz),6.82 (1H,s),6.98(2H,d,J=8.8 Hz),7.13-7.22(3H,m),7.23-7.29(2H, m),7.53(2H,d,J=8.8 Hz),7.79(1H,d,J=8.2 Hz),9.50(1H,s), 9.90(1H,s),12.85(1H,s).

Example 370

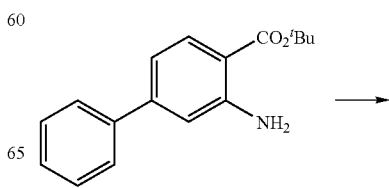

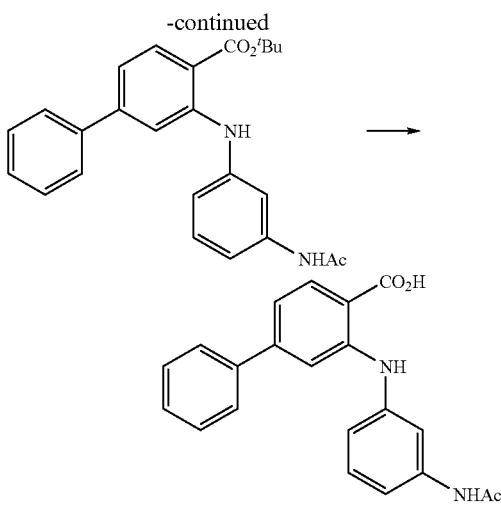

To 2-methyl-2-propanol 2.5 mL solution of tert-butyl 2-amino-4-phenylbenzoate 0.12 g were added cesium carbonate 0.29 g, N-(3-bromophenyl)acetamide 0.14 g, 2-dicyclohexylphosphino-2',4',6'-triisopropylbiphenyl 11 mg, tris(dibenzylideneacetone)dipalladium(0) 4.0 mg and palladium acetate 2.0 mg at room temperature, and it was stirred at 80° C. for 4 hours. Tris(dibenzylideneacetone)dipalladium(0) 4.0 mg, palladium acetate 2.0 mg and 2-dicyclohexylphosphino-2',4',6'-triisopropylbiphenyl 11 mg were added to it at room temperature, and it was stirred at 80° C. for 12 hours. After the reaction mixture was cooled to room temperature, ethyl acetate and water were added to it. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=2:1] to give tert-butyl 2-((3-(acetamido)phenyl)amino)-4-phenylbenzoate.

Trifluoroacetic acid 7.5 mL was added to the obtained tert-butyl 2-((3-(acetamido)phenyl)amino)-4-phenylbenzoate, and it was stirred at room temperature for 2 hours. The solvent was removed under reduced pressure,diisopropyl ether was added to the obtained residue, and solid matter was filtrated to give 2-((3-(acetamido)phenyl)amino)-4-phenylbenzoic acid 0.13 g of a yellow solid.

$^1$H-NMR(DMSO-$d_6$) δ value:

2.05(3H,s),6.96(1H,dd,J=8.1,1.2 Hz),7.09(1H,dd,J=8.3, 1.7 Hz),7.16-7.31(2H,m),7.37-7.49(3H,m),7.52(1H,d,J=1.7 Hz),7.63-7.69(2H,m),7.78(1H,s),8.00(1H,d,J=8.3 Hz),9.75 (1H,s),9.98 (1H,s),13.15(1H,s).

Example 371

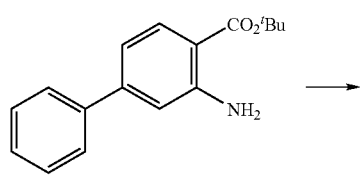

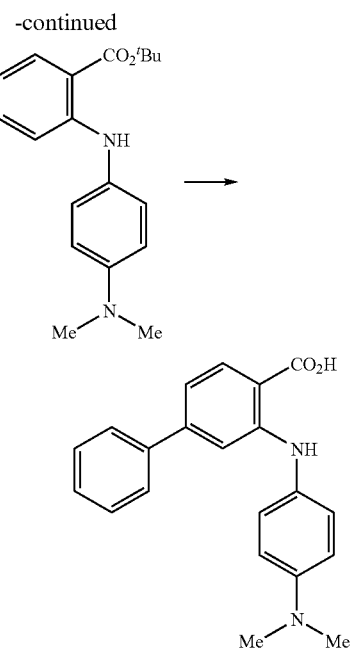

To toluene 3.0 mL suspension of tert-butyl 2-amino-4-phenylbenzoate 0.12 g and cesium carbonate 0.36 g were added 4-bromo-N,N-dimethylaniline 0.18 g, 2-dicyclohexylphosphino-2',4',6'-triisopropylbiphenyl 11 mg, tris(dibenzylideneacetone)dipalladium(0) 4.1 mg and palladium acetate 2.0 mg at room temperature, and it was stirred at 110° C. for 24 hours. 2-Dicyclohexylphosphino-2',4',6'-triisopropylbiphenyl 11 mg, tris(dibenzylideneacetone)dipalladium (0) 4.1 mg and palladium acetate 2.0 mg were added to it, and it was stirred at 110° C. for 21 hours. After the reaction mixture was cooled to room temperature, ethyl acetate and 10% citric acid aqueous solution were added to it, and insoluble matter was filtrated. The organic layer was separated and collected,dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((4-(dimethylamino)phenyl)amino)-4-phenylbenzoate.

Trifluoroacetic acid 5.0 mL was added to the obtained tert-butyl 2-((4-(dimethylamino)phenyl)amino)-4-phenylbenzoate, and it was stirred at room temperature for 3 hours. The solvent was removed under reduced pressure, ethyl acetate and water were added to the obtained residue, and it was adjusted to pH6.5 with saturated sodium hydrogen carbonate aqueous solution. The organic layer was separated and collected,dried over anhydrous magnesium sulfate after washing with saturated sodium chloride aqueous solution, and the solvent was removed under reduced pressure. Ethyl acetate was added to the obtained residue, and solid matter was filtrated to give 2-((4-(dimethylamino)phenyl)amino)-4-phenylbenzoic acid 61 mg of a yellow solid.

$^1$H-NMR(DMSO-$d_6$) δ value:

2.90(6H,s),6.75-6.81(2H,m),6.92(1H,dd,J=8.3,1.6 Hz), 7.07(1H,d,J=1.6 Hz),7.12-7.18(2H,m),7.34-7.53(5H,m), 7.93(1H,d,J=8.3 Hz),9.35-9.50(1H,broad),12.80-13.05(1H, broad).

Example 372

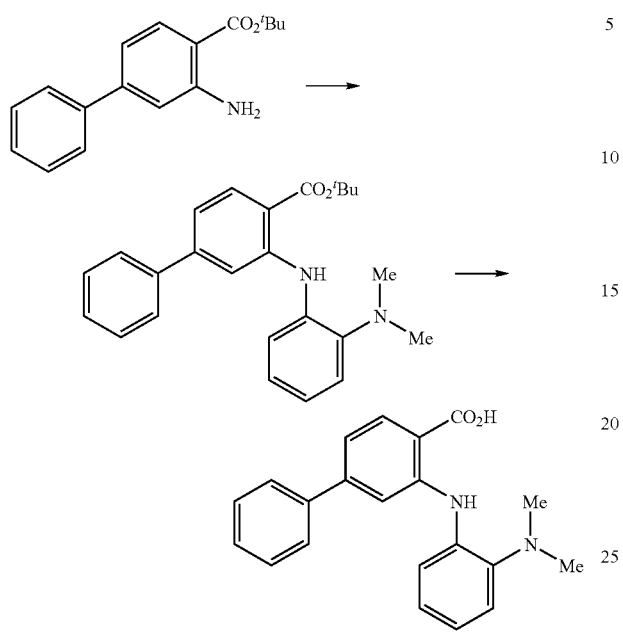

To toluene 3.0 mL suspension of tert-butyl 2-amino-4-phenylbenzoate 0.12 g and cesium carbonate 0.36 g were added 2-bromo-N,N-dimethylaniline 0.18 g, 2-dicyclohexylphosphino-2',4',6'-triisopropylbiphenyl 11 mg, tris(dibenzylideneacetone)dipalladium(0) 4.1 mg and palladium acetate 2.0 mg at room temperature, and it was stirred at 110° C. for 24 hours. 2-Dicyclohexylphosphino-2',4',6'-triisopropylbiphenyl 11 mg, tris(dibenzylideneacetone)dipalladium (0) 4.1 mg and palladium acetate 2.0 mg were added to it, and it was stirred at 110° C. for 21 hours. Cesium carbonate 73 mg, 2-bromo-N,N-dimethylaniline 45 mg, 2-dicyclohexylphosphino-2',4',6'-triisopropyl biphenyl 11 mg, tris(dibenzylideneacetone)dipalladium(0) 4.1 mg and palladium acetate 2.0 mg were added to it, and it was stirred at 110° C. for 24 hours. After the reaction mixture was cooled to room temperature, ethyl acetate and 10% citric acid aqueous solution were added to it, and insoluble matter was filtrated. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((2-(dimethylamino)phenyl)amino)-4-phenylbenzoate.

Trifluoroacetic acid 5.0 mL was added to the obtained tert-butyl 2-((2-(dimethylamino)phenyl)amino)-4-phenylbenzoate, and it was stirred at room temperature for 3 hours. The solvent was removed under reduced pressure, the obtained residue was refined by reversed-phase silica gel column chromatography [eluent; 50-85% acetonitrile/0.1% trifluoroacetic acid aqueous solution], subsequently ethyl acetate and water were added to it, and it was adjusted to pH6.5 with saturated sodium hydrogen carbonate aqueous solution. The organic layer was separated and collected, dried over anhydrous magnesium sulfate after washing with saturated sodium chloride aqueous solution, the solvent was removed under reduced pressure. Hexane was added to the obtained residue, and solid matter was filtrated to give 2-((2-(dimethylamino)phenyl)amino)-4-phenylbenzoic acid 17 mg of a yellow solid.

$^1$H-NMR(DMSO-$d_6$) δ value:
2.65(6H,s),7.00-7.08(3H,m),7.10-7.16(1H,m),7.36-7.50 (5H,m),7.57-7.62(2H,m),7.98(1H,d,J=8.3 Hz),9.67(1H,s), 12.95(1H,s).

Example 373

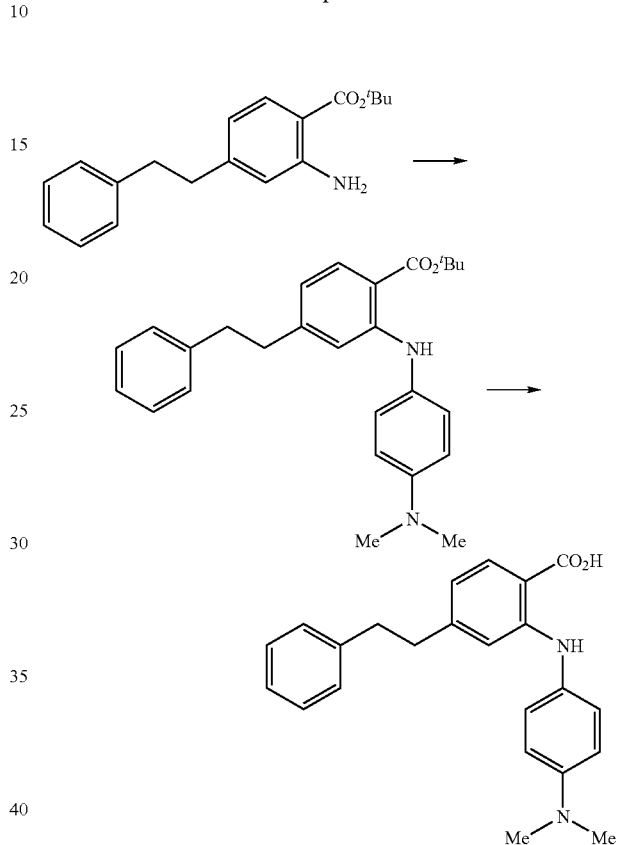

To toluene 3.0 mL suspension of tert-butyl 2-amino-4-phenethylbenzoate 0.12 g and cesium carbonate 0.33 g were added 4-bromo-N,N-dimethylaniline 0.16 g, 2-dicyclohexylphosphino-2',4',6'-triisopropylbiphenyl 9.6 mg, tris(dibenzylideneacetone)dipalladium(0) 3.7 mg and palladium acetate 1.8 mg at room temperature, and it was stirred at 110° C. for 24 hours. 2-Dicyclohexylphosphino-2',4',6'-triisopropylbiphenyl 9.6 mg, tris(dibenzylideneacetone)dipalladium (0) 3.7 mg and palladium acetate 1.8 mg were added to it at room temperature, and it was stirred at 110° C. for 21 hours. After the reaction mixture was cooled to room temperature, ethyl acetate and 10% citric acid aqueous solution were added to it, and insoluble matter was filtrated. The organic layer was separated and collected, dried over anhydrous magnesium sulfate after washing with saturated sodium chloride aqueous solution, and the solvent was removed under reduced pressure. The obtained residue was refined by silica gel column chromatography [Trikonex company, Flash Tube 2008, eluent; hexane:ethyl acetate=10:1] to give tert-butyl 2-((4-(dimethylamino)phenyl)amino)-4-phenethyl benzoate.

Trifluoroacetic acid 5.0 mL was added to tert-butyl 2-((4-(dimethylamino)phenyl)amino)-4-phenethylbenzoate, and it was stirred at room temperature for 3 hours. The solvent was removed under reduced pressure, ethyl acetate and water were added to the obtained residue, and it was adjusted to pH6.5 with saturated sodium hydrogen carbonate aqueous solution. The organic layer was separated and collected, dried over anhydrous magnesium sulfate after washing with saturated sodium chloride aqueous solution, and the solvent was removed under reduced pressure. Diisopropyl ether was added to the obtained residue, solid matter was filtrated to give 2-((4-(dimethylamino)phenyl)amino)-4-phenethylbenzoic acid 83 mg of a pale yellow solid.

$^1$H-NMR(DMSO-d$_6$) δ value:
2.70-2.85(4H,m),2.89(6H,s),6.54(1H,dd,J=8.1,1.6 Hz), 6.63-6.67(1H,m),6.69-6.75(2H,m),6.91-6.98(2H,m),7.12-7.31(5H,m),7.75(1H,d,J=8.1 Hz).

INDUSTRIAL APPLICABILITY

The compounds of the present invention have the inhibitory activity of MMP-13 production and therefore they are useful as, for example, therapeutic agents for rheumatoid arthritis, osteoarthritis, cancer and the other diseases in which MMP-13 is involved.

The invention claimed is:
1. An anthranilic acid compound, or a salt thereof, according to the following general formula:

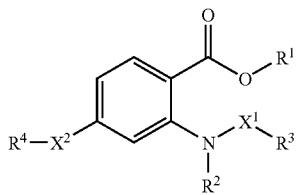

wherein
R$^1$ represents a hydrogen atom or a carboxyl protecting group;
R$^2$ represents a hydrogen atom or an imino protecting group;
R$^3$ represents a a phenyl, or a cycloalkyl which may be substituted with one or more substituents selected from the following group of substituents (1);
R$^4$ represents a phenyl, which may be substituted with one or more substituents selected from the following groups of substituents (2) and (3); or a pyridyl group which may be substituted with one or more substituents selected from the following groups of substituents (2) and (4);
X$^1$ represents an alkylene or alkenylene group or a bond; and
X$^2$ represents a bond, a carbonyl linking group or a linking group selected from the following linking groups —X$^3$—X$^4$—, —X$^4$—X$^3$—, —O—X$^4$— or —X$^4$—C(O)NH—, with the proviso that the bond on the left side of the linking group binds to R$^4$, wherein X$^3$ represents a sulfur atom, an imino group which may be protected, a sulfinyl group, a sulfonyl group or a bond, and X$^4$, wherein both X$^3$ and X$^4$ cannot simultaneously be a bond;
said group of substituents (1) represents a halogen atom, a cyano group, a nitro group, an acyl group, an alkanesulfonyl group, an alkanesulfonamide group, an acetamido group, a carbamoyl group, a sulfamoyl group, a lower alkylamino group, an amino group which may be protected, a hydroxyl group which may be protected, an alkyl group which may be substituted, an alkenyl group which may be substituted, an alkynyl group which may be substituted, an alkoxy group which may be substituted, an aryl group which may be substituted, a cyclic amino group which may be substituted, an aralkyl group which may be substituted or a heterocyclic group which may be substituted;
said group of substituents (2) represents an alkyl, alkenyl, alkynyl, alkoxy, aryl, cyclic amino, aralkyl or heterocyclic group which may be substituted with one or more groups selected from a halogen atom, a cyano group, a nitro group, an amino group, a cyclic amino group, a lower alkylamino group, a carboxyl group, a hydroxyl group, a lower alkyl group, an alkoxy group and an aryl group;
said group of substituents (3) represents a halogen atom, a cyano group, a nitro group, an acyl group, an alkanesulfonyl group, an alkanesulfonamide group, an acetamido group, a carbamoyl group, a sulfamoyl group, a lower alkylamino group, an amino group which may be protected or a hydroxyl group which may be protected; and
said group of substituents (4) represents a cyano group, a nitro group, an acyl group, an alkanesulfonyl group, an alkanesulfonamide group, an acetamido group, a carbamoyl group, a sulfamoyl group, a lower alkylamino group, an amino group which may be protected or a hydroxyl group which may be protected.
2. The anthranilic acid compound, or the salt thereof, according to claim 1, wherein R$^1$ is a hydrogen atom.
3. The anthranilic acid compound, or the salt therof, according to claim 1, wherein R3 is phenyl which may be substituted with one or more substituents selected from the following group of substituents (1a):
a halogen atom, a cyano group, a hydroxyl group, an alkyl group which may be substituted, an alkenyl group which may be substituted, an alkynyl group which may be substituted, an alkoxy group which may be substituted, an aryl group which may be substituted, a cyclic amino group which may be substituted, an aralkyl group which may be substituted or a heterocyclic group which may be substituted.
4. The anthranilic acid compound, or the salt thereof, according to claim 1, wherein X$^2$ represents a carbonyl linking group or a linking group selected from the linking groups —O—X$^{4a}$— or —X$^{4a}$—C(O)NH—, with the proviso that the bond on the left side of the linking group binds to R$^4$, wherein X$^{4a}$ represents an alkylene group which may be substituted or a bond.
5. The anthranilic acid compound, or the salt thereof, according to claim 1, wherein X$^2$ represents a bond, or a linking group selected from the linking groups —X$^{3a}$—X$^{4b}$— or —X$^{4b}$—X$^{3a}$—, with the proviso that the bond on the left side of the linking group binds to R$^4$, wherein X$^{3a}$ represents a sulfur atom, an imino group which may be protected or a bond, and X$^{4b}$ represents an alkylene or alkenylene group which may be substituted with an group selected from an alkyl and phenyl group which may be substituted or a bond, wherein both X$^{3a}$ and X$^{4b}$ cannot simultaneously be a bond.
6. The anthranilic acid compound, or the salt thereof, according to claim 1, wherein X$^2$ is a bond or X$^3$—X$^4$, wherein X$^3$ is a bond and X$^4$ is a substituted or unsubstituted alkylene.
7. A matrix metalloprotease 13 production inhibitor comprising the anthranilic acid compound, or the salt thereof, according to claim 1.

8. A therapeutic agent for rheumatoid arthritis comprising the anthranilic acid compound, or the salt thereof, according to claim 1.

9. The anthranilic acid compound, or the salt thereof, according to claim 1, wherein $R^2$ is a hydrogen atom.

10. The anthranilic acid compound, or the salt thereof, according to claim 1, wherein $R^4$ is a phenyl or bicyclic heterocyclic group which may be substituted with one or more substituents selected from the following groups of substituents (2a) and (3a):
    said group of substituents (2a) represents an alkyl, alkenyl, alkynyl, alkoxy, aryl, cyclic amino, aralkyl or heterocyclic group which may be substituted with one or more groups selected from a halogen atom, a cyano group, a nitro group, an amino group, a cyclic amino group, a lower alkylamino group, a carboxyl group, a hydroxyl group, a lower alkyl group, an alkoxy group and an aryl group; and
    said group of substituents (3a) represents a halogen atom, a cyano group, a nitro group, an acyl group, an alkanesulfonyl group, an alkanesulfonamide group, an acetamido group, a carbamoyl group, a sulfamoyl group, a lower alkylamino group, an amino group which may be protected or a hydroxyl group which may be protected.

11. A composition, comprising the anthranilic acid compound of claim 1 and a pharmaceutically acceptable carrier.

12. A composition, comprising the anthranilic acid compound of claim 2 and a pharmaceutically acceptable carrier.

13. A composition, comprising the anthranilic acid compound of claim 3 and a pharmaceutically acceptable carrier.

14. A composition, comprising the anthranilic acid compound of claim 4 and a pharmaceutically acceptable carrier.

15. A composition, comprising the anthranilic acid compound of claim 5 and a pharmaceutically acceptable carrier.

16. A composition, comprising the anthranilic acid compound of claim 6 and a pharmaceutically acceptable carrier.

17. A composition, comprising the anthranilic acid compound of claim 10 and a pharmaceutically acceptable carrier.

* * * * *